(12) United States Patent
Simon Vecilla et al.

(10) Patent No.: US 10,294,499 B2
(45) Date of Patent: May 21, 2019

(54) BIOSYNTHESIS OF PHENYLPROPANOIDS AND PHENYLPROPANOID DERIVATIVES

(71) Applicant: EVOLVA SA, Reinach (CH)

(72) Inventors: Ernesto Simon Vecilla, Münchenstein (CH); Beata Joanna Lehka, Valby Copenhagen (DK); Carlos Casado Vazquez, Copenhagen (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 15/575,481

(22) PCT Filed: May 27, 2016

(86) PCT No.: PCT/EP2016/061982
§ 371 (c)(1),
(2) Date: Nov. 20, 2017

(87) PCT Pub. No.: WO2016/189121
PCT Pub. Date: Dec. 1, 2016

(65) Prior Publication Data
US 2018/0163235 A1    Jun. 14, 2018

Related U.S. Application Data

(60) Provisional application No. 62/167,595, filed on May 28, 2015.

(51) Int. Cl.

| C12P 7/42  | (2006.01) |
| C12N 9/88  | (2006.01) |
| C12P 7/22  | (2006.01) |
| C12N 1/16  | (2006.01) |
| C12N 1/20  | (2006.01) |
| C12P 13/22 | (2006.01) |

(52) U.S. Cl.
CPC .................. *C12P 7/42* (2013.01); *C12N 1/16* (2013.01); *C12N 1/20* (2013.01); *C12N 9/88* (2013.01); *C12P 7/22* (2013.01); *C12Y 403/01023* (2013.01); *C12P 13/22* (2013.01); *C12Y 203/01074* (2013.01); *C12Y 203/01095* (2013.01)

(58) Field of Classification Search
None
See application file for complete search history.

(56) References Cited

U.S. PATENT DOCUMENTS

| 4,865,973 A  | 9/1989  | Kollerup et al. |
| 5,391,724 A  | 2/1995  | Kindl et al. |
| 5,500,367 A  | 3/1996  | Hain et al. |
| 5,973,230 A  | 10/1999 | Kindl et al. |
| 6,020,129 A  | 2/2000  | Schroder et al. |
| 6,284,523 B1 | 9/2001  | Daugulis et al. |
| 6,521,748 B2 | 2/2003  | Tang |
| 7,604,968 B2 | 10/2009 | Schmidt-Dannert et al. |
| 8,343,739 B2 | 1/2013  | Katz et al. |
| 8,518,677 B2 | 8/2013  | Schmidt et al. |
| 8,569,024 B2 | 10/2013 | Stenhuus et al. |
| 8,895,287 B2 | 11/2014 | Katz et al. |
| 2001/0053847 A1 | 12/2001 | Tang |
| 2004/0023357 A1 | 2/2004  | Breinig et al. |
| 2004/0059103 A1 | 3/2004  | Huang |
| 2004/0078846 A1 | 4/2004  | Desouza et al. |
| 2004/0229326 A1 | 11/2004 | Ben-Bassat et al. |
| 2004/0234671 A1 | 11/2004 | Ector et al. |
| 2005/0003474 A1 | 1/2005  | Desouza et al. |
| 2005/0208643 A1 | 9/2005  | Schmidt-Dannert et al. |
| 2006/0263864 A1 | 11/2006 | Busby et al. |
| 2008/0286844 A1 | 11/2008 | Katz et al. |
| 2009/0035839 A1 | 2/2009  | Katz et al. |
| 2009/0082286 A1 | 3/2009  | Huang et al. |
| 2009/0280543 A1 | 11/2009 | Lim et al. |
| 2011/0086399 A1 | 4/2011  | Smits et al. |
| 2011/0124067 A1 | 5/2011  | Stenhuus et al. |
| 2013/0171328 A1 | 7/2013  | Kishore et al. |
| 2014/0024862 A1 | 1/2014  | Katz et al. |

FOREIGN PATENT DOCUMENTS

| CN | 1277954        | 12/2000 |
| EP | 1 510 586      | 3/2005  |
| EP | 1 715 032      | 10/2006 |
| JP | 2005-53862     | 3/2005  |
| JP | 2001-008695    | 1/2011  |
| KR | 2004-0105110   | 12/2004 |
| WO | WO 00/73485    | 12/2000 |
| WO | WO 02/10407    | 2/2002  |
| WO | WO 2004/049832 | 6/2004  |

(Continued)

OTHER PUBLICATIONS

Louie et al., "Structural Determinants and Modulation of Substrate Specificity in Phenylalanine-Tyrosine Ammonia-Lyases", Dec. 2006, Chemistry & Biology, vol. 13, pp. 1327-1338. DOI 10.1016/j.chembiol.2006.11.011.*
Wang & Zhang, "Inhibitory effects of Broccolini leaf flavonoids on human cancer cells." Scanning, 34(1):1-5 (Jan.-Feb. 2012; Epub Aug. 24, 2011).
Watts et al., "Discovery of a substrate selectivity switch in tyrosine ammonia-lyase, a member of the aromatic amino acid lyase family". Chem Biol. 13:1317-26 (2006).
Watts et al. "Exploring recombinant flavonoid biosynthesis in metabolically engineered *Escherichia coli*" ChemBioChem: A European Journal of Chemical Biology 5(4): Apr. 2004, pp. 500-507.
Watts et al., "Biosynthesis of plant-specific stilbene polyketides in metabolically engineered *Escherichia coli*," BMC Biotechnology 6(22):1-12 (2006).

(Continued)

*Primary Examiner* — Suzanne M Noakes
(74) *Attorney, Agent, or Firm* — McDonnell Boehnen Hulbert & Berghoff LLP

(57) ABSTRACT

Provided herein are recombinant hosts and methods for producing phenylpropanoid and phenylpropanoid derivative compounds. It was found that tyrosine ammonia lyase from *Aeromonas salmonicida* A449 provides improved coumaric acid production.

29 Claims, 3 Drawing Sheets

Specification includes a Sequence Listing.

(56) References Cited

FOREIGN PATENT DOCUMENTS

| WO | WO 2004/092344 | 10/2004 |
|---|---|---|
| WO | WO 2005/012507 | 2/2005 |
| WO | WO 2005/118814 | 12/2005 |
| WO | WO 2006/055322 | 5/2006 |
| WO | WO 2006/089898 | 8/2006 |
| WO | WO 2006/111163 | 10/2006 |
| WO | WO 2006/124999 | 11/2006 |
| WO | WO 2006/125000 | 11/2006 |
| WO | WO 2007/034190 | 3/2007 |
| WO | WO 2008/009728 | 1/2008 |
| WO | WO 2008/065370 | 6/2008 |
| WO | WO 2009/016108 | 2/2009 |
| WO | WO 2009/124879 | 10/2009 |
| WO | WO 2009/124966 | 10/2009 |
| WO | WO 2009/124967 | 10/2009 |
| WO | 2011/140344 A1 | 11/2011 |
| WO | WO 2011/140344 | 11/2011 |
| WO | WO 2011/147818 | 12/2011 |
| ZA | 20048194 | 10/2004 |

OTHER PUBLICATIONS

Weis et al., "Regioselective glucosylation of aromatic compounds: screening of a recombinant glycosyltransferase library to identify biocatalysts." Angew. Chem. Int. Ed. 45(21): 3534-38 (May 2006).
Welch et al., "Designing genes for successful protein expression." Methods in Enzymology, 498:43-66 (2011).
Werck-Reichhart & Feyereisen. Cytochromes P450: a success story. Genome Biology 2000:1:3003.1-3003.9.
Whisstock et al., "Prediction of protein function from protein sequence and structure", Quarterly Reviews of Biophysics 36(3): 307-340 (2003).
Wiebe "Stable production of recombinant proteins in filamentous fungi-problems and improvements." Mycologist. 17:140-144 (2003).
Wiese et al., "Structural organization and differential expression of three stilbene synthase genes located on a 13 kb grapevine DNA fragment." Plant Mol Biol 26(2):667-77 (1994).
Yabusaki et al., "Primary Structure of Saccharomyces cerevisiae NADPH-Cytochrome P450 Reductase Deduced from Nucleotide Sequence of its Cloned Gene", J. Biochem., 103(6):1004-10 (1988).
Yeo et al., "Quantification of pinosylvin in rat plasma by liquid chromatography-tandem mass spectrometry: application to a preclinical pharmacokinetic study." J Chromatogr B Analyt Technol Biomed Life Sci. 931:68-74 (Jul. 2013; Epub May 28, 2013).
Yeo et al., "Pharmacokinetics of pterostilbene in Sprague-Dawley rats: the impacts of aqueous solubility, fasting, dose escalation, and dosing route on bioavailability." Mol Nutr Food Res 57(6):1015-25 (Jun. 2013; Epub Feb. 13, 2013). PMID: 23417986.
Yohei Katsuyama et al., "Precursor-directed biosynthesis of stilbene methyl ethers in Escherichia coli" Biotechnology Journal 2(10):1286-93 (Oct. 2007).
Yoon et al., CrelloxP-mediated in vivo excision of large segments from yeast genome and their amplification based on the 2 mm plasmid-derived system. Gene 1998:223:67-76.
Zahir et al., "Isolation and characterization of novel organic solvent-tolerant bacteria" Extremophiles 10(2):129-38 (2006; Epub Oct. 20, 2005).
Zava & Duwe, "Estrogenic and antiproliferative properties of genistein and other flavonoids in human breast cancer cells in vitro." Nutr. Cancer, 27(1):31-40 (1997).
Zhou et al., "Inhibition of xanthine and monoamine oxidases by stilbenoids from Veratrum taliense." Planta Med. 67(2)158-61 (Mar. 2001). PMID: 11301865.
Zhou et al., "Assessing the regioselectivity of OleD-catalyzed glycosylation with a diverse set of acceptors." J. Nat. Prod. 76(2):279-86 (Feb. 2013; Epub Jan. 29, 2013).
Zhu et al., "A mult-omic map of the lipid-producing yeast Rhodosporidium toruloides." Nature Communications 3:1112 pp. 1-12 (Oct. 2012).
Zwiers et al., ABC transporters and azole susceptibility in laboratory strains of the wheat pathogen Mycosphaerella graminicola. Antimicrob Agents Chemother. Dec. 2002; 46(12):3900-6.
The International Search Report issued in International Application No. PCT/EP2006/060154 (published as WO 2006/089898); dated Jun. 20, 2006, pp. 1-4.
The International Search Report issued in International Application No. PCT/EP2007/057484 (published as WO 2008/009728); dated Oct. 17, 2007, pp. 1-5.
The International Search Report issued in International Application No. PCT/EP2008/059768 (published as WO 2009/016108); dated Apr. 9, 2009, pp. 1-6.
The International Search Report issued in International Application No. PCT/EP2009/053974 (published as WO 2009/124879); dated Oct. 5, 2009, pp. 1-6.
The International Search Report issued in International Application No. PCT/EP2009/054219 (published as WO 2009/124967); dated Oct. 2, 2009, pp. 1-5.
The International Search Report issued in International Application No. PCT/EP2011/058447 (published as WO 2011/147818); dated Aug. 22, 2011, pp. 1-7.
The International Search Report issued in International Application No. PCT/EP2014/067520 (published as WO 2015/028324); dated Mar. 2, 2015, pp. 1-9.
The International Search Report issued in International Application No. PCT/EP2016/060798 (published as WO 2015/028324); dated Jul. 27, 2016, pp. 1-4.
The International Search Report issued in International Application No. PCT/EP2016/061982 (published as WO2016/189121); dated Jul. 29, 2016, pp. 1-7.
Gonzalez-Candelas et al. "The use of transgenic yeasts expressing a gene encoding a glycosyl-hydrolase as a tool to increase resveratrol content in wine." Int J Food Microbiol. 59(3):179-83 (2000).
Greenwald, "Clinical trials in cancer prevention: current results and perspectives for the future." J Nutr, 134(12 Suppl.):3507S-3512S (Dec. 2004).
Guengerich et al., Expression of human cytochrome P450 enzymes in yeast and bacteria and relevance to studies on catalytic specificity. Toxicology. 1993:82:21-37.
Guerra et al., "A novel system of genetic transformation allows multiple integrations of a desired gene in Saccharomyces cerevisiae chromosomes", J Microbiol Methods, vol. 67, pp. 437-445, 2006.
Gustafsson et al., "Codon bias and heterologous protein expression," Trends Biotechnol. 22:346-53 (2004).
Hain et al., "Disease resistance results from foreign phytoalexin expression in a novel plant", Nature, vol. 361, pp. 153-156, 1993.
Hamberger & Hahlbrock. The 4-coumarate:CoA ligase gene family in Arabidopsis thaliana comprises one rare, sinapate-activating and three commonly occurring isoenzymes. Proc Natl Acad Sci USA. 2004:101:2209-14.vol. 101, pp. 2209-2214, 2004.
Hall, "Longevity research. In Vino Vitalis? Compounds Activate Life-Extending Genes." Science 301(5637):1165 (2003).
Hano et al., "Sequential glucosylation determined by NMR in the biosynthesis of mulberroside D, a cis-oxyresveratrol diglucoside, in Morus alba L. cell cultures," Cell. Mol. Life Sci. 53(3):237-41 (Mar. 1997).
Hansen et al., "Substrate specificities of family 1 UGTs gained by domain swapping." Phytochemistry 70(4):473-82 (Mar. 2009; Epub Mar. 2, 2009).
Hart, "Role of phytostilbenes in decay and disease resistance". Annu. Rev. Phytopathology 19, 437-458 (1981).
Hart & Shrimpton, "Role of stilbenes in resistance of wood to decay". Phytopathology 69, 1138-1143 (1979).
Hasemann et al., "Structure and function of cytochromes P450:a comparative analysis of three crystal structures", Structure, 3(1):41-62 (Jan. 1995). PMID: 7743131.
Hegemann & Hock, "Delete and repeat: a comprehensive toolkit for sequential gene knockout in the budding yeast Saccharomyces cerevisiae." Methods Mol Biol., 765:189-206 (2011).
Hemingway et al., "Polyphenols in Ceratocystis minor infected Pinus taeda: Fungal Metabolites, phloem and xylem phenols". J. Agric. Food Chem., 25, 717-722 (1977).

(56) References Cited

OTHER PUBLICATIONS

Herrero et al., Engineering the *Saccharomyces cerevisiae* isoprenoid pathway for de novo production of aromatic monoterpenes in wine, Metabolic Eng., 10(2):78-86 (2008).
Horinouchi et al., "Combinatorial Biosynthesis of Non-bacterial and Unnatural Flavonoids, Stilbenoids and Curcuminoids by Microorganisms," Journal of Antibiotics 61(12):709-28 (2008).
Horinouchi et al., "Combinatorial biosynthesis of plant medicinal polyketides by microorganisms" Current Opinion in Chemical Biology 13(2):197-2014 (Apr. 2009).
Hou et al., "Molecular Mechanisms Behind the Chemopreventive Effects of Anthocyanidins" J Biomed Biotechnol, (5):321-25 (2004).
Huang, "Diet for cancer prevention." Food Sci.(Shipin Kexue; Taipei) 24(6):713-727 (1997).
Hseih et al., "Cloning, expression, site-directed mutagenesis and immunolocalization of phenylalanine ammonia-lyase in Bambusa oldhamii." Phytochemistry 71(17-18):1999-2009 (Dec. 2010; Epub Oct. 27, 2010).
Hubbard et al., "NADPH-Cytochrome P450 Oxidoreductase: Structural Basis for Hydride and Electron Transfer." J. Biol. Chem. 276:29163-70 (2001).
Hwang et al., "Production of Plant-Specific Flavanones by *Escherichia coli* Containing an Artificial Gene Cluster." Appl. Environ. Microbial. 69(5):2699-2706 (2003).
Jang et al. "Cancer Chemopreventive Activity of Resveratrol, a Natural Product Derived from Grapes." Science 275(5297):218-20 (1997).
Jeandet et al. "Effect of Enological Practices on the Resveratrol Isomer Content of Wine." J. Agric. Food Chem. 43, 1995. pp. 316-319 (1995).
Jeandet et al. "Occurence of a resveratrol.cndot.- D-glucoside in wine: Preliminary studies." Vitis 33, pp. 183-184 (1994).
Jeandet et al., "Phytoalexins from the Vitaeae: Biosynthesis, Phytoalexin Gene Expression in Transgenic Plants, Antifungal Activity, and Metabolism", J. Agric. Food Chem., 50(10):2731-41 (2002).
Jiang et al. "Metabolic Engineering of the Phenylpropanoid Pathway in *Saccharomyces cerevisiae*." Applied and Environmental Microbiology 71(6):2962-69 (2005).
Johansson & Hahn-Hagerdal. Overproduction of pentose phosphate pathway enzymes using a new CRE-IoxP expression vector for repeated genomic integration in *Saccharomyces cerevisiae*. Yeast 2002:19:225-231.
Jungwirth & Kuchler. Yeast ABC transporters—a tale of sex, stress, drugs and aging. FEBS Lett. 2006:580:1131-8.
Juretzek et al., "Vectors for gene expression and amplification in the yeast *Yarrowia lipolytica*", Yeast. 18(2):97-113 :2001).
Juvvadi et al., "Genomics reveals traces of fungal phenylpropanoid-flavonoid metabolic pathway in the filamentous fungus *Aspergillus oryzae*." J Microbiol. 43(6):475-486 (2005).
Kaneko, et al., "Cinnamate:Coenzyme A ligase from the Filamentous Bacteria Streptomyces coelicolor A3(2)," J. Bact. 185(1): 20-27 (2003).
Kapetanovic et al., "Pharmacokinetics, oral bioavailability, and metabolic profile of resveratrol and its dimethylether analog, pterostilbene, in rats." Cancer Chemother Pharmacol 68(3):593-601 (Sep. 2011; Epub Nov. 30, 2010).
KiIndl, Biosynthesis of stilbenes. In Higuchi T, ed, Biosynthesis and Biodegradation of Wood Components. Academic Press, London, pp. 349-377. (1985).
Kirino et al., "Analysis and functionality of major polyphenolic components of Polygonum cuspidatum (itadori)." J Nutr Sci Vitaminol 58(4):278-86 (2012).
Kizer et al., "Application of Functional Genomics to Pathway Optimization for Increased Isoprenoid Production." Applied and Environmental Microbiology. 74(10):3229-3241 (2008).
Koopmann et al. "Regulation and Functional Expression of Cinnamate 4-Hydroxylase from Parsley." Plant Physiol. 119(1):49-56 (1999).
Koopman et al., "De novo production of the flavonoid naringenin in engineered *Saccharomyces cerevisiae*." Microb Cell Fact. 11:155 pp. 1-15 (Dec. 2012).
Kopp, "Resveratrol, a phytooestrogen found in red wine. A possible explanation for the conundrum of the "French Paradox"?" Eur. J. Endocrinol. 138, 1998. pp. 619-620.
Kodan et al., "A stilbene synthase from Japanese red pine (*Pinus densiflora*): Implications for phytoalexin accumulationand down-regulation of flavonoid biosynthesis" Proc. Natl. Acad. Sci. 99, 3335-3339 (2002).
Kunji et al., Lactococcus lactis as host for overproduction of functional membrane proteins. Biochim Biophys Acta. 2003:1610:97-108.
Kyndt et al. "Characterization of a bacterial tyrosine ammonia lyase, a biosynthetic enzyme for the photoactive yellow protein." FEBS Lett. 512(1-3):240-44 (2002).
La Grange et al. "Cloning of the Bacillus pumilus beta-xylosidase gene (xynB) and its expression in *Saccharomyces cerevisiae*. Appl. Microbiol." Biotechnol. 47(3):262-266 (1997).
Larronde et al., "New stilbenoid glucosides isolated from Vitis vinifera cell suspension cultures (cv. Cabernet Sauvignon)." Planta Med. 71(9):888-90 (Sep. 2005).
Le Dall et al., "Multiple-copy integration in the yeast *Yarrowia lipolytica*". Curr Genet. 26(1):38-44 (1994).
Lee et al. "Antibacterial and antifungal activity of pinosylvin, a constituent of pine" Fitoterapia, 76(2):258-60 (2005).
Li et al., "De novo production of resveratrol from glucose or ethanol by engineered *Saccharomyces cerevisiae*." Metabolic Engineering 32:1-11 (Nov. 2015; Epub Sep. 4, 2015).
Li et al., "High-density cultivation of oleaginous yeast *Rhodosporidium toruloides* Y4 in fed-batch culture" Enzyme and Microbial Technology, 41(3):312-17 (Aug. 2007).
Lieutier et al., "Changes in phenolic metabolites of Scots pine phloem induced by Ophiostoma brunneo-ciliatum, a bark beetle-associated fungus". Eur. J.For Pathol. 26(3):145-158 (1996).
Abe et al., "Enzymatic formation of long-chain polyketide pyrones by plant type III polyketide synthases", Phytochemistry, vol. 6, pp. 2447-2453 (2004).
Ageitos et al., "Oily yeasts as oleaginous cell factories." Applied Microbiology and Biotechnology, 90(4):1219-27 (May 2011).
Aggarwal et al., "Role of resveratrol in prevention and therapy of cancer: preclinical and clinical studies". Anticancer Res. 24(5A):2783-840 (2004).
Allina et al., "4-coumarate: Coenzyme A ligase in hybrid poplar. Properties of enzymes, cDNA cloning, and analysis of recombinant clones". Plant Physiol. 116, 743-754 (1998).
Allister et al., "Inhibition of microsomal triglyceride transfer protein expression and apolipoprotein B100 secretion by the citrus flavonoid naringenin and by insulin involves activation of the mitogen-activated protein kinase pathway in hepatocytes" Diabetes 54(6):1676-83 (Jun. 2005).
Andrade et al.. The ABC transporter AtrB from Aspergillus nidulans mediates resistance to all major classes of fungicides and some natural toxic compounds. Microbiology. 2000:146:1987-97.
Aoyama et al. "NADPH-cytochrome P-450 reductase of yeast microsomes." Arch. Biochem. Biophys. 185, 1978. pp. 362-369 (1978).
Appert et al., "Structural and catalytic properties of the four phenylalanine ammonia-lyase isoenzymes from parsley (*Petroselinum crispum* Nym.)" FEBS 225:491-99 (1994).
Aury et al., Global trends of whole-genome duplications revealed by the ciliate Paramecium tetraurelia. Nature. Nov. 9, 2006; 444(7116):171-8.
Austin et al., "An Aldol Switch Discovered in Stilbene Synthases Mediated Cyclization Specificity of Type III Polyketide Synthases", Chemistry & Biology, vol. 11, pp. 1179-1194, Sep. 2004.
Baedeker et al., "Autocatalytic Peptide Cyclization during Chain Folding of Histidine Ammonia-Lyase", Structure, vol. 10, pp. 61-67, Jan. 2002.
Baedeker et al., "Structures of two histidine ammonia-lyase modifications and implications for the catalytic mechanism", Eur J. Biochem., vol. 269, pp. 1790-1797, 2002.

(56) References Cited

OTHER PUBLICATIONS

Bankar et al., "Environmental and industrial applications of Yarrowia lipolytica." Appl Microbiol Biotechnol. 84(5):847-65 (Oct. 2009; Epub Aug. 8, 2009).

Banerjee et al., Responses of pathogenic and nonpathogenic yeast species to steroids reveal the functioning and evolution of multidrug resistance transcriptional networks. Eukaryot Cell. 2008:7:68-77.

Bateman et al., "Pfam 3.1: 1313 multiple alignments and profile HMMs match the majority of proteins." Nucl. Acids Res., 27(1):260-62 (Jan. 1999).

Becker et al., "Metabolic engineering of *Saccharomyces cerevisiae* for the synthesis of the wine-related antioxidant resveratrol." FEMS Yeast Research 4:79-85 (2003).

Beekwilder et al., "Production of Resveratrol in Recombinant Microorganisms," Applied and Environmental Microbiology 72(8):5670-72 (2006).

Beopoulos et al., "Yarrowia lipolytica: A model and a tool to understand the mechanisms implicated in lipid accumulation." BIOHIMIE, 91(6):692-6 (Jun. 2009; Epub Feb. 25, 2009).

Berner et al., "Genes and enzymes involved in caffeic acid biosynthesis in the actinomycete Saccharothrix espanaensis", J Bacteriol, 2006:188:2666-73.

Blanquet et al."Recombinant *Saccharomyces cerevisiae* Expressing P450 in Artificial Digestive Systems: a Model for Biodetoxication in the Human Digestive Environment." Applied and Environmental Microbiology, 69(5):2884-2892 (2003).

Boer et al., The genome-wide transcriptional responses of *Saccharomyces cerevisiae* grown on glucose in aerobic chemostat cultures limited for carbon, nitrogen, phosphorus, or sulfur. J Biol. Chem. 2003:278:3265-74.

Bu et al., "High-throughput Caco-2 cell permeability screening by cassette dosing and sample pooling approaches using direct injection/on-line guard cartridge extraction/tandem mass spectrometry," Rapid Communications in Mass Spectrometry 14(6):523-28 (Mar. 2000).

Callemien et al., "Hop as an interesting source of resveratrol for brewers: Optimization of the extraction and quantitative study by liquid chromatography/atmospheric pressure chemical ionization tandem mass spectrometry" J Agric Food Chem. 53(2):424-29 (2005).

Caruso et al., "Structural basis for antioxidant activity of trans-resveratrol: ab initio calculations and crystal and molecular structure", J Agric Food Chem., vol. 52, pp. 7279-7285, 2004.

Celotti et al."Resveratrol content of some wines obtained from dried Valpolicella grapes: Recioto and Amarone." Journal of Chromatography A. 730(1-2):47-52 (1996).

Chen et al., "One-step transformation of the dimorphic yeast *Yarrowia lipolytica*." Appl Microbiol Biotechnol. 48(2):232-5 (1997).

Chenna et al., "Multiple sequence alignment with the Clustal series of programs." Nucl. Acids Res., 31(13):3497-500 (Jul. 2003).

Chloupkova et al., Expression of 25 human ABC transporters in the yeast *Pichia pastoris* and characterization of the purified ABCC3 ATPase activity. Biochemistry. 2007:46:7992-8003.

Cochrane, et al. "The *Arabidopsis phenylalanine* ammonia lyase gene family: kinetic characterization of the four PAL isoforms." Phytochemistry 65, 2004. pp. 1557-1564.

Connolly et al., Heterologous expression of a pleiotropic drug resistance transporter from Phytophthora sojae in yeast transporter mutants. Curr Genet. 2005:48:356-65.

Cordero-Otero et al., "Efficient selection of hygromycin-B-resistant Yarrowia lipolytica transformants". Appl Microbiol Biotechnol. 46(2):143-48 (1996).

Costa et al., "Characterization in vitro and in vivo of the putative multigene 4-coumarate:CoA ligase network in *Arabidopsis*: syringyl lignin and sinapate/sinapyl alcohol derivative formation", Phytochemistry, 66(17):2072-91 (2005).

Couzin, "Scientific community. Aging Research's Family Feud." Science 303(5662):1276-79 (2004).

Decendit et al., "Galloylated catechins and stilbene diglucosides in Vitis vinifera cell suspension cultures" Phytochemistry 60(8):795-98 (Aug. 2002).

Del Sorbo et al., Multidrug resistance in Aspergillus nidulans involves novel ATP-binding cassette transporters. Mol Gen Genet. 1997:254:417-26.

Del Sorbo et al., Cloning and functional characterization of BcatrA, a gene encoding an ABC transporter of the plant pathogenic fungus *Botryotinia fuckeliana* (Botrytis cinerea). Mycol Res. 2008:112:737-46.

Domergue et al., in vivo characterization of the first acyl-GoA Delta6-desaturase from a member of the plant (kingdom, the microalga *Ostreococcus tauri*. Biochem J. Jul. 15, 2005; 389 (Pt 2):483-90.

Ehlting et al., Three 4-coumarate:coenzyme A ligases in *Arabidopsis thaliana* represent two evolutionarily divergent classes in angiosperms. Plant J. 1999:19:9-20.

Erdeniz et al., Cloning-Free PCR-Based Allele Replacement Methods. Genome Res. Jul. 1997: 1174-1183.

Escribano-Bailon et al., "Coupling Reactions between Flavylium Ions and Catechin" Phytochemistry 41(6):1583-92 (1996).

Etschmann et al., Biotechnological production of 2-phenylethanol. Appl Microbial Biotechnol 2002:59:1-8.

Fickers et al., "New disruption cassettes for rapid gene disruption and marker rescue in the yeast *Yarrowia lipolytica*." J Microbiol Methods. 55(3):727-37 (2003).

Filpula et al. "Nucleotide sequence of gene for phenylalanine ammonia-lyase from Rhodotorula rubra." Nucleic Acids Res. 16(23):11381 (1988).

Gao & Ming, "Bioavailability challenges associated with development of anti-cancer phenolics." Mini Rev Med Chem 10(6):550-67 (Jun. 2010).

Gehlert et al., "Stilbene synthase from seedlings of Pinus sylvestris—purification and induction in response to fungal infection". Mol. Plant-Microbe Interaction 3(6):444-49 (1990).

Gehm et al. "Resveratrol, a polyphenolic compound found in grapes and wine, is an agonist for the estrogen receptor." Proc. Natl. Acad. Sci. USA 94, 1997. pp. 14138-14143 (1997).

Gems et al., "An autonomously replicating plasmid transforms Aspergillus nidulans at high frequency". Gene 98(1):61-67 (1991).

Giaever et al., Functional profiling of the *Saccharomyces cerevisiae* genome. Nature. 2002:418:387-91.

Gietz & Schiestl. Applications of high efficiency lithium acetate transformation of intact yeast cells using single-stranded nucleic acids as carrier. Yeast. 1991:7:253-63.

Gilon et al., Degradation signals for ubiquitin system proteolysis in *Saccharomyces cerevisiae*. The EMBO Journal. 1998:17:2759-2766.

Koopman, Frank et al., "Denovo production of the flavonoid naringenin in engineered *Saccharomyces cerevisiae*" Microbial Cell Factories (2012) vol. 11(155), 15 pages.

Watts, Kevin T. et al. "Discovery of a substrate selectivity switch in tyrosine ammonia-lyase, a member of the aromatic amino acid lyase family" Chemistry & Biology (2006) vol. 13, pp. 1317-1326.

Database UniProt [Online] May 15, 2007 (May 15, 2007) SubName: Full=Histidine ammonia-lyase {EC0:0000313:EMBL:AB089050. 1}; XP002760065 retrieved from EBI accession No. Uniprot:A4SJH8.

The International Search Report (ISR) for PCT/EP2016/061982 dated Jul. 20, 2016, pp. 1-6.

Written Opinion of the International Searching Authority for PCT/EP2016/061982 dated Jul. 20, 2016, pp. 1-5.

Limem et al., "Production of phenylpropanoid compounds by recombinant microorganisms expressing plant-specific biosynthesis genes." Process Biochemistry, 43(5):463-479 (May 2008).

Lin et al. "Sequence and analysis of chromosome 2 of the plant *Arabidopsis thaliana*." Nature 402(6763):761-768 (1999).

Lindberg et al., "Antibacterial effects of knotwood extractives on paper mill bacteria". J Ind Microbiol Biotechnol. 31(3):137-147 (2004).

Lobo, "Benefits and risks of estrogen replacement therapy." Am. J. Obstet. Gynecol. 173(3 Pt 2):982-89 (1995).

Luttik et al., "Alleviation of feedback inhibition in *Saccharomyces cerevisiae* aromatic amino acid biosynthesis: Quantification of metabolic impact," Metabolic Eng. 10:141-53 (2008).

(56) References Cited

OTHER PUBLICATIONS

Madzak et al., "Heterologous protein expression and secretion in the non-conventional yeast *Yarrowia lipolytica*: review". J Biotechnol. 109(1-2):63-81 (2004).
Martin et al., "Engineering a mevalonate pathway in *Escherichia coli* for production of terpenoids". Nature biotechnology 21(7):796-802 (2003).
Melchior & Kindl, "Coordinate and elicitor dependent expression of stilbene synthase and phenylalanine ammonialyase genes in *Vitis* cv. Optima." Arch. Biochem. Biophys 288(2):552-57 (1991).
Melchior & Kindl, "Grapevine stilbene synthase cDNA only slightly differing from chalcone synthase cDNA is expressed in *Escherichia coli* into a catalytically active enzyme", FEBS Lett. 268(1):17-20 (Jul. 1990).
Mellanen et al., "Wood-derived estrogens: studies in vitro with breast cancer cell lines and in vivo in trout". Toxicol. App. Pharm. 136(2):381-88 (1996).
Merkulov et al., "Cloning and characterization of the Yarrowia lipolytica squalene synthase (SQS1) gene and functional complementation of the *Saccharomyces cerevisiae* erg9 mutation," Yeast 16(3):197-206 (2000).
Mizutani et al., Isolation of a eDNA and a genomic clone encoding cinnamate 4-hydroxylase from *Arabidopsis* and its expression manner in planta. Plant Physiol. 1997:113:755-63.
Mizutani & Ohta. Two isoforms of NADPH:cytochrome P450 reductase in *Arabidopsis thaliana*. Gene structure. heterologous expression in insect cells. and differential regulation. Plant Physiol. 1998:116:357-67.
Mora-Pale et al., "Metabolic engineering and in vitro biosynthesis of phytochemicals and non-natural analogues". Plant Science 210:10-24 (May 2013).
Morita et al., "Novel polyketides synthesized with a higher plant stilbene synthase". Eur. J. Biochem. 268, 3759-3766 (2001).
Moriya et al.. In vivo robustness analysis of cell division cycle genes in *Saccharomyces cerevisiae*. PLoS Genet. Jul. 2006; 2(7):e111. Epub Jun. 5, 2006. Erratum in: PLoS Genet. Dec. 2006; 2(12):e218.
Muhitch et al.. Transgenic expression of the TRI101 or PDR5 gene increases resistance of tobacco to the phytotoxic effects of the trichothecene 4, 15-diacetoxyscirpenol. Plant Sci. 2000:157:201-207.
Muller et al., "Comparison of expression systems in the yeasts *Saccharomyces cerevisiae, Hansenula polymorpha, Klyveromyces lactis, Schizosaccharomyces pombe* and *Yarrowia lipolytica*. Cloning of two novel promoters from *Yarrowia lipolytica*". Yeast 14(14):1267-83 (1998).
Mumberg et al., Yeast vectors for the controlled expression of heterologous proteins in different genetic backgrounds. Gene. 156(1):119-22 (Apr. 1995).
Nicaud et al., Protein expression and secretion in the yeast *Yarrowia lipolytica*. FEMS Yeast Res. 2(3):371-9 (2002).
Niimi et al., Functional analysis of fungal drug efflux transporters by heterologous expression in S. cerevisiae. Jpn. J. Infect Disease 2005:58:1-7.
Nijveldt et al., "Flavonoids: a review of probable mechanisms of action and potential applications." Am J Clin Nutr, 74(4):418-25 (Oct. 2001).
Nisimoto, "Localization Cytochrome c-binding Domain on NADPH-Cytochrome P-450 Reductase", The Journal of Biological Chemistry, vol. 261, No. 30, pp. 14232-14239, 1986.
Orsini et al., "Isolation, synthesis, and antiplatelet aggregation activity of resveratrol 3-O-beta-D-glucopyranoside and related compounds." J. Nat. Prod. 60(11):1082-87 (Nov. 1997).
Osmani et al., "Catalytic key amino acids and UDP-sugar donor specificity of a plant glucuronosyltransferase, UGT94B1: molecular modeling substantiated by site-specific mutagenesis and biochemical analyses." Plant Physiol. 148(3):1295-1308 (Nov. 2008; Epub Oct. 1, 2008).
Osmani et al., "Substrate specificity of plant UDP-dependent glycosyltransferases predicted from crystal structures and homology modeling." Phytochemistry, 70(3):325-47 (Feb. 2009).

Ozaki et al., "Regioselective glucosidation of-resveratrol inexpressing glucosyltransferase from Phytolacca americana" Biotechnology Letters 34(3):475-81 (Nov. 2011).
Pacher et al., "Antifungal stilbenoids from Stemona collinsae." J Nat Prod. 65 (6):820-827 (2002).
Pan et al., Identification of molecular pathways affected by pterostilbene, a natural dimethylether analog of resveratrol. BMC Med. Genomics. 2008:20:1-7.
Park et al., "Bioconversion of Piceid to Piceid Glucoside Using Amylosucrase from Alteromonas macleodii Deep Ecotype," J. Microbiol. Biotechnol. 22(12):1698-1704 (Dec. 2012).
Park et al., "Enzymatic synthesis of piceid glucosides using maltosyltransferase from Caldicellulosiruptor bescii DSM 6725" J. Agric. Food Chem. 60(33):8183-89 (Aug. 2012; Epub Aug. 8, 2012).
Passorn et al., Heterologous expression of Mucor rouxii delta(12)-desaturase gene in *Saccharomyces cerevisiae*. Biochem. Biophys. Res. Commun. 263 (1):47-51 (1999).
Pignede et al., "Autocloning and amplification of LIP2 in Yarrowia lipolytica." Appl. Environ Microbiol. 2000:66:3283-9.
Porter & Kasper, "NADPH-Cytochrome P-450 Oxidoreductase: Flavin Mononucleotide and Flavin Adenine Dinucleotide Domains Evolved from Different Flavoproteins", Biochemistry, 25:1682-1687 (1986).
Prather et al., "De novo biosynthetic pathways: rational design of microbial chemical factories. Current Opinion in Biotechnology." 19:468-474 (2008).
Preisig-Muller et al., "Characterization of a pine multigene family containing elicitor-responsive stilbene synthase genes". Plant Molecular Biology. 39(2):221-229. (1999).
Pretorius et al., "Meeting the consumer challenge through genetically customized wine-yeast strains," Trends Biotech 20:426-32 (2002).
Punt et al., "Filamentous fungi as cell factories for heterologous protein production," Trends in Biotechnology 20(5):200-206 (2002).
Raiber et al., "Molecular and enzymatic characterization of two stilbene synthases from Eastern white pine (*Pinus strobus*). A single Arg/His difference determines the activity and the pH dependence of the enzymes". FEBS Lett. 361(2-3):299-302 (1995).
Regev-Shoshani et al., "Glycosylation of resveratrol protects it from enzymic oxidation." Biochem J. 374(Pt 1):157-63 (Aug. 2003).
Richter & Wild, "Phenolic compounds in needles of Norway spruce trees in relation to novel forest decline: I. Studies on trees from site of the Northern Black Forest.", Biochem. Biophys. Pflanz 188, 305-320 (1992).
Ritter et al., "Structural Basis for the Entrance into the Phenylpropanoid Metabolism Catalyzed by Phenylalanine Ammonia-Lyase", The Plant Cell, 16(12):3426-3436 (Dec. 2004).
Ro et al. "Functional Characterization and Subcellular Localization of Poplar (*Populus trichocarpa* x *Populus deltoides*) Cinnamate 4-Hydroxylase." Plant Physiol. 126, 2001. pp. 317-329 (2001).
Ro & Douglas, "Reconstitution of the Entry Point of Plant Phenylpropanoid Metabolism in Yeast (*Saccharomyces cerevisiae*)," J. Biol. Chem. 279(4):2600-07 (2004).
Rodriguez et al., "Establishment of a yeast platform strain for production of p-coumaric acid through metabolic engineering of aromatic amino acid biosynthesis." Metab. Eng. 31:181-88 (Sep. 2015; Epub Aug. 18, 2015).
Rogers et al., The pleitropic drug ABC transporters from *Saccharomyces cerevisiae*. J Mol Microbiol Biotechnol. 2001:3:207-14.
Rosemann et al., "Biochemical Plant Responses to Ozone. II. Induction of Stilbene Biosynthesis in Scots Pine (*Pinu sylvestris* L.) Seedlings. Jr." Plant Physiol. 97, 1280-1286 (1991).
Rosler et al. "Maize phenylalanine ammonia-lyase has tyrosine ammonia-lyase activity." Plant Physiol. 113, 1997. pp. 175-179 (1997).
Rother et al ., "An active site homology model of phenylalanine ammonia-lyase from Petroselinum crispum," Eur. J. Biochern. 269(12):3065-75 (2002).
Roupe et al., "Pharmacometrics of Stilbenes: Seguing Towards the Clinic." Curr. Clin. Pharmac. 1, 81-101 (2006).

(56) References Cited

OTHER PUBLICATIONS

Rupasinghe et al., "Common active site architecture and binding strategy of four phenylpropanoid P450s from *Arabidopsis thaliana* as revealsed by molecular modeling", Protein Engineering, 16(10):721-31 (2003).
Saenge et al., "Potential use of oleaginous red yeast *Rhodotorula glutinis* for the bioconversion of crude glycerol from biodiesel plant to lipids and carotenoids." Process Biochemistry, 46(1):210-18 (Jan. 2011).
Samappito et al. "Aromatic and pyrone polyketides synthesized by a stilbene synthase from Rheum tataricum" Phytochemistry, 62(3): Feb. 2003, pp. 313-323.
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis." J Biol Chem. 280(2):899-906 (Jan. 2005; Epub Oct. 7, 2004).
Schanz et al., "Stilbene synthase from Scot's pine (*Pinus sylvestris*)" FEBS Lett. 313(1):71-74 (1992).
Schmidheini et al., "A single point mutation results in a constitutively activated and feedback-resistant chorismate mutase of *Saccharomyces cerevisiae*." Journal of Bacteriology 171(3):1245-53 (Mar. 1989).
Schmidlin et al., "A stress-inducible resveratrol O-methyltransferase involved in the biosynthesis of pterostilbene in grapevine." Plant Physiol 148(3):1630-39 (Nov. 2008; Epub Sep. 17, 2008).
Schoonbeek et al., "The ABC Transporter BcatrB Affects the Sensitivity of Botrytis cinerea to the Phytoalexin Resveratrol and the Fungicide Fenpiclonil," Molecular Plant-Microbe Interactions 14:562-71 (2001).
Schoppner & Kindl, "Purification and properties of a stilbene synthase from induced cell suspension cultures of peanut". J. Biol. Chem. 259, 6806-6811 (1984).
Schneider et al., "The substrate specificity-determining amino acid cod of 4-coumarate:CoA ligase", PNAS, vol. 100, No. 14, pp. 8601-8606, Jul. 2003.
Schroder et al., "Molecular analysis of resveratrol synthase. cDNA clones and relationship with chalcone synthase". Eur J Biochem 172(1): 161-69 (1988).
Schuster & Retey, "Serine-202 is the putative precursor of the active site dehydroalanine of phenylalanine ammonia lyase", FEBS Letters 349(2):252-54 (1994).
Schwede et al., "Crystal Structure of Histidine Ammonia-Lyase Revealing a Novel Polypeptide Modification as the Catalytic Electrophile", Biochemistry, 38(17):5355-61 (1999).
Sengottuvelan & Nalini, "Dietary supplementation of resveratrol suppresses colonic tumour incidence in 1,2-dimethylhydrazine-treated rats by modulating biotransforming enzymes and aberrant crypt foci development." British Journal of Nutrition 96(1):145-53 (2006).
Serazetdinova et al., "Expression of transgenic stilbene synthases in wheat causes the accumulation of unknown stilbene derivatives with antifungal activity." Journal of Plant Physiology 162(9):985-1002 (2005).
Servos et al., Gene SNQ2 of *Saccharomyces cerevisiae*, which confers resistance to 4-nitroquinoline-N-oxide and other chemicals, encodes a 169 kDa protein homologous to ATP-dependent permeases. Mol Gen Genet. Jan. 1993; 236(2-3):214-8.
Wang et al., "Three-dimensional structure of NADPH-cytochrome P450 reductase: Prototype for FMN- and FAD-containing enzymes", Proc. Natl. Acad. Sci. USA, 94:8411-16 (Aug. 1997).
Seshime et al., "Genomic evidences for the existence of a phenylpropanoid metabolic pathway in Aspergillus oryzae." Biochem. Biophys. Res Commun. 337(3):747-51 (2005).
Shao et al., "Phenolic and Triterpenoid glycosides from Aster batangensis" Phytochemistry 41(6):1593-98 (1996).
Shi et al., "Improving production of malonyl coenzyme A-derived metabolites by abolishing Snf1-dependent regulation of Acc1." mBio 6(3):e01130-14 (May 2014).
Sikorski & Hieter, "A system of shuttle vectors and yeast host strains designed for efficient manipulation of DNA in *Saccharomyces cerevisiae*", Genetics, vol. 122(1):19-27 (May 1989).
Skinnider & Stoessl, "The effect of the phytoalexins, lubimin, (-)-maackiain, pinosylvin, and the related compounds dehydroloroglossol and hordatine M on human lymphoblastoid cell lines". Experientia 42(5):568-570 (1986).
Song et al., Engineering tolerance and accumulation of lead and cadmium in transgenic plants. Nat. Biotechnol. 2003:21:914-9.
Sonnhammer et al., "Pfam: multiple sequence alignments and HMM-profiles of protein domains." Nucl. Acids Res. 26(1):320-22 (Jan. 1998).
Sonnhammer et al., "Pfam: a comprehensive database of protein domain families based on seed alignments" Proteins, 28(3):405-20 (Jul. 1997).
Stark et al., "Novel Type of in Situ Extraction: Use of Solvent Containing Microcapsules for the Bioconversion of 2-Phenylethanol From .sub.L-Phenylalanine by *Saccharomyces cerevisiae*", Biotechnology and Bioengineering, vol. 83(4), pp. 376-385, 2003.
Stojanovic et al., "Efficiency and mechanism of the anti-oxidant action of trans-resveratrol and its analogues in the radical liposome oxidation". Arch. Biochem. Biophys. 391(1):79-89 (2001).
STN Search CAS directory pinosylvin chemical properties data, pp. 1-2, 2012.
Stuible et al., "Identification of the Substrate Specificity-conferring Amino Acid Residues of 4-Coumarate:Coenzyme A Ligase Allows the Rational Design of Mutant Enzymes with New Catalytic Properties", The Journal of Biological Chemistry, vol. 276, No. 29, pp. 26893-26897, 2001.
Suga et al., "Endogenous pine wood nematicidal substances in pines, *Pinus massoniana, P. strobus* and *P. palustris*." Phytochemistry 33(6):1395-1401 (1993).
Suh et al., "Identification of amino acid residues important in the cyclization reactions of chalcone and stilbene synthases", Biochem. J. 350(Pt.1):229-35 (2000).
Sun et al., "In vitro testing of drug absorption for drug 'developability' assessment: forming an interface between in vitro preclinical data and clinical outcome." Curr. Opin. Drug Discov. Devel. 7(1):75-85 (Jan. 2004).
Tavares & Gunnarsson. GenBank GU593327.1 Mortierella alpina strain CBS 608.70 delta-6 elongase mRNA, complete cds. Mar. 29, 2010, one page.
Tilburn et al., "Transformation by integration in Aspergillus nidulans", Gene, vol. 26, pp. 205-221, 1983.
Trantas et al. "Metabolic engineering of the complete pathway leading to heterologous biosynthesis of various flavonoids and stilbenoids in *Saccharomyces cerevisiae*", Metab Eng. 11(6):355-66 (2009).
Tropf et al., "Reaction mechanisms of homodimeric plant polyketide synthase (stilbenes and chalcone synthase). A single active site for the condensing reaction is sufficient for synthesis of stilbenes, chalcones, and 6'-deoxychalcones". J. Biol. Chem. 270, 7922-7928 (1995).
Trott et al., "Activation of heat shock and antioxidant responses by the natural product celastrol: transcriptional signatures of a thiol-targeted molecule. Mol Biol Cell. 2008:19:1104-12.
Uhlmann & Ebel, "Molecular Cloning and Expression of 4-Coumarate:Coenzyme A Ligase, an Enzyme Involved in the Resistance Response of Soybean (*Glycine max* L.) against Pathogen Attack", Plant Physiol. 102(4):1147-56 (1993).
Uniprot, Accession No. P32449, ARO4, 2010, www.uniprot.org. last accessed Jun. 8, 2015, pp. 1-8.
Uniprot, Accession No. P32178, ARO7 2010, www.uniprot.org. last accessed Jun. 8, 2015, pp. 1-7.
Uniprot, Accession No. A4SJH8, Histidine ammonia-lyase, 2007; www.uniprot.org. last accessed Jul. 20, 2016, one page.
Urban et al., "Characterization of recombinant plant cinnamate 4-hydroxylase produced in yeast. Kinetic and spectral properties of the major plant P450 of the phenylpropanoid pathway". Eur J Biochem. 222(3):843-50 (1994).

(56) References Cited

OTHER PUBLICATIONS

Urban et al. "Cloning, Yeast Expression, and Characterization of the Coupling of Two Distantly Related *Arabidopsis taliana* NADPH-Cytochrome 450 Reductases with P450 CYP73A5." J. Biol. Chem. 272: 19176-186 (1997).

Vannelli et al., "Functional expression in *Escherichia coli* of the tyrosine-inducible tyrosine ammonia-lyase enzyme from yeast *Trichosporon cutaneum* for production of p-hydroxycinnamic acid." Enzyme and Microbial Technology, 41(4):413-22 (Sep. 2007).

Verduyn et al., "Effect of benzoic acid on metabolic fluxes in yeasts: a continuous-culture study on the regulation of respiration and alcoholic fermentation". Yeast 8, 501-517 (1992).

Vuralhan et al., "Physiological characterization of the ARO10-dependent broad-substrate-specificity 2-oxo acid decarboxylase activity of *Saccharomyces cerevisiae*," App. Env. Microbiol. 71:3276-84 (2005).

Waffo-Teguo et al., "Isolation, identification, and antioxidant activity of three stilbene glucosides newly extracted from vitis vinifera cell cultures" J. Nat. Prod. 61(5):655-57 (May 1998).

Wang et al., "Pterostilbene production by microorganisms expressing resveratrol O-methyltransferase." Ann Microbiol. pp. 1-10 (published online: Jun. 26, 2014).

Wang et al., "Structure, mechanism and engineering of plant natural product glycosyltransferases" FEBS Letters 583(20):3303-09 (Oct. 2009).

Chao et al., "Protective effects of pinostilbene, a resveratrol methylated derivative, against 6-hydroxydopamine-induced neurotoxicity in SH-SY5Y cells," J Nutritional Biochemistry, 21(6):482-89 (Jun. 2010).

Dercks & Creasy, "The significance of stilbene phytoalexins in the Plasmopara viticola—grapevine interaction." Physiological and Molecular Plant Pathology 34:189-202 (1989).

Gakh et al., "Dihdryo-resveratrol—A potent dietary polyphenol" Bioorganic & Medicinal Chemistry Letters 20:6149-51 (2010).

Kang et al., "Biosynthesis of methylated resveratrol analogs through the construction of an artificial biosynthetic pathway in *E.coli*" BMC Biotechnology 14:67, pp. 1-11 (2014).

Kumar & Nambisan, "Antifunal Activity of Diketopiperazines and Stilbenes Against Plant Pathogenic Fungi in Vitro" Appl Biochem Biotechnol. 172:741-54 (2014).

Laavola et al., "Pinosylvin and Monomethylpinosylvin, Constituents of an Extract from the Knot of Pinus sylvestris, Reduce Inflammatory Gene Expression and Inflammatory Responses in Vivo," J Agricultural and Chemistry, 63(13):3445-3453 (Mar. 2015).

Romero-Perez et al., "Piceid, the Major Resveratrol Derivative in Grape Juices," J Agric. Food. Chem., 47(4):1533-36 (Apr. 1999).

Shi et al., "Stilbene Derivatives from Photorhabdus temperata SN259 and Their Antifungal Activities against Phytopathogenic Fungi" Journal of Agricultural and Food Chemistry 65:60-65 (2017; published Dec. 14, 2016).

Shim et al., "Enzymatic Preparation of Phenolic Glucosides by *Streptococcus mutans*," Bull. Korean Chem. Soc., 24(11):1680-82 (2003).

The International Search Report issued in International Application No. PCT/EP2018/062607; dated Jul. 18, 2018, pp. 1-6.

The International Search Report issued in International Application No. PCT/EP2018/062619; dated Jul. 24 2018, pp. 1-6.

GenBank Accession No. AAR06914.1; two pages, published Dec. 28, 2004.

\* cited by examiner

SEQUENCE LISTING

<160> NUMBER OF SEQ ID NOS: 49

<210> SEQ ID NO 1
<211> LENGTH: 531

<212> TYPE: PRT
<213> ORGANISM: Rhodobacter capsulatus

<400> SEQUENCE: 1

```
Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400
```

```
Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
        530

<210> SEQ ID NO 2
<211> LENGTH: 505
<212> TYPE: PRT
<213> ORGANISM: Arabidopsis thaliana

<400> SEQUENCE: 2

Met Asp Leu Leu Leu Glu Lys Ser Leu Ile Ala Val Phe Val Ala
1               5                   10                  15

Val Ile Leu Ala Thr Val Ile Ser Lys Leu Arg Gly Lys Lys Leu Lys
            20                  25                  30

Leu Pro Pro Gly Pro Ile Pro Ile Pro Ile Phe Gly Asn Trp Leu Gln
        35                  40                  45

Val Gly Asp Asp Leu Asn His Arg Asn Leu Val Asp Tyr Ala Lys Lys
    50                  55                  60

Phe Gly Asp Leu Phe Leu Leu Arg Met Gly Gln Arg Asn Leu Val Val
65                  70                  75                  80

Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
```

```
                225                 230                 235                 240
Ile Cys Gln Asp Val Lys Asp Arg Arg Ile Ala Leu Phe Lys Lys Tyr
                    245                 250                 255

Phe Val Asp Glu Arg Lys Gln Ile Ala Ser Ser Lys Pro Thr Gly Ser
                260                 265                 270

Glu Gly Leu Lys Cys Ala Ile Asp His Ile Leu Glu Ala Glu Gln Lys
                275                 280                 285

Gly Glu Ile Asn Glu Asp Asn Val Leu Tyr Ile Val Glu Asn Ile Asn
                290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
                    325                 330                 335

Asp Thr Val Leu Gly Pro Gly Val Gln Val Thr Glu Pro Asp Leu His
                340                 345                 350

Lys Leu Pro Tyr Leu Gln Ala Val Val Lys Glu Thr Leu Arg Leu Arg
                355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
                    405                 410                 415

Arg Pro Glu Arg Phe Glu Glu Ser His Val Glu Ala Asn Gly
                420                 425                 430

Asn Asp Phe Arg Tyr Val Pro Phe Gly Val Gly Arg Arg Ser Cys Pro
                435                 440                 445

Gly Ile Ile Leu Ala Leu Pro Ile Leu Gly Ile Thr Ile Gly Arg Met
                450                 455                 460

Val Gln Asn Phe Glu Leu Leu Pro Pro Pro Gly Gln Ser Lys Val Asp
465                 470                 475                 480

Thr Ser Glu Lys Gly Gly Gln Phe Ser Leu His Ile Leu Asn His Ser
                    485                 490                 495

Ile Ile Val Met Lys Pro Arg Asn Cys
                    500                 505

<210> SEQ ID NO 3
<211> LENGTH: 556
<212> TYPE: PRT
<213> ORGANISM: Arabidopsis thaliana

<400> SEQUENCE: 3

Met Thr Thr Gln Asp Val Ile Val Asn Asp Gln Asn Asp Gln Lys Gln
1               5                   10                  15

Cys Ser Asn Asp Val Ile Phe Arg Ser Arg Leu Pro Asp Ile Tyr Ile
                20                  25                  30

Pro Asn His Leu Pro Leu His Asp Tyr Ile Phe Glu Asn Ile Ser Glu
            35                  40                  45

Phe Ala Ala Lys Pro Cys Leu Ile Asn Gly Pro Thr Gly Glu Val Tyr
        50                  55                  60

Thr Tyr Ala Asp Val His Val Thr Ser Arg Lys Leu Ala Ala Gly Leu
65                  70                  75                  80

His Asn Leu Gly Val Lys Gln His Asp Val Val Met Ile Leu Leu Pro
                85                  90                  95
```

```
Asn Ser Pro Glu Val Val Leu Thr Phe Leu Ala Ala Ser Phe Ile Gly
            100                 105                 110

Ala Ile Thr Thr Ser Ala Asn Pro Phe Phe Thr Pro Ala Glu Ile Ser
        115                 120                 125

Lys Gln Ala Lys Ala Ser Ala Ala Lys Leu Ile Val Thr Gln Ser Arg
    130                 135                 140

Tyr Val Asp Lys Ile Lys Asn Leu Gln Asn Asp Gly Val Leu Ile Val
145                 150                 155                 160

Thr Thr Asp Ser Asp Ala Ile Pro Glu Asn Cys Leu Arg Phe Ser Glu
                165                 170                 175

Leu Thr Gln Ser Glu Glu Pro Arg Val Asp Ser Ile Pro Glu Lys Ile
            180                 185                 190

Ser Pro Glu Asp Val Val Ala Leu Pro Phe Ser Ser Gly Thr Thr Gly
        195                 200                 205

Leu Pro Lys Gly Val Met Leu Thr His Lys Gly Leu Val Thr Ser Val
    210                 215                 220

Ala Gln Gln Val Asp Gly Glu Asn Pro Asn Leu Tyr Phe Asn Arg Asp
225                 230                 235                 240

Asp Val Ile Leu Cys Val Leu Pro Met Phe His Ile Tyr Ala Leu Asn
                245                 250                 255

Ser Ile Met Leu Cys Ser Leu Arg Val Gly Ala Thr Ile Leu Ile Met
            260                 265                 270

Pro Lys Phe Glu Ile Thr Leu Leu Leu Glu Gln Ile Gln Arg Cys Lys
        275                 280                 285

Val Thr Val Ala Met Val Val Pro Pro Ile Val Leu Ala Ile Ala Lys
    290                 295                 300

Ser Pro Glu Thr Glu Lys Tyr Asp Leu Ser Ser Val Arg Met Val Lys
305                 310                 315                 320

Ser Gly Ala Ala Pro Leu Gly Lys Glu Leu Glu Asp Ala Ile Ser Ala
                325                 330                 335

Lys Phe Pro Asn Ala Lys Leu Gly Gln Gly Tyr Gly Met Thr Glu Ala
            340                 345                 350

Gly Pro Val Leu Ala Met Ser Leu Gly Phe Ala Lys Glu Pro Phe Pro
        355                 360                 365

Val Lys Ser Gly Ala Cys Gly Thr Val Val Arg Asn Ala Glu Met Lys
    370                 375                 380

Ile Leu Asp Pro Asp Thr Gly Asp Ser Leu Pro Arg Asn Lys Pro Gly
385                 390                 395                 400

Glu Ile Cys Ile Arg Gly Asn Gln Ile Met Lys Gly Tyr Leu Asn Asp
                405                 410                 415

Pro Leu Ala Thr Ala Ser Thr Ile Asp Lys Asp Gly Trp Leu His Thr
            420                 425                 430

Gly Asp Val Gly Phe Ile Asp Asp Asp Glu Leu Phe Ile Val Asp
        435                 440                 445

Arg Leu Lys Glu Leu Ile Lys Tyr Lys Gly Phe Gln Val Ala Pro Ala
    450                 455                 460

Glu Leu Glu Ser Leu Leu Ile Gly His Pro Glu Ile Asn Asp Val Ala
465                 470                 475                 480

Val Val Ala Met Lys Glu Asp Ala Gly Glu Val Pro Val Ala Phe
                485                 490                 495

Val Val Arg Ser Lys Asp Ser Asn Ile Ser Glu Asp Glu Ile Lys Gln
            500                 505                 510

Phe Val Ser Lys Gln Val Val Phe Tyr Lys Arg Ile Asn Lys Val Phe
```

```
                515                 520                 525
Phe Thr Asp Ser Ile Pro Lys Ala Pro Ser Gly Lys Ile Leu Arg Lys
    530                 535                 540

Asp Leu Arg Ala Arg Leu Ala Asn Gly Leu Met Asn
545                 550                 555

<210> SEQ ID NO 4
<211> LENGTH: 392
<212> TYPE: PRT
<213> ORGANISM: Vitis pseudoreticulata

<400> SEQUENCE: 4

Met Ala Ser Val Glu Glu Ile Arg Asn Ala Gln Arg Ala Lys Gly Pro
1               5                   10                  15

Ala Thr Ile Leu Ala Ile Gly Thr Ala Thr Pro Asp His Cys Val Tyr
                20                  25                  30

Gln Ser Asp Tyr Ala Asp Tyr Tyr Phe Arg Val Thr Lys Ser Glu His
            35                  40                  45

Met Thr Ala Leu Lys Lys Lys Phe Asn Arg Ile Cys Asp Lys Ser Met
    50                  55                  60

Ile Lys Lys Arg Tyr Ile His Leu Thr Glu Glu Met Leu Glu Glu His
65                  70                  75                  80

Pro Asn Ile Gly Ala Tyr Met Ala Pro Ser Leu Asn Ile Arg Gln Glu
                85                  90                  95

Ile Ile Thr Ala Glu Val Pro Lys Leu Gly Lys Glu Ala Ala Leu Lys
            100                 105                 110

Ala Leu Lys Glu Trp Gly Gln Pro Lys Ser Lys Ile Thr His Leu Val
        115                 120                 125

Phe Cys Thr Thr Ser Gly Val Glu Met Pro Gly Ala Asp Tyr Lys Leu
    130                 135                 140

Ala Asn Leu Leu Gly Leu Glu Pro Ser Val Arg Arg Val Met Leu Tyr
145                 150                 155                 160

His Gln Gly Cys Tyr Ala Gly Gly Thr Val Leu Arg Thr Thr Lys Asp
                165                 170                 175

Leu Ala Glu Asn Asn Ala Gly Ala Arg Val Leu Val Val Cys Pro Glu
            180                 185                 190

Ile Thr Val Val Thr Phe Arg Gly Pro Ser Glu Asp Ala Leu Asp Ser
        195                 200                 205

Leu Val Gly Gln Ala Leu Phe Gly Asp Gly Ser Ala Ala Val Ile Val
    210                 215                 220

Gly Ser Asp Pro Asp Ile Ser Ile Glu Arg Pro Leu Phe Gln Leu Val
225                 230                 235                 240

Ser Ala Ala Gln Thr Phe Ile Pro Asn Phe Ala Gly Ala Ile Ala Gly
                245                 250                 255

Asn Leu Arg Glu Val Gly Leu Thr Phe His Leu Trp Pro Asn Val Pro
            260                 265                 270

Thr Leu Ile Ser Glu Asn Ile Glu Asn Cys Leu Thr Gln Ala Phe Asp
        275                 280                 285

Pro Leu Gly Ile Ser Asp Trp Asn Ser Leu Phe Trp Ile Ala His Pro
    290                 295                 300

Gly Gly Pro Ala Ile Leu Asp Ala Val Glu Ala Lys Leu Asn Leu Asp
305                 310                 315                 320

Lys Lys Lys Leu Glu Ala Thr Arg His Val Leu Ser Glu Tyr Gly Asn
                325                 330                 335
```

```
Val Ser Ser Ala Cys Val Leu Phe Ile Leu Asp Glu Met Arg Lys Lys
            340                 345                 350

Ser Leu Lys Gly Glu Arg Ala Thr Thr Gly Glu Gly Leu Gly Trp Gly
        355                 360                 365

Val Leu Phe Gly Phe Gly Pro Gly Leu Thr Ile Glu Thr Val Val Leu
    370                 375                 380

His Ser Ile Pro Met Val Thr Asn
385                 390

<210> SEQ ID NO 5
<211> LENGTH: 711
<212> TYPE: PRT
<213> ORGANISM: Arabidopsis thaliana

<400> SEQUENCE: 5

Met Ser Ser Ser Ser Ser Ser Thr Ser Met Ile Asp Leu Met Ala
1               5                   10                  15

Ala Ile Ile Lys Gly Glu Pro Val Ile Val Ser Asp Pro Ala Asn Ala
                20                  25                  30

Ser Ala Tyr Glu Ser Val Ala Ala Glu Leu Ser Ser Met Leu Ile Glu
        35                  40                  45

Asn Arg Gln Phe Ala Met Ile Val Thr Thr Ser Ile Ala Val Leu Ile
    50                  55                  60

Gly Cys Ile Val Met Leu Val Trp Arg Arg Ser Gly Ser Gly Asn Ser
65                  70                  75                  80

Lys Arg Val Glu Pro Leu Lys Pro Leu Val Ile Lys Pro Arg Glu Glu
                85                  90                  95

Glu Ile Asp Asp Gly Arg Lys Lys Val Thr Ile Phe Phe Gly Thr Gln
                100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
    130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
    195                 200                 205

Tyr Glu His Phe Asn Lys Val Ala Lys Val Val Asp Asp Ile Leu Val
    210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
    275                 280                 285

Glu Asp Ala Lys Phe Asn Asp Ile Asn Met Ala Asn Gly Asn Gly Tyr
    290                 295                 300

Thr Val Phe Asp Ala Gln His Pro Tyr Lys Ala Asn Val Ala Val Lys
305                 310                 315                 320
```

Arg Glu Leu His Thr Pro Glu Ser Asp Arg Ser Cys Ile His Leu Glu
                325                 330                 335

Phe Asp Ile Ala Gly Ser Gly Leu Thr Tyr Glu Thr Gly Asp His Val
            340                 345                 350

Gly Val Leu Cys Asp Asn Leu Ser Glu Thr Val Asp Glu Ala Leu Arg
        355                 360                 365

Leu Leu Asp Met Ser Pro Asp Thr Tyr Phe Ser Leu His Ala Glu Lys
    370                 375                 380

Glu Asp Gly Thr Pro Ile Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430

Thr Glu Ala Glu Arg Leu Lys His Leu Ala Ser Pro Ala Gly Lys Asp
        435                 440                 445

Glu Tyr Ser Lys Trp Val Val Glu Ser Gln Arg Ser Leu Leu Glu Val
    450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Asn Cys Ser Ser Ala
    530                 535                 540

Pro Ile Phe Val Arg Gln Ser Asn Phe Lys Leu Pro Ser Asp Ser Lys
545                 550                 555                 560

Val Pro Ile Ile Met Ile Gly Pro Gly Thr Gly Leu Ala Pro Phe Arg
                565                 570                 575

Gly Phe Leu Gln Glu Arg Leu Ala Leu Val Glu Ser Gly Val Glu Leu
            580                 585                 590

Gly Pro Ser Val Leu Phe Phe Gly Cys Arg Asn Arg Arg Met Asp Phe
        595                 600                 605

Ile Tyr Glu Glu Glu Leu Gln Arg Phe Val Glu Ser Gly Ala Leu Ala
    610                 615                 620

Glu Leu Ser Val Ala Phe Ser Arg Glu Gly Pro Thr Lys Glu Tyr Val
625                 630                 635                 640

Gln His Lys Met Met Asp Lys Ala Ser Asp Ile Trp Asn Met Ile Ser
                645                 650                 655

Gln Gly Ala Tyr Leu Tyr Val Cys Gly Asp Ala Lys Gly Met Ala Arg
            660                 665                 670

Asp Val His Arg Ser Leu His Thr Ile Ala Gln Glu Gln Gly Ser Met
        675                 680                 685

Asp Ser Thr Lys Ala Glu Gly Phe Val Lys Asn Leu Gln Thr Ser Gly
    690                 695                 700

Arg Tyr Leu Arg Asp Val Trp
705                 710

<210> SEQ ID NO 6
<211> LENGTH: 1200

<212> TYPE: DNA
<213> ORGANISM: Hordeum vulgare

<400> SEQUENCE: 6

```
atggctgcag taagattgaa agaagttaga atggcacaga gggctgaagg tttagctaca      60
gttttagcaa tcggtactgc cgttccagct aattgtgttt atcaagctac ctatccagat     120
tattatttta gggttactaa aagtgagcac ttggcagatt taaaggagaa gtttcaaaga     180
atgtgtgaca aatcaatgat tagaaagaga cacatgcact tgaccgagga atatattgatc    240
aagaacccaa agatctgtgc acacatggag acctcattgg atgctagaca cgccatcgca     300
ttagttgaag ttcccaaatt gggccaaggt gcagctgaga aggccattaa ggagtggggc     360
caaccttgt ctaagattac tcatttggta ttttgcacaa catccggcgt tgacatgccc      420
ggtgctgatt accaattaac aaagttgtta ggtttgtccc ctacagtcaa aggttaatg     480
atgtaccaac aaggttgctt tggtggtgca actgttttga gattggcaaa agatatcgct    540
gaaaataata gaggtgccag agtgttagtc gtttgttccg agataactgc tatggccttc    600
agaggtccat gcaagagtca tttagattcc ttggtaggtc atgccttgtt cggtgatggt    660
gccgctgctg caattatagg cgctgaccca gaccaattag acgaacaacc agttttccag    720
ttggtatcag cttctcagac tatattacca gaatcagaag gtgccataga tggccattta    780
acagaagctg gttaactat acatttatta aaagatgttc ctggtttaat ttcagagaac     840
attgaacagg ctttggagga tgcctttgaa cctttaggta ttcataactg gaattcaatt    900
ttctggattg cacatcctgg tggccctgcc attttagaca gagttgaaga tagagtagga    960
ttggataaga agagaatgag ggcttctagg gaagtgttat ctgaatacgg aaatatgtct   1020
agtgcctctg tgttgtttgt gttagatgtc atgaggaaaa gttctgctaa agacggattg   1080
gcaaccacag gagaaggaaa agattgggga gtgttgtttg gattcggacc aggcttgact   1140
gtagaaacct tagtgttgca tagtgtccca gtccctgtcc ctactgcagc ttctgcatga   1200
```

<210> SEQ ID NO 7
<211> LENGTH: 399
<212> TYPE: PRT
<213> ORGANISM: Hordeum vulgare

<400> SEQUENCE: 7

```
Met Ala Ala Val Arg Leu Lys Glu Val Arg Met Ala Gln Arg Ala Glu
 1               5                  10                  15

Gly Leu Ala Thr Val Leu Ala Ile Gly Thr Ala Val Pro Ala Asn Cys
             20                  25                  30

Val Tyr Gln Ala Thr Tyr Pro Asp Tyr Tyr Phe Arg Val Thr Lys Ser
         35                  40                  45

Glu His Leu Ala Asp Leu Lys Glu Lys Phe Gln Arg Met Cys Asp Lys
     50                  55                  60

Ser Met Ile Arg Lys Arg His Met His Leu Thr Glu Glu Ile Leu Ile
 65                  70                  75                  80

Lys Asn Pro Lys Ile Cys Ala His Met Glu Thr Ser Leu Asp Ala Arg
                 85                  90                  95

His Ala Ile Ala Leu Val Glu Val Pro Lys Leu Gly Gln Gly Ala Ala
            100                 105                 110

Glu Lys Ala Ile Lys Glu Trp Gly Gln Pro Leu Ser Lys Ile Thr His
        115                 120                 125

Leu Val Phe Cys Thr Thr Ser Gly Val Asp Met Pro Gly Ala Asp Tyr
    130                 135                 140
```

```
Gln Leu Thr Lys Leu Leu Gly Leu Ser Pro Thr Val Lys Arg Leu Met
145                 150                 155                 160

Met Tyr Gln Gln Gly Cys Phe Gly Gly Ala Thr Val Leu Arg Leu Ala
            165                 170                 175

Lys Asp Ile Ala Glu Asn Asn Arg Gly Ala Arg Val Leu Val Val Cys
        180                 185                 190

Ser Glu Ile Thr Ala Met Ala Phe Arg Gly Pro Cys Lys Ser His Leu
    195                 200                 205

Asp Ser Leu Val Gly His Ala Leu Phe Gly Asp Gly Ala Ala Ala Ala
210                 215                 220

Ile Ile Gly Ala Asp Pro Asp Gln Leu Asp Glu Gln Pro Val Phe Gln
225                 230                 235                 240

Leu Val Ser Ala Ser Gln Thr Ile Leu Pro Glu Ser Glu Gly Ala Ile
            245                 250                 255

Asp Gly His Leu Thr Glu Ala Gly Leu Thr Ile His Leu Leu Lys Asp
        260                 265                 270

Val Pro Gly Leu Ile Ser Glu Asn Ile Glu Gln Ala Leu Glu Asp Ala
    275                 280                 285

Phe Glu Pro Leu Gly Ile His Asn Trp Asn Ser Ile Phe Trp Ile Ala
290                 295                 300

His Pro Gly Gly Pro Ala Ile Leu Asp Arg Val Glu Asp Arg Val Gly
305                 310                 315                 320

Leu Asp Lys Lys Arg Met Arg Ala Ser Arg Glu Val Leu Ser Glu Tyr
            325                 330                 335

Gly Asn Met Ser Ser Ala Ser Val Leu Phe Val Leu Asp Val Met Arg
        340                 345                 350

Lys Ser Ser Ala Lys Asp Gly Leu Ala Thr Thr Gly Glu Gly Lys Asp
    355                 360                 365

Trp Gly Val Leu Phe Gly Phe Gly Pro Gly Leu Thr Val Glu Thr Leu
370                 375                 380

Val Leu His Ser Val Pro Val Pro Val Pro Thr Ala Ala Ser Ala
385                 390                 395

<210> SEQ ID NO 8
<211> LENGTH: 726
<212> TYPE: DNA
<213> ORGANISM: Petunia hybrida

<400> SEQUENCE: 8
atgtctccac cagtttctgt tacaaaaatg caagtcgaaa attatgcttt tgcaccaaca      60
gtgaaccctg ccggttccac caatactttg ttcttagctg gagcaggcca tagaggtcta     120
gagattgaag gaaagtttgt gaaattcaca gccataggcg tataccttga ggaaagtgct     180
atcccatttt tggcagaaaa gtggaaaggt aagacccctc aggagttaac tgatagcgtc     240 gagttctttta gggacgtggt tacaggtcca ttcgaaaagt ttaccagagt aactatgatt     300
ctacctctta caggaaagca atattctgag aaagtcgccg aaaactgtgt tgctcactgg     360
aagggcatag gtacctacac tgatgacgaa ggaagggcaa tcgagaaatt cttggatgtg     420
tttagatcag aaacattccc acctggtgct tccattatgt ttactcagag tccattaggc     480
ttgttaacca tcagctttgc caaggacgat tcagttaccg gtactgcaaa tgctgtaatc     540
gagaacaaac aactatcaga agccgtcctt gaatccatta ttggaaagca tggtgtgagt     600
cctgcagcca aatgctctgt tgccgagaga gtagcagaat tgttaaaaaa gagctatgct     660
```

-continued

```
gaagaggcct cagtgttcgg caaaccagaa accgaaaagt ccacaatacc tgttatcggt      720
gtgtag                                                                  726
```

<210> SEQ ID NO 9
<211> LENGTH: 241
<212> TYPE: PRT
<213> ORGANISM: Petunia hybrida

<400> SEQUENCE: 9

```
Met Ser Pro Pro Val Ser Val Thr Lys Met Gln Val Glu Asn Tyr Ala
1               5                   10                  15

Phe Ala Pro Thr Val Asn Pro Ala Gly Ser Thr Asn Thr Leu Phe Leu
            20                  25                  30

Ala Gly Ala Gly His Arg Gly Leu Glu Ile Glu Gly Lys Phe Val Lys
        35                  40                  45

Phe Thr Ala Ile Gly Val Tyr Leu Glu Glu Ser Ala Ile Pro Phe Leu
    50                  55                  60

Ala Glu Lys Trp Lys Gly Lys Thr Pro Gln Glu Leu Thr Asp Ser Val
65                  70                  75                  80

Glu Phe Phe Arg Asp Val Val Thr Gly Pro Phe Glu Lys Phe Thr Arg
                85                  90                  95

Val Thr Met Ile Leu Pro Leu Thr Gly Lys Gln Tyr Ser Glu Lys Val
            100                 105                 110

Ala Glu Asn Cys Val Ala His Trp Lys Gly Ile Gly Thr Tyr Thr Asp
        115                 120                 125

Asp Glu Gly Arg Ala Ile Glu Lys Phe Leu Asp Val Phe Arg Ser Glu
    130                 135                 140

Thr Phe Pro Pro Gly Ala Ser Ile Met Phe Thr Gln Ser Pro Leu Gly
145                 150                 155                 160

Leu Leu Thr Ile Ser Phe Ala Lys Asp Asp Ser Val Thr Gly Thr Ala
                165                 170                 175

Asn Ala Val Ile Glu Asn Lys Gln Leu Ser Glu Ala Val Leu Glu Ser
            180                 185                 190

Ile Ile Gly Lys His Gly Val Ser Pro Ala Ala Lys Cys Ser Val Ala
        195                 200                 205

Glu Arg Val Ala Glu Leu Leu Lys Lys Ser Tyr Ala Glu Glu Ala Ser
    210                 215                 220

Val Phe Gly Lys Pro Glu Thr Glu Lys Ser Thr Ile Pro Val Ile Gly
225                 230                 235                 240

Val
```

<210> SEQ ID NO 10
<211> LENGTH: 663
<212> TYPE: DNA
<213> ORGANISM: Petunia hybrida

<400> SEQUENCE: 10

```
atgtctccat ctgtttctgt tactaaagtc caagtggaaa attatgtctt cctccaaca       60 gtgaagcctc cagctagtac caaaactttg ttcttaggtg gagcaggcca tagaggtcta      120
gatgttgagg gaaagtttgt gaaattcaca gttattggcg tataccttga agagagcgcc      180
gtccagtttt tggctcctaa gtggaaaggt aagtctgcag aagaattaat acactcagtt      240
gacttcttta gggatatcgt gaccggtcca ttcgagaagt ttactagagt taggttcatt      300
ctacctctta caggaaagca attttccgaa aaagtagccg aaaactgtgt cgctcattgg      360
```

```
aaggcaaccg gcacttatag tgacgccggt agcagagcta tagagaaatt cttgaatgtg    420
gttaagtctg aaacattttt accaggagca tcaatcttgt ttacccagtc ccctttaggt    480
agtctaacta tttctttcac aaaagatgac agcatatccg aagctggcaa cgccgtaatc    540
gagaacaaac agtttagtga ggccgtcctt gagactatta ttggtgaaca cggagttagt    600
ccagctgcca agtgctctat agcagctaga atgtcagaat gttcaaaaa cagcttattt    660 tga                                                                 663
```

<210> SEQ ID NO 11
<211> LENGTH: 220
<212> TYPE: PRT
<213> ORGANISM: Petunia hybrida

<400> SEQUENCE: 11

```
Met Ser Pro Ser Val Ser Val Thr Lys Val Gln Val Glu Asn Tyr Val
1               5                   10                  15

Phe Pro Pro Thr Val Lys Pro Pro Ala Ser Thr Lys Thr Leu Phe Leu
            20                  25                  30

Gly Gly Ala Gly His Arg Gly Leu Asp Val Glu Gly Lys Phe Val Lys
        35                  40                  45

Phe Thr Val Ile Gly Val Tyr Leu Glu Glu Ser Ala Val Gln Phe Leu
    50                  55                  60

Ala Pro Lys Trp Lys Gly Lys Ser Ala Glu Glu Leu Ile His Ser Val
65                  70                  75                  80

Asp Phe Phe Arg Asp Ile Val Thr Gly Pro Phe Glu Lys Phe Thr Arg
                85                  90                  95

Val Arg Phe Ile Leu Pro Leu Thr Gly Lys Gln Phe Ser Glu Lys Val
            100                 105                 110

Ala Glu Asn Cys Val Ala His Trp Lys Ala Thr Gly Thr Tyr Ser Asp
        115                 120                 125

Ala Gly Ser Arg Ala Ile Glu Lys Phe Leu Asn Val Val Lys Ser Glu
    130                 135                 140

Thr Phe Leu Pro Gly Ala Ser Ile Leu Phe Thr Gln Ser Pro Leu Gly
145                 150                 155                 160

Ser Leu Thr Ile Ser Phe Thr Lys Asp Asp Ser Ile Ser Glu Ala Gly
                165                 170                 175

Asn Ala Val Ile Glu Asn Lys Gln Phe Ser Glu Ala Val Leu Glu Thr
            180                 185                 190

Ile Ile Gly Glu His Gly Val Ser Pro Ala Ala Lys Cys Ser Ile Ala
        195                 200                 205

Ala Arg Met Ser Glu Leu Phe Lys Asn Ser Leu Phe
    210                 215                 220
```

<210> SEQ ID NO 12
<211> LENGTH: 2178
<212> TYPE: DNA
<213> ORGANISM: Arabidopsis thaliana

<400> SEQUENCE: 12

```
atggagatta cgggggcaca caagagcaac ggaggaggag tggacgctat gttatgcggc     60
ggagacatca agacaaagaa catggtgatc aacgcggagg atcctctcaa ctggggagct    120
gcagcggagc aaatgaaagg tagccatttg gatgaagtga agagaatggt tgctgagttt    180
aggaagccag ttgtgaatct tggtggtgag actctgacca ttggacaagt ggctgcgatc    240
tcaactattg gtaacagtgt gaaggtggag ctatcggaga cagctagagc cggtgtgaat    300
```

```
gctagtagtg attgggttat ggagagtatg aacaaaggca ctgatagtta tggtgttact      360
actggttttg gtgctacttc tcatcggaga accaaaaacg tgtcgcact  tcagaaggaa      420
cttattagat tccttaacgc cggaatattc ggaagcacga agaaacaag  ccacacattg      480
ccacactccg ccacaagagc cgccatgctt gtacgaatca acactctcct caaggattt       540
tccggtatcc gatttgagat tctcgaagca attaccagtt tcctcaacaa caacatcact      600
ccatctctcc ccctccgtgg tacaatcacc gcctccggag atctcgttcc tctctcctac      660
atcgccggac ttctcaccgg tcgtcccaat tccaagcta  ctggtcccaa cggtgaagct      720
ttaacagcag aggaagcttt caaattagca ggaatcagct ccggattctt tgatctccag      780
cctaaggaag gtctcgcgct agtcaatggc acggcggttg gatctggaat ggcgtcaatg      840
gtgttattcg aaacgaatgt tctctctgtt ttggctgaga ttttgtcggc ggttttcgca      900
gaggtgatga gtggtaagcc tgagttcacc gatcatctca ctcacagact aaacatcat       960
cccggtcaaa tcgaagcggc ggcgataatg gagcatatcc tcgacggaag ctcgtacatg     1020
aaattagctc agaagcttca cgagatggat ccgttacaga aacctaaaca agatcgttac     1080
gctcttcgta cttctcctca atggttaggt cctcaaatcg aagtgatccg ttacgcaacg     1140
aaatcgatcg agcgtgagat taactccgtc aacgataatc cgttgatcga tgtttcgagg     1200
aacaaggcga ttcacggtgg taacttccaa ggaacaccaa tcggagtttc aatggataac     1260
acgagattgg cgatagcagc gattggtaaa ctcatgtttg ctcaattctc agagcttgtg     1320
aatgatttct acaacaatgg tttaccctcg aatctaaccg cttcgaggaa tccaagtttg     1380
gattatggat tcaagggagc tgagattgca atggcttctt attgttcaga gcttcaatac     1440
ttagctaatc ctgtgactag ccatgttcaa tcagcagagc aacataacca agatgtcaac     1500
tctttgggac taatctcgtc tcgcaaaact tctgaagctg ttgatattct caagcttatg     1560
tcaacaacgt tcctcgttgc gatttgtcaa gctgtggatt tgagacattt ggaggagaat     1620
ttgagacaga ctgtgaagaa cactgtctct caagtggcga agaaagttct tactactgga     1680
gtcaatggtg agcttcatcc ttctcgcttc tgcgaaaagg atttactcaa agttgtagac     1740
cgtgaacaag tctacacata cgcggatgat ccttgtagcg caacgtaccc gttgattcag     1800
aagctgagac aagttattgt tgaccatgct ttgatcaatg gtgagagtga agaatgca      1860
gtgacttcaa tcttccataa gattggagct ttcgaggagg agcttaaggc agtgctaccg     1920
aaagaagtgg aagcagcaag agcagcctac gataacggaa catcggctat cccgaacagg     1980
atcaaggaat gtaggtcgta tccattgtat agattcgtga gggaagagct tggaacagag     2040
cttttgaccg gagagaaagt gacgtcgcct ggagaagagt tcgacaaggt tttcacggcg     2100
atttgtgaag gtaaaatcat tgatccgatg atggaatgtc tcaacgagtg gaacggagct     2160
cccattccaa tatgttaa                                                   2178
```

<210> SEQ ID NO 13
<211> LENGTH: 725
<212> TYPE: PRT
<213> ORGANISM: Arabidopsis thaliana

<400> SEQUENCE: 13

Met Glu Ile Asn Gly Ala His Lys Ser Asn Gly Gly Val Asp Ala
1               5                   10                  15

Met Leu Cys Gly Gly Asp Ile Lys Thr Lys Asn Met Val Ile Asn Ala
            20                  25                  30

```
Glu Asp Pro Leu Asn Trp Gly Ala Ala Glu Gln Met Lys Gly Ser
         35                  40                  45

His Leu Asp Glu Val Lys Arg Met Val Ala Glu Phe Arg Lys Pro Val
 50                  55                  60

Val Asn Leu Gly Gly Glu Thr Leu Thr Ile Gly Gln Val Ala Ala Ile
 65                  70                  75                  80

Ser Thr Ile Gly Asn Ser Val Lys Val Glu Leu Ser Glu Thr Ala Arg
                 85                  90                  95

Ala Gly Val Asn Ala Ser Ser Asp Trp Val Met Glu Ser Met Asn Lys
                100                 105                 110

Gly Thr Asp Ser Tyr Gly Val Thr Thr Gly Phe Gly Ala Thr Ser His
                115                 120                 125

Arg Arg Thr Lys Asn Gly Val Ala Leu Gln Lys Glu Leu Ile Arg Phe
130                 135                 140

Leu Asn Ala Gly Ile Phe Gly Ser Thr Lys Glu Thr Ser His Thr Leu
145                 150                 155                 160

Pro His Ser Ala Thr Arg Ala Ala Met Leu Val Arg Ile Asn Thr Leu
                165                 170                 175

Leu Gln Gly Phe Ser Gly Ile Arg Phe Glu Ile Leu Glu Ala Ile Thr
                180                 185                 190

Ser Phe Leu Asn Asn Asn Ile Thr Pro Ser Leu Pro Leu Arg Gly Thr
                195                 200                 205

Ile Thr Ala Ser Gly Asp Leu Val Pro Leu Ser Tyr Ile Ala Gly Leu
                210                 215                 220

Leu Thr Gly Arg Pro Asn Ser Lys Ala Thr Gly Pro Asn Gly Glu Ala
225                 230                 235                 240

Leu Thr Ala Glu Glu Ala Phe Lys Leu Ala Gly Ile Ser Ser Gly Phe
                245                 250                 255

Phe Asp Leu Gln Pro Lys Glu Gly Leu Ala Leu Val Asn Gly Thr Ala
                260                 265                 270

Val Gly Ser Gly Met Ala Ser Met Val Leu Phe Glu Thr Asn Val Leu
                275                 280                 285

Ser Val Leu Ala Glu Ile Leu Ser Ala Val Phe Ala Glu Val Met Ser
290                 295                 300

Gly Lys Pro Glu Phe Thr Asp His Leu Thr His Arg Leu Lys His His
305                 310                 315                 320

Pro Gly Gln Ile Glu Ala Ala Ile Met Glu His Ile Leu Asp Gly
                325                 330                 335

Ser Ser Tyr Met Lys Leu Ala Gln Lys Leu His Glu Met Asp Pro Leu
                340                 345                 350

Gln Lys Pro Lys Gln Asp Arg Tyr Ala Leu Arg Thr Ser Pro Gln Trp
                355                 360                 365

Leu Gly Pro Gln Ile Glu Val Ile Arg Tyr Ala Thr Lys Ser Ile Glu
                370                 375                 380

Arg Glu Ile Asn Ser Val Asn Asp Asn Pro Leu Ile Asp Val Ser Arg
385                 390                 395                 400

Asn Lys Ala Ile His Gly Gly Asn Phe Gln Gly Thr Pro Ile Gly Val
                405                 410                 415

Ser Met Asp Asn Thr Arg Leu Ala Ile Ala Ala Ile Gly Lys Leu Met
                420                 425                 430

Phe Ala Gln Phe Ser Glu Leu Val Asn Asp Phe Tyr Asn Asn Gly Leu
                435                 440                 445

Pro Ser Asn Leu Thr Ala Ser Arg Asn Pro Ser Leu Asp Tyr Gly Phe
```

-continued

```
                   450                 455                 460
Lys Gly Ala Glu Ile Ala Met Ala Ser Tyr Cys Ser Glu Leu Gln Tyr
465                 470                 475                 480

Leu Ala Asn Pro Val Thr Ser His Val Gln Ser Ala Glu Gln His Asn
                    485                 490                 495

Gln Asp Val Asn Ser Leu Gly Leu Ile Ser Ser Arg Lys Thr Ser Glu
                500                 505                 510

Ala Val Asp Ile Leu Lys Leu Met Ser Thr Thr Phe Leu Val Ala Ile
            515                 520                 525

Cys Gln Ala Val Asp Leu Arg His Leu Glu Glu Asn Leu Arg Gln Thr
        530                 535                 540

Val Lys Asn Thr Val Ser Gln Val Ala Lys Lys Val Leu Thr Thr Gly
545                 550                 555                 560

Val Asn Gly Glu Leu His Pro Ser Arg Phe Cys Glu Lys Asp Leu Leu
                565                 570                 575

Lys Val Val Asp Arg Glu Gln Val Tyr Thr Tyr Ala Asp Asp Pro Cys
                580                 585                 590

Ser Ala Thr Tyr Pro Leu Ile Gln Lys Leu Arg Gln Val Ile Val Asp
            595                 600                 605

His Ala Leu Ile Asn Gly Glu Ser Glu Lys Asn Ala Val Thr Ser Ile
        610                 615                 620

Phe His Lys Ile Gly Ala Phe Glu Glu Leu Lys Ala Val Leu Pro
625                 630                 635                 640

Lys Glu Val Glu Ala Ala Arg Ala Ala Tyr Asp Asn Gly Thr Ser Ala
                645                 650                 655

Ile Pro Asn Arg Ile Lys Glu Cys Arg Ser Tyr Pro Leu Tyr Arg Phe
                660                 665                 670

Val Arg Glu Glu Leu Gly Thr Glu Leu Leu Thr Gly Glu Lys Val Thr
            675                 680                 685

Ser Pro Gly Glu Glu Phe Asp Lys Val Phe Thr Ala Ile Cys Glu Gly
        690                 695                 700

Lys Ile Ile Asp Pro Met Met Glu Cys Leu Asn Glu Trp Asn Gly Ala
705                 710                 715                 720

Pro Ile Pro Ile Cys
                725
```

<210> SEQ ID NO 14
<211> LENGTH: 2154
<212> TYPE: DNA
<213> ORGANISM: Arabidopsis thaliana

<400> SEQUENCE: 14

```
atggaccaaa ttgaagcaat gctatgcggt ggtggtgaaa agaccaaggt ggccgtaacg    60
acaaaaactc ttgcagatcc tttgaattgg ggtctggcag ctgaccagat gaaggtagc   120
catctggatg aagttaagaa gatggttgag aatacagaa gaccagtcgt aaatctaggc   180
ggcgagacat tgacgatagg acaggtagct gctatttcga ccgttggcgg ttcagtgaag   240
gtagaacttg cagaaacaag tagagccgga gttaaggctt catcagattg gtcatggaa   300
agtatgaaca agggcacaga ttcctatggc gttaccacag ctttggtgc tacctctcat   360
agaagaacta aaaatggcac tgctttgcaa acagaactga tcagattcct taacgccggt   420
attttcggta atacaaagga aacttgccat acattacccc aatcggcaac aagagctgct   480
atgcttgtta gggtgaacac tttgttgcaa ggttactctg aataaggtt tgaaattctt   540
```

-continued

```
gaggccatca cttcactatt gaaccacaac atttctcctt cgttgccctt aagaggaaca      600
ataactgcca gcggtgattt ggttcccctt tcatatatcg caggcttatt aacgggaaga      660
cctaattcaa aggccactgg tccagacgga gaatccttaa ccgctaagga agcatttgag      720
aaagctggta tttcaactgg tttctttgat ttgcaaccca aggaaggttt agccctggtg      780
aatggcaccg ctgtcggcag cggtatggca tccatggtgt tgtttgaagc taacgtacaa      840
gcagttttgg ccgaagtttt gtccgcaatt tttgccgaag tcatgagtgg aaaacctgag      900
tttactgatc acttgaccca caggttaaaa catcacccag acaaattga agcagcagct      960
atcatggagc acattttgga cggctctagc tacatgaagt tagcccagaa ggttcatgaa     1020
atggaccctt tgcaaaaacc caaacaagat agatatgctt taaggacatc cccacaatgg     1080
cttggccctc aaattgaagt aattagacaa gctacaaagt ctatagaaag agagatcaac     1140
tctgttaacg ataatccact tatttgatgtg tcgaggaata aggcaataca tggaggcaat     1200
ttccagggta cacccatagg agtcagtatg gataatacca ggcttgccat agccgcaatt     1260
ggcaaattaa tgtttgccca attttctgaa ttggtcaatg acttctacaa taacggtttg     1320
ccttcgaatc tgaccgcatc ttctaaccct agtcttgatt atggttccaa aggtgctgag     1380
atagcaatgg caagctattg ttcagagctg caatatctag ccaacccagt aacctctcat     1440
gtacaatcag ccgaacaaca caatcaggat gttaattctt gggcctgat ttcatcaaga     1500
aaaacaagcg aggccgttga tatccttaaa ttaatgtcca acattttt agtgggtata     1560
tgccaggccg tagatttgag acacttggaa gagaatttga cagacagt gaaaaatacc     1620
gtatcacagg ttgcaaaaaa ggttctaact acaggtatca atggtgaatt gcacccatca     1680
agattctgtg aaaaagattt attaaaagtt gtagatagag aacaagtatt tacttacgtt     1740
gacgatccat gtagcgctac ttatccattg atgcagagat tgagacaagt tattgtagat     1800
cacgctttat ccaatggtga aactgagaaa aatgccgtta cttcaatatt ccaaaagata     1860
ggtgcctttg aagaagaact gaaggcagtt ttaccaaagg aagtcgaagc tgctagagcc     1920
gcatacggaa atggtactgc ccctatacca aatagaatca agagtgtag gtcgtaccct     1980
ttgtacagat tcgttagaga agagttggga accaaattac taactggtga aaaagtcgtt     2040
agcccaggtg aagaatttga caaggtattc acagctatgt gcgagggaaa gttgatagat     2100
ccacttatgg attgcttgaa agagtggaat ggtgcaccta ttccaatctg ctaa          2154
```

<210> SEQ ID NO 15
<211> LENGTH: 717
<212> TYPE: PRT
<213> ORGANISM: Arabidopsis thaliana

<400> SEQUENCE: 15

```
Met Asp Gln Ile Glu Ala Met Leu Cys Gly Gly Glu Lys Thr Lys
1               5                   10                  15

Val Ala Val Thr Thr Lys Thr Leu Ala Asp Pro Leu Asn Trp Gly Leu
            20                  25                  30

Ala Ala Asp Gln Met Lys Gly Ser His Leu Asp Glu Val Lys Lys Met
        35                  40                  45

Val Glu Glu Tyr Arg Arg Pro Val Val Asn Leu Gly Gly Glu Thr Leu
    50                  55                  60

Thr Ile Gly Gln Val Ala Ala Ile Ser Thr Val Gly Gly Ser Val Lys
65                  70                  75                  80

Val Glu Leu Ala Glu Thr Ser Arg Ala Gly Val Lys Ala Ser Ser Asp
                85                  90                  95
```

-continued

```
Trp Val Met Glu Ser Met Asn Lys Gly Thr Asp Ser Tyr Gly Val Thr
            100                 105                 110

Thr Gly Phe Gly Ala Thr Ser His Arg Arg Thr Lys Asn Gly Thr Ala
            115                 120                 125

Leu Gln Thr Glu Leu Ile Arg Phe Leu Asn Ala Gly Ile Phe Gly Asn
        130                 135                 140

Thr Lys Glu Thr Cys His Thr Leu Pro Gln Ser Ala Thr Arg Ala Ala
145                 150                 155                 160

Met Leu Val Arg Val Asn Thr Leu Leu Gln Gly Tyr Ser Gly Ile Arg
                165                 170                 175

Phe Glu Ile Leu Glu Ala Ile Thr Ser Leu Leu Asn His Asn Ile Ser
            180                 185                 190

Pro Ser Leu Pro Leu Arg Gly Thr Ile Thr Ala Ser Gly Asp Leu Val
        195                 200                 205

Pro Leu Ser Tyr Ile Ala Gly Leu Leu Thr Gly Arg Pro Asn Ser Lys
    210                 215                 220

Ala Thr Gly Pro Asp Gly Glu Ser Leu Thr Ala Lys Glu Ala Phe Glu
225                 230                 235                 240

Lys Ala Gly Ile Ser Thr Gly Phe Phe Asp Leu Gln Pro Lys Glu Gly
                245                 250                 255

Leu Ala Leu Val Asn Gly Thr Ala Val Gly Ser Gly Met Ala Ser Met
            260                 265                 270

Val Leu Phe Glu Ala Asn Val Gln Ala Val Leu Ala Glu Val Leu Ser
        275                 280                 285

Ala Ile Phe Ala Glu Val Met Ser Gly Lys Pro Glu Phe Thr Asp His
    290                 295                 300

Leu Thr His Arg Leu Lys His His Pro Gly Gln Ile Glu Ala Ala Ala
305                 310                 315                 320

Ile Met Glu His Ile Leu Asp Gly Ser Ser Tyr Met Lys Leu Ala Gln
                325                 330                 335

Lys Val His Glu Met Asp Pro Leu Gln Lys Pro Lys Gln Asp Arg Tyr
            340                 345                 350

Ala Leu Arg Thr Ser Pro Gln Trp Leu Gly Pro Gln Ile Glu Val Ile
        355                 360                 365

Arg Gln Ala Thr Lys Ser Ile Glu Arg Glu Ile Asn Ser Val Asn Asp
    370                 375                 380

Asn Pro Leu Ile Asp Val Ser Arg Asn Lys Ala Ile His Gly Gly Asn
385                 390                 395                 400

Phe Gln Gly Thr Pro Ile Gly Val Ser Met Asp Asn Thr Arg Leu Ala
                405                 410                 415

Ile Ala Ala Ile Gly Lys Leu Met Phe Ala Gln Phe Ser Glu Leu Val
            420                 425                 430

Asn Asp Phe Tyr Asn Asn Gly Leu Pro Ser Asn Leu Thr Ala Ser Ser
        435                 440                 445

Asn Pro Ser Leu Asp Tyr Gly Phe Lys Gly Ala Glu Ile Ala Met Ala
    450                 455                 460

Ser Tyr Cys Ser Glu Leu Gln Tyr Leu Ala Asn Pro Val Thr Ser His
465                 470                 475                 480

Val Gln Ser Ala Glu Gln His Asn Gln Asp Val Asn Ser Leu Gly Leu
                485                 490                 495

Ile Ser Ser Arg Lys Thr Ser Glu Ala Val Asp Ile Leu Lys Leu Met
            500                 505                 510
```

```
Ser Thr Thr Phe Leu Val Gly Ile Cys Gln Ala Val Asp Leu Arg His
        515                 520                 525

Leu Glu Glu Asn Leu Arg Gln Thr Val Lys Asn Thr Val Ser Gln Val
        530                 535                 540

Ala Lys Lys Val Leu Thr Thr Gly Ile Asn Gly Glu Leu His Pro Ser
545                 550                 555                 560

Arg Phe Cys Glu Lys Asp Leu Leu Lys Val Val Asp Arg Glu Gln Val
                565                 570                 575

Phe Thr Tyr Val Asp Asp Pro Cys Ser Ala Thr Tyr Pro Leu Met Gln
                580                 585                 590

Arg Leu Arg Gln Val Ile Val Asp His Ala Leu Ser Asn Gly Glu Thr
        595                 600                 605

Glu Lys Asn Ala Val Thr Ser Ile Phe Gln Lys Ile Gly Ala Phe Glu
        610                 615                 620

Glu Glu Leu Lys Ala Val Leu Pro Lys Glu Val Glu Ala Ala Arg Ala
625                 630                 635                 640

Ala Tyr Gly Asn Gly Thr Ala Pro Ile Pro Asn Arg Ile Lys Glu Cys
                645                 650                 655

Arg Ser Tyr Pro Leu Tyr Arg Phe Val Arg Glu Glu Leu Gly Thr Lys
                660                 665                 670

Leu Leu Thr Gly Glu Lys Val Val Ser Pro Gly Glu Phe Asp Lys
        675                 680                 685

Val Phe Thr Ala Met Cys Glu Gly Lys Leu Ile Asp Pro Leu Met Asp
        690                 695                 700

Cys Leu Lys Glu Trp Asn Gly Ala Pro Ile Pro Ile Cys
705                 710                 715

<210> SEQ ID NO 16
<211> LENGTH: 2151
<212> TYPE: DNA
<213> ORGANISM: Rhodosporidium toruloides

<400> SEQUENCE: 16
atggctccat cattggattc tatttctcat tcttttgcaa acgtgttgc atctgcaaaa      60 caagctgtta atggtgcatc tactaatttg gcagttgctg ttctcattt accaactacc     120 caagttacac aagttgatat tgttgaaaag atgttagcag cacctactga ttctaccttg     180
gaattggatg ttactctttt aaatttaggt gatgttgttt ctgcagctag aaagggtaga     240
ccagttagag ttaaagattc tgatgaaatt agatctaaaa ttgataaatc tgttgaattt     300
ttgagatctc aattatcaat gtcagtttat ggtgttacaa ctggtttcgg tggttcagct     360
gatactagaa ctgaagatgc aatttcttta caaaaggcat gttggaaca tcaattatgt     420 ggtgttttgc cttcatcatt cgattctttt agattaggta gaggtttaga aaactctttg     480
ccattagaag ttgttagagg tgcaatgaca attagagtta attctttaac aagaggtcat     540
tctgctgtta gattggttgt tttagaagct ttgactaact ttttgaacca tggtattact     600
ccaattgttc cattaagagg tacaatttct gcatctggtg atttgtctcc tttgtcttat     660
attgcagctg ctatttcagg tcatccagat tcaaaggttc atgttgttca tgaaggtaag     720
gaaaagattt tatatgcaag agaagctatg gctttattta tttagaacc agttgtttta     780 ggtcctaagg aaggtttagg tttagttaac ggtacagctg tttcagcatc tatggctacc     840
ttagctttgc atgatgctca tatgttatct tgttatctc aatcattaac agctatgact     900
gttgaagcta tggttggtca tgctggttct tttcatccat tcttgcatga tgttaccaga     960
```

```
cctcatccaa cacaaattga agttgctggt aatattagaa agttgttaga aggttctaga      1020
ttcgcagttc atcatgaaga agaagttaaa gttaaggatg atgaaggtat tttgagacaa      1080
gatagatacc cattgagaac ttcaccacaa tggttgggtc cattggtttc tgatttgatt      1140
catgctcatg cagttttgac cattgaagca ggtcaatcta aacagataa tccattgatt      1200 gatgttgaaa acaaaacatc acatcatggt ggtaattttc aagcagctgc tgttgctaat      1260
acaatggaaa agacaagatt aggtttggca caaattggta agttaaattt cacacaatta      1320
actgaaatgt tgaatgcagg tatgaataga ggtttgccat cttgtttggc agctgaagat      1380
ccttcattat cttatcattg taaaggtttg gatattgcag cagcagctta tacttcagaa      1440
ttaggtcatt tagcaaatcc agttactaca catgttcaac cagctgaaat ggctaatcaa      1500
gctgttaatt ctttagcatt gatttcagct agaagaacca ctgaatcaaa cgatgttttg      1560
tcattattat tagctactca tttatattgt gttttacaag ctattgattt gagagcaatt      1620
gaatttgaat ttaaaaagca atttggtcca gctattgttt cattaattga tcaacatttt      1680
ggttctgcaa tgactggttc aaatttgaga gatgaattag ttgaaaaggt taacaagacc      1740
ttggctaaaa gattagaaca aactaactct tacgatttgg ttccaagatg catgatgct      1800 ttttcttttg ctgcaggtac agttgttgaa gttttgtcat ctacctcatt gtctttggca      1860
gctgttaacg cttggaaagt tgctgctgct gaatcagcta tttcattaac tagacaagtt      1920
agagaaactt tttggtctgc tgcttcaact tcttcacctg ctttgtctta cttgtctcca      1980
agaactcaaa ttttgtacgc tttcgttaga gaagaattgg gtgttaaagc tagaagaggt      2040
gatgttttct taggtaagca agaagttact attggttcta atgttctaa aatttacgaa      2100 gctattaaat caggtagaat taataacgtt ttgttgaaga tgttagcata a              2151

<210> SEQ ID NO 17
<211> LENGTH: 716
<212> TYPE: PRT
<213> ORGANISM: Rhodosporidium toruloides

<400> SEQUENCE: 17

Met Ala Pro Ser Leu Asp Ser Ile Ser His Ser Phe Ala Asn Gly Val
1               5                   10                  15

Ala Ser Ala Lys Gln Ala Val Asn Gly Ala Ser Thr Asn Leu Ala Val
            20                  25                  30

Ala Gly Ser His Leu Pro Thr Thr Gln Val Thr Gln Val Asp Ile Val
        35                  40                  45

Glu Lys Met Leu Ala Ala Pro Thr Asp Ser Thr Leu Glu Leu Asp Gly
    50                  55                  60

Tyr Ser Leu Asn Leu Gly Asp Val Val Ser Ala Ala Arg Lys Gly Arg
65                  70                  75                  80

Pro Val Arg Val Lys Asp Ser Asp Glu Ile Arg Ser Lys Ile Asp Lys
                85                  90                  95

Ser Val Glu Phe Leu Arg Ser Gln Leu Ser Met Ser Val Tyr Gly Val
            100                 105                 110

Thr Thr Gly Phe Gly Gly Ser Ala Asp Thr Arg Thr Glu Asp Ala Ile
        115                 120                 125

Ser Leu Gln Lys Ala Leu Leu Glu His Gln Leu Cys Gly Val Leu Pro
    130                 135                 140

Ser Ser Phe Asp Ser Phe Arg Leu Gly Arg Gly Leu Glu Asn Ser Leu
145                 150                 155                 160

Pro Leu Glu Val Val Arg Gly Ala Met Thr Ile Arg Val Asn Ser Leu
```

-continued

```
                165                 170                 175
Thr Arg Gly His Ser Ala Val Arg Leu Val Val Leu Glu Ala Leu Thr
            180                 185                 190
Asn Phe Leu Asn His Gly Ile Thr Pro Ile Val Pro Leu Arg Gly Thr
            195                 200                 205
Ile Ser Ala Ser Gly Asp Leu Ser Pro Leu Ser Tyr Ile Ala Ala Ala
            210                 215                 220
Ile Ser Gly His Pro Asp Ser Lys Val His Val His Glu Gly Lys
225                 230                 235                 240
Glu Lys Ile Leu Tyr Ala Arg Glu Ala Met Ala Leu Phe Asn Leu Glu
            245                 250                 255
Pro Val Val Leu Gly Pro Lys Glu Gly Leu Gly Leu Val Asn Gly Thr
            260                 265                 270
Ala Val Ser Ala Ser Met Ala Thr Leu Ala Leu His Asp Ala His Met
            275                 280                 285
Leu Ser Leu Leu Ser Gln Ser Leu Thr Ala Met Thr Val Glu Ala Met
            290                 295                 300
Val Gly His Ala Gly Ser Phe His Pro Phe Leu His Asp Val Thr Arg
305                 310                 315                 320
Pro His Pro Thr Gln Ile Glu Val Ala Gly Asn Ile Arg Lys Leu Leu
            325                 330                 335
Glu Gly Ser Arg Phe Ala Val His His Glu Glu Val Lys Val Lys
            340                 345                 350
Asp Asp Glu Gly Ile Leu Arg Gln Asp Arg Tyr Pro Leu Arg Thr Ser
            355                 360                 365
Pro Gln Trp Leu Gly Pro Leu Val Ser Asp Leu Ile His Ala His Ala
            370                 375                 380
Val Leu Thr Ile Glu Ala Gly Gln Ser Thr Thr Asp Asn Pro Leu Ile
385                 390                 395                 400
Asp Val Glu Asn Lys Thr Ser His His Gly Gly Asn Phe Gln Ala Ala
            405                 410                 415
Ala Val Ala Asn Thr Met Glu Lys Thr Arg Leu Gly Leu Ala Gln Ile
            420                 425                 430
Gly Lys Leu Asn Phe Thr Gln Leu Thr Glu Met Leu Asn Ala Gly Met
            435                 440                 445
Asn Arg Gly Leu Pro Ser Cys Leu Ala Ala Glu Asp Pro Ser Leu Ser
            450                 455                 460
Tyr His Cys Lys Gly Leu Asp Ile Ala Ala Ala Tyr Thr Ser Glu
465                 470                 475                 480
Leu Gly His Leu Ala Asn Pro Val Thr Thr His Val Gln Pro Ala Glu
            485                 490                 495
Met Ala Asn Gln Ala Val Asn Ser Leu Ala Leu Ile Ser Ala Arg Arg
            500                 505                 510
Thr Thr Glu Ser Asn Asp Val Leu Ser Leu Leu Leu Ala Thr His Leu
            515                 520                 525
Tyr Cys Val Leu Gln Ala Ile Asp Leu Arg Ala Ile Glu Phe Glu Phe
            530                 535                 540
Lys Lys Gln Phe Gly Pro Ala Ile Val Ser Leu Ile Asp Gln His Phe
545                 550                 555                 560
Gly Ser Ala Met Thr Gly Ser Asn Leu Arg Asp Glu Leu Val Glu Lys
            565                 570                 575
Val Asn Lys Thr Leu Ala Lys Arg Leu Glu Gln Thr Asn Ser Tyr Asp
            580                 585                 590
```

```
Leu Val Pro Arg Trp His Asp Ala Phe Ser Phe Ala Ala Gly Thr Val
        595                 600                 605

Val Glu Val Leu Ser Ser Thr Ser Leu Ser Leu Ala Ala Val Asn Ala
    610                 615                 620

Trp Lys Val Ala Ala Glu Ser Ala Ile Ser Leu Thr Arg Gln Val
625                 630                 635                 640

Arg Glu Thr Phe Trp Ser Ala Ala Ser Thr Ser Ser Pro Ala Leu Ser
                645                 650                 655

Tyr Leu Ser Pro Arg Thr Gln Ile Leu Tyr Ala Phe Val Arg Glu Glu
            660                 665                 670

Leu Gly Val Lys Ala Arg Arg Gly Asp Val Phe Leu Gly Lys Gln Glu
        675                 680                 685

Val Thr Ile Gly Ser Asn Val Ser Lys Ile Tyr Glu Ala Ile Lys Ser
    690                 695                 700

Gly Arg Ile Asn Asn Val Leu Leu Lys Met Leu Ala
705                 710                 715

<210> SEQ ID NO 18
<211> LENGTH: 1596
<212> TYPE: DNA
<213> ORGANISM: Rhodobacter capsulatus

<400> SEQUENCE: 18
atgaccctgc aatctcaaac agctaaagat tgtttggctt tggatggtgc cttgacatta      60
gttcaatgcg aagcgatagc aacccataga agtagaatct ctgtaacacc agccctacgt     120
gagagatgtg ctagagcaca tgctaggtta aacatgcaa tagccgaaca gcgacacata      180
tatgggataa cgacaggctt cgggccactt gctaacaggc tgatcggagc agaccagggt     240
gctgaattac aacagaacct tatctaccat ttggcaaccg gagttggccc caaattatca     300
tgggccgaag ccagagcttt aatgctcgct cgtttgaata gtatactaca aggtgcttct     360
ggtgctagcc ctgaaacaat tgataggatc gttgcagtct taaatgccgg atttgccccg     420
gaagtcccag cccaaggaac cgttggtgct tcgggtgact taactccgtt agcacacatg     480
gtattagcat tgcaaggcag aggtcgtatg attgatcctt cagggagagt tcaagaagcc     540
ggcgctgtca tggataggtt gtgtggaggc ccttaacat tggctgccag agatggcctc      600 gcctagtaa atggtacatc tgccatgaca gctattgccg cattgaccgg tgtggaggct      660
gcaagagcga ttgatgcagc gcttagacat tccgcagtct tgatggaggt cctgtcaggg     720
catgctgagg cttggcaccc tgcctttgcg gaattgcgtc cgcatccagg acaattacgc     780
gccactgaga ggttagctca agcattggac ggcgcaggta gagtctgccg gactcttaca     840
gccgctaggc gtctaactgc agctgatctg agaccagaag atcatccagc tcaagatgca     900
tattcacttc gagtagttcc tcagctggtt ggtgccgtat gggatacgtt ggattggcac     960
gacagggttt gacttgcga acttaactcc gtgaccgaca atccaatttt ccccgagggt    1020
tgtgcggttc cagcactaca cggtggaaac tttatgggcg tacatgtggc actagcttct    1080
gacgctttaa atgcagcgtt ggttacatta gctggtctag ttgaaaggca gattgcaaga    1140
cttactgatg agaagttgaa taagggtttg cctgcttttt tgcatggagg ccaagcaggt    1200
ttacaatcag gtttcatggg agctcaggtt actgctactg ctttgctagc ggaaatgaga    1260
gctaacgcga ctcccgtgtc cgttcaaagc ctcagcacca atggtgcaaa tcaagacgtg    1320
gtaagtatgg gtacgattgc cgcgagacga gcaagagctc aacttttacc tctgtctcaa    1380
```

```
atccaagcga ttttggcact ggctcttgca caagccatgg atctcctaga cgatcctgaa   1440
ggacaagccg gttggtcctt aacggcaaga gatttaagag accgtatacg ggctgtcagt   1500
ccagggttgc gcgcagatag accactagcg ggtcatattg aagctgtggc tcaaggtcta   1560
agacacccct cggcagctgc cgatccacct gcttaa                             1596
```

<210> SEQ ID NO 19
<211> LENGTH: 531
<212> TYPE: PRT
<213> ORGANISM: Rhodobacter capsulatus

<400> SEQUENCE: 19

```
Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335
```

```
Phe Pro Glu Gly Cys Ala Val Pro Ala Leu His Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530
```

<210> SEQ ID NO 20
<211> LENGTH: 1596
<212> TYPE: DNA
<213> ORGANISM: Rhodobacter capsulatus

<400> SEQUENCE: 20

```
atgaccttac aatcccaaac tgccaaagac tgcttagcct tagacggtgc cttgaccttg     60
gttcaatgtg aagcaattgc cacacataga tccagaataa gtgtcacccc agctttgaga    120
gaaagatgcg ctagagcaca tgccagatta gaacacgcta ttgcagaaca aagacacatc    180
tatggtataa ctacaggttt tggtcctttg ctaatagat taataggtgc cgatcaaggt    240
gctgaattgc aacaaaactt aatctaccat ttggctactg gtgttggtcc aaaattgtct    300
tgggccgaag ctagagcatt gatgttggca agattgaact caatcttgca aggtgcatct    360
ggtgcctcac ctgaaacaat cgacagaatt gttgctgtct aaacgctgg tttcgcacca    420
gaagtccctg cccaaggtac tgtaggtgct tccggtgact tgacaccatt ggcacatatg    480
gttttggcct acaaggtag aggtagaatg attgatccta gtggtagagt tcaagaagcc    540
ggtgctgtca tggacagatt atgtggtggt ccattgactt tagctgcaag agatggtttg    600
gctttagtta atggtacttc tgccatgaca gctatcgccg ctttgacagg tgttgaagca    660
gccagagcta ttgatgctgc attaagacat tccgcagtat taatgaagt tttgagtggt    720
catgcagaag cctggcaccc agcttttgca gaattgagac acacccctgg tcaattaaga    780
gctaccgaaa gattagccca gctttggat ggtgcaggta gagtttgcag aaccttgact    840
gccgctagaa gattgacagc agccgactta agaccagaag atcatcctgc aagacgcgcc    900
tattctttga gagttgtccc acaattagtt ggtgctgtct gggatacttt ggactggcac    960
```

```
gatagagtag ttacctgtga attgaactca gtcactgata acccaatatt tcctgaaggt    1020
tgcgctgtac ctgcattaca tggtggtaat ttcatgggtg tacacgttgc attggcctcc    1080
gacgctttaa acgctgcatt agtaacattg gctggtttag ttgaaagaca aatcgcaaga    1140
ttgaccgatg aaaagttgaa taagggtttg ccagcatttt tgcatggtgg tcaagcaggt    1200
ttacaatcag gtttcatggg tgctcaagtt acagctaccg cattgttagc agaaatgaga    1260
gccaacgcta cccctgtctc tgtacaatct ttgtcaacta atggtgctaa ccaagatgtc    1320
gtatcaatgg gtactatcgc cgctagaaga gcaagagccc aattgttgcc attgtctcaa    1380
atccaagcaa tcttggcttt agcattggcc caagctatgg acttgttaga tgaccctgaa    1440
ggtcaagcag gttggtcctt gacagccaga gacttaagag atagaattag agctgttagt    1500
ccaggtttga gagctgatag accttttagca ggtcatatag aagcagtcgc acaaggtttg    1560
agacatccat ccgccgcagc agaccctcca gcctaa                              1596
```

<210> SEQ ID NO 21
<211> LENGTH: 531
<212> TYPE: PRT
<213> ORGANISM: Rhodobacter capsulatus

<400> SEQUENCE: 21

```
Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190

Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
```

```
                260                 265                 270
Gly Arg Val Cys Arg Thr Leu Thr Ala Ala Arg Arg Leu Thr Ala Ala
            275                 280                 285

Asp Leu Arg Pro Glu Asp His Pro Ala Gln Asp Ala Tyr Ser Leu Arg
        290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530

<210> SEQ ID NO 22
<211> LENGTH: 1536
<212> TYPE: DNA
<213> ORGANISM: Saccharothrix espanaensis

<400> SEQUENCE: 22
atgacacagg tagttgaaag gcaggcagat aggcttagtt ccagggaata tcttgccagg      60
gtcgtcaggt ccgctggttg ggatgctggt ttgacttcct gtactgatga ggaaatcgtg     120
agaatgggtg ctagtgccag aacaattgaa gagtacttga agtccgataa acctatatac     180
ggcttaacac aaggatttgg tccacttgtt ctatttgatg ccgatagtga attagagcaa     240
ggaggttctt taatctctca tctaggtaca ggccaaggtg ctcctttggc cccagaagtg     300
tcaagactaa tcttatggtt gagaatacag aatatgagaa aaggttattc cgcagtgtca     360
cctgtattct ggcagaagtt agccgatcta tggaataagg gtttcacacc agctattcca     420
aggcacggta ctgtctccgc atctggcgat ttgcagccac ttgctcatgc tgctttagca     480
ttcactggcg ttggagaagc atggacaaga gatgctgacg gcagatggag cactgttcct     540
```

```
gcagtagacg ctttggctgc tttgggtgca gaaccatttg attggccagt tagagaggca    600
ttagcttttg ttaatggtac tggcgcctca ttggcagtag ccgtgctaaa ccataggagt    660
gctttaagat tagtgagagc ctgtgccgtg ttgtccgcaa ggttagccac attgcttggt    720
gccaatcctg agcattatga tgtaggtcat ggcgttgcaa gaggccaagt tggtcaattg    780
actgcagcag aatggatcag gcaaggttta cctagaggta tggtcagaga cggaagtagg    840
ccattgcaag aaccatactc cttaagatgt gctcctcaag ttttaggtgc cgttttggac    900
cagttagatg gagctggtga cgtattagct agggaagtcg acggttgtca ggacaatcct    960
ataacttacg aaggagagtt gttgcatggt ggtaatttcc atgcaatgcc agttggtttc    1020
gcatctgatc aaataggttt agcaatgcat atggccgctt acttggcaga aaggcagctt    1080
ggtttattag ttagccctgt tacaaacggt gaccttccac caatgttaac ccctagggct    1140
ggtagaggcg caggactagc aggtgtgcag atatccgcta ccagttttgt tagtagaatt    1200
aggcagttgg tgtttcctgc aagcttgaca actttgccta ccaacggatg gaatcaagat    1260
cacgtcccaa tggcattgaa tggcgcaaat tcagtattcg aagccttaga gttgggatgg    1320
ttaactgttg gtagcttggc agtaggtgtt gcccaattag ccgccatgac aggtcacgct    1380
gctgagggtg tttgggcaga acttgctggt atttgccctc cacttgatgc tgatagacct    1440
ttgggagcag aagtgagggc tgctagggat cttttgtctg cccacgctga tcaattgtta    1500
gtcgatgaag ctgatggaaa agacttcgga taatga                             1536
```

<210> SEQ ID NO 23
<211> LENGTH: 510
<212> TYPE: PRT
<213> ORGANISM: Saccharothrix espanaensis

<400> SEQUENCE: 23

```
Met Thr Gln Val Val Glu Arg Gln Ala Asp Arg Leu Ser Ser Arg Glu
1               5                   10                  15

Tyr Leu Ala Arg Val Val Arg Ser Ala Gly Trp Asp Ala Gly Leu Thr
            20                  25                  30

Ser Cys Thr Asp Glu Glu Ile Val Arg Met Gly Ala Ser Ala Arg Thr
        35                  40                  45

Ile Glu Glu Tyr Leu Lys Ser Asp Lys Pro Ile Tyr Gly Leu Thr Gln
    50                  55                  60

Gly Phe Gly Pro Leu Val Leu Phe Asp Ala Asp Ser Glu Leu Glu Gln
65                  70                  75                  80

Gly Gly Ser Leu Ile Ser His Leu Gly Thr Gly Gln Gly Ala Pro Leu
                85                  90                  95

Ala Pro Glu Val Ser Arg Leu Ile Leu Trp Leu Arg Ile Gln Asn Met
            100                 105                 110

Arg Lys Gly Tyr Ser Ala Val Ser Pro Val Phe Trp Gln Lys Leu Ala
        115                 120                 125

Asp Leu Trp Asn Lys Gly Phe Thr Pro Ala Ile Pro Arg His Gly Thr
    130                 135                 140

Val Ser Ala Ser Gly Asp Leu Gln Pro Leu Ala His Ala Ala Leu Ala
145                 150                 155                 160

Phe Thr Gly Val Gly Glu Ala Trp Thr Arg Asp Ala Asp Gly Arg Trp
                165                 170                 175

Ser Thr Val Pro Ala Val Asp Ala Leu Ala Ala Leu Gly Ala Glu Pro
            180                 185                 190

Phe Asp Trp Pro Val Arg Glu Ala Leu Ala Phe Val Asn Gly Thr Gly
```

```
                195                 200                 205
Ala Ser Leu Ala Val Ala Val Leu Asn His Arg Ser Ala Leu Arg Leu
    210                 215                 220

Val Arg Ala Cys Ala Val Leu Ser Ala Arg Leu Ala Thr Leu Leu Gly
225                 230                 235                 240

Ala Asn Pro Glu His Tyr Asp Val Gly His Gly Val Ala Arg Gly Gln
                245                 250                 255

Val Gly Gln Leu Thr Ala Ala Glu Trp Ile Arg Gln Gly Leu Pro Arg
            260                 265                 270

Gly Met Val Arg Asp Gly Ser Arg Pro Leu Gln Glu Pro Tyr Ser Leu
        275                 280                 285

Arg Cys Ala Pro Gln Val Leu Gly Ala Val Leu Asp Gln Leu Asp Gly
    290                 295                 300

Ala Gly Asp Val Leu Ala Arg Glu Val Asp Gly Cys Gln Asp Asn Pro
305                 310                 315                 320

Ile Thr Tyr Glu Gly Glu Leu Leu His Gly Gly Asn Phe His Ala Met
                325                 330                 335

Pro Val Gly Phe Ala Ser Asp Gln Ile Gly Leu Ala Met His Met Ala
            340                 345                 350

Ala Tyr Leu Ala Glu Arg Gln Leu Gly Leu Leu Val Ser Pro Val Thr
        355                 360                 365

Asn Gly Asp Leu Pro Pro Met Leu Thr Pro Arg Ala Gly Arg Gly Ala
    370                 375                 380

Gly Leu Ala Gly Val Gln Ile Ser Ala Thr Ser Phe Val Ser Arg Ile
385                 390                 395                 400

Arg Gln Leu Val Phe Pro Ala Ser Leu Thr Thr Leu Pro Thr Asn Gly
                405                 410                 415

Trp Asn Gln Asp His Val Pro Met Ala Leu Asn Gly Ala Asn Ser Val
            420                 425                 430

Phe Glu Ala Leu Glu Leu Gly Trp Leu Thr Val Gly Ser Leu Ala Val
        435                 440                 445

Gly Val Ala Gln Leu Ala Ala Met Thr Gly His Ala Ala Glu Gly Val
    450                 455                 460

Trp Ala Glu Leu Ala Gly Ile Cys Pro Pro Leu Asp Ala Asp Arg Pro
465                 470                 475                 480

Leu Gly Ala Glu Val Arg Ala Ala Arg Asp Leu Leu Ser Ala His Ala
                485                 490                 495

Asp Gln Leu Leu Val Asp Glu Ala Asp Gly Lys Asp Phe Gly
            500                 505                 510

<210> SEQ ID NO 24
<211> LENGTH: 2151
<212> TYPE: DNA
<213> ORGANISM: Petroselinum crispum

<400> SEQUENCE: 24
atggaaaatg gtaatggtgc tactacaaat ggccatgtta acggtaatgg aatggatttt     60
tgtatgaaaa ccgaggaccc attgtattgg ggcattgcag ccgaagctat gactggttct    120
cacttagatg aggtaaagaa aatggtcgca gaatacagaa agcctgtggt taaactaggt    180
ggagaaacac ttaccatatc acaagtagcc gctatctcag caagggacgg aagtggtgtc    240
actgtggagt tgtccgaagc tgctagagca ggagttaagg cttcttcaga ttggtaatg    300 gactccatga acaaaggtac agatagttat ggcgtcacca ctggtttcgg agccacaagc    360
```

```
cataggagaa ccaagcaggg cggcgcatta caaaaagaac taattagatt cttgaatgct      420
ggtatattcg gaaacggttc tgataatact ttgccacact cagctaccag ggcagctatg      480
ttagttagaa tcaacacttt gttacagggc tactccggaa ttagatttga atccttgaa      540
gccatcacca agtttctaaa ccaaaatatt acaccttgct tgccattaag ggtactatt      600
accgcaagtg gcgacctagt gcctttgtct tacatagctg gtttacttac tggtagacca      660
aacagcaaag ccgttggtcc tactggcgta atcttgtcac cagaagaggc ctttaagtta      720
gctggtgtcg aaggaggttt ctttgaattg caacctaaag aaggccttgc cttggtgaat      780
ggaacagcag ttggttccgg tatggccagt atggtattat cgaagctaa cattctagcc      840
gtcttggcag aggttatgtc tgctatattt gccgaagtga tgcagggcaa gccagagttc      900
accgatcact taactcacaa acttaaacat catcctggac aaatcgaggc agctgccatt      960
atggaacaca tattggatgg ctccgcatac gttaaggctg cacaaaagtt gcatgaaatg     1020
gacccactac agaagcctaa caagataggg tatgctttga aacctcacc tcagtggtta     1080
ggtccacaaa tcgaggtaat tagaagctcc actaagatga ttgaaaggga gatcaatagt     1140
gtcaacgaca atcctcttat cgatgtgtca agaaacaaag ccattcacgg cggaaatttt     1200
caaggtaccc caataggcgt ttctatggac aacacaagac tagcaatcgc tgccattgga     1260
aagttgatgt ttgcacagtt cagcgagtta gtgaatgatt tttacaataa cggccttcct     1320
tccaacctat ctggcggcag gaacccatca ttagattatg gattcaaagg tgctgaaata     1380
gccatggcat cctactgtag cgagctacag ttttttggcta atcctgtcac taaccatgtt     1440
caatccgccg aacagcacaa tcaagacgtg aacagtttag gtcttatttc atctagaaag     1500
accagtgagg ccgttgagat attgaaacta atgtccacaa cttttcttagt aggcttgtgc     1560
caggctattg atcttagaca cttagaagaa aatctaaagt caaccgtcaa aaacacagtt     1620
tctagtgtgg ctaaaagggt attgactatg ggagtcaatg gtgagttaca tccaagcaga     1680
ttttgtgaaa aggacctttt gagggttgtg gatagagaat acatattcgc ctacatcgat     1740
gacccttgca gtgcaacata tccactaatg cagaaactaa gacaaacatt ggttgagcac     1800
gctcttaaga atggcgataa cgaaggaat ttgagtactt ctattttca gaaaatagca     1860
accttcgagg acgaactaaa ggcattgtta cctaaagaag tagagagtgc tagggccgca     1920
ctagaaagtg gaaacccagc tatccctaat agaattgaag agtgtaggtc ctacccactt     1980
tataagtttg tcagaaagga gttgggtaca gaatacttaa ccggcgagaa ggttactagt     2040
ccaggcgaag aatttgagaa agtgttcata gccatgagta agggagaaat tatcgatcca     2100
ttgttagagt gtttggagtc ctggaacggt gcaccactac ctatttgcta a              2151

<210> SEQ ID NO 25
<211> LENGTH: 716
<212> TYPE: PRT
<213> ORGANISM: Petroselinum crispum

<400> SEQUENCE: 25

Met Glu Asn Gly Asn Gly Ala Thr Thr Asn Gly His Val Asn Gly Asn
1               5                   10                  15

Gly Met Asp Phe Cys Met Lys Thr Glu Asp Pro Leu Tyr Trp Gly Ile
            20                  25                  30

Ala Ala Glu Ala Met Thr Gly Ser His Leu Asp Glu Val Lys Lys Met
        35                  40                  45

Val Ala Glu Tyr Arg Lys Pro Val Val Lys Leu Gly Gly Glu Thr Leu
    50                  55                  60
```

```
Thr Ile Ser Gln Val Ala Ala Ile Ser Ala Arg Asp Gly Ser Gly Val
 65                  70                  75                  80

Thr Val Glu Leu Ser Glu Ala Ala Arg Ala Gly Val Lys Ala Ser Ser
             85                  90                  95

Asp Trp Val Met Asp Ser Met Asn Lys Gly Thr Asp Ser Tyr Gly Val
            100                 105                 110

Thr Thr Gly Phe Gly Ala Thr Ser His Arg Arg Thr Lys Gln Gly Gly
            115                 120                 125

Ala Leu Gln Lys Glu Leu Ile Arg Phe Leu Asn Ala Gly Ile Phe Gly
            130                 135                 140

Asn Gly Ser Asp Asn Thr Leu Pro His Ser Ala Thr Ala Ala Ala Met
145                 150                 155                 160

Leu Val Arg Ile Asn Thr Leu Leu Gln Gly Tyr Ser Gly Ile Arg Phe
                165                 170                 175

Glu Ile Leu Glu Ala Ile Thr Lys Phe Leu Asn Gln Asn Ile Thr Pro
                180                 185                 190

Cys Leu Pro Leu Arg Gly Thr Ile Thr Ala Ser Gly Asp Leu Val Pro
                195                 200                 205

Leu Ser Tyr Ile Ala Gly Leu Leu Thr Gly Arg Pro Asn Ser Lys Ala
210                 215                 220

Val Gly Pro Thr Gly Val Ile Leu Ser Pro Glu Glu Ala Phe Lys Leu
225                 230                 235                 240

Ala Gly Val Glu Gly Gly Phe Phe Glu Leu Gln Pro Lys Glu Gly Leu
                245                 250                 255

Ala Leu Val Asn Gly Thr Ala Val Gly Ser Gly Met Ala Ser Met Val
                260                 265                 270

Leu Phe Glu Ala Asn Ile Leu Ala Val Leu Ala Glu Val Met Ser Ala
            275                 280                 285

Ile Phe Ala Glu Val Met Gln Gly Lys Pro Glu Phe Thr Asp His Leu
            290                 295                 300

Thr His Lys Leu Lys His His Pro Gly Gln Ile Glu Ala Ala Ala Ile
305                 310                 315                 320

Met Glu His Ile Leu Asp Gly Ser Ala Tyr Val Lys Ala Ala Gln Lys
                325                 330                 335

Leu His Glu Met Asp Pro Leu Gln Lys Pro Lys Gln Asp Arg Tyr Ala
                340                 345                 350

Leu Arg Thr Ser Pro Gln Trp Leu Gly Pro Gln Ile Glu Val Ile Arg
                355                 360                 365

Ser Ser Thr Lys Met Ile Glu Arg Glu Ile Asn Ser Val Asn Asp Asn
370                 375                 380

Pro Leu Ile Asp Val Ser Arg Asn Lys Ala Ile His Gly Gly Asn Phe
385                 390                 395                 400

Gln Gly Thr Pro Ile Gly Val Ser Met Asp Asn Thr Arg Leu Ala Ile
                405                 410                 415

Ala Ala Ile Gly Lys Leu Met Phe Ala Gln Phe Ser Glu Leu Val Asn
                420                 425                 430

Asp Phe Tyr Asn Asn Gly Leu Pro Ser Asn Leu Ser Gly Gly Arg Asn
                435                 440                 445

Pro Ser Leu Asp Tyr Gly Phe Lys Gly Ala Glu Ile Ala Met Ala Ser
            450                 455                 460

Tyr Cys Ser Glu Leu Gln Phe Leu Ala Asn Pro Val Thr Asn His Val
465                 470                 475                 480
```

```
Gln Ser Ala Glu Gln His Asn Gln Asp Val Asn Ser Leu Gly Leu Ile
                485                 490                 495

Ser Ser Arg Lys Thr Ser Glu Ala Val Glu Ile Leu Lys Leu Met Ser
            500                 505                 510

Thr Thr Phe Leu Val Gly Leu Cys Gln Ala Ile Asp Leu Arg His Leu
        515                 520                 525

Glu Glu Asn Leu Lys Ser Thr Val Lys Asn Thr Val Ser Ser Val Ala
    530                 535                 540

Lys Arg Val Leu Thr Met Gly Val Asn Gly Glu Leu His Pro Ser Arg
545                 550                 555                 560

Phe Cys Glu Lys Asp Leu Leu Arg Val Val Asp Arg Glu Tyr Ile Phe
                565                 570                 575

Ala Tyr Ile Asp Asp Pro Cys Ser Ala Thr Tyr Pro Leu Met Gln Lys
            580                 585                 590

Leu Arg Gln Thr Leu Val Glu His Ala Leu Lys Asn Gly Asp Asn Glu
        595                 600                 605

Arg Asn Leu Ser Thr Ser Ile Phe Gln Lys Ile Ala Thr Phe Glu Asp
    610                 615                 620

Glu Leu Lys Ala Leu Leu Pro Lys Glu Val Glu Ser Ala Arg Ala Ala
625                 630                 635                 640

Leu Glu Ser Gly Asn Pro Ala Ile Pro Asn Arg Ile Glu Glu Cys Arg
                645                 650                 655

Ser Tyr Pro Leu Tyr Lys Phe Val Arg Lys Glu Leu Gly Thr Glu Tyr
            660                 665                 670

Leu Thr Gly Glu Lys Val Thr Ser Pro Gly Glu Phe Glu Lys Val
        675                 680                 685

Phe Ile Ala Met Ser Lys Gly Glu Ile Ile Asp Pro Leu Leu Glu Cys
    690                 695                 700

Leu Glu Ser Trp Asn Gly Ala Pro Leu Pro Ile Cys
705                 710                 715

<210> SEQ ID NO 26
<211> LENGTH: 2112
<212> TYPE: DNA
<213> ORGANISM: Aspergillus niger

<400> SEQUENCE: 26
atgttggaca agcacatccc agacggtcac ttagaaacca ctagcgccca ctggagggat      60
ttaaaccaag ttgttcaaaa cggtgaatta tctattgacg ttactccttt gtccttggcc     120
gatgttgttg ctgtcgctaa gtatggttgc aaccaagat tgactgacaa gccagagact      180
attgatgcta ttaacggttc tgtcatcgcc ttggctgaat gtttaaggga tggtcatcac     240
atttacggtt taacactgg ttttggtggt tctgccgatt ccagaaccaa ccagaccact     300
actttgcaaa gctccttgtt gcaattgttg caatccggta tcttaactgc ttctgacact     360
accaatgaag gtttgcagtt gaacttgcaa ggtcaaagca gccattctat gccatctgag     420
tgggttaaag ctaccatgtt ggttcgttct aactctgtcg ctagaggcca ttctgctgtc     480
agcttgccag ctatttccgc catttttgaga ttgatcagag aagatatcgt cccagttatt     540
ccattgagag gtactatctc cgcttccggt gacttgatgc cattggctta cgttgtcggt     600
gccattgaag ttctccagg tatttacgtt agagtcaagg atggttctga acatcaagtc     660
gttaccgctc aaaaggccct acaaactatc ggtgctaagg tgttactttt ggcccctaaa     720
gagggtttag gtttggtcaa tggtactgct gcttctggtg ccttagctgg tttggttttg     780
```

```
tatgaggctc atcaattggc cgtcttggct caagctgtca ccgccttaac tgtcgaagct    840
attcaaggtt ctaccgaatc ctttcaccct tttatcgctc aagtccgtcc acatgaaggt    900
cagatcgagg ctgctgaaaa catcctatct ctattaaaag gtagcttgtt ggccagaggt    960
agctctacta cccaaaccag aaccggtcta gtccaagaca gatactcctt gagaactgct   1020
tctcaatgga tcggtcctca attggaagat ttattgttgg ccgacagaca ggtccaagtc   1080
gaactaaatt ctaccagcga caacccatta atcgatactg ttctaaaac tttctacact    1140 ggtggtaact tccaagctac cagcattacc tccgctatgg aaaagactag gttggctttg   1200
caaatgttcg gtaagatgtt attcgtccaa tgtaatgaaa tgatcgaccc aaacttgaac   1260
aacggtctac ctaccaactt ggttgctgat gacccatcct tgtccttcac catgaaaggc   1320
gtcgatatca acatggctgc ttatatgtct gaattggctt acttggctaa tccagtctcc   1380
tcccacgttc aaactgctga atgcaaaac caagccttga actccttggc tttcgttagc    1440
gctaggtata ctatgaaagc tgttgatatc gtctctatga tgggtgcttg tgctttgtat   1500
gtcgcttgtc aagccttaga cttgagggtc ttgcaattgc gtttcttcca aagagtccaa   1560
ggtgtcgcta agaaatcgc tcacggtgcc tttggtaagg ccttggaacc tttcgaaatc    1620
gaccaggttg ctgatcactt gtctgaagct attcaaaact cctggccatc tacctctagg   1680
ttggacttga gagacagatg caaaagggtt gctgaaatgt tatcccagt cttgttcggt    1740 gctttgttgc aaattatccc acagaacaga caaacctctg attattcac cgccatctct    1800 gcttgtaaga tgatttccgt ttttaagttg gaaggcgttt acagagaagt tttcgctgaa   1860
ttttgcactt cccaacctac cgctgacttt ttgggtaccg gtactaagga aatctacacc   1920
ttcatcagac acgacttgag agtcccattc caccagggtt tcgtcgaaca tccatccgcc   1980
tctcaaaccg acttaccaga aactatcaac ggtagagtta aaaagaccgt cggtggttgg   2040
atttctgtcg tttacgaagc cttgagaaat ggtaccttaa gcggtactat tttgaactcc   2100
ttccaacaat aa                                                       2112
```

<210> SEQ ID NO 27
<211> LENGTH: 703
<212> TYPE: PRT
<213> ORGANISM: Aspergillus niger

<400> SEQUENCE: 27

```
Met Leu Asp Lys His Ile Pro Asp Gly His Leu Glu Thr Thr Ser Ala
1               5                   10                  15

His Trp Arg Asp Leu Asn Gln Val Val Gln Asn Gly Glu Leu Ser Ile
            20                  25                  30

Asp Gly Tyr Ser Leu Ser Leu Ala Asp Val Val Ala Val Ala Lys Tyr
        35                  40                  45

Gly Cys Gln Pro Arg Leu Thr Asp Lys Pro Glu Thr Ile Asp Ala Ile
    50                  55                  60

Asn Gly Ser Val Ile Ala Leu Ala Glu Cys Leu Arg Asp Gly His His
65                  70                  75                  80

Ile Tyr Gly Val Asn Thr Gly Phe Gly Gly Ser Ala Asp Ser Arg Thr
                85                  90                  95

Asn Gln Thr Thr Thr Leu Gln Ser Leu Leu Gln Leu Leu Gln Ser
            100                 105                 110

Gly Ile Leu Thr Ala Ser Asp Thr Thr Asn Glu Gly Leu Gln Leu Asn
        115                 120                 125

Leu Gln Gly Gln Ser Ser His Ser Met Pro Ser Glu Trp Val Lys Ala
```

-continued

```
            130                 135                 140
Thr Met Leu Val Arg Ser Asn Ser Val Ala Arg Gly His Ser Ala Val
145                 150                 155                 160

Ser Leu Pro Ala Ile Ser Ala Ile Leu Arg Leu Ile Arg Glu Asp Ile
                165                 170                 175

Val Pro Val Ile Pro Leu Arg Gly Thr Ile Ser Ala Ser Gly Asp Leu
                180                 185                 190

Met Pro Leu Ala Tyr Val Val Gly Ala Ile Glu Gly Ser Pro Gly Ile
                195                 200                 205

Tyr Val Arg Val Lys Asp Gly Ser Glu His Gln Val Thr Ala Gln
        210                 215                 220

Lys Ala Leu Gln Thr Ile Gly Ala Lys Gly Val Thr Leu Gly Pro Lys
225                 230                 235                 240

Glu Gly Leu Gly Leu Val Asn Gly Thr Ala Ala Ser Gly Ala Leu Ala
                245                 250                 255

Gly Leu Val Leu Tyr Glu Ala His Gln Leu Ala Val Leu Ala Gln Ala
                260                 265                 270

Val Thr Ala Leu Thr Val Glu Ala Ile Gln Gly Ser Thr Glu Ser Phe
                275                 280                 285

His Pro Phe Ile Ala Gln Val Arg Pro His Glu Gly Gln Ile Glu Ala
        290                 295                 300

Ala Glu Asn Ile Leu Ser Leu Leu Lys Gly Ser Leu Leu Ala Arg Gly
305                 310                 315                 320

Ser Ser Thr Thr Gln Thr Arg Thr Gly Leu Val Gln Asp Arg Tyr Ser
                325                 330                 335

Leu Arg Thr Ala Ser Gln Trp Ile Gly Pro Gln Leu Glu Asp Leu Leu
                340                 345                 350

Leu Ala Asp Arg Gln Val Gln Val Glu Leu Asn Ser Thr Ser Asp Asn
        355                 360                 365

Pro Leu Ile Asp Thr Gly Ser Lys Thr Phe Tyr Thr Gly Gly Asn Phe
        370                 375                 380

Gln Ala Thr Ser Ile Thr Ser Ala Met Glu Lys Thr Arg Leu Ala Leu
385                 390                 395                 400

Gln Met Phe Gly Lys Met Leu Phe Val Gln Cys Asn Glu Met Ile Asp
                405                 410                 415

Pro Asn Leu Asn Asn Gly Leu Pro Thr Asn Leu Val Ala Asp Asp Pro
                420                 425                 430

Ser Leu Ser Phe Thr Met Lys Gly Val Asp Ile Asn Met Ala Ala Tyr
                435                 440                 445

Met Ser Glu Leu Ala Tyr Leu Ala Asn Pro Val Ser Ser His Val Gln
450                 455                 460

Thr Ala Glu Met Gln Asn Gln Ala Leu Asn Leu Ala Phe Val Ser
465                 470                 475                 480

Ala Arg Tyr Thr Met Lys Ala Val Asp Ile Val Ser Met Met Gly Ala
                485                 490                 495

Cys Ala Leu Tyr Val Ala Cys Gln Ala Leu Asp Leu Arg Val Leu Gln
                500                 505                 510

Leu Arg Phe Phe Gln Arg Val Gln Gly Val Ala Lys Glu Ile Ala His
                515                 520                 525

Gly Ala Phe Gly Lys Ala Leu Glu Pro Phe Glu Ile Asp Gln Val Ala
        530                 535                 540

Asp His Leu Ser Glu Ala Ile Gln Asn Ser Trp Pro Ser Thr Ser Arg
545                 550                 555                 560
```

```
Leu Asp Leu Arg Asp Arg Cys Lys Arg Val Ala Glu Met Phe Ile Pro
            565                 570                 575

Val Leu Phe Gly Ala Leu Leu Gln Ile Ile Pro Gln Asn Arg Gln Thr
        580                 585                 590

Ser Asp Leu Phe Thr Ala Ile Ser Ala Cys Lys Met Ile Ser Val Phe
        595                 600                 605

Lys Leu Glu Gly Val Tyr Arg Glu Val Phe Ala Glu Phe Cys Thr Ser
    610                 615                 620

Gln Pro Thr Ala Asp Phe Leu Gly Thr Gly Thr Lys Glu Ile Tyr Thr
625                 630                 635                 640

Phe Ile Arg His Asp Leu Arg Val Pro Phe His Gln Gly Phe Val Glu
            645                 650                 655

His Pro Ser Ala Ser Gln Thr Asp Leu Pro Glu Thr Ile Asn Gly Arg
        660                 665                 670

Val Lys Lys Thr Val Gly Gly Trp Ile Ser Val Val Tyr Glu Ala Leu
    675                 680                 685

Arg Asn Gly Thr Leu Ser Gly Thr Ile Leu Asn Ser Phe Gln Gln
        690                 695                 700
```

<210> SEQ ID NO 28
<211> LENGTH: 2073
<212> TYPE: DNA
<213> ORGANISM: Puccinia graminis

<400> SEQUENCE: 28

| | |
|---|---|
| atggctcatg ctgatttgtg ctccgctatt tctagagaat ggaagaaca catctccaac | 60 |
| aagagagaaa ttatcttgga cggtcatggt ttgacttcta ctggtgttgt tggtgctgct | 120 |
| agatacaatg ttcaagccaa gatttctaac gatccagcct tgattactgt cgttgaagaa | 180 |
| tctgttgaat tcttggcctc taagttggat actgctatct atggtgttac caccttctct | 240 |
| gaaagattag atccaagacc aactaacgct tgcaactttt actttcaagg ttctgctgat | 300 |
| accagatctg attctactgc tgacttgcaa atggctttct ggaacatca agtttctggt | 360 |
| gttttgccat tgtcctctag atctacttct gctggtttgt atttgtccga tccaatgaac | 420 |
| aatgttatgc ctgaagctat taccagaggt gccattttga ttagaatcaa ctctttggtt | 480 |
| agaggtcact ccgctttgag atttcaagtt ttggaaactt tgatcacctt gttgaacaag | 540 |
| aacttgactc caatggttcc attgagaggt tctatttctg cttctggtga tttgatgcct | 600 |
| ttgtcttatg ttgctgctgc aatttgtggt catccagcca ttagaattat cgatagatct | 660 |
| tcagccgatg gtcacatcga attatgcca gcttctgatg ctttgactaa gcacggtatt | 720 |
| actccaatag ttttgggtcc aaaagaaggt ttggccatct ctaatggtac tgcttttcct | 780 |
| gcatctgctg cttgtttggt tgctcatgat tctcatatgt tgttgatgtt ggctcaaggt | 840 |
| ttgacatcta tgactgttga agctatgatg ggtcaagctc aatctttcga tcctttcatt | 900 |
| cacgaaactt gtagaccaca tccaggtcaa gttgaagttg ctaagactat cagatctatg | 960 |
| ttcgaaggtt ccagattggt tatccacatg gatgaagaaa gatccgttga tcaagaaaag | 1020 |
| gaccaaggta tcttgagaca agatagatat gctttgagaa ctgctccaca atggttgggt | 1080 |
| ccacaattag aagaattggt tactgtcaac aagaccttgt gcagagaaat caatgctact | 1140 |
| actgataacc cattgatcga catcaagaac aaaaagatct tgaacggtgg taacttccaa | 1200 |
| gccatgtcta ttaccaattc tatggaaaag accagatcct ccttggaatc cattggtaaa | 1260 |
| ttgtctttcg ctcaagccat cgaattgatg aactgtacta tgtctaaagg tttgccttct | 1320 |

-continued

```
tgtttggctg gtgatgaacc atctactaat taccatacaa agggtttgga tattaacatg  1380
gctgcttaca ctgctgaatt gggttttttg gcttctccag tttctaccca tgttcaatct  1440
gctgaacaac acaatcaatc cgttaactca ttggctttgg tttctgccag atacacaatt  1500
caagctgtcg aagttttgtc catgttgttg tcatctcact tgtacgttgt ctgcatggct  1560
attgatttga gagttatcga ccaaatgttt caaaagaat tgaagggttt gttgccagtt  1620
ttgttggatt cccattttaa gtctagacca actcaagctg ctgatccatt gattggtgct  1680
ttagcttcta gattggaagc tactgcttct ttggattctg aagctagatt tttgtccgct  1740
ttcaagcaaa ccttgcatgt tattttagcc ttcccagttg atttggaaga agctagaagt  1800
tggccatcat ttgctgcttc tcaatctact ttgttgtaca agagaaccag agatcaatac  1860
ttcgaaaact ccgaatcttt cttggctgaa aagtggttgg gtaaaaagaa caagcacttg  1920
taccacttcg tcagaaaaga attaggtatc ggtcctagaa gaggtgatgt tagattgggt  1980
agacatgaag gttccgtttc cattgatgtt tctaagatct acgaatccgt cagatccggt  2040
gaattataca agtttatgaa cagaatgttt taa                                2073
```

<210> SEQ ID NO 29
<211> LENGTH: 690
<212> TYPE: PRT
<213> ORGANISM: Puccinia graminis

<400> SEQUENCE: 29

```
Met Ala His Ala Asp Leu Cys Ser Ala Ile Ser Arg Glu Leu Glu Glu
1               5                   10                  15

His Ile Ser Asn Lys Arg Glu Ile Ile Leu Asp Gly His Gly Leu Thr
            20                  25                  30

Ser Thr Gly Val Val Gly Ala Ala Arg Tyr Asn Val Gln Ala Lys Ile
        35                  40                  45

Ser Asn Asp Pro Ala Leu Ile Thr Val Glu Glu Ser Val Glu Phe
    50                  55                  60

Leu Ala Ser Lys Leu Asp Thr Ala Ile Tyr Gly Val Thr Thr Phe Ser
65                  70                  75                  80

Glu Arg Leu Asp Pro Arg Pro Thr Asn Ala Cys Asn Phe Tyr Phe Gln
                85                  90                  95

Gly Ser Ala Asp Thr Arg Ser Asp Ser Thr Ala Asp Leu Gln Met Ala
            100                 105                 110

Phe Leu Glu His Gln Val Ser Gly Val Leu Pro Leu Ser Ser Arg Ser
        115                 120                 125

Thr Ser Ala Gly Leu Tyr Leu Ser Asp Pro Met Asn Asn Val Met Pro
    130                 135                 140

Glu Ala Ile Thr Arg Gly Ala Ile Leu Ile Arg Ile Asn Ser Leu Val
145                 150                 155                 160

Arg Gly His Ser Ala Leu Arg Phe Gln Val Leu Glu Thr Leu Ile Thr
                165                 170                 175

Leu Leu Asn Lys Asn Leu Thr Pro Met Val Pro Leu Arg Gly Ser Ile
            180                 185                 190

Ser Ala Ser Gly Asp Leu Met Pro Leu Ser Tyr Val Ala Ala Ile
        195                 200                 205

Cys Gly His Pro Ala Ile Arg Ile Ile Asp Arg Ser Ser Ala Asp Gly
    210                 215                 220

His Ile Glu Ile Met Pro Ala Ser Asp Ala Leu Thr Lys His Gly Ile
225                 230                 235                 240
```

-continued

Thr Pro Ile Val Leu Gly Pro Lys Glu Gly Leu Ala Ile Ser Asn Gly
            245                 250                 255

Thr Ala Phe Ser Ala Ser Ala Ala Cys Leu Val Ala His Asp Ser His
        260                 265                 270

Met Leu Leu Met Leu Ala Gln Gly Leu Thr Ser Met Thr Val Glu Ala
        275                 280                 285

Met Met Gly Gln Ala Gln Ser Phe Asp Pro Phe Ile His Glu Thr Cys
        290                 295                 300

Arg Pro His Pro Gly Gln Val Glu Val Ala Lys Thr Ile Arg Ser Met
305                 310                 315                 320

Phe Glu Gly Ser Arg Leu Val Ile His Met Asp Glu Glu Arg Ser Val
            325                 330                 335

Asp Gln Glu Lys Asp Gln Gly Ile Leu Arg Gln Asp Arg Tyr Ala Leu
            340                 345                 350

Arg Thr Ala Pro Gln Trp Leu Gly Pro Gln Leu Glu Glu Leu Val Thr
            355                 360                 365

Val Asn Lys Thr Leu Cys Arg Glu Ile Asn Ala Thr Thr Asp Asn Pro
            370                 375                 380

Leu Ile Asp Ile Lys Asn Lys Ile Leu Asn Gly Asn Phe Gln
385                 390                 395                 400

Ala Met Ser Ile Thr Asn Ser Met Glu Lys Thr Arg Ser Ser Leu Glu
            405                 410                 415

Ser Ile Gly Lys Leu Ser Phe Ala Gln Ala Ile Glu Leu Met Asn Cys
            420                 425                 430

Thr Met Ser Lys Gly Leu Pro Ser Cys Leu Ala Gly Asp Glu Pro Ser
            435                 440                 445

Thr Asn Tyr His Thr Lys Gly Leu Asp Ile Asn Met Ala Ala Tyr Thr
            450                 455                 460

Ala Glu Leu Gly Phe Leu Ala Ser Pro Val Ser Thr His Val Gln Ser
465                 470                 475                 480

Ala Glu Gln His Asn Gln Ser Val Asn Ser Leu Ala Leu Val Ser Ala
            485                 490                 495

Arg Tyr Thr Ile Gln Ala Val Glu Val Leu Ser Met Leu Leu Ser Ser
            500                 505                 510

His Leu Tyr Val Val Cys Met Ala Ile Asp Leu Arg Val Ile Asp Gln
            515                 520                 525

Met Phe Gln Lys Glu Leu Lys Gly Leu Leu Pro Val Leu Leu Asp Ser
            530                 535                 540

His Phe Lys Ser Arg Pro Thr Gln Ala Ala Asp Pro Leu Ile Gly Ala
545                 550                 555                 560

Leu Ala Ser Arg Leu Glu Ala Thr Ala Ser Leu Asp Ser Glu Ala Arg
            565                 570                 575

Phe Leu Ser Ala Phe Lys Gln Thr Leu His Val Ile Leu Ala Phe Pro
            580                 585                 590

Val Asp Leu Glu Glu Ala Arg Ser Trp Pro Ser Phe Ala Ala Ser Gln
            595                 600                 605

Ser Thr Leu Leu Tyr Lys Arg Thr Arg Asp Gln Tyr Phe Glu Asn Ser
            610                 615                 620

Glu Ser Phe Leu Ala Glu Lys Trp Leu Gly Lys Asn Lys His Leu
625                 630                 635                 640

Tyr His Phe Val Arg Lys Glu Leu Gly Ile Gly Pro Arg Arg Gly Asp
            645                 650                 655

Val Arg Leu Gly Arg His Glu Gly Ser Val Ser Ile Asp Val Ser Lys
            660                 665                 670

Ile Tyr Glu Ser Val Arg Ser Gly Glu Leu Tyr Lys Phe Met Asn Arg
        675                 680                 685

Met Phe
    690

<210> SEQ ID NO 30
<211> LENGTH: 1563
<212> TYPE: DNA
<213> ORGANISM: Aeromonas salmonicida

<400> SEQUENCE: 30

```
atgaacaagt ccgaaatgaa gtacgttacc tttggtgctg aaccattgac cattgaagat      60
gttgttgctt tggctgaaag aagagctaga ccagctttga atagagatcc agcttttatg     120
gccagaattc aaagaggtgc tgatttcttg gatagattat ggccgaagaa aggtgttatc     180
tacggtgtta ctactggtta tggtgattct gttactagac agttccagc  tgaattggtt     240
ccagaattgc cattgcattt gactagattt catggttgtg gtttgggtga agatttggaa     300
ttggatgctg gtagagctgt tttggctact agattgtgtt cttggctca  aggtgtttct     360
ggtgtttcac caggtttgtt ggaaagatta tgttggttgt tggaacaaga cttgatccca     420
agaattcctg aagaaggttc tgttggtgct tctggtgatt tgactccatt gtcttatgtt     480
gctgctgtat tggttggtga agagaattg  catcacgacg gtgctttaag accagctgct     540
gaagtttatc aagaattggg tattacccca ttgaccttaa gaccaaaaga aggtttggct     600
ttgatgaacg gtacttctgt tatgactgct ttagcttgtt tggcttatgc tagagctgat     660
tacttaatgc aattggccac tagaattacc gccttggttt ctgttgctat gggtggtaat     720
gcttttcatt tcgacgaaag attattcgcc gttaagccac atccaggtat gcaaggtatt     780
gctgcttggt tgagatctga tttggttgct ggtgaattgc aagacattc  tgatagattg     840
caagacagat actctttgag atgtgcccca catgttattg gtgttgttgc agattctttg     900
ccatggtgga gacaattgat tgaaaacgaa ttgaactccg ccaacgataa cccattgatt     960
gatggtgaag gtgaacatgt tatgcatggt ggtcattttt acggtggtca tattgctatg    1020
gctatggatt ctatgaagac cgctattgct aatttggccg atttgttgga cagacaattg    1080
gctcaattgg ttgataccaa gtttaatggt ggtttgccat ctaatttgtc tggtgctcca    1140
gctggtagac aaatgatcaa tcatggtttt aaggccgttc aaattggtgt tagtgcttgg    1200
actgctgaag ctttgaaaca aactatgcca gcttctgttt tctccagatc taccgaatgt    1260
cacaatcaag acaaagtctc catgggtaca attgctgcta gagatgcttt gagagttttg    1320
actttgactg aacaagttgg tgctgcttgt tgttggctg  ctgttcaagg tgtagaattg    1380
agattagctc aacctactcc attcactaga ccattatctc cagctttagc tcacatggtt    1440
caacaagtta gagctgaatt tgccccatta ttggaagata gagccttaga caagaattg     1500
agagctttga ttgccagaat cagattgaga cactaccctt tgtaccaaga atcctctttg    1560
tga                                                                  1563
```

<210> SEQ ID NO 31
<211> LENGTH: 520
<212> TYPE: PRT
<213> ORGANISM: Aeromonas salmonicida

<400> SEQUENCE: 31

```
Met Asn Lys Ser Glu Met Lys Tyr Val Thr Phe Gly Ala Glu Pro Leu
1               5                   10                  15

Thr Ile Glu Asp Val Val Ala Leu Ala Glu Arg Arg Ala Arg Pro Ala
                20                  25                  30

Leu Asn Arg Asp Pro Ala Phe Met Ala Arg Ile Gln Arg Gly Ala Asp
            35                  40                  45

Phe Leu Asp Arg Leu Leu Ala Glu Glu Gly Val Ile Tyr Gly Val Thr
    50                  55                  60

Thr Gly Tyr Gly Asp Ser Val Thr Arg Pro Val Pro Ala Glu Leu Val
65                  70                  75                  80

Pro Glu Leu Pro Leu His Leu Thr Arg Phe His Gly Cys Gly Leu Gly
                85                  90                  95

Glu Asp Leu Glu Leu Asp Ala Gly Arg Ala Val Leu Ala Thr Arg Leu
            100                 105                 110

Cys Ser Leu Ala Gln Gly Val Ser Gly Val Ser Pro Gly Leu Leu Glu
    115                 120                 125

Arg Leu Cys Trp Leu Leu Glu Gln Asp Leu Ile Pro Arg Ile Pro Glu
130                 135                 140

Glu Gly Ser Val Gly Ala Ser Gly Asp Leu Thr Pro Leu Ser Tyr Val
145                 150                 155                 160

Ala Ala Val Leu Val Gly Glu Arg Glu Leu His His Asp Gly Ala Leu
                165                 170                 175

Arg Pro Ala Ala Glu Val Tyr Gln Glu Leu Gly Ile Thr Pro Leu Thr
            180                 185                 190

Leu Arg Pro Lys Glu Gly Leu Ala Leu Met Asn Gly Thr Ser Val Met
    195                 200                 205

Thr Ala Leu Ala Cys Leu Ala Tyr Ala Arg Ala Asp Tyr Leu Met Gln
210                 215                 220

Leu Ala Thr Arg Ile Thr Ala Leu Val Ser Val Ala Met Gly Gly Asn
225                 230                 235                 240

Ala Phe His Phe Asp Glu Arg Leu Phe Ala Val Lys Pro His Pro Gly
                245                 250                 255

Met Gln Gly Ile Ala Ala Trp Leu Arg Ser Asp Leu Val Ala Gly Glu
            260                 265                 270

Leu Pro Arg His Ser Asp Arg Leu Gln Asp Arg Tyr Ser Leu Arg Cys
    275                 280                 285

Ala Pro His Val Ile Gly Val Val Ala Asp Ser Leu Pro Trp Trp Arg
290                 295                 300

Gln Leu Ile Glu Asn Glu Leu Asn Ser Ala Asn Asp Asn Pro Leu Ile
305                 310                 315                 320

Asp Gly Glu Gly Glu His Val Met His Gly Gly His Phe Tyr Gly Gly
                325                 330                 335

His Ile Ala Met Ala Met Asp Ser Met Lys Thr Ala Ile Ala Asn Leu
            340                 345                 350

Ala Asp Leu Leu Asp Arg Gln Leu Ala Gln Leu Val Asp Thr Lys Phe
    355                 360                 365

Asn Gly Gly Leu Pro Ser Asn Leu Ser Gly Ala Pro Ala Gly Arg Gln
370                 375                 380

Met Ile Asn His Gly Phe Lys Ala Val Gln Ile Gly Val Ser Ala Trp
385                 390                 395                 400

Thr Ala Glu Ala Leu Lys Gln Thr Met Pro Ala Ser Val Phe Ser Arg
                405                 410                 415

Ser Thr Glu Cys His Asn Gln Asp Lys Val Ser Met Gly Thr Ile Ala
```

```
                420             425             430
Ala Arg Asp Ala Leu Arg Val Leu Thr Leu Thr Glu Gln Val Gly Ala
            435                 440                 445

Ala Cys Leu Leu Ala Ala Val Gln Gly Val Glu Leu Arg Leu Ala Gln
            450                 455                 460

Pro Thr Pro Phe Thr Arg Pro Leu Ser Pro Ala Leu Ala His Met Val
465                 470                 475                 480

Gln Gln Val Arg Ala Glu Phe Ala Pro Leu Leu Glu Asp Arg Ala Leu
                485                 490                 495

Glu Gln Glu Leu Arg Ala Leu Ile Ala Arg Ile Arg Leu Arg His Tyr
            500                 505                 510

Pro Leu Tyr Gln Glu Ser Ser Leu
            515                 520

<210> SEQ ID NO 32
<211> LENGTH: 1602
<212> TYPE: DNA
<213> ORGANISM: Ralstonia metallidurans

<400> SEQUENCE: 32
atgccacatg ctcatccagc tgatattgat ggtcatcatt tgactccaga taccgttgct     60
gctattgcta gaggtcaaag agctgctata gttccagaac cagttttggg taaagttgct    120
gatgctagag ctagatttga acaagttgct gctgcaaatg ttccaatcta tggtgtttct    180
actggtttcg gtgaattggt tcataactgg gttgatatcg aacatggtag agccttgcaa    240
gaaaacttgt tgagatcaca ttgtgctggt gttggtcctt gtttttctag atgaagtt     300 agagctatga tggttgctag agcaaatgct ttggctagag ttattctgc tgttagacca    360 gcagttatcg aacaattatt gaagtacttg aagccggta ttactccagc tgttccacaa    420
gttggttctt gggtgcttc tggtgatttg ctccattgt ctcatgttgc tattaccttg    480
attggtgaag gtaaggtttt gactgaagat ggtggtactg ctccaactgc tgaagttttg    540
agagaaagag gtattacacc attggctttg gcttacaaag aaggtttggc tttgattaac    600
ggtacttctg ctatgacagg tgtttcttgt ttgttgttgg aaactttgag agcccaagtt    660
caacaagctg aaattattgc tgcttttggca ttggaaggtt tgtctgcttc agctgatgct    720
tttatggctc atggtcatga tattgctaaa ccacatccag tcaaattag atctgctgct    780 aatatgagag cttttgttggc tgattctgct agattgtctg gtcatggtga attgtctgct    840
gaaatgaaaa ctagagctgg tgaagctaag aatactggta ctggtgtttt cattcaaaag    900
gcctacacct tgagatgtat cccacaagtt ttaggtgcag ttagagatac cttggatcat    960
tgtgctactg ttgtcgaaag agaattgaac tcctctaacg ataaccctt gttctttgaa   1020 gatggtgaat tattccacgg tggtaacttt catggtcaac aagtagcttt tgccatggat   1080
tttttggcta ttgctgcaac tcaattgggt gttgtttctg aaagaagatt gaacagatta   1140
ttgtccccac acttgaacaa caatttgcca gcttttttgg cagctgctaa cgaaggttta   1200
tcttgtggtt tgctggtgc tcaatatcca gctactgctt tgattgctga aaacagaact   1260
atttgctccc cagcctctat tcaatctgtt ccatcaaatg gtgataatca agacgttgtc   1320
tccatgggtt taattgcagc tagaaacgct agaagaatct ggacaacaa tcaatatatc   1380 ttggccttgg aattattggc ttcttgtcaa gctgctgaat ggctggtgc tgttgaacaa   1440 ttggctccag ctggtagagc tgttttttgct tttgttagag aaagagtccc attcttgtcc   1500
atcgatagat atatgaccga tgacattgaa gctatggctg ctttgttgag acaaggtgct   1560
```
ttggttgaag ttgttagagg tgctggtatt gaattggcct aa         1602

<210> SEQ ID NO 33
<211> LENGTH: 533
<212> TYPE: PRT
<213> ORGANISM: Ralstonia metallidurans

<400> SEQUENCE: 33

```
Met Pro His Ala His Pro Ala Asp Ile Asp Gly His His Leu Thr Pro
1               5                   10                  15

Asp Thr Val Ala Ala Ile Ala Arg Gly Gln Arg Ala Ala Ile Val Pro
            20                  25                  30

Glu Pro Val Leu Gly Lys Val Ala Asp Ala Arg Ala Arg Phe Glu Gln
        35                  40                  45

Val Ala Ala Ala Asn Val Pro Ile Tyr Gly Val Ser Thr Gly Phe Gly
    50                  55                  60

Glu Leu Val His Asn Trp Val Asp Ile Glu His Gly Arg Ala Leu Gln
65                  70                  75                  80

Glu Asn Leu Leu Arg Ser His Cys Ala Gly Val Gly Pro Leu Phe Ser
                85                  90                  95

Arg Asp Glu Val Arg Ala Met Met Val Ala Arg Ala Asn Ala Leu Ala
            100                 105                 110

Arg Gly Tyr Ser Ala Val Arg Pro Ala Val Ile Glu Gln Leu Leu Lys
        115                 120                 125

Tyr Leu Glu Ala Gly Ile Thr Pro Ala Val Pro Gln Val Gly Ser Leu
    130                 135                 140

Gly Ala Ser Gly Asp Leu Ala Pro Leu Ser His Val Ala Ile Thr Leu
145                 150                 155                 160

Ile Gly Glu Gly Lys Val Leu Thr Glu Asp Gly Gly Thr Ala Pro Thr
                165                 170                 175

Ala Glu Val Leu Arg Glu Arg Gly Ile Thr Pro Leu Ala Leu Ala Tyr
            180                 185                 190

Lys Glu Gly Leu Ala Leu Ile Asn Gly Thr Ser Ala Met Thr Gly Val
        195                 200                 205

Ser Cys Leu Leu Leu Glu Thr Leu Arg Ala Gln Val Gln Gln Ala Glu
    210                 215                 220

Ile Ile Ala Ala Leu Ala Leu Glu Gly Leu Ser Ala Ser Ala Asp Ala
225                 230                 235                 240

Phe Met Ala His Gly His Asp Ile Ala Lys Pro His Pro Gly Gln Ile
                245                 250                 255

Arg Ser Ala Ala Asn Met Arg Ala Leu Leu Ala Asp Ser Ala Arg Leu
            260                 265                 270

Ser Gly His Gly Glu Leu Ser Ala Glu Met Lys Thr Arg Ala Gly Glu
        275                 280                 285

Ala Lys Asn Thr Gly Thr Gly Val Phe Ile Gln Lys Ala Tyr Thr Leu
    290                 295                 300

Arg Cys Ile Pro Gln Val Leu Gly Ala Val Arg Asp Thr Leu Asp His
305                 310                 315                 320

Cys Ala Thr Val Val Glu Arg Glu Leu Asn Ser Ser Asn Asp Asn Pro
                325                 330                 335

Leu Phe Phe Glu Asp Gly Glu Leu His Gly Gly Asn Phe His Gly
            340                 345                 350

Gln Gln Val Ala Phe Ala Met Asp Phe Leu Ala Ile Ala Ala Thr Gln
        355                 360                 365
```

Leu Gly Val Val Ser Glu Arg Arg Leu Asn Arg Leu Leu Ser Pro His
    370                 375                 380

Leu Asn Asn Asn Leu Pro Ala Phe Leu Ala Ala Ala Asn Glu Gly Leu
385                 390                 395                 400

Ser Cys Gly Phe Ala Gly Ala Gln Tyr Pro Ala Thr Ala Leu Ile Ala
                405                 410                 415

Glu Asn Arg Thr Ile Cys Ser Pro Ala Ser Ile Gln Ser Val Pro Ser
                420                 425                 430

Asn Gly Asp Asn Gln Asp Val Val Ser Met Gly Leu Ile Ala Ala Arg
            435                 440                 445

Asn Ala Arg Arg Ile Leu Asp Asn Asn Gln Tyr Ile Leu Ala Leu Glu
    450                 455                 460

Leu Leu Ala Ser Cys Gln Ala Ala Glu Leu Ala Gly Ala Val Glu Gln
465                 470                 475                 480

Leu Ala Pro Ala Gly Arg Ala Val Phe Ala Phe Val Arg Glu Arg Val
                485                 490                 495

Pro Phe Leu Ser Ile Asp Arg Tyr Met Thr Asp Asp Ile Glu Ala Met
                500                 505                 510

Ala Ala Leu Leu Arg Gln Gly Ala Leu Val Glu Val Val Arg Gly Ala
            515                 520                 525

Gly Ile Glu Leu Ala
    530

<210> SEQ ID NO 34
<211> LENGTH: 1620
<212> TYPE: DNA
<213> ORGANISM: Streptomyces globisporus

<400> SEQUENCE: 34
atggccttga ctcaagtcga aactgaaatc gttccagttt ctgttgatgg tgaaactttg      60
actgttgaag ccgttagaag agttgctgaa gaaagagcta ctgttgacgt tccagctgaa     120
tctattgcta agctcaaaaa gtccagagaa atcttcgaag gtattgccga caaaacatt      180 ccaatctacg tgttactac tggttacggt gaaatgatct atatgcaagt cgacaagtcc      240
aaagaagttg aattgcaaac taacttggtc agatctcatt ctgctggtgt tggtccatta     300
ttcgctgaag atgaagctag agctatagtt gctgctagat tgaatacttt ggctaaaggt     360
cattcagctg tcagaccaat tatcttggaa agattggctc aatacttgaa cgaaggtatc     420
actccagcta ttccagaaat tggttctttg ggtgcttctg gtgatttggc tccattgtct     480
catgttgctt ctactttgat tggtgaaggt tacgttttga gagatggtag accagttgaa     540
actgctcaag ttttggctga agaggtatt gaaccattgg aattgagatt caaagaaggt     600
ttggccttga ttaacggtac ttctggtatg actggtttgg gttctttagt tgttggtaga     660
gctttggaac aagctcaaca agctgaaata gttaccgcct tgttgataga agctgttaga     720
ggttctactt ctccattctt agctgaaggt catgatattg ctagaccaca tgaaggtcaa     780
attgatactg ctgctaatat gagagctttg atgagaggtt ctggtttgac agttgaacat     840
gctgatttga agagagaatt acaaaaggac aaagaagccg gtaaggacgt tcaaagatct     900
gaaatctact tgcaaaaggc ctactccttg agagctattc ctcaagttgt aggtgcagtt     960
agagatacct tgtatcatgc tagacacaag ttgagaatcg aattgaattc cgctaacgac    1020 aacccctttgt tctttgaagg taagaaaatt ttccacggtg ccaactttca tggtcaacct    1080
attgcttttg ctatggactt cgttaccatt gctttgactc aattgggtgt tttagccgaa    1140

```
agacaaatca acagagttttt gaacagacac ttgtcttacg gtttgccaga attttttggtt    1200 tcaggtgatc caggtttaca ttctggtttt gctggtgctc aatatccagc tactgctttg    1260
gttgctgaaa acagaactat tggtccagct tctacacaat ctgttccatc taatggtgat    1320
aatcaagacg ttgtctccat gggtttgatt tctgctagaa atgcaagaag agtcttgtcc    1380
aacaacaaca agattttggc agtcgaatat ttggctgctg ctcaagctgt tgatatttct    1440
ggtagattcg atggtttgtc tccagctgct aaagcaactt atgaagctgt aagaagattg    1500
gttccaacct tgggtgttga cagatatatg gctgatgata ttgaattggt tgccgatgct    1560
ttgtctagag gtgaattttt gagagccatt gctagagaaa ccgacatcca attgagataa    1620
```

<210> SEQ ID NO 35
<211> LENGTH: 539
<212> TYPE: PRT
<213> ORGANISM: Streptomyces globisporus

<400> SEQUENCE: 35

```
Met Ala Leu Thr Gln Val Glu Thr Glu Ile Val Pro Val Ser Val Asp
1               5                   10                  15

Gly Glu Thr Leu Thr Val Glu Ala Val Arg Arg Val Ala Glu Glu Arg
            20                  25                  30

Ala Thr Val Asp Val Pro Ala Glu Ser Ile Ala Lys Ala Gln Lys Ser
        35                  40                  45

Arg Glu Ile Phe Glu Gly Ile Ala Glu Gln Asn Ile Pro Ile Tyr Gly
    50                  55                  60

Val Thr Thr Gly Tyr Gly Glu Met Ile Tyr Met Gln Val Asp Lys Ser
65                  70                  75                  80

Lys Glu Val Glu Leu Gln Thr Asn Leu Val Arg Ser His Ser Ala Gly
                85                  90                  95

Val Gly Pro Leu Phe Ala Glu Asp Glu Ala Arg Ala Ile Val Ala Ala
            100                 105                 110

Arg Leu Asn Thr Leu Ala Lys Gly His Ser Ala Val Arg Pro Ile Ile
        115                 120                 125

Leu Glu Arg Leu Ala Gln Tyr Leu Asn Glu Gly Ile Thr Pro Ala Ile
    130                 135                 140

Pro Glu Ile Gly Ser Leu Gly Ala Ser Gly Asp Leu Ala Pro Leu Ser
145                 150                 155                 160

His Val Ala Ser Thr Leu Ile Gly Glu Gly Tyr Val Leu Arg Asp Gly
                165                 170                 175

Arg Pro Val Glu Thr Ala Gln Val Leu Ala Glu Arg Gly Ile Glu Pro
            180                 185                 190

Leu Glu Leu Arg Phe Lys Glu Gly Leu Ala Leu Ile Asn Gly Thr Ser
        195                 200                 205

Gly Met Thr Gly Leu Gly Ser Leu Val Val Gly Arg Ala Leu Glu Gln
    210                 215                 220

Ala Gln Gln Ala Glu Ile Val Thr Ala Leu Leu Ile Glu Ala Val Arg
225                 230                 235                 240

Gly Ser Thr Ser Pro Phe Leu Ala Glu Gly His Asp Ile Ala Arg Pro
                245                 250                 255

His Glu Gly Gln Ile Asp Thr Ala Ala Asn Met Arg Ala Leu Met Arg
            260                 265                 270

Gly Ser Gly Leu Thr Val Glu His Ala Asp Leu Arg Arg Glu Leu Gln
        275                 280                 285
```

Lys Asp Lys Glu Ala Gly Lys Asp Val Gln Arg Ser Glu Ile Tyr Leu
290                 295                 300

Gln Lys Ala Tyr Ser Leu Arg Ala Ile Pro Gln Val Val Gly Ala Val
305                 310                 315                 320

Arg Asp Thr Leu Tyr His Ala Arg His Lys Leu Arg Ile Glu Leu Asn
            325                 330                 335

Ser Ala Asn Asp Asn Pro Leu Phe Phe Glu Gly Lys Glu Ile Phe His
            340                 345                 350

Gly Ala Asn Phe His Gly Gln Pro Ile Ala Phe Ala Met Asp Phe Val
            355                 360                 365

Thr Ile Ala Leu Thr Gln Leu Gly Val Leu Ala Glu Arg Gln Ile Asn
370                 375                 380

Arg Val Leu Asn Arg His Leu Ser Tyr Gly Leu Pro Glu Phe Leu Val
385                 390                 395                 400

Ser Gly Asp Pro Gly Leu His Ser Gly Phe Ala Gly Ala Gln Tyr Pro
                405                 410                 415

Ala Thr Ala Leu Val Ala Glu Asn Arg Thr Ile Gly Pro Ala Ser Thr
            420                 425                 430

Gln Ser Val Pro Ser Asn Gly Asp Asn Gln Asp Val Val Ser Met Gly
            435                 440                 445

Leu Ile Ser Ala Arg Asn Ala Arg Arg Val Leu Ser Asn Asn Asn Lys
450                 455                 460

Ile Leu Ala Val Glu Tyr Leu Ala Ala Ala Gln Ala Val Asp Ile Ser
465                 470                 475                 480

Gly Arg Phe Asp Gly Leu Ser Pro Ala Ala Lys Ala Thr Tyr Glu Ala
                485                 490                 495

Val Arg Arg Leu Val Pro Thr Leu Gly Val Asp Arg Tyr Met Ala Asp
                500                 505                 510

Asp Ile Glu Leu Val Ala Asp Ala Leu Ser Arg Gly Glu Phe Leu Arg
            515                 520                 525

Ala Ile Ala Arg Glu Thr Asp Ile Gln Leu Arg
530                 535

<210> SEQ ID NO 36
<211> LENGTH: 2163
<212> TYPE: DNA
<213> ORGANISM: Rhodotorula graminis

<400> SEQUENCE: 36
atggccccat ctttggattc tttggctact actttggcta acggtttcac taatggttct      60
catgctgctc caacaaaatc tgctgctggt ccaacttctg ctttgagaag aactccaggt     120
ttggatggtc atgctgcaca tcaatctcaa ttggaaatcg ttcaagaatt attgtccgat     180
ccaaccgatg atgttgttga attgtctggt tactctttga ccgttagaga tgttgtaggt     240
gctgctagaa aaggtagaag agttagagtt caaaacgacg acgaaattag agccagagtt     300
gataagtctg ttgatttctt gaaggcccaa ttgcaaaact ctgtttacgg tgttactact     360
ggttttggtg gttctgctga tacaagaact gaagatgctg tttccttgca aaaggccttg     420
attgaacatc aattgtgtgg tgttactcca acctctgttt cttcattttc tgttggtaga     480
ggtttggaaa acaccttgcc attggaagtt gttagaggtg ctatggttat tagagtcaac     540
tcattgacta gaggtcattc cgctgttaga ttggttgttt tggaagcttt gaccaacttc     600
ttgaaccata gaattactcc aatcgtccca ttgagaggtt ctatttctgc ttctggtgat     660
ttgtctccat tgtcttatat tgctggtgct attactggtc acccagatgt taaggttcat     720

-continued

```
gttttacatg aaggtactga aaagatcatg ttcgccagag aagctatttc tttgtttggt    780
ttggaagcag ttgtcttggg tccaaaagaa ggtttgggtt tggttaatgg tactgctgtt    840
tcagcttcta tggctacttt gtcattgcat gattcccaca tgttgtcctt gttgtctcaa    900
gctttaactg ccttgactgt tgaagctatg gttggtcaac aaggttcttt tgctccattc    960
attcatgatg tctgtagacc acatccaggt caagttgaag ttgctagaaa catcagaact   1020
ttgttgtccg gttcatcttt cgctgttgaa catgaagaag aagttaaggt taaggacgac   1080
gaaggtattt tgagacaaga tagatatcca ttgagaactt ccccacaatt tttgggtcca   1140
ttggttgaag atatgatgca tgcttactct accttgtcct tagaaaacaa cactactacc   1200
gataaccctt tgttggatgt cgaaaacaaa caaactgctc atggtggtaa ttttcaagct   1260
tctgctgtct ctatctctat ggaaaaaact agattggctt tggccttgat cggtaagttg   1320
aatttcactc aatgcaccga attattgaac gctgctatga atagaggttt accatcttgt   1380
ttggctgctg aagatccatc tttgaactat catggtaagg gtttggatat tcatattgct   1440
gcttacgctt cagaattggg tcatttggct aatccagtta ctactttgt tcaaccagcc    1500
gaaatgggta atcaagccgt taattcttta gccttgattt ccgctagaag aactgctgaa   1560
gctaacgatg ttttgtcttt gttgttggct tctcacttgt actgtacatt gcaagcagtt   1620
gatttgagag ccatggaatt ggatttcaag aagcaattcg atcctttgtt gcctaccttg   1680
ttacaacaac atttgggtac tggtttggac gttaatgctt tggctttaga agtcaagaag   1740
gctttgaaca agagattgga acaaactacc acctacgatt tggaacctag atggcatgat   1800
gctttttctt atgctactgg tactgtcgtt gaattattga gttcttcccc atctgctaac   1860
gttactttga ctgctgttaa cgcttggaaa gttgcatctg ctgaaaaggc tatttccttg   1920
acaagagaag tcagaaacag attctggcaa actccatctt ctcaagctcc agctcatgct   1980
tatttgtcac caagaactag agtcttgtac tccttcgtta gagaagaatt aggtgtccaa   2040
gctagaagag gtgatgtttt tgttggtgtt caacaagaaa ccatcggttc caatgtttca   2100
agaatctacg aagccattaa ggacggtaga atcaatcacg ttttggttaa gatgttggct   2160
taa                                                                 2163
```

<210> SEQ ID NO 37
<211> LENGTH: 720
<212> TYPE: PRT
<213> ORGANISM: Rhodotorula graminis

<400> SEQUENCE: 37

```
Met Ala Pro Ser Leu Asp Ser Leu Ala Thr Thr Leu Ala Asn Gly Phe
1               5                   10                  15

Thr Asn Gly Ser His Ala Ala Pro Thr Lys Ser Ala Ala Gly Pro Thr
            20                  25                  30

Ser Ala Leu Arg Arg Thr Pro Gly Leu Asp Gly His Ala Ala His Gln
        35                  40                  45

Ser Gln Leu Glu Ile Val Gln Glu Leu Leu Ser Asp Pro Thr Asp Asp
    50                  55                  60

Val Val Glu Leu Ser Gly Tyr Ser Leu Thr Val Arg Asp Val Val Gly
65                  70                  75                  80

Ala Ala Arg Lys Gly Arg Arg Val Arg Val Gln Asn Asp Asp Glu Ile
                85                  90                  95

Arg Ala Arg Val Asp Lys Ser Val Asp Phe Leu Lys Ala Gln Leu Gln
            100                 105                 110
```

-continued

```
Asn Ser Val Tyr Gly Val Thr Gly Phe Gly Ser Ala Asp Thr
        115                 120                 125

Arg Thr Glu Asp Ala Val Ser Leu Gln Lys Ala Leu Ile Glu His Gln
130                 135                 140

Leu Cys Gly Val Thr Pro Thr Ser Val Ser Ser Phe Ser Val Gly Arg
145                 150                 155                 160

Gly Leu Glu Asn Thr Leu Pro Leu Glu Val Val Arg Gly Ala Met Val
                165                 170                 175

Ile Arg Val Asn Ser Leu Thr Arg Gly His Ser Ala Val Arg Leu Val
                180                 185                 190

Val Leu Glu Ala Leu Thr Asn Phe Leu Asn His Arg Ile Thr Pro Ile
                195                 200                 205

Val Pro Leu Arg Gly Ser Ile Ser Ala Ser Gly Asp Leu Ser Pro Leu
210                 215                 220

Ser Tyr Ile Ala Gly Ala Ile Thr Gly His Pro Asp Val Lys Val His
225                 230                 235                 240

Val Leu His Glu Gly Thr Glu Lys Ile Met Phe Ala Arg Glu Ala Ile
                245                 250                 255

Ser Leu Phe Gly Leu Glu Ala Val Val Leu Gly Pro Lys Glu Gly Leu
                260                 265                 270

Gly Leu Val Asn Gly Thr Ala Val Ser Ala Ser Met Ala Thr Leu Ser
                275                 280                 285

Leu His Asp Ser His Met Leu Ser Leu Leu Ser Gln Ala Leu Thr Ala
                290                 295                 300

Leu Thr Val Glu Ala Met Val Gly Gln Gln Gly Ser Phe Ala Pro Phe
305                 310                 315                 320

Ile His Asp Val Cys Arg Pro His Pro Gly Gln Val Glu Val Ala Arg
                325                 330                 335

Asn Ile Arg Thr Leu Leu Ser Gly Ser Ser Phe Ala Val Glu His Glu
                340                 345                 350

Glu Glu Val Lys Val Lys Asp Glu Gly Ile Leu Arg Gln Asp Arg
        355                 360                 365

Tyr Pro Leu Arg Thr Ser Pro Gln Phe Leu Gly Pro Leu Val Glu Asp
370                 375                 380

Met Met His Ala Tyr Ser Thr Leu Ser Leu Glu Asn Asn Thr Thr Thr
385                 390                 395                 400

Asp Asn Pro Leu Leu Asp Val Glu Asn Lys Gln Thr Ala His Gly Gly
                405                 410                 415

Asn Phe Gln Ala Ser Ala Val Ser Ile Ser Met Glu Lys Thr Arg Leu
                420                 425                 430

Ala Leu Ala Leu Ile Gly Lys Leu Asn Phe Thr Gln Cys Thr Glu Leu
                435                 440                 445

Leu Asn Ala Ala Met Asn Arg Gly Leu Pro Ser Cys Leu Ala Ala Glu
450                 455                 460

Asp Pro Ser Leu Asn Tyr His Gly Lys Gly Leu Asp Ile His Ile Ala
465                 470                 475                 480

Ala Tyr Ala Ser Glu Leu Gly His Leu Ala Asn Pro Val Thr Thr Phe
                485                 490                 495

Val Gln Pro Ala Glu Met Gly Asn Gln Ala Val Asn Ser Leu Ala Leu
                500                 505                 510

Ile Ser Ala Arg Arg Thr Ala Glu Ala Asn Asp Val Leu Ser Leu Leu
                515                 520                 525
```

| | | | | | | | | | | | | |
|---|---|---|---|---|---|---|---|---|---|---|---|---|
| Leu | Ala | Ser | His | Leu | Tyr | Cys | Thr | Leu | Gln | Ala | Val | Asp | Leu | Arg | Ala |
| | | 530 | | | | 535 | | | | 540 | | | | | |

Leu Ala Ser His Leu Tyr Cys Thr Leu Gln Ala Val Asp Leu Arg Ala
            530                 535                 540

Met Glu Leu Asp Phe Lys Lys Gln Phe Asp Pro Leu Leu Pro Thr Leu
545                 550                 555                 560

Leu Gln Gln His Leu Gly Thr Gly Leu Asp Val Asn Ala Leu Ala Leu
                565                 570                 575

Glu Val Lys Lys Ala Leu Asn Lys Arg Leu Glu Gln Thr Thr Thr Tyr
                580                 585                 590

Asp Leu Glu Pro Arg Trp His Asp Ala Phe Ser Tyr Ala Thr Gly Thr
            595                 600                 605

Val Val Glu Leu Leu Ser Ser Ser Pro Ser Ala Asn Val Thr Leu Thr
            610                 615                 620

Ala Val Asn Ala Trp Lys Val Ala Ser Ala Glu Lys Ala Ile Ser Leu
625                 630                 635                 640

Thr Arg Glu Val Arg Asn Arg Phe Trp Gln Thr Pro Ser Ser Gln Ala
                645                 650                 655

Pro Ala His Ala Tyr Leu Ser Pro Arg Thr Arg Val Leu Tyr Ser Phe
                660                 665                 670

Val Arg Glu Glu Leu Gly Val Gln Ala Arg Arg Gly Asp Val Phe Val
                675                 680                 685

Gly Val Gln Gln Glu Thr Ile Gly Ser Asn Val Ser Arg Ile Tyr Glu
690                 695                 700

Ala Ile Lys Asp Gly Arg Ile Asn His Val Leu Val Lys Met Leu Ala
705                 710                 715                 720

<210> SEQ ID NO 38
<211> LENGTH: 2106
<212> TYPE: DNA
<213> ORGANISM: Bambusa oldhamii

<400> SEQUENCE: 38

```
atggctggta atggtccaat cgttaaggat gatccattga attggggtgc tgctgctgca      60
gaattgactg gttctcattt tgatgaagtc aagagaatgg ttgcccaatt cagagaacct     120
gttattaaga ttgaaggtgc ctctttgaga gttggtcaag ttgctgctgt tgctcaagct     180
aaagatgttt ctggtgttgc tgttgaattg gatgaagaag ctagaccaag agttaaggct     240
tcttctgaat ggattttgaa ctgttttggct catggtggtg atatctatgg tgttactact     300
ggttttggtg gtacttccca tagaagaaca aaagatggtc cagcattgca agttgaatta     360
ttgagacatt tgaacgccgg tattttcggt actggtactg atggtcatac tttgccatct     420
gaagttacta gagctgctat gttggttaga atcaacactt tgttgcaagg ttactccggt     480
atcagattcg aaatttttgga agccattacc aagttgatca atactggtgt tacaccatgt     540
ttgccattga gaggtactat tactgcttct ggtgatttgg ttccattgtc ttatattgcc     600
ggtttgatta ctggtagacc aaatgctcaa gcagttgctc cagatggtag aaaagttgat     660
gctgctgaag cttttaagat tgctggtata gaaggtggtt tcttcaagtt gaacccaaaa     720
gaaggtttgg ctatcgttaa cggtacttct gttggttctg cttttggctgc tactgtcttg     780
tatgattgca atgttttggc cgttttgtcc gaagtttttgt ctgctgttttt ttgcgaagtt     840
atgaacggta agccagaata cactgatcat ttgacccata agttgaaaca tcacccaggt     900
tctattgaag ctgctgctat tatggaacat attttggctg ttcctctctt catgtcccat     960
gctaaaaaag ttacgaaaat ggacccttttg ttgaagccta gcaagatag atatgctttg    1020
agaacttctc acaatggttt gggtccacaa attgaagtta agagcagcc accaagtcc    1080
```

```
atcgaaagag aagttaattc cgttaatgac aacccagtta tcgatgttca tagaggtaag    1140
gctttacatg gtggtaattt tcaaggtact ccaatcggtg tttctatgga caacactaga    1200
ttggctattg ctaacatcgg taagttgatg ttcgctcaat tttccgaatt ggtcaacgaa    1260
ttctacaaca acggtttgac ttctaatttg gccggttcta gaaatccatc tttggattac    1320
ggtttcaagg gtactgaaat tgctatggct tcttactgct ccgaattgca atatttggct    1380
aacccaatca ccaaccatgt tcaatctgct gaacaacaca atcaagacgt taactctttg    1440
ggtttggttt ctgctagaaa aacagctgaa gccgttgata tcttgaagtt gatgagttct    1500
acttacatgt tgctttgtg ccaagctgtt gatttgagac acttggaaga aaacatcaag    1560
tcctctgtta agaactgcgt tacccaagtt gctaaaaagg ttttgactat gaacccaacc    1620
ggtgatttgt catctgctag attttctgaa aagaacttgt tgaccgccat tgatagagaa    1680
gctgttttca cttatgctga tgatccttgt tctgctaact acccattgat gcaaaaattg    1740
agagccgttt tggttgatca tgctttgaca tctggtgatg ctgaaagaga accttctgtt    1800
ttctctaaga tcaccaagtt cgaagaagaa ttgagatctg ctttgccaag agaaattgaa    1860
gcagctagag ttgcagttgc tgatggtaca gctccaattg ctaatagaat caaagaatcc    1920
agatccttcc cagtctacag attcgttaga gaagaattag gttgcgttta cttgaccggt    1980
gaaaaattga atctccagg tgaagaatgc aacaaggttt tcattggtat ctcccaaggt    2040
aaattgatcg acccaatgtt ggaatgcttg aaagaatgga atggtgaacc attgccaatc    2100
aactga                                                              2106

<210> SEQ ID NO 39
<211> LENGTH: 701
<212> TYPE: PRT
<213> ORGANISM: Bambusa oldhamii

<400> SEQUENCE: 39

Met Ala Gly Asn Gly Pro Ile Val Lys Asp Asp Pro Leu Asn Trp Gly
1               5                   10                  15

Ala Ala Ala Ala Glu Leu Thr Gly Ser His Phe Asp Glu Val Lys Arg
            20                  25                  30

Met Val Ala Gln Phe Arg Glu Pro Val Ile Lys Ile Glu Gly Ala Ser
        35                  40                  45

Leu Arg Val Gly Gln Val Ala Val Ala Gln Ala Lys Asp Val Ser
    50                  55                  60

Gly Val Ala Val Glu Leu Asp Glu Glu Ala Arg Pro Arg Val Lys Ala
65                  70                  75                  80

Ser Ser Glu Trp Ile Leu Asn Cys Leu Ala His Gly Gly Asp Ile Tyr
                85                  90                  95

Gly Val Thr Thr Gly Phe Gly Thr Ser His Arg Arg Thr Lys Asp
            100                 105                 110

Gly Pro Ala Leu Gln Val Glu Leu Leu Arg His Leu Asn Ala Gly Ile
        115                 120                 125

Phe Gly Thr Gly Thr Asp Gly His Thr Leu Pro Ser Glu Val Thr Arg
    130                 135                 140

Ala Ala Met Leu Val Arg Ile Asn Thr Leu Leu Gln Gly Tyr Ser Gly
145                 150                 155                 160

Ile Arg Phe Glu Ile Leu Glu Ala Ile Thr Lys Leu Ile Asn Thr Gly
                165                 170                 175

Val Thr Pro Cys Leu Pro Leu Arg Gly Thr Ile Thr Ala Ser Gly Asp
```

```
                180                 185                 190
Leu Val Pro Leu Ser Tyr Ile Ala Gly Leu Ile Thr Gly Arg Pro Asn
            195                 200                 205

Ala Gln Ala Val Ala Pro Asp Gly Arg Lys Val Asp Ala Ala Glu Ala
            210                 215                 220

Phe Lys Ile Ala Gly Ile Glu Gly Gly Phe Lys Leu Asn Pro Lys
225                 230                 235                 240

Glu Gly Leu Ala Ile Val Asn Gly Thr Ser Val Gly Ser Ala Leu Ala
                245                 250                 255

Ala Thr Val Leu Tyr Asp Cys Asn Val Leu Ala Val Leu Ser Glu Val
            260                 265                 270

Leu Ser Ala Val Phe Cys Glu Val Met Asn Gly Lys Pro Glu Tyr Thr
            275                 280                 285

Asp His Leu Thr His Lys Leu Lys His His Pro Gly Ser Ile Glu Ala
            290                 295                 300

Ala Ala Ile Met Glu His Ile Leu Ala Gly Ser Ser Phe Met Ser His
305                 310                 315                 320

Ala Lys Lys Val Asn Glu Met Asp Pro Leu Leu Lys Pro Lys Gln Asp
                325                 330                 335

Arg Tyr Ala Leu Arg Thr Ser Pro Gln Trp Leu Gly Pro Gln Ile Glu
            340                 345                 350

Val Ile Arg Ala Ala Thr Lys Ser Ile Glu Arg Glu Val Asn Ser Val
            355                 360                 365

Asn Asp Asn Pro Val Ile Asp Val His Arg Gly Lys Ala Leu His Gly
            370                 375                 380

Gly Asn Phe Gln Gly Thr Pro Ile Gly Val Ser Met Asp Asn Thr Arg
385                 390                 395                 400

Leu Ala Ile Ala Asn Ile Gly Lys Leu Met Phe Ala Gln Phe Ser Glu
                405                 410                 415

Leu Val Asn Glu Phe Tyr Asn Asn Gly Leu Thr Ser Asn Leu Ala Gly
            420                 425                 430

Ser Arg Asn Pro Ser Leu Asp Tyr Gly Phe Lys Gly Thr Glu Ile Ala
            435                 440                 445

Met Ala Ser Tyr Cys Ser Glu Leu Gln Tyr Leu Ala Asn Pro Ile Thr
            450                 455                 460

Asn His Val Gln Ser Ala Glu Gln His Asn Gln Asp Val Asn Ser Leu
465                 470                 475                 480

Gly Leu Val Ser Ala Arg Lys Thr Ala Glu Ala Val Asp Ile Leu Lys
                485                 490                 495

Leu Met Ser Ser Thr Tyr Met Val Ala Leu Cys Gln Ala Val Asp Leu
            500                 505                 510

Arg His Leu Glu Glu Asn Ile Lys Ser Ser Val Lys Asn Cys Val Thr
            515                 520                 525

Gln Val Ala Lys Lys Val Leu Thr Met Asn Pro Thr Gly Asp Leu Ser
            530                 535                 540

Ser Ala Arg Phe Ser Glu Lys Asn Leu Leu Thr Ala Ile Asp Arg Glu
545                 550                 555                 560

Ala Val Phe Thr Tyr Ala Asp Asp Pro Cys Ser Ala Asn Tyr Pro Leu
                565                 570                 575

Met Gln Lys Leu Arg Ala Val Leu Val Asp His Ala Leu Thr Ser Gly
            580                 585                 590

Asp Ala Glu Arg Glu Pro Ser Val Phe Ser Lys Ile Thr Lys Phe Glu
            595                 600                 605
```

```
Glu Leu Arg Ser Ala Leu Pro Arg Glu Ile Glu Ala Ala Arg Val
    610             615                 620

Ala Val Ala Asp Gly Thr Ala Pro Ile Ala Asn Arg Ile Lys Glu Ser
625             630                 635                 640

Arg Ser Phe Pro Val Tyr Arg Phe Val Arg Glu Glu Leu Gly Cys Val
            645                 650                 655

Tyr Leu Thr Gly Glu Lys Leu Lys Ser Pro Gly Glu Glu Cys Asn Lys
            660                 665                 670

Val Phe Ile Gly Ile Ser Gln Gly Lys Leu Ile Asp Pro Met Leu Glu
            675                 680                 685

Cys Leu Lys Glu Trp Asn Gly Glu Pro Leu Pro Ile Asn
    690                 695                 700

<210> SEQ ID NO 40
<211> LENGTH: 1785
<212> TYPE: DNA
<213> ORGANISM: Neosartorya fischeri

<400> SEQUENCE: 40
atgccagctt cttgggttag aggtactatg ttggttagat gtaactctaa cgctagaggt      60
cattctgctg tttctttgcc agctattgaa tccttgttga gattgatcga aaaccacatt     120
actccagttg ttccattgag aggttctatt tctgcttctg gtgatttgat gccattgtct     180
tatattgctg gtgctattga aggttcccca gatgtttatg ttcaagttca agattccgac     240
aagaccagaa tcatgaattc tagagatgct tgttgtcca ctggtttgga agctcaaact      300
ttgggtccaa agaaggtttt ggtttggtt aatggtactt ctgcttcagc tgctttggct     360
tctttggcta tgtatgaagc tcatcaattg gccgttttgg ttcaagcttt gtctgctttg    420
actgttgaag ctttgatggg taatgctgaa tctttccatc cattcatttc cgccattaga    480
ccacatgatg tcaaattga atgtgccaga acgtcatgt cttcttgca aggttctcaa       540
ttggctcaaa acttggaaag aaacttgaag acagaaaca gaccaggttt gatccaagat     600
agatacgctt tgagaactgt tccacaatgg attggtccac aattggaaga tttgttgttg    660
gcccatagac aagttaccgt tgaattgaac tcttcttgcg ataacccatt ggttgatgct    720
caatccgatg atattttcta cggtggtaat ttccaagccg tttctattac atctgctatg    780
gaaaagacta gaacctgctt gcaaatgttc ggtagattgt tgtttgctca agccaccgaa    840
ttgattgatc catctttgaa caatggtttg cctaccaatt tggttgctga tgatccatcc    900
ttgtctttca ctatgaaggg tgttgatatt ccatggcttt cttacatggc tgaattggct    960
tacttggcta atccagtttc ttctcatgtt caaaccgccg aaatgcacaa tcaatctgtt   1020
aattctatgg ccttcgtttc ctctagatac actatgcaag ctgtcgaaat cgtttctttg   1080
atgtgtgctt gctctgttta cattggttgc caagctttgg atttgagagt cttgcatttg   1140
acattcttgc aaagatctac cccacaattg catactttga cctctcatt gttctccgaa    1200
cacttgtttg aaccagattt ggctactttg aatgaagcct tgtctaccca tattcaaaag   1260
tcttggccaa ctactaccag attgaacatt accgatagag ttgaagaagt tgttacctcc   1320
gctattccaa ttttgtgtag aactttcgct tcttccactg gtacatctac ttctcaagct   1380
ccaactttct ctgatttgga aacctggaaa tctagagctt cagctttgtt gaacgaaatc   1440
taccaagata ctgctcatgc cttcttctct taccaacata tgaagaaat gttgggtact    1500
tcctctaaga tcttgtacca aaccgttaga agacaattgg gtgttccatt tcatcaaggt   1560
```

```
ttcattgaac atccaaccgc tcaatctgat actttgggtg gtagaccaaa aaagactgtt    1620
ggttcttgga tctccattat ctacgaagct attagagaag gtagattgat ggatcctttg    1680
atggcatctt tacaagctgg tgttgctggt gaatcagata ctgaagctgt tgatacttta    1740
aaggacggtt cttctggtaa gtgttcttct tcaggtttgg actga                    1785
```

<210> SEQ ID NO 41
<211> LENGTH: 594
<212> TYPE: PRT
<213> ORGANISM: Neosartorya fischeri

<400> SEQUENCE: 41

```
Met Pro Ala Ser Trp Val Arg Gly Thr Met Leu Val Arg Cys Asn Ser
1               5                   10                  15

Asn Ala Arg Gly His Ser Ala Val Ser Leu Pro Ala Ile Glu Ser Leu
            20                  25                  30

Leu Arg Leu Ile Glu Asn His Ile Thr Pro Val Val Pro Leu Arg Gly
        35                  40                  45

Ser Ile Ser Ala Ser Gly Asp Leu Met Pro Leu Ser Tyr Ile Ala Gly
    50                  55                  60

Ala Ile Glu Gly Ser Pro Asp Val Tyr Val Gln Val Gln Asp Ser Asp
65                  70                  75                  80

Lys Thr Arg Ile Met Asn Ser Arg Asp Ala Leu Leu Ser Thr Gly Leu
                85                  90                  95

Glu Ala Gln Thr Leu Gly Pro Lys Glu Gly Leu Gly Leu Val Asn Gly
            100                 105                 110

Thr Ser Ala Ser Ala Ala Leu Ala Ser Leu Ala Met Tyr Glu Ala His
        115                 120                 125

Gln Leu Ala Val Leu Val Gln Ala Leu Ser Ala Leu Thr Val Glu Ala
    130                 135                 140

Leu Met Gly Asn Ala Glu Ser Phe His Pro Phe Ile Ser Ala Ile Arg
145                 150                 155                 160

Pro His Asp Gly Gln Ile Glu Cys Ala Arg Asn Val Met Ser Phe Leu
                165                 170                 175

Gln Gly Ser Gln Leu Ala Gln Asn Leu Glu Arg Asn Leu Lys Asp Arg
            180                 185                 190

Asn Arg Pro Gly Leu Ile Gln Asp Arg Tyr Ala Leu Arg Thr Val Pro
        195                 200                 205

Gln Trp Ile Gly Pro Gln Leu Glu Asp Leu Leu Leu Ala His Arg Gln
    210                 215                 220

Val Thr Val Glu Leu Asn Ser Ser Cys Asp Asn Pro Leu Val Asp Ala
225                 230                 235                 240

Gln Ser Asp Asp Ile Phe Tyr Gly Gly Asn Phe Gln Ala Val Ser Ile
                245                 250                 255

Thr Ser Ala Met Glu Lys Thr Arg Thr Cys Leu Gln Met Phe Gly Arg
            260                 265                 270

Leu Leu Phe Ala Gln Ala Thr Glu Leu Ile Asp Pro Ser Leu Asn Asn
        275                 280                 285

Gly Leu Pro Thr Asn Leu Val Ala Asp Pro Ser Leu Ser Phe Thr
    290                 295                 300

Met Lys Gly Val Asp Ile Ser Met Ala Ser Tyr Met Ala Glu Leu Ala
305                 310                 315                 320

Tyr Leu Ala Asn Pro Val Ser Ser His Val Gln Thr Ala Glu Met His
                325                 330                 335
```

Asn Gln Ser Val Asn Ser Met Ala Phe Val Ser Ser Arg Tyr Thr Met
                340                 345                 350

Gln Ala Val Glu Ile Val Ser Leu Met Cys Ala Cys Ser Val Tyr Ile
            355                 360                 365

Gly Cys Gln Ala Leu Asp Leu Arg Val Leu His Leu Thr Phe Leu Gln
        370                 375                 380

Arg Ser Thr Pro Gln Leu His Thr Leu Thr Ser His Leu Phe Ser Glu
385                 390                 395                 400

His Leu Phe Glu Pro Asp Leu Ala Thr Leu Asn Glu Ala Leu Ser Thr
                405                 410                 415

His Ile Gln Lys Ser Trp Pro Thr Thr Thr Arg Leu Asn Ile Thr Asp
            420                 425                 430

Arg Val Glu Glu Val Val Thr Ser Ala Ile Pro Ile Leu Cys Arg Thr
        435                 440                 445

Phe Ala Ser Ser Thr Gly Thr Ser Thr Ser Gln Ala Pro Thr Phe Ser
    450                 455                 460

Asp Leu Glu Thr Trp Lys Ser Arg Ala Ser Ala Leu Leu Asn Glu Ile
465                 470                 475                 480

Tyr Gln Asp Thr Ala His Ala Phe Phe Ser Tyr Gln His Thr Glu Glu
                485                 490                 495

Met Leu Gly Thr Ser Ser Lys Ile Leu Tyr Gln Thr Val Arg Arg Gln
            500                 505                 510

Leu Gly Val Pro Phe His Gln Gly Phe Ile Glu His Pro Thr Ala Gln
        515                 520                 525

Ser Asp Thr Leu Gly Gly Arg Pro Lys Lys Thr Val Gly Ser Trp Ile
    530                 535                 540

Ser Ile Ile Tyr Glu Ala Ile Arg Glu Gly Arg Leu Met Asp Pro Leu
545                 550                 555                 560

Met Ala Ser Leu Gln Ala Gly Val Ala Gly Glu Ser Asp Thr Glu Ala
                565                 570                 575

Val Asp Thr Leu Lys Asp Gly Ser Gly Lys Cys Ser Ser Ser Gly
            580                 585                 590

Leu Asp

<210> SEQ ID NO 42
<211> LENGTH: 2148
<212> TYPE: DNA
<213> ORGANISM: Rhodotorula glutinis

<400> SEQUENCE: 42
atgtccttga gaagagatca cggtgttaga agattgggta gacatccaga tggtggtaga      60
gatttggctg ctgaaggtgt tagattgcat attgctttgt ctccattctc ctcaagaaga     120
gcttctactg attctagagg tccattcgct ttcgaaaaca gtttgttgga acatcaattg     180
tgcggtgttt tgccaacttc tatggatggt tttgctttgg ttctggtttt ggaaaattct     240
ttgccattgg aagttgttag aggtgctatg actttgagag tcaactcttt gacaagaggt     300
cattctgctg ttagaatcgt tgttttggaa gctttgacta acttcttgaa ccatggtatt     360
actccaatcg ttccattgag aggtactatt tctgcttctg tgatttgtc accattgtct     420 tatattgctg cttccattac tggtcaccca gattctaaag ttcatgttga tggtcaaatc     480
atgtccgctc aagaagctat tgcattgaaa ggtttacaac cagttgtctt gggtccaaaa     540
gaaggtttgg gttagttaa tggtactgct gtttcagctt ctatggctac tttggctttg     600
actgatgctc atgttttgtc tttgttggct caagctaata ctgctttgac agttgaagct     660

```
atggttggtc atgctggttc ttttcatcca ttcttgcatg atgttactag accagctcca    720
gatccagaca gaggtagagc tgctacttta ggtttgttgt tggaaggttc taagtactgc    780
ttgtctacta tgagaccaag atccagatct agaactacta gagcttcttc tggtagaact    840
gatacaagat ctgctgctag acctagattt gtcgttttca gaattccatc cttgtctgcc    900
catagatctg atcctttgtt gttatgttct ggtgctcaat ggttgggtcc attggtttct    960
gatatgattc atgcccattc tgtcttgtct ttagaagctg gtcaatctac tactgacaac   1020
ccattgattg acttggaaaa caagatgact catcatggtg gtgcttttat ggcttcttca   1080
gttggtaaca ctatggaaaa agattggtt tccccatctc atttgtgggc tagattggct   1140
tctttatctt ctccaagatg ttctactcca gcttgtactg ctagatttcc accagcttca   1200
ccaccaagaa ctagattgtg tccaactaca gctagagttt ctacttctcc accattgcat   1260
actttgagat cctctgttac ttctagaacc caatccagac caactttctc tagacaaaga   1320
tgggctatta agatctac cagatctcca tcttctagac cagttgctcc tcctagaaga   1380
acaacttctt ctagatcatc atctcctcca acttcaactg cttcttgtag aagatccact   1440
tgtgctagat ggtcatcctc tactagaaag tctttatcaa gatggtcccc aacctgttct   1500
tcatctactt tagctagatc aagacaacct acctccagaa caagatcagc taatagatct   1560
acttctggtt gctccagaac tacaagaact acttcatctt ctggtggtac aaccagatca   1620
agaagtagac cagcaccatc atctaaacca tctccaggta ctagatgtag atctagagca   1680
tctacaccag gtagaagtag agctttgaga agaccttctc catctcctgc tccatgtgct   1740
actagatcag gtcctcgtcg tagaagaaga agaccaagaa gttcaactag tagaagaggt   1800
ttggcttcct gtactagatc ttcaggtaaa acatctgctt caagaccagc tgctgctact   1860
agtacttcag cttcaagaag atcaagatcc ggtccaactt ctgctgcatc aacaagaaga   1920
tccagaactg ctgctttgtt gagatcatct tcaagatgtt ggcacaagag aactttggtt   1980
caagcttcat tggctagaga ttctaagttg ccattttttgc caggtagatt gagacaaaga   2040
agattcccac cagattgtca ttttccacat gctccatatc cattgggttt cagatctcat   2100
tctggtccag ttgaaaccca tatttctttc ggtagaagac catattaa                2148
```

<210> SEQ ID NO 43
<211> LENGTH: 715
<212> TYPE: PRT
<213> ORGANISM: Rhodotorula glutinis

<400> SEQUENCE: 43

```
Met Ser Leu Arg Arg Asp His Gly Val Arg Arg Leu Gly Arg His Pro
1               5                   10                  15

Asp Gly Gly Arg Asp Leu Ala Ala Glu Gly Val Arg Leu His Ile Ala
            20                  25                  30

Leu Ser Pro Phe Ser Ser Arg Arg Ala Ser Thr Asp Ser Arg Gly Pro
        35                  40                  45

Phe Ala Phe Glu Asn Ser Leu Leu Glu His Gln Leu Cys Gly Val Leu
    50                  55                  60

Pro Thr Ser Met Asp Gly Phe Ala Leu Gly Ser Gly Leu Glu Asn Ser
65                  70                  75                  80

Leu Pro Leu Glu Val Val Arg Gly Ala Met Thr Leu Arg Val Asn Ser
                85                  90                  95

Leu Thr Arg Gly His Ser Ala Val Arg Ile Val Val Leu Glu Ala Leu
            100                 105                 110
```

```
Thr Asn Phe Leu Asn His Gly Ile Thr Pro Ile Val Pro Leu Arg Gly
            115                 120                 125

Thr Ile Ser Ala Ser Gly Asp Leu Ser Pro Leu Ser Tyr Ile Ala Ala
    130                 135                 140

Ser Ile Thr Gly His Pro Asp Ser Lys Val His Val Asp Gly Gln Ile
145                 150                 155                 160

Met Ser Ala Gln Glu Ala Ile Ala Leu Lys Gly Leu Gln Pro Val Val
                165                 170                 175

Leu Gly Pro Lys Glu Gly Leu Gly Leu Val Asn Gly Thr Ala Val Ser
            180                 185                 190

Ala Ser Met Ala Thr Leu Ala Leu Thr Asp Ala His Val Leu Ser Leu
            195                 200                 205

Leu Ala Gln Ala Asn Thr Ala Leu Thr Val Glu Ala Met Val Gly His
        210                 215                 220

Ala Gly Ser Phe His Pro Phe Leu His Asp Val Thr Arg Pro Ala Pro
225                 230                 235                 240

Asp Pro Asp Arg Gly Arg Ala Ala Thr Leu Gly Leu Leu Glu Gly
                245                 250                 255

Ser Lys Tyr Cys Leu Ser Thr Met Arg Pro Arg Ser Arg Ser Arg Thr
        260                 265                 270

Thr Arg Ala Ser Ser Gly Arg Thr Asp Thr Arg Ser Ala Ala Arg Pro
    275                 280                 285

Arg Phe Val Val Phe Arg Ile Pro Ser Leu Ser Ala His Arg Ser Asp
    290                 295                 300

Pro Leu Leu Leu Cys Ser Gly Ala Gln Trp Leu Gly Pro Leu Val Ser
305                 310                 315                 320

Asp Met Ile His Ala His Ser Val Leu Ser Leu Glu Ala Gly Gln Ser
                325                 330                 335

Thr Thr Asp Asn Pro Leu Ile Asp Leu Glu Asn Lys Met Thr His His
            340                 345                 350

Gly Gly Ala Phe Met Ala Ser Ser Val Gly Asn Thr Met Glu Lys Arg
        355                 360                 365

Leu Val Ser Pro Ser His Leu Trp Ala Arg Leu Ala Ser Leu Ser Ser
    370                 375                 380

Pro Arg Cys Ser Thr Pro Ala Cys Thr Ala Arg Phe Pro Pro Ala Ser
385                 390                 395                 400

Pro Pro Arg Thr Arg Leu Cys Pro Thr Thr Ala Arg Val Ser Thr Ser
            405                 410                 415

Pro Pro Leu His Thr Leu Arg Ser Ser Val Thr Ser Arg Thr Gln Ser
            420                 425                 430

Arg Pro Thr Phe Ser Arg Gln Arg Trp Ala Ile Arg Arg Ser Thr Arg
            435                 440                 445

Ser Pro Ser Ser Arg Pro Val Ala Pro Pro Arg Arg Thr Thr Ser Ser
    450                 455                 460

Arg Ser Ser Ser Pro Pro Thr Ser Thr Ala Ser Cys Arg Arg Ser Thr
465                 470                 475                 480

Cys Ala Arg Trp Ser Ser Ser Thr Arg Lys Ser Leu Ser Arg Trp Ser
            485                 490                 495

Pro Thr Cys Ser Ser Thr Leu Ala Arg Ser Arg Gln Pro Thr Ser
            500                 505                 510

Arg Thr Arg Ser Ala Asn Arg Ser Thr Ser Gly Cys Ser Arg Thr Thr
            515                 520                 525
```

-continued

```
Arg Thr Thr Ser Ser Ser Gly Gly Thr Thr Arg Ser Arg Ser Arg Pro
            530                 535                 540

Ala Pro Ser Ser Lys Pro Ser Pro Gly Thr Arg Cys Arg Ser Arg Ala
545                 550                 555                 560

Ser Thr Pro Gly Arg Ser Arg Ala Leu Arg Arg Pro Ser Pro Ser Pro
                565                 570                 575

Ala Pro Cys Ala Thr Arg Ser Gly Pro Arg Arg Arg Arg Arg Arg Pro
            580                 585                 590

Arg Ser Ser Thr Ser Arg Arg Gly Leu Ala Ser Cys Thr Arg Ser Ser
                595                 600                 605

Gly Lys Thr Ser Ala Ser Arg Pro Ala Ala Thr Ser Thr Ser Ala
    610                 615                 620

Ser Arg Arg Ser Arg Ser Gly Pro Thr Ser Ala Ala Ser Thr Arg Arg
625                 630                 635                 640

Ser Arg Thr Ala Ala Leu Leu Arg Ser Ser Arg Cys Trp His Lys
                645                 650                 655

Arg Thr Leu Val Gln Ala Ser Leu Ala Arg Asp Ser Lys Leu Pro Phe
            660                 665                 670

Leu Pro Gly Arg Leu Arg Gln Arg Arg Phe Pro Pro Asp Cys His Phe
675                 680                 685

Pro His Ala Pro Tyr Pro Leu Gly Phe Arg Ser His Ser Gly Pro Val
            690                 695                 700

Glu Thr His Ile Ser Phe Gly Arg Arg Pro Tyr
705                 710                 715

<210> SEQ ID NO 44
<211> LENGTH: 2070
<212> TYPE: DNA
<213> ORGANISM: Trichosporon cutaneum

<400> SEQUENCE: 44
atgttcatcg aaactaacgt tgctaagcca gcttctacta aggctatgaa tgctggttct      60
gctaaagctg ctccagttga accatttgct acttatgctc attctcaagc tactaagacc     120
gtttctattg atggtcatac aatgaaggtt ggtgatgttg ttgctgttgc tagacatggt     180
gctaaagttg aattggctgc ttctgttgct ggtccagtta gagcttcagt tgatttcaaa     240
gaatccaaaa agcacacctc catctacggt gttactactg ttttggtgg ttcagctgat      300
acaagaactt ctgatactga agccttgcaa atctccttgt ggaacatca attgtgtggt      360
ttcttgccaa ctgatgctac ttacgaaggt atgttgttgg ctgctatgcc aattccaata     420
gttagaggtg ctatggctgt tagagttaat tcttgtgtta gaggtcactc cggtgttaga     480
ttggaagttt tacaatcttt cgccgacttc atcaacagag gtttggttcc atgtgttcca     540
ttgagaggta ctatttctgc ttctggtgat tgtctccat gtcttatat tgctggtgct       600
atttgtggtc acccagatgt taaggttttt gatactgctg cttctccacc aactgttttg     660
acttctcctg aagctattgc taagtacggt ttgaaaactg ttaagttggc ctccaaagaa     720
ggtttgggtt tggttaatgg tactgctgtt tctgctgctg ctggtgcatt ggcattatat     780
gatgctgaat gtttggccat catgtcccaa actaacacag ttttgactgt tgaagctttg     840
gatggtcatg ttggttcttt tgctccattc atccaagaaa ttagaccaca tgcaggtcaa     900
attgaagctg ccagaaatat cagacatatg ttgggtggtt ctaagttggc tgttcatgaa     960
gaatctgaat tattggctga tcaagacgcc ggtattttga dacaagatag atatgctttg    1020
agaacctccg ctcaatggat tggtccacaa ttggaagctt taggtttggc cagacaacaa    1080
```

```
attgaaaccg aattgaactc taccaccgat aacccattga ttgatgttga aggtggtatg    1140
tttcatcacg gtggtaattt tcaagctatg gcagttactt ctgctatgga ttctgctaga    1200
attgtcttgc aaaacttggg taaattgtcc ttcgctcaag tcactgaatt gatcaactgt    1260
gaaatgaatc acgtttgcc atctaatttg gcaggtctg aaccatctac taattaccat     1320
tgcaagggtt tggatattca ttgtggtgct tattgtgctg aattgggttt tttggctaac    1380
ccaatgtcta accatgttca atctaccgaa atgcacaatc aatccgttaa ctctatggct    1440
tttgcttccg ctagaagaac tatggaagct aacgaagttt tgtccttgtt gttgggttca    1500
caaatgtact gtgctaccca agccttggat ttgagagtta tggaagttaa gttcaagatg    1560
gccattgtca agttgttgaa cgaaactttg accaagcact tgctgctttt tttgactcca    1620
gaacaattgg ctaagttgaa cactcatgct gctatcacct tgtacaaaag attgaatcaa    1680
accccatctt gggattccgc tccaagattt gaagatgctg ctaaacattt ggttggtgtt    1740
attatggatg ccttgatggt taacgatgat atcactgact tgactaactt gccaaagtgg    1800
aagaaagaat cgctaaaga agctggtaac ttgtacagat ccattttggt tgctactact     1860
gctgatggta aaacgatttt ggaaccagct gaatatttgg gtcaaactag agctgtttac    1920
gaagccgtta gatcagaatt gggtgtcaaa gttagaagag gtgatgtagc tgaaggtaag    1980
agtggtaaat ctatcggttc ttccgttgcc aaaatcgttg aagctatgag agatggtaga    2040
ttgatgggtg ctgttggtaa gatgttctga                                     2070
```

<210> SEQ ID NO 45
<211> LENGTH: 689
<212> TYPE: PRT
<213> ORGANISM: Trichosporon cutaneum

<400> SEQUENCE: 45

```
Met Phe Ile Glu Thr Asn Val Ala Lys Pro Ala Ser Thr Lys Ala Met
1               5                   10                  15

Asn Ala Gly Ser Ala Lys Ala Ala Pro Val Glu Pro Phe Ala Thr Tyr
            20                  25                  30

Ala His Ser Gln Ala Thr Lys Thr Val Ser Ile Asp Gly His Thr Met
        35                  40                  45

Lys Val Gly Asp Val Val Ala Val Ala Arg His Gly Ala Lys Val Glu
    50                  55                  60

Leu Ala Ala Ser Val Ala Gly Pro Val Arg Ala Ser Val Asp Phe Lys
65                  70                  75                  80

Glu Ser Lys Lys His Thr Ser Ile Tyr Gly Val Thr Thr Gly Phe Gly
                85                  90                  95

Gly Ser Ala Asp Thr Arg Thr Ser Asp Thr Glu Ala Leu Gln Ile Ser
            100                 105                 110

Leu Leu Glu His Gln Leu Cys Gly Phe Leu Pro Thr Asp Ala Thr Tyr
        115                 120                 125

Glu Gly Met Leu Leu Ala Ala Met Pro Ile Pro Ile Val Arg Gly Ala
    130                 135                 140

Met Ala Val Arg Val Asn Ser Cys Val Arg Gly His Ser Gly Val Arg
145                 150                 155                 160

Leu Glu Val Leu Gln Ser Phe Ala Asp Phe Ile Asn Arg Gly Leu Val
                165                 170                 175

Pro Cys Val Pro Leu Arg Gly Thr Ile Ser Ala Ser Gly Asp Leu Ser
            180                 185                 190
```

-continued

Pro Leu Ser Tyr Ile Ala Gly Ala Ile Cys Gly His Pro Asp Val Lys
    195                 200                 205

Val Phe Asp Thr Ala Ala Ser Pro Pro Thr Val Leu Thr Ser Pro Glu
210                 215                 220

Ala Ile Ala Lys Tyr Gly Leu Lys Thr Val Lys Leu Ala Ser Lys Glu
225                 230                 235                 240

Gly Leu Gly Leu Val Asn Gly Thr Ala Val Ser Ala Ala Gly Ala
                245                 250                 255

Leu Ala Leu Tyr Asp Ala Glu Cys Leu Ala Ile Met Ser Gln Thr Asn
            260                 265                 270

Thr Val Leu Thr Val Glu Ala Leu Asp Gly His Val Gly Ser Phe Ala
        275                 280                 285

Pro Phe Ile Gln Glu Ile Arg Pro His Ala Gly Gln Ile Glu Ala Ala
    290                 295                 300

Arg Asn Ile Arg His Met Leu Gly Gly Ser Lys Leu Ala Val His Glu
305                 310                 315                 320

Glu Ser Glu Leu Leu Ala Asp Gln Asp Ala Gly Ile Leu Arg Gln Asp
                325                 330                 335

Arg Tyr Ala Leu Arg Thr Ser Ala Gln Trp Ile Gly Pro Gln Leu Glu
            340                 345                 350

Ala Leu Gly Leu Ala Arg Gln Gln Ile Glu Thr Glu Leu Asn Ser Thr
        355                 360                 365

Thr Asp Asn Pro Leu Ile Asp Val Glu Gly Gly Met Phe His His Gly
    370                 375                 380

Gly Asn Phe Gln Ala Met Ala Val Thr Ser Ala Met Asp Ser Ala Arg
385                 390                 395                 400

Ile Val Leu Gln Asn Leu Gly Lys Leu Ser Phe Ala Gln Val Thr Glu
                405                 410                 415

Leu Ile Asn Cys Glu Met Asn His Gly Leu Pro Ser Asn Leu Ala Gly
            420                 425                 430

Ser Glu Pro Ser Thr Asn Tyr His Cys Lys Gly Leu Asp Ile His Cys
        435                 440                 445

Gly Ala Tyr Cys Ala Glu Leu Gly Phe Leu Ala Asn Pro Met Ser Asn
    450                 455                 460

His Val Gln Ser Thr Glu Met His Asn Gln Ser Val Asn Ser Met Ala
465                 470                 475                 480

Phe Ala Ser Ala Arg Arg Thr Met Glu Ala Asn Glu Val Leu Ser Leu
                485                 490                 495

Leu Leu Gly Ser Gln Met Tyr Cys Ala Thr Gln Ala Leu Asp Leu Arg
            500                 505                 510

Val Met Glu Val Lys Phe Lys Met Ala Ile Val Lys Leu Leu Asn Glu
        515                 520                 525

Thr Leu Thr Lys His Phe Ala Ala Phe Leu Thr Pro Glu Gln Leu Ala
    530                 535                 540

Lys Leu Asn Thr His Ala Ala Ile Thr Leu Tyr Lys Arg Leu Asn Gln
545                 550                 555                 560

Thr Pro Ser Trp Asp Ser Ala Pro Arg Phe Glu Asp Ala Ala Lys His
                565                 570                 575

Leu Val Gly Val Ile Met Asp Ala Leu Met Val Asn Asp Asp Ile Thr
            580                 585                 590

Asp Leu Thr Asn Leu Pro Lys Trp Lys Lys Glu Phe Ala Lys Glu Ala
        595                 600                 605

Gly Asn Leu Tyr Arg Ser Ile Leu Val Ala Thr Thr Ala Asp Gly Arg

Asn Asp Leu Glu Pro Ala Glu Tyr Leu Gly Gln Thr Arg Ala Val Tyr
625                 630                 635                 640

Glu Ala Val Arg Ser Glu Leu Gly Val Lys Val Arg Arg Gly Asp Val
            645                 650                 655

Ala Glu Gly Lys Ser Gly Lys Ser Ile Gly Ser Ser Val Ala Lys Ile
            660                 665                 670

Val Glu Ala Met Arg Asp Gly Arg Leu Met Gly Ala Val Gly Lys Met
            675                 680                 685

Phe

<210> SEQ ID NO 46
<211> LENGTH: 2214
<212> TYPE: DNA
<213> ORGANISM: Phanerochaete chrysosporium

<400> SEQUENCE: 46

| | | |
|---|---|---|
| atgccatcca gaatcgacta ctacacttct tctggtaatg gttacgccca atccagaaaa | 60 |
| tcttctgcta tctatccagc ttctgcttct actggtcatg ctgctccatc tactgaaaga | 120 |
| aaaccagaat tattggacaa gttcgttgaa gcctacgacg aattgcaatc ttacagaaa | 180 |
| ggtaagccag ttatcgttga tggtcataac ttgtctattc cagctgttgc tgctacagct | 240 |
| agatttggtg ctgctgttgt tttggacgaa atcctgaaa ctcacgaaag agtcttgcaa | 300 |
| tctagaagag ttatcgtcga taaggtcagt acccaaagat ctgtttatgg tgtttctaca | 360 |
| ggttttggtg ttctgctga tacaagaact tctgatccat gcaattggg tcatgccttg | 420 |
| ttacaacatc aacacgttgg tgttttgcca actcaaactg aatctccatt gccagctttg | 480 |
| ccattgggtg atccattagc tactacttct atgcctgaag cttgggttag aggtgctatt | 540 |
| ttgattagaa tgaactcctt gatcagaggt cactctggtg ttagatggga attgattgaa | 600 |
| aagatgggtg aattattgag agaaaacatc accccattgg ttccattgag aggttctatt | 660 |
| tctgcttcag gtgatttgtc tccattgtct tatattgccg gtactttgat tggttcccca | 720 |
| gctattagag ttttgatgg tccagcttca tatggtgcca gaagaatttt gccatccaat | 780 |
| attgctttgg ccaatcatgg tgttgctcca attccattgt catccaaaga acatttgggt | 840 |
| atcttgaacg gtactgcttt tcagcttct gttggtgctt tggctttgaa tgaagctgtt | 900 |
| catttgtctt tgttggctca agtatgtact gctatgggta ctgaagctat gattggtgca | 960 |
| gttggttctt tcgatgcttt cattcatgat actgctagac acatccagg tcaagttgaa | 1020 |
| gttgctagaa atgttagaac cttgttggaa gattctcaaa tggctgttaa ggccgaagat | 1080 |
| gaagttcata ttgctgaaga tgaaggtgaa ttgagacaag acagataccc attgagaact | 1140 |
| gctgctcaat ttttgggtcc acaaatcgaa gatattttgt ctgctcacga aaccgttacc | 1200 |
| ttggaatgta attctactac cgataaccca ttgatcgatg gtgaaactgg tactgttcat | 1260 |
| catggtggta attttcaagc tatggccgtt actaatgcta tggaaaaaac agattggct | 1320 |
| atccatcata tcggtaagtt gttgtttgct caagctaccg aattgatcaa cccaatgatg | 1380 |
| aatagaggtt tgccacctaa tttggctgct actgatccat ctcataatta ctttgctaag | 1440 |
| ggtgttgata ttcatttggc agcttacgtt ggtgaattgg gtttttggc ttctccagtt | 1500 |
| tcctcccata ttcaatctgc tgaaatgcat aatcaagccg ttaattcctt ggctttggtt | 1560 |
| tctgctagat ataccatttc cgcttttgat gtcttatctt tgttgactgc tgcttacttg | 1620 |
| tacgttttgt gtcaagcttt ggatttgaga gctatgcata acgacttgca atcatctttg | 1680 |

-continued

```
tcagccatcg ttagagaatt attaccaaag cactttccat ccgctgctaa aagagctgac    1740
gctttgttgc caattttgga aagaactatt ttcagagcct tgaactcctc ttcttctgct    1800
gactgtaaag ctagaatggt ttcagttgct gcttcaacta ctactccatt ggttgatttt    1860
ttgtcagctg atgcagcttt ggcatctgaa ttggctaata ttactgcttt cagaaccgaa    1920
ttagctacca gagctgctga tgctttgact actttgagaa ctcaatattt ggaaggtgct    1980
agaggtgcag ctccagcatc taaatacttg ggtaaaacta gaccagtcta cgaatttgtt    2040
agagtcactt tgaacgttcc aatgcacggt agagaaaact tgcataactt tgaaatgggt    2100
ccaggtgttg aagatggtat tattggtaac aacatctcca ccatctacga agcaattaga    2160
gatggtaaga tgcaaaacgt cgtaatgcaa ttggtcaagt ccattaaggc ttaa          2214

<210> SEQ ID NO 47
<211> LENGTH: 737
<212> TYPE: PRT
<213> ORGANISM: Phanerochaete chrysosporium

<400> SEQUENCE: 47

Met Pro Ser Arg Ile Asp Tyr Tyr Thr Ser Gly Asn Gly Tyr Ala
1               5                   10                  15

Gln Ser Arg Lys Ser Ser Ala Ile Tyr Pro Ala Ser Ala Ser Thr Gly
                20                  25                  30

His Ala Ala Pro Ser Thr Glu Arg Lys Pro Glu Leu Leu Asp Lys Phe
            35                  40                  45

Val Glu Ala Tyr Asp Glu Leu Gln Ser Tyr Arg Glu Gly Lys Pro Val
        50                  55                  60

Ile Val Asp Gly His Asn Leu Ser Ile Pro Ala Val Ala Ala Thr Ala
65                  70                  75                  80

Arg Phe Gly Ala Ala Val Val Leu Asp Glu Asn Pro Glu Thr His Glu
                85                  90                  95

Arg Val Leu Gln Ser Arg Arg Val Ile Val Asp Lys Val Ser Thr Gln
            100                 105                 110

Arg Ser Val Tyr Gly Val Ser Thr Gly Phe Gly Gly Ser Ala Asp Thr
        115                 120                 125

Arg Thr Ser Asp Pro Leu Gln Leu Gly His Ala Leu Leu Gln His Gln
    130                 135                 140

His Val Gly Val Leu Pro Thr Gln Thr Glu Ser Pro Leu Pro Ala Leu
145                 150                 155                 160

Pro Leu Gly Asp Pro Leu Ala Thr Thr Ser Met Pro Glu Ala Trp Val
                165                 170                 175

Arg Gly Ala Ile Leu Ile Arg Met Asn Ser Leu Ile Arg Gly His Ser
            180                 185                 190

Gly Val Arg Trp Glu Leu Ile Glu Lys Met Gly Glu Leu Leu Arg Glu
        195                 200                 205

Asn Ile Thr Pro Leu Val Pro Leu Arg Gly Ser Ile Ser Ala Ser Gly
    210                 215                 220

Asp Leu Ser Pro Leu Ser Tyr Ile Ala Gly Thr Leu Ile Gly Ser Pro
225                 230                 235                 240

Ala Ile Arg Val Phe Asp Gly Pro Ala Ser Tyr Gly Ala Arg Arg Ile
                245                 250                 255

Leu Pro Ser Asn Ile Ala Leu Ala Asn His Gly Val Ala Pro Ile Pro
            260                 265                 270

Leu Ser Ser Lys Glu His Leu Gly Ile Leu Asn Gly Thr Ala Phe Ser
```

```
                275                 280                 285
Ala Ser Val Gly Ala Leu Ala Leu Asn Glu Ala Val His Leu Ser Leu
290                 295                 300
Leu Ala Gln Val Cys Thr Ala Met Gly Thr Glu Ala Met Ile Gly Ala
305                 310                 315                 320
Val Gly Ser Phe Asp Ala Phe Ile His Asp Thr Ala Arg Pro His Pro
                325                 330                 335
Gly Gln Val Glu Val Ala Arg Asn Val Arg Thr Leu Leu Glu Asp Ser
                340                 345                 350
Gln Met Ala Val Lys Ala Glu Asp Val His Ile Ala Glu Asp Glu
                355                 360                 365
Gly Glu Leu Arg Gln Asp Arg Tyr Pro Leu Arg Thr Ala Ala Gln Phe
370                 375                 380
Leu Gly Pro Gln Ile Glu Asp Ile Leu Ser Ala His Glu Thr Val Thr
385                 390                 395                 400
Leu Glu Cys Asn Ser Thr Thr Asp Asn Pro Leu Ile Asp Gly Glu Thr
                405                 410                 415
Gly Thr Val His His Gly Gly Asn Phe Gln Ala Met Ala Val Thr Asn
                420                 425                 430
Ala Met Glu Lys Thr Arg Leu Ala Ile His His Ile Gly Lys Leu Leu
                435                 440                 445
Phe Ala Gln Ala Thr Glu Leu Ile Asn Pro Met Met Asn Arg Gly Leu
450                 455                 460
Pro Pro Asn Leu Ala Ala Thr Asp Pro Ser His Asn Tyr Phe Ala Lys
465                 470                 475                 480
Gly Val Asp Ile His Leu Ala Ala Tyr Val Gly Glu Leu Gly Phe Leu
                485                 490                 495
Ala Ser Pro Val Ser Ser His Ile Gln Ser Ala Glu Met His Asn Gln
                500                 505                 510
Ala Val Asn Ser Leu Ala Leu Val Ser Ala Arg Tyr Thr Ile Ser Ala
                515                 520                 525
Leu Asp Val Leu Ser Leu Leu Thr Ala Ala Tyr Leu Tyr Val Leu Cys
530                 535                 540
Gln Ala Leu Asp Leu Arg Ala Met His Asn Asp Leu Gln Ser Ser Leu
545                 550                 555                 560
Ser Ala Ile Val Arg Glu Leu Leu Pro Lys His Phe Pro Ser Ala Ala
                565                 570                 575
Lys Arg Ala Asp Ala Leu Leu Pro Ile Leu Glu Arg Thr Ile Phe Arg
                580                 585                 590
Ala Leu Asn Ser Ser Ser Ser Ala Asp Cys Lys Ala Arg Met Val Ser
                595                 600                 605
Val Ala Ala Ser Thr Thr Thr Pro Leu Val Asp Phe Leu Ser Ala Asp
                610                 615                 620
Ala Ala Leu Ala Ser Glu Leu Ala Asn Ile Thr Ala Phe Arg Thr Glu
625                 630                 635                 640
Leu Ala Thr Arg Ala Ala Asp Ala Leu Thr Thr Leu Arg Thr Gln Tyr
                645                 650                 655
Leu Glu Gly Ala Arg Gly Ala Ala Pro Ala Ser Lys Tyr Leu Gly Lys
                660                 665                 670
Thr Arg Pro Val Tyr Glu Phe Val Arg Val Thr Leu Asn Val Pro Met
                675                 680                 685
His Gly Arg Glu Asn Leu His Asn Phe Glu Met Gly Pro Gly Val Glu
                690                 695                 700
```

```
Asp Gly Ile Ile Gly Asn Asn Ile Ser Thr Ile Tyr Glu Ala Ile Arg
705                 710                 715                 720

Asp Gly Lys Met Gln Asn Val Val Met Gln Leu Val Lys Ser Ile Lys
                725                 730                 735

Ala

<210> SEQ ID NO 48
<211> LENGTH: 2142
<212> TYPE: DNA
<213> ORGANISM: Rhodotorula glutinis

<400> SEQUENCE: 48
atggccccat ccgttgattc tattgctact tctgttgcta actccttgtc caatggttta      60
catgctgctg ctgcagctaa tggtggtgat gttcataaga aaactgctgg tgctggttct     120
ttgttgccaa ctactgaaac tactcaattg acatcgtcg aaagaatttt ggctgatgct     180
ggtgcaacta tcaaatcaa attggatggt tacactttga ccttgggtga tgttgttggt     240
gctgctagaa gaggtagatc tgttaaggtt gctgattccc cacatatcag agaaaagatt     300
gatgcctctg tcgaattctt gagaacccaa ttggataact ctgtttacgg tgttactact     360
ggttttggtg ttctgctga tacaagaact gaagatgcta tctccttgca aaaggctttg     420
ttggaacatc aattgtgtgg tgttttgcca acttctatgg atggttttgc tttgggtaga     480
ggtttggaaa attcattgcc attggaagtt gttagaggtg ccatgactat cagagttaat     540
tctttgacta gaggtcactc cgctgttaga atagttgttt ggaagctttt gactaacttc     600
ttgaaccatg gtattactcc aatcgttcca ttgagaggta ctatttctgc ttctggtgat     660
ttgtctccat tgtcttatat tgctgcttcc attactggtc acccagattc taaagttcat     720
gttgatggta agatcatgtc cgctcaagaa gctattgctt tgaaaggttt acaaccagtt     780
gtcttgggtc caaaagaagg tttgggtttg gttaatggta ctgctgtttc agcttctatg     840
gctacattgg ctttgactga tgctcatgtt ttgtctttgt tggctcaagc tttaactgct     900
ttgacagttg aagctatggt tggtcatgct ggttcatttc tccattctt gcatgatgtt     960
actagaccac atccaaccca aattgaagtt gccagaaaca ttagaacctt gttggaaggt    1020
tccaagtatg ctgttcatca cgaaactgaa gttaaggtta aggatgacga aggtatcttg    1080
agacaagata gatacccatt gagatgttct ccacaatggt tgggtccatt ggtttctgat    1140
atgattcatg ctcatgccgt cttgtcttta gaagctggtc aatctactac tgacaaccca    1200
ttgattgact ggaaaacaa gatgactcat catggtggtg ttttatggc ttcttctgta    1260
ggtaacacta tggaaagac tagattggct gttgctttga tgggtaaggt ttctttcact    1320
caattgaccg aaatgttgaa cgctggtatg aatagagctt tgccatcatg tttggctgct    1380
gaagatccat ctttatctta ccactgtaag ggtttggata ttgcagctgc tgcttatact    1440
tctgaattgg tcatttggc taacccagtt tctactcatg ttcaaccagc tgaaatgggt    1500
aatcaagcta tcaattcttt ggccttgatt ccgctagaa gaacagctga agctaatgat    1560
gttttgagtt tgttgttggc tacccacttg tattgcgttt tacaagctgt tgatttgaga    1620
gccatggaat tcgaacatac caaagctttc gaacctatgg tcaccgaatt attgaagcaa    1680
cattttggtg ctttggctac cgctgaagtt gaagataagg taagaaagtc catctacaag    1740
agattgcaac aaaacaattc ctacgatttg aacaaagat ggcacgatac tttttcagtt    1800
gctactggtg ctgttgttga agctttggca ggtcaagaag tatctttggc ttcttttgaat   1860
```

```
gcttggaaag ttgcttgtgc tgaaaaggct attgcattga ctagatccgt tagagattct   1920
ttttgggctg ctccatcttc ttcatctcca gctttgaaat acttgtctcc aagaactaga   1980
gtcttgtact ccttcgttag agaagaagtt ggtgttaagg caagaagagg tgacgtttat   2040
ttgggtaaac aagaagtcac catcggtaca aacgtttcca gaatctatga agccattaag   2100
tccggtagaa ttgctccagt tttggttaag atgatggcct ga                     2142
```

<210> SEQ ID NO 49
<211> LENGTH: 713
<212> TYPE: PRT
<213> ORGANISM: Rhodotorula glutinis

<400> SEQUENCE: 49

```
Met Ala Pro Ser Val Asp Ser Ile Ala Thr Ser Val Ala Asn Ser Leu
1               5                   10                  15

Ser Asn Gly Leu His Ala Ala Ala Ala Asn Gly Gly Asp Val His
            20                  25                  30

Lys Lys Thr Ala Gly Ala Gly Ser Leu Leu Pro Thr Thr Glu Thr Thr
        35                  40                  45

Gln Leu Asp Ile Val Glu Arg Ile Leu Ala Asp Ala Gly Ala Thr Asp
    50                  55                  60

Gln Ile Lys Leu Asp Gly Tyr Thr Leu Thr Leu Gly Asp Val Val Gly
65                  70                  75                  80

Ala Ala Arg Arg Gly Arg Ser Val Lys Val Ala Asp Ser Pro His Ile
                85                  90                  95

Arg Glu Lys Ile Asp Ala Ser Val Glu Phe Leu Arg Thr Gln Leu Asp
            100                 105                 110

Asn Ser Val Tyr Gly Val Thr Thr Gly Phe Gly Gly Ser Ala Asp Thr
        115                 120                 125

Arg Thr Glu Asp Ala Ile Ser Leu Gln Lys Ala Leu Leu Glu His Gln
130                 135                 140

Leu Cys Gly Val Leu Pro Thr Ser Met Asp Gly Phe Ala Leu Gly Arg
145                 150                 155                 160

Gly Leu Glu Asn Ser Leu Pro Leu Glu Val Val Arg Gly Ala Met Thr
                165                 170                 175

Ile Arg Val Asn Ser Leu Thr Arg Gly His Ser Ala Val Arg Ile Val
            180                 185                 190

Val Leu Glu Ala Leu Thr Asn Phe Leu Asn His Gly Ile Thr Pro Ile
        195                 200                 205

Val Pro Leu Arg Gly Thr Ile Ser Ala Ser Gly Asp Leu Ser Pro Leu
    210                 215                 220

Ser Tyr Ile Ala Ala Ser Ile Thr Gly His Pro Asp Ser Lys Val His
225                 230                 235                 240

Val Asp Gly Lys Ile Met Ser Ala Gln Glu Ala Ile Ala Leu Lys Gly
                245                 250                 255

Leu Gln Pro Val Val Leu Gly Pro Lys Glu Gly Leu Gly Leu Val Asn
            260                 265                 270

Gly Thr Ala Val Ser Ala Ser Met Ala Thr Leu Ala Leu Thr Asp Ala
        275                 280                 285

His Val Leu Ser Leu Leu Ala Gln Ala Leu Thr Ala Leu Thr Val Glu
    290                 295                 300

Ala Met Val Gly His Ala Gly Ser Phe His Pro Phe Leu His Asp Val
305                 310                 315                 320

Thr Arg Pro His Pro Thr Gln Ile Glu Val Ala Arg Asn Ile Arg Thr
```

```
                    325                 330                 335
Leu Leu Glu Gly Ser Lys Tyr Ala Val His His Glu Thr Glu Val Lys
            340                 345                 350

Val Lys Asp Asp Glu Gly Ile Leu Arg Gln Asp Arg Tyr Pro Leu Arg
            355                 360                 365

Cys Ser Pro Gln Trp Leu Gly Pro Leu Val Ser Asp Met Ile His Ala
            370                 375                 380

His Ala Val Leu Ser Leu Glu Ala Gly Gln Ser Thr Thr Asp Asn Pro
385                         390                 395                 400

Leu Ile Asp Leu Glu Asn Lys Met Thr His His Gly Gly Ala Phe Met
                405                 410                 415

Ala Ser Ser Val Gly Asn Thr Met Glu Lys Thr Arg Leu Ala Val Ala
                420                 425                 430

Leu Met Gly Lys Val Ser Phe Thr Gln Leu Thr Glu Met Leu Asn Ala
                435                 440                 445

Gly Met Asn Arg Ala Leu Pro Ser Cys Leu Ala Ala Glu Asp Pro Ser
            450                 455                 460

Leu Ser Tyr His Cys Lys Gly Leu Asp Ile Ala Ala Ala Tyr Thr
465                 470                 475                 480

Ser Glu Leu Gly His Leu Ala Asn Pro Val Ser Thr His Val Gln Pro
                485                 490                 495

Ala Glu Met Gly Asn Gln Ala Ile Asn Ser Leu Ala Leu Ile Ser Ala
            500                 505                 510

Arg Arg Thr Ala Glu Ala Asn Asp Val Leu Ser Leu Leu Leu Ala Thr
            515                 520                 525

His Leu Tyr Cys Val Leu Gln Ala Val Asp Leu Arg Ala Met Glu Phe
            530                 535                 540

Glu His Thr Lys Ala Phe Glu Pro Met Val Thr Glu Leu Leu Lys Gln
545                 550                 555                 560

His Phe Gly Ala Leu Ala Thr Ala Glu Val Glu Asp Lys Val Arg Lys
                565                 570                 575

Ser Ile Tyr Lys Arg Leu Gln Gln Asn Asn Ser Tyr Asp Leu Glu Gln
            580                 585                 590

Arg Trp His Asp Thr Phe Ser Val Ala Thr Gly Ala Val Val Glu Ala
            595                 600                 605

Leu Ala Gly Gln Glu Val Ser Leu Ala Ser Leu Asn Ala Trp Lys Val
            610                 615                 620

Ala Cys Ala Glu Lys Ala Ile Ala Leu Thr Arg Ser Val Arg Asp Ser
625                 630                 635                 640

Phe Trp Ala Ala Pro Ser Ser Ser Pro Ala Leu Lys Tyr Leu Ser
                645                 650                 655

Pro Arg Thr Arg Val Leu Tyr Ser Phe Val Arg Glu Glu Val Gly Val
            660                 665                 670

Lys Ala Arg Arg Gly Asp Val Tyr Leu Gly Lys Gln Gly Val Thr Ile
            675                 680                 685

Gly Thr Asn Val Ser Arg Ile Tyr Glu Ala Ile Lys Ser Gly Arg Ile
            690                 695                 700

Ala Pro Val Leu Val Lys Met Met Ala
705                 710
```

BIOSYNTHESIS OF PHENYLPROPANOIDS AND PHENYLPROPANOID DERIVATIVES

This application is a U.S. National Stage Application of International Application No. PCT/EP2016/061982, filed May 27, 2016, and claims the benefit of U.S. Provisional Application No. 62/167,595, filed May 28, 2015, the disclosures of each of which are explicitly incorporated by reference herein in their entirety.

BACKGROUND OF THE INVENTION

Field of the Invention

The invention disclosed herein relates generally to the field of genetic engineering. Particularly, the invention disclosed herein provides methods for biosynthetic production of phenylpropanoids and phenylpropanoid derivatives, such as chalcones and stilbenes.

Description of Related Art

Phenylpropanoids are a diverse family of phenolic compounds produced biosynthetically in plants from phenolic amino acid precursors. Phenylpropanoids and their derivatives have desirable applications, for example in the food and healthcare industries.

An exemplary phenylpropanoid derivative is naringenin, a compound that is also an intermediate in the production of downstream phenylpropanoid derivatives. Naringenin has the chemical structure:

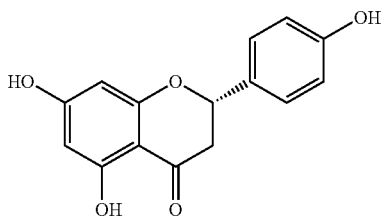 [SMILES: O=C1C[C@@H](c2ccc(O)cc2)Oc2cc(O)cc(O)c21]

Naringenin is produced naturally in plants, and also biosynthetically in cells genetically engineered with components of a flavonoid biosynthesis pathway (see e.g., Koopman et al., (2012) *Microbial Cell Factories* 2012, 11:155). For example, cells engineered to produce coumaroyl-CoA are further engineered with recombinant genes expressing proteins that convert coumaroyl-CoA to naringenin.

Another exemplary phenylpropanoid derivative is the stilbene resveratrol, which is also an intermediate in the production of other downstream phenylpropanoid derivatives. Resveratrol has the chemical structure:

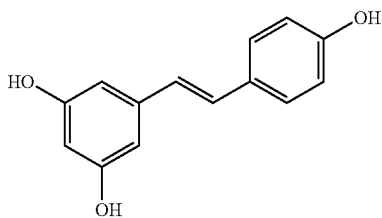 [SMILES: Oc1ccc(/C=C/c2cc(O)cc(O)c2)cc1]

Resveratrol is also produced using a coumaroyl-CoA precursor molecule.

Generally, stilbenes, including resveratrol, and chalcones are produced in plants and yeast through the phenylpropanoid pathway as illustrated by the reactions shown in FIG. 1 and as described in U.S. 2008/0286844, which is incorporated by reference in its entirety herein.

In yeast, the starting metabolites are malonyl-CoA and either phenylalanine or tyrosine. The amino acid L-phenylalanine is converted into trans-cinnamic acid through non-oxidative deamination by L-phenylalanine ammonia lyase (PAL). Next, trans-cinnamic acid is hydroxylated at the para-position to 4-coumaric acid (4-hydroxycinnamic acid) by cinnamate-4-hydroxylase (C4H), a cytochrome P450 monooxygenase enzyme, in conjunction with NADPH:cytochrome P450 reductase (CPR). Alternatively, the amino acid L-tyrosine is directly converted into 4-coumaric acid by tyrosine ammonia lyase (TAL). The 4-coumaric acid from either pathway is subsequently activated to 4-coumaroyl-CoA by the action of 4-coumarate-CoA ligase (4CL). Within the phenylpropanoid pathway, 4-coumaroyl-CoA represents the key branching point from which phenylpropanoid derivatives, including chalcones and stilbenes, are derived. Stilbenes are synthesized via stilbene synthase (STS), also known as resveratrol synthase (RS), catalyzing condensation of a phenylpropane unit of 4-coumaroyl-CoA with malonyl-CoA, resulting in formation of resveratrol. Conversely, chalcones are synthesized via condensation of a phenylpropane unit of 4-coumaroyl-CoA with malonyl-CoA and chalcone synthase (CHS), resulting in the formation of tetrahydroxychalcone.

Current methods of producing naringenin, resveratrol, and other phenylpropanoid derivatives are limited by pathways that compete for phenylpropanoids, such as coumaroyl-CoA, as a substrate. For example, cells engineered to produce naringenin also produce phloretic acid by an unknown mechanism (see e.g., Koopman et al., (2012) *Microbial Cell Factories* 2012, 11:155). Phloretic acid is a side product of the phenylpropanoid pathway. It is a dihydro-phenylpropanoid, which are converted from a phenylpropanoid (e.g., p-coumaroyl-CoA) to a dihydrophenylpropanoid (e.g., p-dihydrocoumaroyl-CoA). However, the enzymes responsible for producing dihydrophenylpropanoids (and reducing naringenin production) are presently unknown.

Phenylalanine ammonia lyase (PAL), which converts L-phenylalanine to ammonia and trans-cinnamic acid, and Tyrosine ammonia lyase (TAL), which converts L-tyrosine into p-coumaric acid, are both members of the aromatic amino acid lyase family. The third member of the aromatic amino acid lyase family is histidine ammonia lyase (HAL), which converts histidine to trans-urocanic acid. Most ammonia lyases have an affinity to both phenylalanine and tyrosine, with a strong preference for phenylalanine. These enzymes are called PAL/TALs. Watts, K. T. et al. (2006), identified a single active site residue as responsible for substrate specificity, and reported that replacing the active site residue His89 with Phe in *Rhodobacter sphaeroides* TAL switched its substrate selectivity from tyrosine to phenylalanine (Watts, K. T. et al. (2006) *Chemistry & Biology* 13, 1317-1326).

Generally, PAL is a more active enzyme than TAL and, therefore, has been preferred for the production of phenylpropanoids in yeast strains such as *Saccharomyces cerevisiae* (see e.g. U.S. Pat. No. 8,895,287). However, finding and introducing an active, specific TAL in strains that produce phenylpropanoids and phenylpropanoid derivatives, such as *S. cerevisiae*, may result in a substantial increase in the carbon flux going through the phenylpropanoid pathway and, therefore, in an increased production of phenylpropanoids or phenylpropanoid derivatives, including chalcones and stilbenes.

Expression of the heterologous phenylpropanoid pathway through use of both PAL and TAL has been reported (see Koopman, F. et al., 2012, *Microbial Cell Factories*, 11:155). Koopman, F. et al. (2012) id., used TAL from *Rhodobacter capsulatus* (RcTAL). However, even after deregulating synthesis of aromatic amino acids, thereby increasing the available tyrosine, RcTAL shows very poor activity and, thus, cannot be used in industrial applications. Accordingly, there remains a need for expression of active, specific TALs in yeast, which produces high yields of phenylpropanoids or phenylpropanoid derivatives.

SUMMARY OF THE INVENTION

It is against the above background that the present invention provides certain advantages and advancements over the prior art.

Although this invention disclosed herein is not limited to specific advantages or functionality, the invention disclosed herein provides a recombinant host comprising a recombinant gene encoding a tyrosine ammonia lyase (TAL) polypeptide, wherein the host is capable of producing a phenylpropanoid or a phenylpropanoid derivative compound, and wherein the TAL polypeptide uses tyrosine as a preferred substrate.

The invention further provides a method of producing a phenylpropanoid or a phenylpropanoid derivative compound, comprising growing a recombinant host as described herein in a culture medium under conditions in which the recombinant genes are expressed, wherein the phenylpropanoid or the phenylpropanoid derivative compound is synthesized by the recombinant host.

In some aspects, the gene encoding the TAL polypeptide encodes a polypeptide having the amino acid sequence set forth in SEQ ID NO:31.

In some aspects, the gene encoding the TAL polypeptide encodes a polypeptide having at least 65% identity to the amino acid sequence set forth in SEQ ID NO:31.

In some aspects, the gene encoding the TAL polypeptide is overexpressed in the recombinant host.

In some aspects, the recombinant host containing the TAL gene is capable of producing an increased yield of a phenylpropanoid or a phenylpropanoid derivative compound, as compared to a recombinant host not comprising the gene encoding a TAL polypeptide.

In some aspects, the recombinant host containing the TAL gene produces an increased yield of a phenylpropanoid or a phenylpropanoid derivative compound, as compared to a recombinant host not comprising the gene encoding a TAL polypeptide.

In some aspects, the recombinant host containing the TAL gene produces an increased yield of one or more of (1) resveratrol and (2) coumaric acid, as compared to a recombinant host not comprising the gene encoding the TAL polypeptide.

In some aspects of the recombinant host or methods disclosed herein, the recombinant host further comprises a recombinant gene encoding:
 (a) a stilbene synthase (STS) polypeptide; or
 (b) a chalcone synthase (CHS) polypeptide.

In some aspects of the recombinant host or methods disclosed herein, the recombinant host further comprises one or more of:
 (a) a gene encoding a L-phenylalanine ammonia lyase (PAL) polypeptide;
 (b) a gene encoding a cinnamate-4-hydroxylase (C4H) polypeptide;
 (c) a gene encoding a NADPH:cytochrome P450 reductase polypeptide;
 (d) a gene encoding a 4-coumarate-CoA ligase (4CL) polypeptide; or
 (e) a gene encoding a chalcone isomerase (CHI) polypeptide
 wherein at least one of the genes is a recombinant gene.

In some aspects of the recombinant host or methods disclosed herein, the phenylpropanoid compound is coumaric acid.

In some aspects of the recombinant host or methods disclosed herein, the phenylpropanoid derivative compound is a stilbenoid compound or a chalcone compound.

In some aspects of the recombinant host or methods disclosed herein, the stilbene is resveratrol or a resveratrol derivative.

In some aspects of the recombinant host or methods disclosed herein, the chalcone is naringenin or a naringenin derivative.

In some aspects of the recombinant host or methods disclosed herein, the recombinant host comprises a microorganism that is a yeast cell, a plant cell, a mammalian cell, an insect cell, a fungal cell, or a bacterial cell.

In some aspects of the recombinant host or methods disclosed herein, the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

In some aspects of the recombinant host or methods disclosed herein, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

In some aspects of the recombinant host or methods disclosed herein, the yeast cell is a *Saccharomycete*.

In some aspects of the recombinant host or methods disclosed herein, the yeast cell is a cell from the *Saccharomyces cerevisiae* species.

In some aspects, the method disclosed herein further comprises recovering the phenylpropanoid or the phenylpropanoid derivative compound from the culture media.

In some aspects, the method disclosed herein further comprises isolating the phenylpropanoid or the phenylpropanoid derivative compound from the culture medium.

These and other features and advantages will be more fully understood from the following detailed description taken together with the accompanying claims.

BRIEF DESCRIPTION OF THE DRAWINGS

The following detailed description can be best understood when read in conjunction with the following drawings in which.

DETAILED DESCRIPTION

Figure 1:
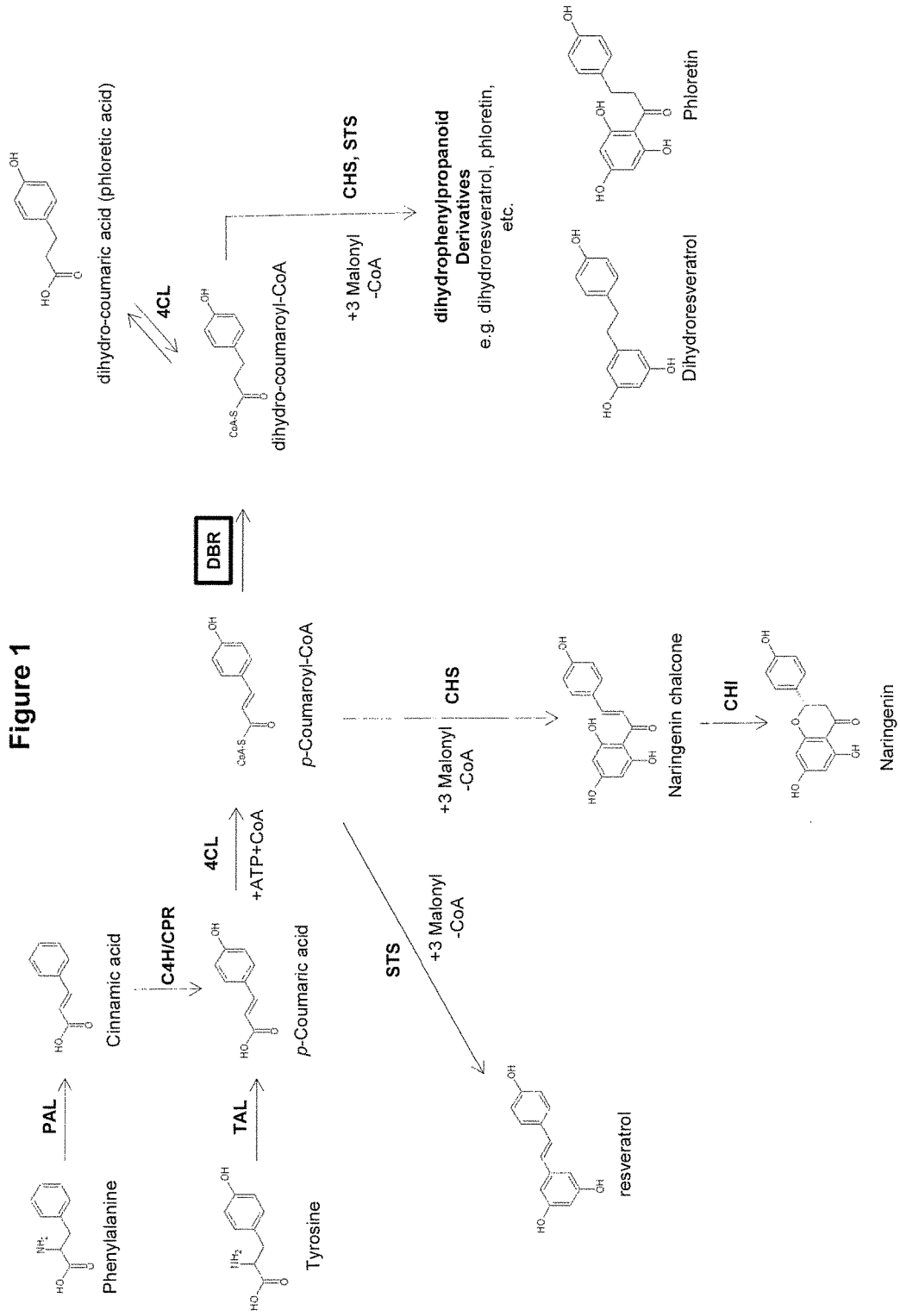
FIG. 1 shows the phenylpropanoid pathway branching from p-coumaroyl-CoA to a variety of phenylpropanoid derivatives. Two branches of the pathway are shown, with exemplary phenylpropanoid derivatives produced by two PKS type III enzymes: chalcone synthase (CHS) and stilbene synthase (STS). Also shown is a branch producing dihydrophenylpropanoid derivatives via the action of a reductase enzyme. Other enzyme abbreviations are: phenylalanine lyase (PAL or TAL); cinnamate-4-hydroxylase (C4H) which requires the activity of a reductase (CPR); 4-Coumaroyl-CoA ligase (4CL); and chalcone isomerase (CHI).

All publications, patents and patent applications cited herein are hereby expressly incorporated by reference for all purposes.

Because many phenylpropanoid derivatives are useful as, inter alia, pharmaceutical compounds, there is a need for efficient methods of their production. For example, the chalcone naringenin, and the stilbene resveratrol, are useful for controlling blood sugar levels, as well as other potential uses to improve human health.

Accordingly, provided herein are materials and methods useful for biosynthesis of phenylpropanoid derivatives, including chalcones and stilbenes. In certain embodiments, the disclosure provides recombinant hosts and methods for biosynthesis of naringenin and other chalcones. In alternative embodiments, the disclosure provides recombinant hosts and methods for biosynthesis of resveratrol and other stilbenes.

Before describing the disclosed methods and compositions in detail, a number of terms will be defined. As used herein, the singular forms "a", "an", and "the" include plural referents unless the context clearly dictates otherwise. For example, reference to a "nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining the present invention it is noted that the terms "increase", "increases", "increased", "greater", "higher", and "lower" are utilized herein to represent non-quantitative comparisons, values, measurements, or other representations to a stated reference or control.

For the purposes of describing and defining the present invention, it is noted that the terms such as "preferred substrate" and "primary substrate" are interchangeable and utilized herein to represent non-quantitative comparisons, values, measurements, or other representations regarding stated substrates.

For the purposes of describing and defining this invention it is noted that the terms "substantial" and "substantially" are utilized herein to represent the inherent degree of uncertainty that can be attributed to any quantitative comparison, value, measurement, or other representation. The terms "substantial" and "substantially" are also utilized herein to represent the degree by which a quantitative representation can vary from a stated reference without resulting in a change in the basic function of the subject matter at issue.

Methods well known to those skilled in the art can be used to construct the genetic expression constructs and recombinant cells disclosed herein. These methods include in vitro recombinant DNA techniques, synthetic techniques, in vivo recombination techniques, and polymerase chain reaction (PCR) techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "recombinant host," "host cell," and "recombinant host cell" can be used interchangeably. As used herein, the term "recombinant host" is intended to refer to a host, the genome of which has been augmented by at least one DNA sequence. Such DNA sequences include but are not limited to genes or DNA sequences that are not naturally present, that are not normally transcribed into RNA, nor translated into protein ("expressed") natively in the cell, and other genes or DNA sequences one desires to introduce into a host. It will be appreciated that typically the genome of a recombinant host described herein is augmented through stable introduction of one or more recombinant genes. Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "gene" refers to a polynucleotide unit comprised of at least one of the DNA sequences disclosed herein, or any DNA sequences encoding the amino acid sequences disclosed herein, or any DNA sequence that hybridizes to the complement of the coding sequence disclosed herein. Preferably, the term includes coding and non-coding regions, and preferably all sequences necessary for normal gene expression including promoters, enhancers, and other regulatory sequences.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species, or can be a DNA sequence that originated from or is present in the same species, but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. The recombinant genes are particularly encoded by cDNA.

As used herein, the term "engineered biosynthetic pathway" refers to a biosynthetic pathway that occurs in a recombinant host, as described herein, and does not naturally occur in the host. In some embodiments, the engineered biosynthetic pathway comprises enzymes naturally produced by the host, wherein in certain embodiments the extent and amount of expression of the genes encoding these enzymes are altered in the recombinant host; in some embodiments these enzymes are underexpressed, or their expression is eliminated, in the recombinant host.

As used herein, the term "endogenous" gene refers to a gene that originates from and is produced or synthesized within a particular organism, tissue, or cell.

As used herein, the terms "heterologous sequence" and "heterologous coding sequence" are used to describe a sequence derived from a species other than the recombinant host. In some embodiments, the recombinant host is an S. cerevisiae cell, and a heterologous sequence is derived from an organism other than S. cerevisiae. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular microorganism is obtained, using appropriate codon bias tables for that microorganism. Nucleic acids may also be optimized to a GC-content preferable to a particular microorganism, and/or to reduce the number of repeat sequences. As isolated nucleic acids, these modified sequences can exist as purified molecules and can be incorporated into a vector or a virus for use in constructing modules for recombinant nucleic acid constructs. In addition, heterologous nucleic acids can be modified for increased or even optimal expression in the relevant microorganism. Thus, in some embodiments of the methods and compositions disclosed herein, heterologous nucleic acids have been codon optimized for expression in the relevant microorganism. Codon optimization may be performed by routine methods known in the art (See e.g., Welch, M., et al. (2011), Methods in Enzymology 498:43-66).

Chalcone and Stilbene Synthesis

As used herein, the terms "chalcone" and "chalconoid" are interchangeable and refer to derivatives the compound of formula (I):

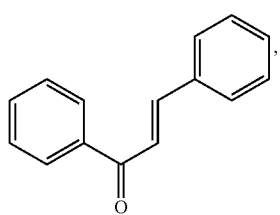

(I)

wherein formula (I) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the terms "stilbene" and "stilbenoid" are interchangeable and refer to compounds based on the compound of formula (II):

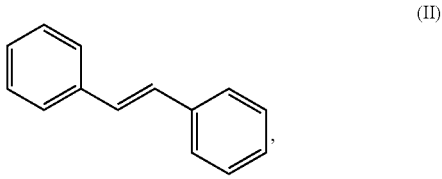 [SMILES: C(=C\c1ccccc1)/c1ccccc1]

(II)

wherein formula (II) may be substituted at one or more suitable positions. Exemplary substituents include, but are not limited to, halogen, cyano, nitro, $C_1$-$C_6$ alkyl, $C_1$-$C_6$ haloalkyl, $C_1$-$C_6$ hydroxyalkyl, hydroxy, $C_1$-$C_6$ alkoxy, thiol, $C_1$-$C_6$ alkylthio, amino, $C_1$-$C_6$ alkyl amino, di-$C_1$-$C_6$ alkyl amino, carboxyl, $C_1$-$C_6$ alkoxycarbonyl, amido, and glycosyl.

As used herein, the term "phenylpropanoid" refers to compounds based on a 3-phenylprop-2-enoate backbone. Examples of such compounds include, but are not limited to, cinnamic acid, coumaric acid, caffeic acid, ferulic acid, 5-hydroxyferulic acid, sinapinic acid, cinnamoyl-CoA, p-coumaroyl-CoA, and the like.

As used herein, the term "phenylpropanoid derivative" refers to any compound derived from, synthesized from, or biosynthesized from a phenylpropanoid; i.e. a phenylpropanoid derivative includes any compound for which a phenylpropanoid compound is a precursor or intermediate. Examples of phenylpropanoid derivatives include, but are not limited to, stilbenoid compounds and chalcone compounds. Specific examples of phenylpropanoid derivatives include, but are not limited to, naringenin, resveratrol, pinosylvin, pinocembrin chalcone, and pinocembrin.

As used herein, the term "dihydrophenylpropanoid" refers to compounds based on a phenylpropanoate backbone. Examples of such compounds include, but are not limited to, dihydrocinnamic acid, phloretic acid, 3,4-dihydroxyhydrocinnamic acid, hydroferulic acid, dihydrocoumaroyl-CoA, dihydrocinnamoyl-CoA, and the like.

As used herein, the term "dihydrophenylpropanoid derivative" refers to any compound derived from, synthesized from, or biosynthesized from a dihydrophenylpropanoid; i.e. a dihydrophenylpropanoid derivative includes any compound for which a dihydrophenylpropanoid compound is a precursor or intermediate. Examples of dihydrophenylpropanoid derivatives include, but are not limited to, dihydrostilbenoid compounds and dihydrochalcone compounds. Specific examples of dihydrophenylpropanoid derivatives include, but are not limited to, phloretin, phlorizin, dihydropinosylvin, dihydropinosylvincarboxylate, 3-O-methyldihydropinosylvincarboxylate, 4-isoprenyl-3-O-methyldihydropinosylvincarboxylate (amorfrutin 1), 3-O-methyldihydropinosylvin, 4-isoprenyl-3-O-methyldihydropinosylvin (amorfrutin 2), 5-hydroxy-lunularic acid, and dihydroresveratrol.

As used herein, the terms "phenylpropanoid pathway," "phenylpropanoid derivative pathway," "phenylpropanoid derivative synthesis pathway," and "phenylpropanoid derivative biosynthesis pathway" are interchangeable and refer to any biosynthesis pathway in which a phenylpropanoid is a precursor or intermediate.

"Optional" or "optionally" means that the subsequently described event or circumstance may or may not occur, and that the description includes instances where said event or circumstance occurs and instances in which it does not.

As used herein, "reduced expression" refers to expression of a gene or protein at a level lower than the native expression of the gene or protein. For example, in some embodiments the activity of a reductase is reduced by decreasing the amount of protein product, or expression, of a gene encoding the reductase.

Reduction or elimination (i.e., disruption) of expression of a gene can be accomplished by any known method, including insertions, missense mutations, frame shift mutations, deletion, substitutions, or replacement of a DNA sequence, or any combinations thereof. Insertions include the insertion of the entire genes, which may be of any origin. Reduction or elimination of gene expression can, for example, comprise altering or replacing a promoter, an enhancer, or splice site of a gene, leading to inhibition of production of the normal gene product partially or completely. In some embodiments, reduction or elimination of gene expression comprises altering the total level of the protein product expressed in the cell or organism. In other embodiments, disruption of a gene comprises reducing or eliminating the activity of the protein product of the gene in a cell or organism. In some embodiments of the disclosure, the disruption is a null disruption, wherein there is no significant expression of the gene. In some embodiments the disruption of a gene in a host or organism occurs on both chromosomes, in which case it is a homozygous disruption. In other embodiments the disruption of a gene in a host or organism occurs on only one chromosome, leaving the other chromosomal copy intact, in which case it is a heterozygous gene disruption. In still other embodiments each copy of a gene in a host or organism is disrupted differently.

Reduction or elimination of gene expression may also comprise gene knock-out or knock-down. A "gene knock-out" refers to a cell or organism in which the expression of one or more genes is eliminated. A "gene knock-down" refers to a cell or organism in which the level of one or more genes is reduced, but not completely eliminated.

In some embodiments, the recombinant host further comprises one or more polypeptides of a phenylpropanoid derivative biosynthesis pathway. In some embodiments, recombinant genes are provided that catalyze formation of intermediates in the biosynthesis of chalcones, stilbenes, or other phenylpropanoid derivatives. Intermediates comprise, inter alia, cinnamic acid, cinnamoyl-CoA, p-coumaric acid, p-coumaroyl CoA, naringenin, and resveratrol.

In some embodiments, a L-phenylalanine ammonia lyase (PAL) polypeptide can be expressed, overexpressed, or recombinantly expressed in said microorganism. In some embodiments, said PAL is a PAL (EC 4.3.1.5) from a plant belonging to the genus of *Arabidopsis, Brassica, Citrus, Phaseolus, Pinus, Populus, Solanum, Prunus, Vitis, Zea, Agastache, Ananas, Asparagus, Bromheadia, Bambusa, Beta, Betula, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeurn, Helianthus, Ipomoea, Lactuca, Lithospermum, Lotus, Lycopersicon, Medicago, Malus, Manihot, Medicago, Mesembryanthemum, Nicotiana, Olea, Oryza, Pisum, Persea, Petroselinurn, Phalaenopsis, Phyllostachys, Physcomitrella, Picea, Pyrus, Quercus, Raphanus, Rehmannia, Rubus, Sorghum, Sphenostylis, Stellaria, Stylosanthes, Triticum, Trifolium, Triticum, Vaccinium, Vigna,* or *Zinnia* or a microorganism belonging to the genus *Agaricus, Aspergillus, Ustilago, Rhodobacter,* or *Rhodotorula*. See, e.g., WO 2006/089898, which has been incorporated by reference in its entirety. In some embodiments, the PAL is an *Arabidopsis thaliana* PAL, e.g., *A. thaliana* PAL2 (SEQ ID NO:15).

In some embodiments, a tyrosine ammonia lyase (TAL) polypeptide can be expressed, overexpressed, or recombinantly expressed in said microorganism. In some embodiments, said TAL is capable of using both tyrosine and phenylalanine as substrates. In some embodiments, said TAL does not use phenylalanine as its primary or preferred substrate. In some embodiments, said TAL uses tyrosine as its primary or preferred substrate. In some embodiments, said TAL has a Km for Phenylalanine which is higher than its Km for Tyrosine and/or said TAL has a Kcat for Phenylalanine which is lower than its Kcat for Tyrosine. In some embodiments, said TAL is a TAL (EC 4.3.1.5) from yeast belonging to the genus *Rhodotorula* or a bacterium belonging to the genus *Rhodobacter*. See, e.g., WO 2006/089898, which has been incorporated by reference in its entirety. In some embodiments, the TAL is a *Rhodobacter capsulatus* TAL, e.g., *R. capsulatus* TAL (SEQ ID NO:1). In some embodiments, the TAL is an *Aeromonas salmonicida* TAL, e.g., *A. salmonicida* subsp. *salmonicida* A449 (Asal) TAL (SEQ ID NO:31).

In some embodiments, a cinnamate 4-hydroxylase (C4H) polypeptide can be expressed, overexpressed, or recombinantly expressed in said microorganism. In some embodiments, said C4H is a C4H (EC 1.14.13.11) from a plant belonging to the genus of *Arabidopsis, Citrus, Phaseolus, Pinus, Populus, Solanum, Vitis, Zea, Ammi, Avicennia, Camellia, Camptotheca, Catharanthus, Glycine, Helianthus, Lotus, Mesembryanthemum, Physcomitrella, Ruta, Saccharum,* or *Vigna* or from a microorganism belonging to the genus *Aspergillus*. See, e.g., WO 2006/089898, which has been incorporated by reference in its entirety. See, e.g., WO 2006/089898, which has been incorporated by reference in its entirety. In some embodiments, the C4H is *Arabidopsis thaliana* C4H (SEQ ID NO:2).

In some embodiments, a 4-coumarate-CoA ligase (4CL) polypeptide can be expressed, overexpressed, or recombinantly expressed in said microorganism. In some embodiments, said 4CL can be a 4CL (EC 6.2.1.12) from a plant belonging to the genus of *Abies, Arabidopsis, Brassica, Citrus, Larix, Phaseolus, Pinus, Populus, Solanum, Vitis, Zea,* e.g., *Z. mays, Agastache, Amorpha, Cathaya, Cedrus, Crocus, Festuca, Glycine, Juglans, Keteleeria, Lithospermum, Lolium, Lotus, Lycopersicon, Malus, Medicago, Mesembryanthemum, Nicotiana, Nothotsuga, Oryza, Pelargonium, Petroselinum, Physcomitrella, Picea, Prunus, Pseudolarix, Pseudotsuga, Rosa, Rubus, Ryza, Saccharum, Suaeda, Thellungiella, Triticum,* or *Tsuga,* a microorganism belonging to the genus *Aspergillus, Neurospora, Yarrowia, Mycosphaerella, Mycobacterium, Neisseria, Streptomyces,* or *Rhodobacter,* or a nematode belonging to the genus *Ancylostoma, Caenorhabditis, Haemonchus, Lumbricus, Meloidogyne, Strongyloidus,* or *Pristionchus*. See, e.g., WO 2006/089898, which has been incorporated by reference in its entirety. In some embodiments, the 4CL is an *Arabidopsis thaliana* 4CL, e.g., *A. thaliana* 4CL2 (SEQ ID NO:3).

In some embodiments, the disclosure provides a recombinant host engineered to express recombinant polypeptides that catalyze the formation of stilbenoids from p-coumaroyl-CoA. Thus, in some embodiments, recombinant host further comprises one or more stilbene synthase genes.

In some embodiments, a stilbene synthase (STS) polypeptide can be expressed, overexpressed, or recombinantly expressed in said microorganism. In some embodiments, said STS is an STS (EC 2.3.1.95) from a plant belonging to the genus of *Arachis, Rheum, Vitis, Pinus, Piceea, Lilium, Eucalyptus, Parthenocissus, Cissus, Calochortus, Polygonum, Gnetum, Artocarpus, Nothofagus, Phoenix, Festuca, Carex, Veratrum, Bauhinia*, or *Pterolobium*. See, e.g., WO 2006/089898, which has been incorporated by reference in its entirety. In some embodiments, the STS is *Vitis* pseudoreticulata STS (SEQ ID NO:4).

In some embodiments, an NADPH:cytochrome P450 reductase (CPR) polypeptide can be expressed, overexpressed, or recombinantly expressed in said microorganism. In some embodiments, said CPR is a CPR (EC 1.6.2.4) from a plant belonging to genus *Arabidopsis*, e.g., *A. thaliana*, a plant belonging to genus Citrus, e.g., Citrus× *sinensis*, or Citrus× *paradisi*, a plant belonging to genus *Phaseolus*, e.g., *P. vulgaris*, a plant belonging to genus *Pinus*, e.g., *P. taeda*, a plant belonging to genus *Populus*, e.g., *P. deltoides, R. tremuloides*, or *R. trichocarpa*, a plant belonging to genus *Solanum*, e.g., *S. tuberosum*, a plant belonging to genus *Vitis*, e.g., *Vitis vinifera*, a plant belonging to genus *Zea*, e.g., *Z. mays*, or other plant genera, e.g., *Ammi, Avicennia, Camellia, Camptotheca, Catharanthus, Glycine, Helianthus, Lotus, Mesembryanthemum, Physcomitrella, Ruta, Saccharum*, or *Vigna*. See, e.g., WO 2006/089898, which has been incorporated by reference in its entirety. In some embodiments, the CPR is an *Arabidopsis thaliana* CPR, e.g., *A. thaliana* ATR2 (SEQ ID NO:5).

In some embodiments, the disclosure provides recombinant host engineered to express recombinant polypeptides that catalyze the formation of phenylpropanoid derivatives, such as chalcones and stilbenoids.

In some embodiments, a chalcone synthase (CHS) polypeptide can be expressed, overexpressed, or recombinantly expressed in said microorganism. In some embodiments, said CHS is a *Hordeum vulgare* CHS, e.g., *H. vulgare* CHS2 (SEQ ID NO:7).

In some embodiments, a chalcone isomerase (CHI) polypeptide can be expressed, overexpressed, or recombinantly expressed in said microorganism. In some embodiments, the CHI is a *Petunia hybrida* CHI, e.g., *P. hybrida* CHI1 (SEQ ID NO:9) or *P. hybrida* CHI2 (SEQ ID NO:11).

In another aspect, the disclosure provides methods of producing a chalcone or a stilbene compound, comprising growing a recombinant host as disclosed herein in a culture medium under conditions in which the recombinant genes are expressed, and wherein said compound is synthesized by the recombinant host.

In some embodiments, the methods of the disclosure are used to produce a chalcone compound. In some embodiments, the chalcone compound is naringenin or a naringenin derivative. In addition to naringenin, some embodiments disclosed herein are useful for producing other chalcones, e.g., Isoliquiritigenin (liquiritigenin chalcone), Butein (Butin chalcone), Pinocembrin chalcone, Eriodictyol chalcone and Homoeriodictyol chalcone.

In some embodiments, the methods of the disclosure are used to produce a stilbenoid compound. In some embodiments the stilbene compound is resveratrol. In addition to resveratrol, some embodiments of the present disclosure are useful for producing other stilbenoids, e.g. Piceatannol, Dihydroresveratrol, Resveratrol 3-O-glucoside (Piceid, polydatin), epsilon-Viniferin, delta-Viniferin and Pallidol.

In some embodiments, the methods of producing a chalcone or a stilbene compound further comprise harvesting the said compound. In some embodiments, the methods of producing a chalcone or a stilbene compound further comprise isolating said compound.

Functional Homologs

Functional homologs of the polypeptides described above may also be suitable for use in producing phenylpropanoid derivatives in a recombinant host as provided herein. A functional homolog is a polypeptide that has sequence similarity to a reference polypeptide, and that carries out one or more of the biochemical or physiological function(s) of the reference polypeptide. A functional homolog and the reference polypeptide can be a natural occurring polypeptide, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide-polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of phenylpropanoid or phenylpropanoid derivative biosynthesis pathway polypeptides. Sequence analysis can involve BLAST, Reciprocal BLAST, or PSI-BLAST analysis of non-redundant databases using, e.g., a phenylalanine ammonia lyase, tyrosine ammonia lyase, chalcone isomerase, or stilbene synthase amino acid sequence as the reference sequence. Amino acid sequence is, in some instances, deduced from the nucleotide sequence. Those polypeptides in the database that have greater than 40% sequence identity are candidates for further evaluation for suitability as a phenylpropanoid derivative biosynthesis pathway polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in phenylpropanoid derivative biosynthesis pathway polypeptides, e.g., conserved functional domains.

Conserved regions can be identified by locating a region within the primary amino acid sequence of a phenylpropanoid derivative biosynthesis pathway polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.*, 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate to identify such homologs.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, homologs suitable for producing naringenin in a recombinant host include recombinant homologs of chalcone synthase and/or chalcone isomerase genes.

Methods to modify the substrate specificity of a given polypeptide, such as, for example, a phenylalanine ammonia lyase, tyrosine ammonia lyase, chalcone synthase, chalcone isomerase, or stilbene synthase, are known to those skilled in the art, and include without limitation site-directed/rational mutagenesis approaches, random directed evolution approaches and combinations in which random mutagenesis/saturation techniques are performed near the active site of the enzyme. For example see Osmani et al., 2009, Phytochemistry 70: 325-347.

A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200% of the length of the reference sequence. A functional homolog polypeptide typically has a length that is from 95% to 105% of the length of the reference sequence, e.g., 90, 93, 95, 97, 99, 100, 105, 110, 115, or 120% of the length of the reference sequence, or any range between. A % identity for any candidate nucleic acid or polypeptide relative to a reference nucleic acid or polypeptide can be determined as follows. A reference sequence (e.g., a nucleic acid sequence or an amino acid sequence described herein) is aligned to one or more candidate sequences using the computer program ClustalW (version 1.83, default parameters), which allows alignments of nucleic acid or polypeptide sequences to be carried out across their entire length (global alignment). Chenna et al., 2003, *Nucleic Acids Res.* 31(13):3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: % age; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: % age; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that functional homologs, e.g. of enzymes involved in phenylpropanoid derivative biosynthesis, can include additional amino acids that are not involved in the enzymatic activities carried out by the enzymes.

Recombinant Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also can include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

Recombinant Hosts

Recombinant hosts can be used to express polypeptides for phenylpropanoid derivative production, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a phenylpropanoid derivative production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

The constructed and genetically engineered microorganisms provided herein can be cultivated using conventional fermentation processes, including, inter alia, chemostat, batch, fed-batch cultivations, continuous perfusion fermentation, and continuous perfusion cell culture.

Carbon sources of use in the instant method include any molecule that can be metabolized by the recombinant host to facilitate growth and/or production of the phenylpropanoid derivative. Examples of suitable carbon sources include, but are not limited to, sucrose (e.g., as found in molasses), fructose, xylose, ethanol, glycerol, glucose, cellulose, starch, cellobiose or other glucose comprising polymer. In embodiments employing yeast as a host, for example, carbons sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis* 32, *Rhodoturula mucilaginosa, Phaffia rhodozyma* UBV-AX, *Xanthophyllomyces dendrorhous, Fusarium fujikuroi/Gibberella fujikuroi, Candida utilis, Candida glabrata, Candida albicans*, and *Yarrowia lipolytica*.

In some embodiments, a microorganism can be a prokaryote such as *Escherichia coli, Saccharomyces cerevisiae, Rhodobacter sphaeroides, Rhodobacter capsulatus*, or *Rhodoturula toruloides*.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *Saccharomyces cerevisiae*.

In some embodiments, a microorganism can be an algal cell such as *Blakeslea trispora, Dunaliella salina, Haematococcus pluvialis, Chlorella* sp., *Undaria pinnatifida, Sargassum, Laminaria japonica, Scenedesmus almeriensis* species.

In some embodiments, a microorganism can be a cyanobacterial cell such as *Blakeslea trispora, Dunaliella sailna, Haematococcus pluvialis, Chlorella* sp., *Undaria pinnatifida, Sargassum, Laminaria japonica, Scenedesmus almeriensis*.

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*. Generally, *A. niger* is cultured for the industrial production of a number of food ingredients such as citric acid and gluconic acid, and thus species such as *A. niger* are generally suitable for producing phenylpropanoid derivatives.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberelia*, and *Phanerochaete* spp.

*Agaricus, Gibberella*, and *Phanerochaete* spp. can be useful because they are known to produce large amounts of isoprenoids in culture. Thus, precursors for producing large amounts of phenylpropanoid derivatives are already produced by endogenous genes.

*Arxula adeninivorans (Blastobotrys adeninivorans)*

*Arxula adeninivorans* is a dimorphic yeast (it grows as a budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica.*

*Yarrowia lipolytica* is a dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorganism. *Yarrowia lipolyptica* can accumulate lipid content to approximately 40% of its dry cell weight and is a model organism for lipid accumulation and remobilization. See e.g. Nicaud, 2012, Yeast 29(10):409-18; Beopoulos et al., 2009, Biohimie 91(6):692-6; Bankar et al., 2009, *Appl Microbiol Biotechnol.* 84(5):847-65.

*Rhodotorula* sp.

*Rhodotorula* is a unicellular, pigmented yeast. The oleaginous red yeast, *Rhodotorula glutinis*, has been shown to produce lipids and carotenoids from crude glycerol (Saenge et al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is an oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Rhodobacter* spp.

*Rhodobacter* can be used as the recombinant microorganism platform. Similar to *E. coli*, there are libraries of mutants available as well as suitable plasmid vectors, allowing for rational design of various modules to enhance product yield. Isoprenoid pathways have been engineered in membranous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Candida boidinii*

*Candida boidinii* is a methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH.

*Hansenula polymorpha (Pichia anqusta)*

*Hansenula polymorpha* is another methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes.

*Kluyveromyces lactis*

*Kluyveromyces lactis* is yeast regularly applied to producing kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale.

*Pichia pastoris*

*Pichia pastoris* is a methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans).

*Physcomitrella* spp.

*Physcomitrella* mosses, when grown in suspension culture, have characteristics similar to yeast or other fungal cultures. This genera is becoming an important type of cell for producing plant secondary metabolites, which can be difficult to produce in other types of cells.

Methods of Producing Phenylpropanoid Derivatives

Recombinant hosts described herein can be used in methods to produce phenylpropanoid derivatives.

For example, the method can include growing the recombinant host in a culture medium under conditions in which phenylpropanoid derivative biosynthesis genes are expressed. The recombinant host can be grown in a fed batch or continuous process. Typically, the recombinant host is grown in a fermentor at a defined temperature(s) for a desired period of time. Depending on the particular host used in the method, other recombinant genes such as phenylalanine ammonia lyase (PAL), tyrosine ammonia lyase (TAL), cinnamate 4-hydroxylase (C4H), cytochrome P450 reductase (CPR), 4-coumarate-CoA ligase (4CL), stilbene synthase (STS), chalcone synthase (CHS), or chalcone isomerase (CHI) can also be present and expressed. Levels of substrates and intermediates, e.g., phenylalanine, tyrosine, cinnamic acid, coumaric acid, dihydrocinnamic acid or phloretic acid, can be determined by extracting samples from culture media for analysis according to published methods. In some embodiments, the culture medium does not contain a phenylpropanoid precursor or intermediate from an external source (i.e., phenylpropanoid precursors or intermediates are not added to the culture medium).

The genes described herein can be expressed in yeast using any of a number of known promoters. Strains that overproduce phenylpropanoids are known and can be used as acceptor molecules in the production of phenylpropanoids or phenylpropanoid derivatives.

In some embodiments, enzymes may be screened for TAL and/or PAL activity. In some embodiments, the corresponding DNA sequence for the enzymes to be screened for PAL and TAL activity are codon optimized for optimal expression in *Saccharomyces cerevisiae*. In some embodiments, each PAL/TAL enzyme is cloned together with all necessary genes for the production of naringenin from cinnamic acid (C4H-CPR, 4CL, CHS and CHI), to measure PAL+TAL activity, or from coumaric acid (4CL, CHS and CHI), to measure TAL activity alone. In some embodiments, the genes are then introduced in a single step into a *Saccharo-*

*myces cerevisiae* yeast strain which does not produce phenylpropanoids or phenylpropanoid derivatives ("non-producer yeast strain").

In some embodiments, transformants are inoculated in a 96 deep well plate and incubated overnight in 500 μl of SC-URA medium at 30° C. and 400 rpm. In some embodiments, 50 μl of the overnight culture are inoculated to a new 96 deep well plate containing 500 μl of DELFT medium plus 4% w/v glucose. In some embodiments, after 72 hours of growth under the same conditions, the OD600 is measured to estimate cell growth and samples taken to measure cinnamic acid, coumaric acid, naringenin and phloretic acid by HPLC as follows. In some embodiments, a sample of the culture (300 μl) is mixed with 96% EtOH (300 μl) on a shaking table and centrifuged. In some embodiments, supernatant (100 μl) is used for HPLC analysis. In some embodiments, measurements are taken using pure compounds as standards.

In some embodiments, the TAL gene is encoded by the nucleotide sequence of any one of SEQ ID NOS:12, 14, 16, 18, 20, 22, 24, 26, 28, 30, 32, 34, 36, 38, 40, 42, 44, 46 or 48. In some embodiments, the TAL polypeptide is any one of SEQ ID NOS:13, 15, 17, 19, 21, 23, 25, 27, 29, 31, 33, 35, 37, 39, 41, 43, 45, 47 or 49. In some embodiments, the TAL polypeptide is from *Aeromonas salmonicida* subsp. *salmonicida* A449 (Asal) (SEQ ID NO:31). In some embodiments, the TAL polypeptide has at least 50% identity to the amino acid sequence in SEQ ID NO:31. In some embodiments, the TAL polypeptide has at least 65% identity to the amino acid sequence in SEQ ID NO:31. In some embodiments, the TAL gene is encoded by the nucleotide sequence of SEQ ID NO:30. In some embodiments, the TAL gene has at least 60% identity to SEQ ID NO:30.

In some embodiments, the TAL activity of Asal is comparable with previously known TALs from *Rhodotorula graminis* (Vanneli, J. et al. (2007), *Enzyme and Microbial Technology* 41, 413-422) and PAL4 from *Bambusa oldhamii* (Hseih, L. et al. (2010), *Phytochemistry* 71) while Asal possess much higher specificity that the two mentioned TALs (see e.g., FIG. 2). In some embodiments, the Asal TAL also has higher activity than previously reported specific TALs as RcTAL from *Rodobacter capsulatus* (Koopman, F. et al. (2012); Kyndt, J A. et al. (2002), *FEBS Letters* 512, 240-244) and Sam8 from *Saccharothrix espanaensis* (Berner, M. et al. (2006), *J Bacterial*. April; 188(7):2666-73) (see e.g., FIG. 2). In some embodiments, the activity of Asal TAL is more than five (5) times as active as previously reported specific TALs, such as, for example but not limited to, RcTAL from *R. capsulatus* and Sam8 from *S. espanaensis*.

After the recombinant host has been grown in culture for the desired period of time, phenylpropanoid derivatives (such as naringenin or resveratrol) can then be recovered from the culture using various techniques known in the art. In some embodiments, a permeabilizing agent can be added to aid the feedstock entering into the host, and to aid in product release from the host. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound(s) can then be further purified by preparative HPLC according to methods known in the art.

It will be appreciated that the various genes and modules discussed herein can be present in two or more recombinant hosts rather than a single host. When a plurality of recombinant host is used, they can be grown in a mixed culture to produce phenylpropanoid derivatives.

Alternatively, the two or more hosts each can be grown in a separate culture medium and the product of the first culture medium, e.g., a naringenin or resveratrol precursor, can be introduced into second culture medium to be converted into a subsequent intermediate, or into an end product such as, for example, naringenin. The product produced by the second, or final host is then recovered. It will also be appreciated that in some embodiments, a recombinant host is grown using nutrient sources other than a culture medium and utilizing a system other than a fermentor.

In some embodiments, phenylpropanoid derivatives are produced in vivo through expression of one or more enzymes involved in a phenylpropanoid derivative biosynthetic pathway in a recombinant host. For example, a naringenin-producing or resveratrol-producing recombinant host expressing recombinant genes encoding, one or more of an *Arabidopsis thaliana* phenylalanine ammonia lyase (PAL2) polypeptide, a gene encoding a *Ammi majus* cinnamate 4-hydroxylase (CH4) polypeptide, a gene encoding a *Arabidopsis thaliana* 4-coumarate-CoA ligase (4CL2) polypeptide, a gene encoding a *Hordeum vulgare* chalcone synthase 2 (CHS2) polypeptide, a gene encoding a cytochrome P450 reductase (CPR1) polypeptide can be used to produce a chalcone compound, e.g. naringenin, in vivo.

In some embodiments, phenylpropanoid derivatives are produced in vivo through expression of one or more enzymes involved in a phenylpropanoid derivative biosynthetic pathway in a recombinant host. For example, a naringenin-producing or resveratrol-producing recombinant host expressing recombinant genes encoding, one or more of an *Aeromonas salmonicida* tyrosine ammonia lyase (Asal TAL) polypeptide, a gene encoding a *Arabidopsis thaliana* 4-coumarate-CoA ligase (4CL2) polypeptide, a gene encoding a *Hordeum vulgare* chalcone synthase 2 (CHS2) polypeptide, a gene encoding a cytochrome P450 reductase (CPR1) polypeptide can be used to produce a chalcone compound, e.g. naringenin, in vivo.

As another example, a stilbenoid (such as resveratrol)-producing recombinant host wherein one or more genes encoding a *Saccharomyces cerevisiae* trans-2-enoyl-CoA reductase polypeptide are underexpressed or unexpressed, and expressing recombinant genes encoding one or more of an *Arabidopsis thaliana* phenylalanine ammonia lyase (PAL2) polypeptide, a gene encoding a *Ammi majus* cinnamate 4-hydroxylase (CH4) polypeptide, a gene encoding a *Arabidopsis thaliana* 4-coumarate-CoA ligase (4CL2) polypeptide, and a gene encoding a stilbene synthase (STS) polypeptide, can be used to produce a stilbenoid compound, e.g. resveratrol, in vivo.

As another example, a stilbenoid (such as resveratrol)-producing recombinant host wherein one or more genes encoding a *Saccharomyces cerevisiae* trans-2-enoyl-CoA reductase polypeptide are underexpressed or unexpressed, and expressing recombinant genes encoding one or more of an *Aeromonas salmonicida* tyrosine ammonia lyase (Asal TAL) polypeptide, a gene encoding a *Arabidopsis thaliana* 4-coumarate-CoA ligase (4CL2) polypeptide, and a gene encoding a stilbene synthase (STS) polypeptide, can be used to produce a stilbenoid compound, e.g. resveratrol, in vivo.

In some embodiments, phenylpropanoid derivatives are produced through contact of a precursor of the desired compound with one or more enzymes involved in the phenylpropanoid derivative biosynthesis pathway in vitro. For example, contacting tyrosine with a tyrosine ammonia lyase, a 4-coumarate-CoA ligase and a chalcone synthase polypeptide can result in production of a naringenin or naringenin derivative compound in vitro. In some embodiments, a naringenin precursor is produced through contact of an upstream naringenin precursor with one or more enzymes involved in the naringenin pathway in vitro.

In some embodiments, a phenylpropanoid derivative precursor is produced by bioconversion. For bioconversion to occur, a recombinant host expressing one or more enzymes involved in the phenylpropanoid derivative biosynthesis pathway takes up and modifies a phenylpropanoid derivative precursor in the cell; following modification in vivo, the phenylpropanoid derivative remains in the cell and/or is excreted into the culture medium. For example, a recombinant host expressing a gene encoding a tyrosine ammonia lyase, a 4-coumarate-CoA ligase and a chalcone synthase polypeptide can take up tyrosine and convert it to naringenin in the cell; following conversion in vivo, a naringenin compound is excreted into the culture medium.

In some embodiments, phenylpropanoid derivatives as disclosed herein are isolated and purified to homogeneity (e.g., at least 90%, 92%, 94%, 96%, or 98% pure). In other embodiments, phenylpropanoid derivatives are isolated as an extract from a recombinant host or in vitro production method. In this respect, phenylpropanoid derivatives may be isolated, but not necessarily purified to homogeneity. Desirably, the amount of phenylpropanoid derivatives produced can be from about 1 mg/L to about 20,000 mg/L or higher. For example about 1 to about 100 mg/L, about 30 to about 100 mg/L, about 50 to about 200 mg/L, about 100 to about 500 mg/L, about 100 to about 1,000 mg/L, about 250 to about 5,000 mg/L, about 1,000 to about 15,000 mg/L, or about 2,000 to about 10,000 mg/L of phenylpropanoid derivatives can be produced. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

In some embodiments, a resveratrol-producing yeast strain without TAL activity is transformed with a plasmid containing the TAL gene from *Aeromonas salmonicida* (Asal TAL, SEQ ID NO:31). In some embodiments, the plasmid allows multiple integration of the TAL gene at the Ty1 regions present throughout the yeast genome. In some embodiments, the TAL gene is under the control of the strong promoter pPGK1 and results in overexpression of the gene.

In some embodiments, the resulting strain in which the TAL gene is overexpressed is compared with the direct parental strain (control) which contains all necessary genes leading to resveratrol production. In some embodiments, levels of resveratrol and pathway intermediates (coumaric and phloretic acid) are measured after growing the indicated strains for 3 days in minimal medium. In some embodiments, extraction of compounds is carried out by mixing ethanol with a fermentation sample to a final concentration of 50% by volume, and centrifugation for 5 minutes at 3222×g.

In some embodiments, resveratrol titers are increased by at least 25% in the daughter strain in which *A. salmonicida* (Asal) TAL is overexpressed over the control parent strain. In some embodiments, a 25% increase in resveratrol titer is an increase in resveratrol production of approximately 375 mg/L. In some embodiments, coumaric acid accumulation is increased by 2.5 times in the daughter strain in which Asal TAL is overexpressed over the control parent strain. In some embodiments, a 2.5 times increase in coumaric acid accumulation is an increase of approximately 108 mg/L, when compared with the control parent strain. In some embodiments, the potential resveratrol flux, measured as the sum of resveratrol and major side products, is increased by 26.2% in the new strain harboring and overexpressing Asal TAL.

EXAMPLES

The Examples that follow are illustrative of specific embodiments disclosed herein and various uses thereof. They are set forth for explanatory purposes only and are not to be taken as limiting.

Example 1: Screening of TAL Enzymes

PAL/TAL enzymes were screened for PAL and TAL activity. The nucleotide and amino acid sequences are identified herein as SEQ ID NOS:12-49.

Each nucleotide sequence was codon optimized for optimal expression in *Saccharomyces cerevisiae*. Each PAL/TAL enzyme was cloned together with all necessary genes for the production of naringenin from cinnamic acid (C4H-CPR, 4CL, CHS and CHI), to measure PAL and TAL activity, or coumaric acid (4CL, CHS and CHI), to measure TAL activity alone. The genes were then introduced in a single step into a *S. cerevisiae* yeast strain which does not produce phenylpropanoids or phenylpropanoid derivatives ("non-producer yeast strain").

Transformants were inoculated in a 96 deep well plate and incubated overnight in 500 μl of SC-URA medium at 30° C. and 400 rpm. Subsequently, 50 μl of the overnight culture was inoculated to a new 96 deep well plate containing 500 μl of DELFT medium plus 4% w/v glucose. After 72 hours of growth under the same conditions, the OD600 was measured to estimate cell growth and samples were taken to measure cinnamic acid, coumaric acid, naringenin and phloretic acid by HPLC as follows. A sample of the culture (300 μl) was mixed with 96% EtOH (300 μl) on a shaking table and centrifuged. Supernatant (100 μl) was used for HPLC analysis. Measurements were taken using pure compounds as standards. Phloretin could not be measured because the peak overlaps with cinnamic acid.

Figure 2:
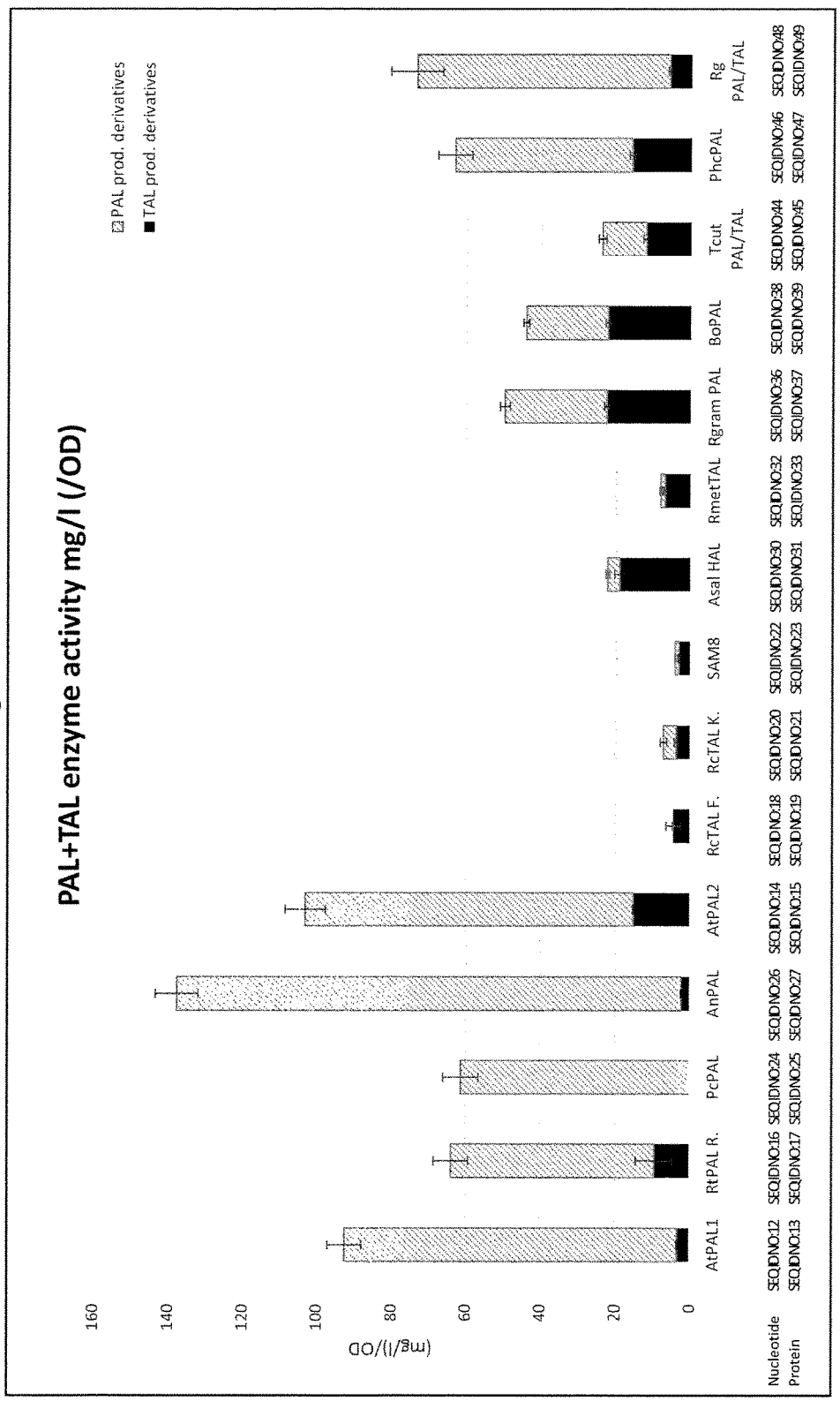
FIG. 2 shows the PAL and TAL activity of fifteen different enzymes, via production of products of the phenylpropanoid pathway derived from either cinnamic acid as a result of PAL activity or coumaric acid as a result of TAL activity.

FIG. 2 shows that the TAL from *Aeromonas salmonicida* subsp. *salmonicida* A449 (Asal) (SEQ ID NOS:30 and 31) possesses much higher specificity to tyrosine as a substrate than the TAL from *Rhodotorula graminis* (SEQ ID NOS:36 and 37) (Vanneli, J. et al. (2007), *Enzyme and Microbial Technology* 41, 413-422) and PAL4 from *Bambusa oldhamii* (SEQ ID NOS:38 and 39) (Hseih, L. et al. (2010), *Phytochemistry* 71). FIG. 2 also shows that Asal TAL has more than five times the activity of both RcTAL from *Rodobacter capsulatus* (SEQ ID NOS:20 and 21) (Koopman, F. et al. (2012); Kyndt, J A. et al. (2002), *FEBS Letters* 512, 240-244) and Sam8 from *Saccharothrix espanaensis* (SEQ ID NOS:22 and 23) (Berner, M. et al. (2006), *J Bacteriol*. April; 188(7):2666-73).

Example 2: Resveratrol Production in a Resveratrol-Producing Strain Overexpressing *Aeromonas salmonicida* TAL (SEQ ID NOS:30 and 31)

A resveratrol-producing yeast strain without TAL activity was transformed with a plasmid containing the TAL gene from *Aeromonas salmonicida* (Asal TAL, SEQ ID NOS:30 and 31). The plasmid allowed multiple integration of the TAL gene at the Ty1 regions present throughout the yeast genome. The TAL gene was under the control of the strong promoter pPGK1 and results in overexpression of the gene.

The resulting strain in which the TAL gene was overexpressed was compared with the direct parental strain (control) which contained all necessary genes leading to resveratrol production.

Levels of resveratrol and pathway intermediates (coumaric and phloretic acid) were measured after growing the indicated strains for 3 days in minimal medium. Extraction of compounds was carried out by mixing ethanol with a fermentation sample to a final concentration of 50% by volume, and centrifugation for 5 minutes at 3222×g.

Figure 3:
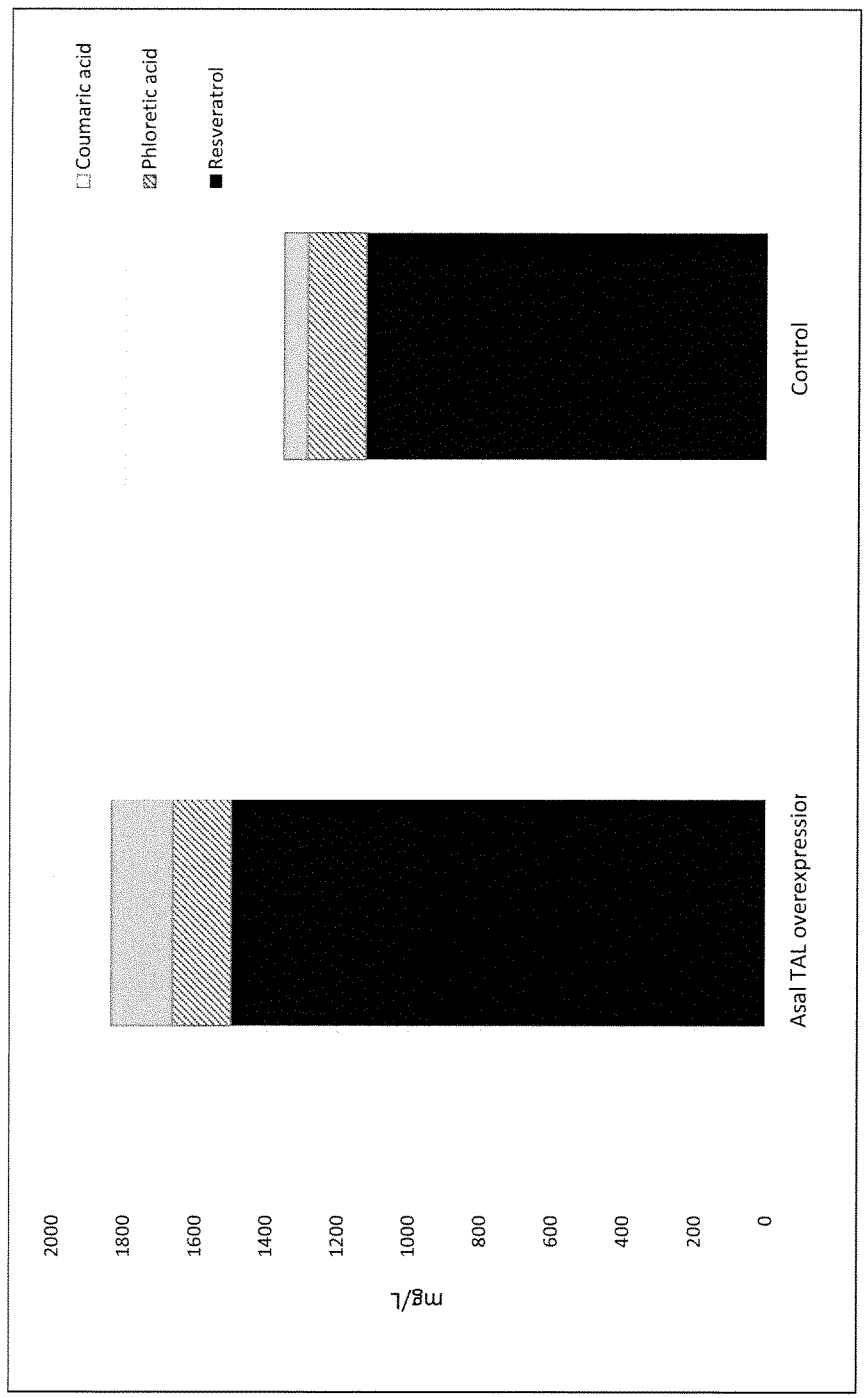
FIG. 3 shows production of resveratrol and secondary metabolites in a resveratrol-producing yeast strain overexpressing Asal TAL and the direct parental resveratrol-producing yeast strain which contained all necessary genes leading to resveratrol production (control). Secondary metabolites are likely produced due to conversion of starting metabolites malonyl-CoA, phenylalanine and/or tyrosine into intermediates (e.g., coumaric acid) and side produces (e.g., phloretic acid), rather than resveratrol.

The results show that resveratrol titers were increased by 25% (an increase of approximately 375 mg/L) in the daughter strain in which *A. salmonicida* TAL was overexpressed. Additionally, coumaric acid accumulation was shown to be increased by 2.5 times (an increase of approximately 108 mg/L) when compared with the control parent strain. Overall, the potential resveratrol flux measured as the sum of resveratrol and major side products was increased by 26.2% in the new strain harboring and overexpressing Asal TAL. (FIG. 3).

Sequences

TABLE 1

Nucleic acid and amino acid sequences.

SEQ ID NO: 1    Protein sequence from tyrosine ammonia lyase (TAL) of *Rhodobacter capsulatus*

MTLQSQTAKDCLALDGALTLVQCEAIATHRSRISVTPALRERCARAHARLEHAIAEQRHIYGITTGFGPLANRLIG
ADQGAELQQNLIYHLATGVGPKLSWAEARALMLARLNSILQGASGASPETIDRIVAVLNAGFAPEVPAQGTVGASG
DLTPLAHMVLALQGRGRMIDPSGRVQEAGAVMDRLCGGPLTLAARDGLALVNGTSAMTAIAALTGVEAARAIDAAL
RHSAVLMEVLSGHAEAWHPAFAELRPHPGQLRATERLAQALDGAGRVCRTLTAARRLTAADLRPEDHPAQDAYSLR
VVPQLVGAVWDTLDWHDRVVTCELNSVTDNPIFPEGCAVPALHGGNFMGVHVALASDALNAALVTLAGLVERQIAR
LTDEKLNKGLPAFLHGGQAGLQSGFMGAQVTATALLAEMRANATPVSVQSLSTNGANQDVVSMGTIAARRARAQLL
PLSQIQAILALALAQAMDLLDDPEGQAGWSLTARDLRDRIRAVSPGLRADRPLAGHIEAVAQGLRHPSAAADPPA

SEQ ID NO: 2    Protein sequence from cinnamate 4-hydroxylase (C4H) of *Arabidopsis thaliana*

MDLLLLEKSLIAVFVAVILATVISKLRGKKLKLPPGPIPIPIFGNWLQVGDDLNHRNLVDYAKKFGDLFLLRMGQR
NLVVVSSPDLTKEVLLTQGVEFGSRTRNVVFDIFTGKGQDMVETVYGEHWRKMRRIMTVPFFTNKVVQQNREGWEF
EAASVVEDVKKNPDSATKGIVLRKRLQLMMYNNMFRIMFDRRFESEDDPLFLRLKALNGERSRLAQSFEYNYGDFI
PILRPFLRGYLKICQDVKDRRIALFKKYFVDERKQIASSKPTGSEGLKCAIDHILEAEQKGEINEDNVLYIVENIN
VAAIETTLWSIEWGIAELVNHPEIQSKLRNELDTVLGPGVQVTEPDLHKLPYLQAVVKETLRLRMAIPLLVPHMNL
HDAKLAGYDIPAESKILVNAWWLANNPNSWKKPEEFRPERFFEEESHVEANGNDFRYVPFGVGRRSCPGIILALPI
LGITIGRMVQNFELLPPPGQSKVDTSEKGGQFSLHILNHSIIVMKPRNC

SEQ ID NO: 3    Protein sequence from 4-coumarate-CoA ligase 2 (4CL2) of *Arabidopsis thaliana*

MTTQDVIVNDQNDQKQCSNDVIFRSRLPDIYIPNHLPLHDYIFENISEFAAKPCLINGPTGEVYTYADVHVTSRKL
AAGLHNLGVKQHDVVMILLPNSPEVVLTFLAASFIGAITTSANPFFTPAEISKQAKASAAKLIVTQSRYVDKIKNL
QNDGVLIVTTDSDAIPENCLRFSELTQSEEPRVDSIPEKISPEDVVALPFSSGTTGLPKGVMLTHKGLVTSVAQQV
DGENPNLYFNRDDVILCVLPMFHIYALNSIMLCSLRVGATILIMPKFEITLLLEQIQRCKVTVAMVVPPIVLAIAK
SPETEKYDLSSVRMVKSGAAPLGKELEDAISAKFPNAKLGQGYGMTEAGPVLAMSLGFAKEPFPVKSGACGTVVRN
AEMKILDPDTGDSLPRNKPGEICIRGNQIMKGYLNDPLATASTIDKDGWLHTGDVGFIDDDDELFIVDRLKELIKY
KGFQVAPAELESLLIGHPEINDVAVVAMKEEDAGEVPVAFVVRSKDSNISEDEIKQFVSKQVVFYKRINKVFFTDS
IPKAPSGKILRKDLRARLANGLMN

SEQ ID NO:4    Protein sequence from stilbene synthase (STS) *Vitis pseudoreticulata*
MASVEEIRNAQRAKGPATILAIGTATPDHCVYQSDYADYYFRVIKSEHMTALKKKENRICDKSMIKKRYIHLTEEM
LEEHPNIGAYMAPSLNIRQEIITAEVPKLGKEAALKALKEWGQPKSKITHLVECTTSGVEMPGADYKLANLLGLEP
SVRRVMLYHQGCYAGGTVLRTTKDLAENNAGARVLVVCPEITVVTFRGPSEDALDSLVGQALFGDGSAAVIVGSDP
DISIERPLFQLVSAAQTFIPNFAGAIAGNLREVGLIFHLWPNVPTLISENIENCLTQAFDPLGISDWNSLFWIAHP
GGPAILDAVEAKLNLDKKKLEATRHVLSEYGNVSSACVLFILDEMRKKSLKGERATTGEGLGWGVLFGEGPGLTIE
TVVLHSIPMVTN SEQ ID NO: 5    Protein sequence from NADPH: cytochrome P450 reductase (CPR) of *Arabidopsis thaliana* ATR2

MSSSSSSSTSMIDLMAAIIKGEPVIVSDPANASAYESVAAELSSMLIENRQFAMIVTTSIAVLIGCIVMLVWRRSG
SGNSKRVEPLKPLVIKPREEEIDDGRKKVTIFFGTQTGTAEGFAKALGEEAKARYEKTRFKIVDLDDYAADDDEYE
EKLKKEDVAFFFLATYGDGEPTDNAARFYKWFTEGNDRGEWLKNLKYGVFGLGNRQYEHENKVAKVVDDILVEQGA
QRLVQVGLGDDDQCIEDDFTAWREALWPELDTILREEGDTAVATPYTAAVLEYRVSIHDSEDAKENDINMANGNGY
TVFDAQHPYKANVAVKRELHTPESDRSCIHLEFDIAGSGLTYETGDHVGVLCDNLSETVDEALRLLDMSPDTYFSL
HAEKEDGTPISSSLPPPFPPCNLRTALTRYACLLSSPKKSALVALAAHASDPTEAERLKHLASPAGKDEYSKWVE
SQRSLLEVMAEFPSAKPPLGVFFAGVAPRLQPRFYSISSSPKIAETRIHVTCALVYEKMPTGRIHKGVCSTWMKNA
VPYEKSENCSSAPIFVRQSNFKLPSDSKVPIIMIGPGTGLAPERGELQERLALVESGVELGPSVLEFGCRNRRMDF
IYEEELQRFVESGALAELSVAFSREGPTKEYVQHKMMDKASDIWNMISQGAYLYVCGDAKGMARDVHRSLHTIAQE
QGSMDSTKAEGFVKNLQTSGRYLRDVW

SEQ ID NO: 6    DNA sequence encoding chalcone synthase (CHS2) of *Hordeum vulgare*, codon optimized for expression in *S. cerevisiae*
ATGGCTGCAGTAAGATTGAAAGAAGTTAGAATGGCACAGAGGGCTGAAGGTTTAGCTACAGTTTTAGCAATCGGTA
CTGCCGTTCCAGCTAATTGTGTTTATCAAGCTACCTATCCAGATTATTATTTTAGGGTTACTAAAAGTGAGCACTT
GGCAGATTTAAAGGAGAAGTTTCAAAGAATGTGTGACAAATCAATGATTAGAAAGAGACACATGCACTTGACCGAG
GAAATATTGATCAAGAACCCAAAGATCTGTCACACATGGAGACCTCATTGGATGCTAGACACGCCATCGCATTAG
TTGAAGTTCCCAAATTGGGCCAAGGTGCAGCTGAGAAGGCCATTAAGGAGTGGGGCCAACCCTTGTCTAAGATTAC
TCATTTGGTATTTTGCACAACATCCGGCGTTGACATGCCCGGTGCTGATTACCAATTAACAAAGTTGTTAGGTTTG
TCCCCTACAGTCAAAAGGTTAATGATGTACCAACAAGGTTGCTTTGGTGGTGCAACTGTTTTGAGATTGGCAAAAG TABLE 1-continued Nucleic acid and amino acid sequences.

ATATCGCTGAAAATAATAGAGGTGCCAGAGTGTTAGTCGTTTGTTCCGAGATAACTGCTATGGCCTTCAGAGGTCC
ATGCAAGAGTCATTTAGATTCCTTGGTAGGTCATGCCTTGTTCGGTGATGGTGCCGCTGCTGCAATTATAGGCGCT
GACCCAGACCAATTAGACGAACAACCAGTTTTCCAGTTGGTATCAGCTTCTCAGACTATATTACCAGAATCAGAAG
GTGCCATAGATGGCCATTTAACAGAAGCTGGTTTAACTATACATTTATTAAAAGATGTTCCTGGTTTAATTTCAGA
GAACATTGAACAGGCTTTGGAGGATGCCTTTGAACCTTTAGGTATTCATAACTGGAATTCAATTTTCTGCATTGCA
CATCCTGGTGGCCCTGCCATTTTAGACAGAGTTGAAGATAGATAGGATTGGATAAGAAGAGAATGAGGGCTTCTA
GGGAAGTGTTATCTGAATACGGAAATATGTCTAGTGCCTCTGTGTTGTTTGTGTTAGATGTCATGAGGAAAAGTTC
TGCTAAAGACGGATTGGCAACCACAGGAGAAGGAAAAGATTGGGGAGTGTTGTTTGGATTCGGACCAGGCTTGACT
GTAGAAACCTTAGTGTTGCATAGTGTCCCAGTCCCTGTCCCTACTGCAGCTTCTGCATGA

SEQ ID NO: 7    Protein sequence of CHS2 from Hordeum vulgare
MAAVRLKEVRMAQRAEGLATVLAIGTAVPANCVYQATYPDYYFRVTKSEHLADLKEKFQRMCDKSMIRKRHMHLTE
EILIKNPKICAHMETSLDARHAIALVEVPKLGQGAAEKAIKEWGQPLSKITHLVFCTTSGVDMPGADYQLTKLLGL
SPTVKRLMMYQQGCFGGATVLRLAKDTAENNRGARVLVVCSEITAMAFRGPCKSHLDSLVGHALFGDGAAAAIIGA
DPDQLDEQPVFQLVSASQTILPESEGAIDGHLTEAGLTIHLLKDVPGLISENTEQALEDAFEPLGIHNWNSIFWIA
HPGGPAILDRVEDRVGLDKKRMRASREVLSEYGNMSSASVLEVLDVMRKSSAKDGLATTGEGKDWGVLFGEGPGLT
VETLVLHSVPVPVPTAASA SEQ ID NO: 8    DNA sequence encoding chalcone isomerase A (CHI-A) of Petunia
                hybrida
ATGTCTCCACCAGTTTCTGTTACAAAAATGCAAGTCGAAAATTATGCTTTTGCACCAACAGTGAACCCTGCCGGTT
CCACCAATACTTTGTTCTTAGCTGGAGCAGGCCATAGAGGTCTAGAGATTGAAGGAAAGTTTGTGAAATTCACAGC
CATAGGCGTATACCTTGAGGAAAGTGCTATCCCATTTTTGGCAGAAAAGTGGAAAGGTAAGACCCCTCAGGAGTTA
ACTGATAGCGTCGAGTTCTTTAGGGACGTGGTTACAGGTCCATTCGAAAAGTTTACCAGAGTAACTATGATTCTAC
CTCTTACAGGAAAGCAATATTCTGAGAAAGTCGCCGAAAACTGTGTTGCTCACTGGAAGGGCATAGGTACCTACAC
TGATGACGAAGGAAGGGCAATCGAGAAATTCTTGGATGTGTTTAGATCAGAAACATTCCCACCTGGTGCTTCCATT
ATGTTTACTCAGAGTCCATTAGGCTTGTTAACCATCAGCTTTGCCAAGGACGATTCAGTTAGGGGTACTGCAAATG
CTGTAATCGAGAACAAACAACTATCAGAAGCCGTCCTTGAATCCATTATTGGAAAGCATGGTGTGAGTCCTGCAGC
CAAATGCTCTGTTGCCGAGAGAGTAGCAGAATTGTTGAGCTATGCTGAAGAGGCCTCAGTGTTCGGCAAA
CCAGAAACCGAAAAGTCCACAATACCTGTTATCGGTGTGTAG SEQ ID NO: 9    Protein sequence of CHI-A (CHI1) from Petunia hybrida
MSPPVSVTKMQVENYAFAPTVNPAGSTNTLFLAGAGHRGLEIEGKFVKFTAIGVYLEESAIPFLAEKWKGKTPQEL
TDSVEFFRDVVTGPFEKFTRVTMILPLTGKQYSEKVAENCVAHWKGIGTYTDDEGRAIEKELDVERSETFPPGASI
MFTQSPLGLLTISFAKDDSVTGTANAVIENKQLSEAVLESIIGKHGVSPAAKCSVAERVAELLKKSYAEEASVFGK
PETEKSTIPVIGV SEQ ID NO: 10   DNA sequence encoding chalcone isomerase B (CHI-B) of Petunia
                hybrida
ATGTCTCCATCTGTTTCTGTTACTAAAGTCCAAGTGGAAAATTATGTCTTTCCTCCAACAGTGAAGCCTCCAGCTA
GTACCAAAACTTTGTTCTTAGGTGGAGCAGGCCATAGAGGTCTAGATGTTGAGGGAAAGTTTGTGAAATTCACAGT
TATTGGCGTATACCTTGAAGAGAGCGCCGTCCAGTTTTTGGCTCCTAAGTGGAAAGGTAAGTCTGCAGAAGAATTA
ATACACTCAGTTGACTTCTTTAGGGATATCGTGACCGGTCCATTCGAGAAGTTTACTAGAGTTAGGTTCATTCTAC
CTCTTACAGGAAAGCAATTTTCCGAAAAGTAGCCGAAAACTGTGTCGCTCATTGGAAGGCAACCGGCACTTATAG
TGACGCCGGTAGCAGAGCTATAGAGAAATTCTTGAATGTGGTTAAGTCTGAAACATTTTTACCAGGAGCATCAATC
TTGTTTACCCAGTCCCCTTTAGGTAGTCTAACTATTTCTTTCACAAAAGATGACAGCATATCCGAAGCTGGCAACG
CCGTAATCGAGAACAAACAGTTTAGTGAGGCCGTCCTTGAGACTATTATTGGTGAACACGGAGTTAGTCCAGCTGC
CAAGTGCTCTATAGCAGCTAGAATGTCAGAATTGTTCAAAAACAGCTTATTTTGA SEQ ID NO: 11   Protein sequence of CHI-B (CHI2) from Petunia hybrida
MSPSVSVTKVQVENYVETPTVKPPASTKTLFLGGAGHRGLDVEGKFVKFTVIGVYLEESAVQFLAPKWKGKSAEEL
IHSVDFFRDIVTGPFEKETRVRFILPLTGKQFSEKVAENCVAHWKATGTESDAGSRAIEKFLNVVKSETFLPGASI
LFTQSPLGSLTISFTKDDSISEAGNAVIENKQFSEAVLETIIGEHGVSPAAKCSIAARMSELEKNSLF SEQ ID NO: 12   DNA sequence encoding phenylalanine ammonia lyase 1 (PAL1) from
                Arabidopsis thaliana codon optimized for expression in S. cerevisiae
ATGGAGATTAACGGGGCACACAAGAGCAACGAGGAGGAGTGGACCTATGTTATGCGGCGGAGACATCAAGACAA
AGAACATGGTGATCAACGCGGAGGATCCTCTCAACTGGGGAGCTGCAGCGGAGCAAATGAAAGGTAGCCATTTGGA
TGAAGTGAAGAGAATGGTTGCTGAGTTTAGGAAGCCAGTTGTGAATCTTGGTGGTGAGACTCTGACCATTGGACAA
GTGGCTGCGATCTCAACTATTGGTAACAGTGTGAAGGTGGAGCTATCGGAGACAGCTAGAGCCGGTGTGAATGCTA
GTAGTGATTGGGTTATGGAGAGTATGAACAAAGGCACTGATAGTTATGGTGTTACTACTGGTTTTGGTGCTACTTC
TCATCGGAGAACCAAAACGGTGTCGCACTTCAGAAGGAACTTATTAGATTCCTTAACGCCGGAATATTCGGAAGC
ACGAAAGAAACAAGCCACACATTGCCACACTCCGCCACAAGAGCCGCCATGCTTGTACGAATCAACACTCTCCTCC
AAGGATTTTCCGGTATCCGATTTGAGATTCTCGAAGCAATTACCAGTTTCCTCAACAACAACATCACTCCATCTCT
CCCCCTCCGTGGTACAATCACCGCCTCCGGAGATCTCGTTCCTCTCTCACATCGCCGGACTTCTCACCGGTCGT
CCCAATTCCAAAGCTACTGGTCCCAACGGTGAAGCTTTAACAGCAGAGGAAGCTTTCAAATTAGCAGGAATCAGCT
CCGGATTCTTTGATCTCCAGCCTAAGGAAGGTCTCGCGCTAGTCAATGGCACGGCGGTTGGATCTGGAATGGCGTC
AATGGTGTTATTCGAAACGAATGTTCTCTCTGTTTTGGCTGAGATTTGTCGGCGGTTTTCGCAGAGGTGATGAGT
GGTAAGCCTGAGTTCACCGATCATCTCACTCACAGACTTAAACATCATCCCGGTCAAATCGAAGCGGCGGCGATAA
TGGAGCATATCCTCGACGGAAGCTCGTACATGAAATTAGCTCAGAAGCTTCACGAGATGGATCCGTTACAGAAACC
TAAACAAGATCGTTACGCTCTTCGTACTTCTCCTCAATGGTTAGGTCCTCAAATCGAAGTGATCCGTTACGCAACG
AAATCGATCGAGCGTGAGATTAACTCCGTAACGATAATCCGTTGATCGATGTTTCGAGGAACAAGGCGATTCACG
GTGGTAACTTCCAAGGAACACCAATCGGAGTTTCAATGGATAACACCAGATTGGCCATAGCAGCGATTGGTAAACT
CATGTTTGCTCAATTCTCAGAGCTTGTGAATGATTTCTACAACAATGGTTTACCCTCGAATCTAACCGCTTCGAGG
AATCCAAGTTTGGATTATGGATTCAAGGGAGCTGAGATTGCAATGGCTTCTTATTGTTCAGAGCTTCAATACTTAG
CTAATCCTGTGACTAGCCATGTTCAATCAGCAGAGCAACATAACCAAGATGTCAACTCTTTGGGACTAATCTCGTC
TCGCAAAACTTCTGAAGCTGTTGATATTCTCAAGCTTATGTCAACAACGTTCCTCGTTGCGATTTGTCAAGCTGTG
GATTTGAGACATTTGGAGGAGAATTTGAGACAGACTGTGAAGAACACTGTCTCTCAAGTGGCGAAGAAAGTTCTTA TABLE 1-continued Nucleic acid and amino acid sequences.

```
CTACTGGAGTCAATGGTGAGCTTCATCCTTCTCGCTTCTGCGAAAAGGATTTACTCAAAGTTGTAGACCGTGAACA
AGTCTACACATACGCGGATGATCCTTGTAGCGCAACGTACCCGTTGATTCAGAAGCTGAGACAAGTTATTGTTGAC
CATGCTTTGATCAATGGTGAGAGTGAGAAGAATGCAGTGACTTCAATCTTCCATAAGATTGGAGCTTTCGAGGAGG
AGCTTAAGGCAGTGCTACCGAAAGAAGTGGAAGCAGCAAGAGCAGCCTACGATAACGGAACATCGGCTATCCCGAA
CAGGATCAAGGAATGTAGGTCGTATCCATTGTATAGATTCGTGAGGGAAGAGCTTGGAACAGAGCTTTTGACCGGA
GAGAAAGTGACGTCGCCTGGAGAAGAGTTCGACAAGGTTTTCACGGCGATTTGTGAAGGTAAAATCATTGATCCGA
TGATGGAATGTCTCAACGAGTGGAACGGAGCTCCCATTCCAATATGTTAA

SEQ ID NO: 13    Protein sequence of PAL1 from Arabidopsis thaliana
MEINGAHKSNGGGVDAMLCGGDIKTKNMVINAEDELNWGAAAEQMKGSHEDEVKRMVAEFRKPVVNEGGETLTIGQ
VAAISTIGNSVKVELSETARAGVNASSDWVMESMNKGTDSYGVTTGFGATSHRRTKNGVALQKELIRELNAGIFGS
TKETSHTLPHSATRAAMLVRINTLLQGFSGIRFEILEAITSFLNNNITPSLPLRGTITASGDINPLEYIAGELTGR
PNSKATGPNGEALTAEEAFKLAGISSGEFDLQPKEGLALVNGTAVGSGMASMVEFETNVLSVLAEILSAVFAEVMS
GKPEFTDHLTHRLKHHPGQIEAAATMEHILDGSSYMKLAQKLHEMDPLQKPKQDRYALRTSPQWEGPQIEVIRYAT
KSIEREINSVNDNPLIDVSRNKAIHGGNFQGTPIGVSMDNTRLAIAAIGKLMFAQFSELVNDFYNNGLPSNLTASR
NPSEDYGFKGAEIAMASYCSELQYLANPVTSHVQSAEQHNQDVNSLGLISSRKTSEAVDILKLMSTTFLVAICQAV
DLRHLEENLRQTVKNTVSQVAKKVETTGVNGELHPSRECEKDELKVVDREQVYTYADDPCSATYPLIQKLRQVIVD
HALINGESEKNAVTSIFHKIGAFEEELKAVLPKEVEAARAAYDNGTSAIPNRIKECRSYPLYRFVREELGTELLTG
EKVTSPGEEFDKVFTAICEGKIIDPMMECLNEWNGAPIPIC SEQ ID NO: 14    DNA sequence encoding phenylalanine ammonia lyase 2 (PAL2) from
                 Arabidopsis thaliana codon optimized for expression in S. cerevisiae
ATGGACCAAATTGAAGCAATGCTATGCGGTGGTGGTGAAAAGACCAAGGTGGCCGTAACGACAAAAACTCTTGCAG
ATCCTTTGAATTGGGGTCTGGCAGCTGACCAGATGAAAGGTAGCCATCTGGATGAAGTTAAGAAGATGGTTGAGGA
ATACAGAAGACCAGTCGTAAATCTAGGCGGCGAGACATTGACGATAGGACAGGTAGCTGCTATTTCGACCGTTGGC
GGTTCAGTGAAGGTAGAACTTGCAGAAACAAGTAGAGCCGGAGTTAAGGCTTCATCAGATTGGGTCATGGAAAGTA
TGAACAAGGGCACAGATTCCTATGGCGTTACCACAGGCTTTGGTGCTACCTCTCATAGAAGAACTAAAAATGGCAC
TGCTTTGCAAACAGAACTGATCAGATTCCTTAACGCCGGTATTTTCGGTAATACAAAGGAAACTTGCCATACATTA
CCCCAATCGGCAACAAGAGCTGCTATGCTTGTTAGGGTGAACACTTTGTTGCAAGGTTACTCTGGAATAAGGTTTG
AAATTCTTGAGGCCATCACTTCACTATTGAACCACAACATTTCTCCTTCGTTGCCCTTAAGAGGAACAATAACTGC
CAGCAGTGATTTGGTTCCCCTTTCATATATCGCAGGCTTATTAACGGGAAGACCTAATTCAAAGGCCACTGGTCCA
GACGGAGAATCCTTAACCGCTAAGGAAGCATTTGAGAAAGCTGGTATTTCAACTGGTTTCTTTGATTTGCAACCCA
AGGAAGGTTTAGCCCTGGTGAATGGCACCGCTGTCGGCAGCGGTATGGCATCCATGGTGTTGTTTGAAGCTAACGT
ACAAGCAGTTTTGGCCGAAGTTTTGTCCGCAATTTTTGCCGAAGTCATGAGTGGAAAACCTGAGTTTACTGATCAC
TTGACCCACAGGTTAAAACATCACCCAGGACAAATTGAAGCAGCAGCTATCATGGAGCACATTTTGGACGGCTCTA
GCTACATGAAGTTAGCCCAGAAGGTTCATGAAATGGACCCTTTGCAAAAACCCAAACAAGATAGAATATGCTTTAAG
GACATCCCCACAATGGCTTGGCCCTCAAATTGAAGTAATTAGACAAGCTACAAAGTCTATAGAAAGAGAGATCAAC
TCTGTTAACGATAATCCACTTATTGATGTGTCGAGGAATAAGGCAATACATGGAGGCAATTTCCAGGGTACACCCA
TAGGAGTCAGTATGGATAATACCAGGCTTGCCATAGCCGCAATTGGCAAATTAATGTTTGCCCAATTTTCTGAATT
GGTCAATGACTTCTACAATAACGGTTTGCCTTCGAATCTGACCGCATCTTCTAACCCTAGTCTTGATTATGGTTTC
AAAGGTGCTGAGATAGCAATGGCAAGCTATTGTTCAGAGCTGCAATATCTAGCCAACCCAGTAACCTCTCATGTAC
AATCAGCCGAACAACACAATCAGGATGTTAATTCTTTGGGCCTGATTTCATCAAGAAAAACAAGCGAGGCCGTTGA
TATCCTTAAATTAATGTCCACAACATTTTTAGTGGGTATATGCCAGGCCGTAGATTTGAGACACTTGGAAGAGAAT
TTGAGACGACAGTGAAAAATACCGTATCACAGGTTGCAAAAAAGGTTCTAACTACAGGTATCAATGGTGAGCTTGC
ACCCATCAAGATTCTGTGAAAAAGATTTATTAAAAGTTGTAGATAGAGAACAAGTATTTACTTACGTTGACGATCC
ATGTAGCGCTACTTATCCATTGATGCAGAGATTGAGACAAGTTATTGTAGATCACGCTTTATCCAATGGTGAAACT
GAGAAAAATGCCGTTACTTCAATATTCCAAAAGATAGGTGCCTTTGAAGAAGAACTGAAGGCAGTTTTACCAAAGG
AAGTCGAAGCTGCTAGAGCCCGCATACGGAAATGGTACTGCCCCTATACCAAATAGAATCAAAGAGTGTAGGTCGTA
CCCTTTGTACAGATTCGTTAGAGAAGAGTTGGGAACCAAATTACTAACTGGTGAAAAGTCGTTAGCCCAGGTGAA
GAATTTGACAAGGTATTCACAGCTATGTGCGAGGGAAAGTTGATAGATCCACTTATGGATTGCTTGAAAGAGTGGA
ATGGTGCACCTATTCCAATCTGCTAA SEQ ID NO: 15    Protein sequence of PAL2 from Arabidopsis thaliana
MDQIEAMLCGGGEKTKVAVTTKTLADPLNWGLAADQMKGSHLDEVKKMVEEYRRPVVNLGGETLTIGQVAAISTVG
GSVKVELAETSRAGVKASSDWVMESMNKGTDSYGVTTGFGATSHRRTKNGTALQTELIRFLNAGIFGNTKETCHTL
PQSATRAAMLVRVNTLLQGYSGIRFEILEAITSLLNHNISPSLPLRGTITASGDINPLSYIAGELTGRPNSKATGP
DGESLTAKEAFEKAGISTGFFDLQPKEGLALVNGTAVGSGMASMVLFEANVQAVLAEVLSAIFAEVMSGKPEFTDH
LTHRLKHHPGQIEAAAIMEHILDGSSYMKLAQKVHEMDPLQKPKQDRYALRTSPQWEGPQIEVIRQATKSIEREIN
SVNDNPLIDVSRNKAIHGGNFQGTPIGVSMDNTRLAIAAIGKLMFAQFSELVNDFYNNGLPSNLTASSNPSLDYGF
KGAEIAMASYCSELQYLANPVTSHVQSAEQHNQDVNSLGLISSRKTSEAVDILKLMSTTELVGICQAVDERHLEEN
LRQTVKNTVSQVAKKVETTGINGELHPSRECEKDLLKVVDREQVFTYVDDPCSATYPLMQRLRQVIVDHALSNGET
EKNAVTSIFQKIGAFEEELKAVLPKEVEAARAAYGNGTAPIPNRIKECRSYPLYREVREELGTKELTGEKVVSPGE
EFDKVETAMCEGKLIDPLMDCLKEWNGAPIPIC SEQ ID NO: 16    DNA sequence encoding phenylalanine ammonia lyase/tyrosine
                 ammonia lyase (PAL/TAL) from Rhodosporidium toruloides codon
                 optimized for expression in S. cerevisiae
ATGGCTCCATCATTGGATTCTATTTCTCATTCTTTTGCAAACGGTGTTGCATCTGCAAACAAGCTGTTAATGGTG
CATCTACTAATTTGGCAGTTGCTGGTTCTCATTTACCAACTACCCAAGTTACACAAGTTGATATTGTTGAAAAGAT
GTTAGCAGCACCTACTGATTCTACCTTGGAATTGGATGGTTACTCTTTAAATTTAGGTGATGTTGTTTCTGCAGCT
AGAAAGGGTAGACCAGTTAGAGTTAAAGATTCTGATGAAATTAGATCTAAAATTGATAAATCTGTTGAATTTTTGA
GATCTCAATTATCAATGTCAGTTTATGGTGTTACAACTGGTTTCGGTGGTTCAGCTGATACTAGAACTGAAGATGC
AATTTCTTTACAAAAGGCATTGTTGGAACATCAATTATGTGGTGTTTTGCCTTCATCATTCGATTCTTTTAGATTA
GGTAGAGGTTTAGAAAACTCTTTGCCATTAGAAGTTGTTAGAGGTGCAATGACAATTAGAGTTAATTCTTTAACAA
GAGGTCATTCTGCTGTTAGATTGGTTGTTTTAGAAGCTTTGACTAACTTTTTGAACCATGGTATTACTCCAATTGT
TCCATTAAGAGGTACAATTTCTGCATCTGGTGATTTGTCTCCTTTGTCTTATATTGCAGCTGCTATTTCAGGTCAT
CCAGATTCAAAGGTTCATGTTGTTCATGAAGGTAAGGAAAAGATTTTATATGCAAGAGAAGCTATGGCTTTATTTA
ATTTAGAACCAGTTGTTTTAGGTCCTAAGGAAGGTTTAGGTTTAGTTAACGGTACAGCTGTTTCAGCATCTATGGC
```

TABLE 1-continued

Nucleic acid and amino acid sequences.

```
TACCTTAGCTTTGCATGATGCTCATATGTTATCTTTGTTATCTCAATCATTAACAGCTATGACTGTTGAAGCTATG
GTTGGTCATGCTGGTTCTTTTCATCCATTCTTGCATGATGTTACCAGACCTCATCCAACACAAATTGAAGTTGCTG
GTAATATTAGAAAGTTGTTAGAAGGTTCTAGATTCGCAGTTCATCATGAAGAAGAAGTTAAAGTTAAGGATGATGA
AGGTATTTTGAGACAAGATAGATACCCATTGAGAACTTCACCACAATGGTTGGGTCATTGGTTTCTGATTTGATT
CATGCTCATGCAGTTTTGACCATTGAAGCAGGTCAATCTACAACAGATAATCCATTGATTGATGTTGAAAACAAAA
CATCACATCATGGTGGTAATTTTCAAGCAGCTGCTGTTGCTAATACAATGGAAAAGACAAGATTAGGTTTGGCACA
AATTGGTAAGTTAAATTTCACACAATTAACTGAAATGTTGAATGCAGGTATGAATAGAGGTTTGCCATCTTGTTTG
GCAGCTGAAGATCCTTCATTATCTTATCATTGTAAAGGTTTGGATATTGCAGCAGCAGCTTATACTTCAGAATTAG
GTCATTTAGCAAATCCAGTTACTACACATGTTCAACCAGCTGAAATGGCTAATCAAGCTGTTAATTCTTTAGCATT
GATTTCAGCTAGAAGAACCACTGAATCAAACGATGTTTTGTCATTATTATTAGCTACTCATTTATATTGTGTTTTA
CAAGCTATTGATTTGAGAGCAATTGAATTTGAATTTAAAAAGCAATTTGGTCCAGCTATTGTTTCATTAATTGATC
AACATTTTGGTTCTGCAATGACTGGTTCAAATTTGAGAGATGAATTAGTTGAAAAGGTTAACAAGACCTTGGCTAA
AAGATTAGAACAAACTAACTCTTACGATTTGGTTCCAAGATGGCATGATGCTTTTTCTTTTGCTGCAGGTACAGTT
GTTGAAGTTTTGTCATCTACCTCATTGTCTTTGGCAGCTGTTAACGCTTGGAAAGTTGCTGCTGCTGAATCAGCTA
TTTCATTAACTAGACAAGTTAGAGAAACTTTTTGGTCTGCTGCTTCAACTTCTTCAACTTGCTTTGTCTTACTTGTC
TCCAAGAACTCAAATTTTGTACGCTTTCGTTAGAGAAGAATTGGGTGTTAAAGCTAGAAGAGGTGATGTTTTCTTA
GGTAAGCAAGAAGTTACTATTGGTTCTAATGTTTCTAAAATTTACGAAGCTATTAAATCAGGTAGAATTAATAACG
TTTTGTTGAAGATGTTAGCATAA
```

SEQ ID NO: 17    Protein sequence of PAL/TAL from Rhodosporidium toruloides
MAPSLDSISHSFANGVASAKQAVNGASTNLAVAGSHLPTTQVTQVDIVEKMLAAPTDSTLELDGYSLNLGDVVSAA
RKGRPVRVKDSDEIRSKIDKSVEFLRSQLSMSVYGVTTGEGGSADTRTEDAISLQKALLEHQLCGVLPSSEDSFRL
GRGLENSLPLEVVRGAMTIRVNSLTRGHSAVRLVVLEALTNELNHGITPIVPLRGTISASGDLSPLSYTAAAISGH
PDSKVHVVHEGKEKILYAREAMALFNLEPVVLGPKEGLGLVNGTAVSASMATLALHDAHMLSLLSQSLTAMTVEAM
VGHAGSFHPFLHDVTRPHPTQIEVAGNIRKLLEGSRFAVHHEEEVKVKDDEGILRQDRYPLRTSPQWLGPLVSDLI
HAHAVLTIEAGQSTTDNPLIDVENKTSHHGGNFQAAAVANTMEKTRLGLAQIGKLNFTQLTEMLNAGMNRGLPSCL
AAEDPSLSYHCKGLDIAAAAYTSELGHLANPVTTHVQPAEMANQAVNSLALISARRTTESNDVLSLLLATHLYCVL
QATDLRAIEFEFKKQFGPAIVSLIDQHFGSAMTGSNLRDELVEKVNKTLAKRLEQTNSYDLVPRWHDAFSFAAGTV
VEVLSSTSLSLAAVNAWKVAAAESAISLTRQVRETEWSAASTSSPALSYLSPRTQILYAFVREELGVKARRGDVFL
GKQEVTIGSNVSKIYEAIKSGRINNVLLKMLA SEQ ID NO: 18    DNA sequence encoding tyrosine ammonia lyase (TAL) from
                 Rhodobacter capsulatus codon optimized for expression in S.
                 cerevisiae (Fluxome)
```
ATGACCCTGCAATCTCAAACAGCTAAAGATTGTTTGGCTTTGGATGGTGCCTTGACATTAGTTCAATGCGAAGCGA
TAGCAACCCATAGAAGTAGAATCTCTGTAACACCAGCCCTACGTGAGAGATGTGCTAGAGCACATGCTAGGTTAGA
ACATGCAATAGCCGAACAGCGACACATATATGGGATAACGACAGGCTTCGGGCCACTTGCTAACAGGCTGATCGGA
GCAGACCAGGGTGCTGAATTACAACAGAACCTTATCTACCATTTGGCAACCGGAGTTGGCCCCAAATTATCATGGG
CCGAAGCCAGAGCTTTAATGCTCGCTCGTTTGAATAGTATACTACAAGGTGCTTCTGGTGCTAGCCCTGAAACAAT
TGATAGGATCGTTGCAGTCTTAAATGCCGGATTTGCCCCGGAAGTCCCAGCCCAAGGAACCGTTGGTGCTTCGGGT
GACTTAACTCCGTTAGCACACATGGTATTAGCATTGCAAGGCAGAGGTCGTATGATTGATCCTTCAGGGAGAGTTC
AAGAAGCCGGCGCTGTCATGGATAGGTTGTGTGGAGGCCCTTTAACATTCCCTGCCAGAGATGGCCTCGCCTTACT
AAATGGTACATCTGCCATGACAGCTATTGCCGCATTGACCGGTGTGGAGGCTGCAAGAGCGATTGATGCAGCGCTT
AGACATTCCGCAGTCTTGATGGAGGTCCTGTCAGGGCATGCTGAGGCTTGGCACCCTGCCTTTGCGGAATTGCGIC
CGCATCCAGGACAATTACGCGCCACTGAGAGGTTAGCTCAAGCATTGGACGGCGCAGGTAGAGTCTGCCGGACTCT
TACAGCCGCTAGGCGTCTAACTGCAGCTGATCTGAGACCAGAAGATCATCCAGCTCAAGATGCATATTCACTTCGA
GTAGTTCCTCAGCTGGTTGGTGCCGTATGGGATACGTTGGATTGGCACGACAGGGTTGTGACTTGCGAACTTAACT
CCGTGACCGACAATCCAATTTTCCCCGAGGGTTGTGCGGTTCCAGCACTACACGGTGGAAACTTTATGGGCGTACA
TGTGGCACTAGCTTCTGACGCTTTAAATGCAGCGTTGGTTACATTAGCTGGTCTAGTTGAAAGGCAGATTGCAAGA
CTTACTGATGAGAAGTTGAATAAGGGTTTGCCTGCTTTTTTGCATGGAGGCCAAGCAGGTTTACAATCAGGTTTCA
TGGGAGCTCAGGTTACTGCTACTGCTTTGCTAGCGGAAATGAGAGCTAACGCGACTCCCGTGTCCGTTCAAAGCCT
CAGCACCAATGGTGCAAATCAAGACGTGGTAAGTATGGGTACGATTGCCGCGAGACGAGCAAGAGCTCAACTTTTA
CCTCTGTCTCAAATCCAAGCGATTTTGGCACTCCCTCTTGCACAAGCCATGGATCTTCCTAGACGATCCTGAAGGAC
AAGCCGGTTGGTCCTTAACGGCAAGAGATTTAAGAGACCGTATACGGGCTGTCAGTCCAGGGTTGCGCGCAGATAG
ACCACTAGCGGGTCATATTGAAGCTGTGGCTCAAGGTCTAAGACACCCCTCGGCAGCTGCCGATCCACCTGCTTAA
```

SEQ ID NO: 19    Protein sequence of TAL from Rhodobacter capsulatus (Fluxome)
MTLQSQTAKDCLALDGALTLVQCEAIATHRSRISVTPALRERCARAHARLEHAIAEQRHIYGITTGFGPLANRLIC
ADQGAELQQNLIYHLATGVGPKLSWAEARALMLARLNSILQGASGASPETIDRIVAVLNAGFAPEVPAQGTVGASG
DLTPLAHMVLALQGRGRMIDPSGRVQEAGAVMDRLCGGPLTLAARDGLALVNGTSAMTAIAALTGVEAARAIDAAL
RHSAVLMEVLSGHAEAWHPAFAELRPHPGQLRATERLAQALDGAGRVCRTLTAARRLTAADLRPEDHPAQDAYSLR
VVPQLVGAVWDTLDWHDRVVTCELNSVTDNPIFPEGCAVPALHGGNFMGVHVALASDALNAALVTLAGLVERQIAR
LTDEKLNKGLPAELHGGQAGLQSGFMGAQVTATALLAEMRANATPVSVQSLSTNGANQDVVSMGTIAARRARAQLL
PLSQIQATLALALAQAMDLLDDPEGQAWSLTARDLRDRIRAVSPGLRADRPLAGHIEAVAQGLRHPSAAADPPA SEQ ID NO: 20    DNA sequence encoding tyrosine ammonia lyase (TAL) from
                 Rhodobacter capsulatus codon optimized for expression in S.
                 cerevisiae (see Koopman, F. et al. (2012))
```
ATGACCTTACAATCCCAAACTGCCAAAGACTGCTTAGCCTTAGACGGTGCCTTGACCTTGGTTCAATGTGAAGCAA
TTGCCACACATAGATCCAGAATAAGTGTCACCCCAGCTTTGAGAGAAAGATGCGCTAGAGCACATGCCAGATTAGA
ACACGCTATTGCAGAACAAAGACACATCTATGGTATAACTACAGGTTTTGGTCCTTTGGCTAATAGATTAATAGGT
GCCGATCAAGGTGCTGAATTGCAACAAAACTTAATCTACCATTTGGCTACTGGTGTTGGTCCAAAATTGTCTTGGG
CCGAAGCTAGAGCATTGATGTTGGCAAGATTGAACTCAATCTTGCAAGGTGCATCTGGTGCCTCACCTGAAACAAT
CGACAGAATTGTTGCTGTCTTAAACGCTGGTTTCGCACCAGAAGTCCCTGCCCAAGGTACTGTAGGTGCTTCCGGT
GACTTGACACCATTGGCACATATGGTTTTGGCCTTACAAGGTAGAGGTAGAATGATTGATCCTAGTGGTAGAGTTC
AAGAAGCCGGTGCTGTCATGGACAGATTATGTGGTGGTCCATTGACTTTAGCTGCAAGAGATGGTTTGGCTTTAGT
TAATGGTACTTCTGCCATGACAGCTATCGCCGCTTTGACAGGTGTTGAAGCAGCCAGAGCTATTGATGCTGCATTA
AGACATTCCGCAGTATTAATGGAAGTTTTGAGTGGTCATGCAGAAGCCTGGCACCCAGCTTTTGCAGAATTGAGAC TABLE 1-continued Nucleic acid and amino acid sequences.

CACACCCTGGTCAATTAAGAGCTACCGAAAGATTAGCCCAAGCTTTGGATGGTGCAGGTAGAGTTTGCAGAACCTT
GACTGCCGCTAGAAGATTGACAGCAGCCGACTTAAGACCAGAAGATCATCCTGCACAAGACGCCTATTCTTTGAGA
GTTGTCCCACAATTAGTTGGTGCTGTCTGGGATACTTTGGACTGGCACGATAGAGTAGTTACCTGTGAATTGAACT
CAGTCACTGATAACCCAATATTTCCTGAAGGTTGCGCTGTACCTGCATTACATGGTGGTAATTTCATGGGTGTACA
CGTTGCATTGGCCTCCGACGCTTTAAACGCTGCATTAGTAACATTGGCTGGTTTAGTTGAAAGACAAATCGCAAGA
TTGACCGATGAAAAGTTGAATAAGGGTTTGCCAGCATTTTTGCATGGTGGTCAAGCAGGTTTACAATCAGGTTTCA
TGGGTGCTCAAGTTACAGCTACCGCATTGTTAGCAGAAATGAGAGCCAACGCTACCCCTGTCTCTGTACAATCTTT
GTCAACTAATGGTGCTAACCAAGATGTCGTATCAATGGGTACTATCGCCGCTAGAAGAGCAAGAGCCCAATTGTTG
CCATTGTCTCAAATCCAAGCAATCTTGGCTTTAGCATTGGCCCAAGCTATGGACTTGTTAGATGACCCTGAAGGTC
AAGCAGGTTGGTCCTTGACAGCCAGAGACTTAAGAGATAGAATTAGAGCTGTTAGTCCAGGTTTGAGAGCTGATAG
ACCTTTAGCAGGTCATATAGAAGCAGTCGCACAAGGTTTGAGACATCCATCCGCCGCAGCAGACCCTCCAGCCTAA

SEQ ID NO: 21    Protein sequence of TAL from *Rhodobacter capsulatus* (see
                 Koopman, F. et al, (2012))
MTLQSQTAKDCLALDGALTLVQCEATATHRSRISVTPALRERCARAHARLEHATAEQRHIYGITTGFGPLANRLIG
ADQGAELQQNLIYHLATGVGPKLSWAEARALMLARLNSILQGASGASPETIDRIVAVLNAGFAPEVPAQGTVGASG
DLTPLAHMVLALQGRGRMIDPSGRVQEAGAVMDRLCGGPLTLAARDGLALVNGTSAMTAIAALTGVEAARAIDAAL
RHSAVLMEVLSGHAEAWHPAFAELRPHPGQLRATERLAQALDGAGRVCRTLTAARRLTAADLRPEDHPAQDAYSLR
VVPQLVGAVWDTLDWHDRVVTCELNSVTDNPIFPEGCAVPALHGGNMVRDGSRPLQEPYSLRCAPQVLGAVLDQLDG
LTDEKLNKGLPAFLHGGQAGLQSGFMGAQVTATALLAEMRANATPVSVQSLSTNGANQDVVSMGTIAARRARAQLL
PLSQIQATLALALAQAMDLLDDPEGQAGWSLTARDLRDRIRAVSPGLRADRPLAGHIEAVAQGLRHPSAAADPPA SEQ ID NO: 22    DNA sequence encoding tyrosine ammonia lyase (TAL) (SAM8) from
                 *Saccharothrix espanaensis* codon optimized for expression in *S.
                 cerevisiae*
ATGACACAGGTAGTTGAAAGGCAGGCAGATAGGCTTAGTTCCAGGGAATATCTTGCCAGGGTCGTCAGGTCCGCTG
GTTGGGATGCTGGTTTGACTTCCTGTACTGATGAGGAAATCGTGAGAATGGGTGCTAGTGCCAGAACAATTGAAGA
GTACTTGAAGTCCGATAAACCTATATACGGCTTAACACAAGGATTTGGTCCACTTGTTCTATTTGATGCCGATAGT
GAATTAGAGCAAGGAGGTTCTTTAATCTCTCATCTAGGTACAGGCCAAGGTGCTCCTTTGGCCCCAGAAGTGTCAA
GACTAATCTTATGGTTGAGAATACAGAATATGAGAAAAGGTTATTCCGCAGTGTCACCTGTATTCTGGCAGAAGTT
AGCCGATCTATGGAATAAGGGTTTCACACCAGCTATTCCAAGGCACGGTACTGTCTCCGCATCTGGCGATTTGCAG
CCACTTGCTCATGCTGCTTTAGCATTCACTGGCGTTGGAGAAGCATGGACAAGAGATGCTGACGGCAGATGGAGCA
CTGTTCCTGCAGTAGACGCTTTGGCTGCTTTGGGTGCAGAACATTTGATTGGCCAGTTAGAGAGGCATTAGCTTTT
TGTTAATGGTACTGGCGCCTCATTGGCAGTAGCCGTGCTAAACCATAGGAGTGCTTTAAGATTAGTGAGAGCCTGT
GCCGTGTTGTCCGCAAGGTTAGCTCACATTGCTTGGTGCCAATCCTGAGCATTATGATGTAGGTCATGGCGTTGCAA
GAGGCCAAGTTGGTCAATTGACTGCAGCAGAATGGATCAGACAAGGTTTACCTAGAGGTATGGTCAGAGACGGAAG
TAGGCCATTGCAAGAACCATACTCCTTAAGATGTGCTCCTCAAGTTTTAGGTGCCGTTTTGGACCAGTTAGATGGA
GCTGGTGACGTATTAGCTAGGGAAGTCGACGGTTGTCAGGACAATCCTATAACTTACGAAGGAGAGTTGTTGCATG
GTGGTAATTTCCATGCAATGCCAGTTGGTTTCGCATCTGATCAAATAGGTTTAGCAATGCATATGGCCGCTTACTT
GGCAGAAAGGCAGCTTGGTTTATTAGTTAGCCCTGTTACAAACGGTGACCTTCCACCAATGTTAACCCCTAGGGCT
GGTAGAGGCGCAGGACTAGCAGGTGTGCAGATATCCGCTACCAGTTTTGTTAGTAGAATTAGGCAGTTGGTGTTTC
CTGCAAGCTTGACAACTTTGCCTACCAACGGATGAATCAAGATCACGTCCCAATGGCATTGAATGGCGCAAATTC
AGTATTCGAAGCCTTAGAGTTGGGATGGTTAACTGTTGGTAGCTTGGCAGTAGGTGTTGCCCAATTAGCCGCCATG
ACAGGTCACGCTGCTGAGGGTGTTTGGGCAGAACTTGCTGGTATTTGCCCTCCACTTGATGCTGATAGACCTTTGG
GAGCAGAAGTGAGGGCTGCTAGGGATCTTTTGTCTGCCCACGCTGATCAATTGTTAGTCGATGAAGCTGATGGAAA
AGACTTCGGATAATGA SEQ ID NO: 23    Protein sequence of TAL (SAM8) from *Saccharothrix espanaensis*
MTQVVERQADRLSSREYLARVVRSAGWDAGLTSCTDEEIVRMGASARTIEEYLKSDKPIYGLTQGFGPLVLFDADS
ELEQGGSLISHLGTGQGAPLAPEVSRLILWLRIQNMRKGYSAVSPVFWQKLADLWNKGETPAIPRHGTVSASGDLQ
PLAHAALAFTGVGEAWTRDADGRWSTVPAVDALAALGAEPFDWPVREALAFVNGTGASLAVAVLNHRSALRLVRAC
AVLSARLATLLGANPEHYDVGHGVARGQVGQLTAAEWIRQGLPRGMVRDGSRPLQEPYSLRCAPQVLGAVLDQLDG
AGDVLAREVDGCQDNPITYEGELLHGGNFHAMPVGFASDQIGLAMHMAAYLAERQLGLLVSPVTNGDLPPMLTPRA
GRGAGLAGVQISATSFVSRIRQLVFPASLTTLPTNGWNQDHVPMALNGANSVFEALELGWLTVGSLAVGVAQLAAM
TGHAAEGVWAELAGICPPLDADRPLGAEVRAARDLLSAHADQLLVDEADGKDFG SEQ ID NO: 24    DNA sequence encoding phenylalanine ammonia lyase (PAL) from
                 *Petroselinum crispum* codon optimized for expression in *S.
                 cerevisiae*
ATGGAAAATGGTAATGGTGCTACTACAAATGGCCATGTTAACGGTAATGGAATGGATTTTTGTATGAAAACCGAGG
ACCCATTGTATTGGGCATTGCAGCCGAAGCTATGACTGGTTCTCACTTAGATGAGGTAAAGAAAATGGTCGCAGA
ATACAGAAAGCCTGTGGTTAAACTAGGTGGAGAAACACTTACCATATCACAAGTAGCCGCTATCTCAGCAAGGGAC
GGAAGTGGTGTCACTGTGGAGTTGTCCGAAGCTGCTAGAGCAGGAGTTAAGGCTTCTTCAGATTGGGTAATGGACT
CCATGAACAAAGGTACAGATAGTTATGGCGTCACCACTGGTTTCGGAGCCACAAGCCATAGGAGAACCAAGCAGGG
CGGCGCATTACAAAAAGAACTAATTAGATCTTGAATGCTGGTATACCTGGTTCTGATAATACTTTGCCA
CACTCAGCTACCAGGGCAGCTATGTTAGTTAGAATCAACACTTTGTTACAGGGCTACTCCGGAATTAGATTTGAAA
TCCTTGAAGCCATCACCAAGTTTCTAAACCAAAATATTACACCTTGCTTGCCATTAAGGGGTACTATTACCGCAAG
TGGCGACCTAGTGCCTTTGTCTTACATAGCTGGTTTACTTACTGGTAGACCAAACAGCAAAGCCGTTGGTCCTACT
GGCGTAATCTTGTCACCAGAAGAGGCCTTTAAGTTAGCTGGTGTCGAAGGAGGTTTCTTTGAATTGCAACCTAAAG
AAGGCCTTGCCTTGGTGAATGGAACAGCAGTTGGTTCCGGTATGGCCAGTATGGTATTATTCGAAGCTAACATTCT
AGCCGTCTTGGCAGAGGTTATGTCTGCTATATTTGCCGAAGTGATGCAGGGCAAGCCAGAGTTCACCGATCACTTA
ACTCACAAACTTAAACATCATCCTGGACAAATCGAGGCAGCTGCCATTATGAACACATATTGGATGGCTCCGCAT
ACGTTAAGGCTGCACAAAGTTGCATGAAATGGACCCACTACAGAGACCTAAGAGAATAGGATGGTATGCTTTGAGAAC
CTCACCTCAGTGGTTAGGTCCACAAATCGAGGTAATTAGAAGCTCCACTAAGATGATTGAAAGGGAGATCAATAGT
GTCAACGACAATCCTCTTATCGATGTGTCAAGAAACAAAGCCATTCACGGCGGAAATTTTCAAGGTACCCCAATAG
GCGTTTCTATGGACAACACAAGACTAGCAATCGCTGCCATTGGAAAGTTGATGTTTGCACAGTTCAGCGAGTTAGT
GAATGATTTTTACAATAACGGCCTTCCTTCCAACCTATCTGGCGGCAGGAACCCATCATTAGATTATGGATTCAAA
GGTGCTGAAATAGCCATGGCATCCTACTGTAGCGAGCTACAGTTTTGGCTAATCCTGTCACTAACCATGTTCAAT TABLE 1-continued Nucleic acid and amino acid sequences.

CCGCCGAACAGCACAATCAAGACGTGAACAGTTTAGGTCTTATTTCATCTAGAAAGACCAGTGAGGCCGTTGAGAT
ATTGAAACTAATGTCCACAACTTTCTTAGTAGGCTTGTGCCAGGCTATTGATCTTAGACACTTAGAAGAAAATCTA
AAGTCAACCGTCAAAAACACAGTTTCTAGTGTGGCTAAAAGGGTATTGACTATGGGAGTCAATGGTGAGTTACATC
CAAGCAGATTTTGTGAAAAGGACCTTTTGAGGGTTGTGGATAGAGAATACATATTCGCCTACATCGATGACCCTTG
CAGTGCAACATATCCACTAATGCAGAAACTAAGACAAACATTGGTTGAGCACGCTCTTAAGAATGGCGATAACGAA
AGGAATTTGAGTACTTCTATTTTTCAGAAAATAGCAACCTTCGAGGACGAACTAAAGGCATTGTTACCTAAAGAAG
TAGAGAGTGCTAGGGCCGCACTAGAAAGTGGAAACCCAGCTATCCCTAATAGAATTGAAGAGTGTAGGTCCTACCC
ACTTTATAAGTTTGTCAGAAAGGAGTTGGGTACAGAATACTTAACCGGCGAGAAGGTTACTAGTCCAGGCGAAGAA
TTTGAGAAAGTGTTCATAGCCATGAGTAAGGGAGAAATTATCGATCCATTGTTAGAGTGTTTGGAGTCCTGGAACG
GTGCACCACTACCTATTTGCTAA

SEQ ID NO: 25 Protein sequence of PAL from *Petroselinum crispum*
MENGNGATTNGHVNGNGMDECMKTEDPLYWGIAAEAMTGSHLDEVKKMVAEYRKPVVKLGGETLTISQVAAISARD
GSGVTVELSEAARAGVKASSDWVMDSMNKGTDSYGVTTGFGATSHRRTKQGGALQKELIRFLNAGIFGNGSDNTLP
HSATRAAMLVRINTLLQGYSGIRFEILEAITKELNQNITPCLPLRGTITASGDLVPLSYTAGLLTGRPNSKAVGPT
GVILSPEEAFKLAGVEGGFFELQPKEGLALVNGTAVGSGMASMVLFEANILAVLAEVMSAIFAEVMQGKPEFTDHL
THKLKHHPGQIEAAAIMEHILDGSAYVKAAQKLHEMDPLQKPKQDRYALRTSPQWLGPQIEVIRSSTKMIEREINS
VNDNPLIDVSRNKAIHGGNFQGTPIGVSMDNTRLAIAAIGKLMFAQFSELVNDFYNNGLPSNLSGGRNPSLDYGFK
GAEIAMASYCSELQFLANPVTNHVQSAEQHNQDVNSLGLISSRKTSEAVEILKLMSTTFLVGLCQATDLRHLEENL
KSTVKNTVSSVAKRVLTMGVNGELHPSRFCEKDLLRVVDREYIFAYIDDPCSATYPLMQKLRQTLVEHALKNGDNE
RNLSTSIFQKIATFEDELKALLPKEVESARAALESGNPAIPNRIEECRSYPLYKFVRKELGTEYLTGEKVTSPGEE
FEKVFIAMSKGEIIDPLLECLESWNGAPLPIC SEQ ID NO: 26 DNA sequence encoding phenylalanine ammonia lyase (PAL) from *Aspergillus niger* codon optimized for expression in *S. cerevisiae*
ATGTTGGACAAGCACATCCCAGACGGTCACTTAGAAACCACTAGCGCCCACTGGAGGGATTTAAACCAAGTTGTTC
AAAACGGTGAATTATCTATTGACGGTTACTCCTTGTCCTTGGCCGATGTTGTTGCTGTCGCTAAGTATGGTTGCCA
ACCAAGATTGACTGACAAGCCAGAGACTATTGATGCTATTAACGGTTCTGTCATCGCCTTGGCTGAATGTTTAAGG
GATGGTCATCACATTTACGGTGTTAACACTGGTTTTGGTGGTTCTGCCGATTCCAGAACCAACCAGACCACTACTT
TGCAAAGCTCCTTGTTGCAATTGTTGCAATCCGGTATCTTAACTGCTTCTGACACTACCAATGAAGGTTTGCAGTT
GAACTTGCAAGGTCAAAGCAGCCATTCTATGCCATCTGAGTGGGTTAAAGCTACCATGTTGGTTCGTTCTAACTCT
GTCGCTAGAGGCCATTCTGCTGTCAGCTTGCCAGCTATTTCCGCCATTTTGAGATTGATCAGAGAAGATATCGTCC
CAGTTATTCCATTGAGAGGTACTATCTCCGCTTCCGGTGACTTGATGCCATTGGCTTACGTTGTCGGTGCCATTGA
AGGTTCTCCAGGTATTTACGTTAGAGTCAAGGATGGTTCTGAACATCAAGTCGTTACCGCTCAAAAGGCCCTACAA
ACTATCGGTGCTAAGGGTGTTACTTTGGGCCCTAAAGAGGGTTTAGGTTTGGTCAATGGTACTGCTGCTTCTGGTG
CCTTAGCTGGTTTGGTTTTGTATGAGGCTCATCAATTGGCCGTCTTGGCTCAAGCTGTCACCGCCTTAACTGTCGA
AGCTATTCAAGGTTCTACCGAATCCTTTCACCCTTTTATCGCTCAAGTCCGTCCACATGAAGGTCAGATCGAGGCT
GCTGAAAACATCCTATCTCTATTAAAAGGTAGCTTGTTGGCCAGAGGTAGCTCTACTACCCAAACCAGAACCGGTC
TAGTCCAAGACAGATACTCCTTGAGAACTGCTTCTCAATGGATCGGTCCTCAATTGGAAGATTTATTGTTGGCCGA
CAGACAGGTCCAAGTCGAACTAAATTCTACCAGCGACAACCCATTAATCGATACTGGTTCTAAAACTTTCTACACT
GGTGGTAACTTCCAAGCTACCAGCATTACCTCCGCTATGGAAAAGACTAGGTTGGCTTTGCAAATGTTCGGTAAGA
TGTTATTCGTCCAATGTAATGAAATGATCGACCCAAACTTGAACAACGGTCTACCTACCAACTTGGTTGCTGATGA
CCCATCCTTGTCCTTCACCATGAAAGGCGTCGATATCAACATGGCTGCTTATATGTCTGAATTGGCTTACTTGGCT
AATCCAGTCTCCTCCCACGTTCAAACTGCTGAAATGCAAAACCAAGCCTTGAACTCCTTGGCTTTCGTTAGCGCTA
GGTATACTATGAAAGCTGTTGATATCGTCTCTATGATGGGTGCTTGTGCTTTGTATGTCGCTTGTCAAGCCTTAGA
CTTGAGGGTOTTGCAATTGCGTTTCTTCCAAAGAGTCCAAGGTGTCGCTAAAGAAATCGCTCACGGTGCCTTTGGT
AAGGCCTTGGAACCTTTCGAAATCGACCAGGTTGCTGATCACTTGTCTGAAGCTATTCAAAACTCCTGGCCATCTA
CCTCTAGGTTGGACTTGAGAGACAGATGCAAAAGGGTTGCTGAAATGTTTATCCCAGTCTTGTTCGGTGCTTTGTT
GCAAATTATCCCACAGAACAGACAAACCTCTGATTTATTCACCGCCATCTCTOCTTGTAAGATGATTTCCGTTTTT
AAGTTGGAAGGCGTTTACAGAGAAGTTTTCGCTGAATTTTGCACTTCCCAACCTACCGCTGACTTTTTGGGTACCG
GTACTAAGGAAATCTACACCTTCATCAGACACGACTTGAGAGTCCCATTCCACCAGGGTTTCGTCGAACATCCATC
CGCCTCTCAAACCGACTTACCAGAAACTATCAACGGTAGAGTTAAAAAGACCGTCGGTGGTTGGATTTCTGTCGTT
TACGAAGCCTTGAGAAATGGTACCTTAAGCGGTACTATTTTGAACTCCTTCCAACAATAA SEQ ID NO: 27 Protein sequence of PAL from *Aspergillus niger*
MLDKHIPDGHLETTSAHWRDLNQVVQNGELSIDGYSLSLADVVAVAKYGCQPRLTDKPETIDAINGSVIALAECLR
DGHHIYGVNTGFGGSADSRTNQTTTLQSSLLQLLQSGILTASDTTNEGLQLNLQGQSSHSMPSEWVKATMLVRSNS
VARGHSAVSLPAISAILRLIREDIVPVIPLRGTISASGDLMPLAYVVGAIEGSPGIYVRVKDGSEHQVVTAQKALQ
TIGAKGVTLGPKEGLGLVNGTAASGALAGLVLYEAHQLAVLAQAVTALTVEAIQGSTESFHPFIAQVRPHEGQIEA
AENILSLLKGSLLARGSSTTQTRTGLVQDRYSLRTASQWIGPQLEDLLLADRQVQVELNSTSDNPLIDTGSKTFYT
GGNFQATSITSAMEKTRLALQMFGKMLFVQCNEMIDPNLNNGLPTNLVADDPSLSFTMKGVDINMAAYMSELAYLA
NPVSSHVQTAEMQNQALNSLAFVSARYTMKAVDIVSMMGACALYVACQALDLRVLQLRFFQRVQGVAKEIAHGAFG
KALEPFEIDQVADHLSEAIQNSWPSTSRLDLRDRCKRVAEMFIPVLFGALLQIIPQNRQTSDLFTAISACKMISVF
KLEGVYREVFAEFCTSQPTADFLGTGTKEIYTFIRHDLRVPFHQGFVEHPSASQTDLPETINGRVKKTVGGWISVV
YEALRNGTLSGTILNSFQQ SEQ ID NO: 28 DNA sequence encoding phenylalanine ammonia lyase (PAL) from *Puccinia graminis* f. sp. *tritici* codon optimized for expression in *S. cerevisiae*
ATGGCTCATGCTGATTTGTGCTCCGCTATTTCTAGAGAATTGGAAGAACACATCTCCAACAAGAGAGAAATTATCT
TGGACGGTCATGGTTTGACTTCTACTGGTGTTGTTGGTGCTGCTAGATACAATGTTCAAGCCAAGATTTCTAACGA
TCCAGCCTTGATTACTGTCGTTGAAGAATCTGTTGAATTCTTGGCCTCTAAGTTGGATACTGCTATCTATGGTGTT
ACCACCTTCTCTGAAAGATTAGATCCAAGACCAACTAACGCTTGCAACTTTTACTTTCAAGGTTCTGCTGATACCA
GATCTGATTCTACTGCTGACTTGCAAATGGCTTTCTTGGAACATCAAGTTTCTGGTGTTTTGCCATTGTCCTCTAG
ATCTACTTCTGCTGGTTTGTATTTGTCCGATCCAATGAACAATGTTATGCCTGAAGCTATTACCAGAGGTGCCATT
TTGATTAGAATCAACTCTTTGGTTAGAGGTCACTCCGCTTTGAGATTTCAAGTTTTGGAAACTTTGATCACCTTGT
TGAACAAGAACTTGACTCCAATGGTTCCATTGAGAGGTTCTATTTCTGCTTCTGGTGATTTGATGCCTTTGTCTTA
TGTTGCTGCTGCAATTTGTGGTCATCCAGCCATTAGAATTATCGATAGATCTTCAGCCGATGGTCACATCGAAATT

TABLE 1-continued

Nucleic acid and amino acid sequences.

```
ATGCCAGCTTCTGATGCTTTGACTAAGCACGGTATTACTCCAATAGTTTTGGGTCCAAAAGAAGGTTTGGCCATCT
CTAATGGTACTGCTTTTTCTGCATCTGCTGCTTGTTTGGTTGCTCATGATTCTCATATGTTGTTGATGTTGCTG
AGGTTTGACATCTATGACTGTTGAAGCTATGATGGGTCAAGCTCAATCTTTCGATCCTTTCATTCACGAAACTTGT
AGACCACATCCAGGTCAAGTTGAAGTTGCTAAGACTATCAGATCTATGTTCGAAGGTTCCAGATTGGTTATCCACA
TGGATGAAGAAAGATCCGTTGATCAAGAAAAGGACCAAGGTATCTTGAGACAAGATAGATATGCTTTGAGAACTGC
TCCACAATGGTTGGGTCCACAATTAGAAGAATTGGTTACTGTCAACAAGACCTTGTGCAGAGAAATCAATGCTACT
ACTGATAACCCATTGATCGACATCAAGAACAAAAAGATCTTGAACGGTGGTAACTTCCAAGCCATGTCTATTACCA
ATTCTATGGAAAAGACCAGATCCTCCTTGGAATCCATTGGTAAATTGTCTTTCGCTCAAGCCATCGAATTGATGAA
CTGTACTATGTCTAAAGGTTTGCCTTCTTGTTTGGCTGGTGATGAACCATCTACTAATTACCATACAAAGGGTTTG
GATATTAACATGGCTGCTTACACTGCTGAATTGGGTTTTTTGGCTTCTCCAGTTTCTACCCATGTTCAATCTGCTG
AACAACACAATCAATCCGTTAACTCATTGGCTTTGGTTTCTGCCAGATACACAATTCAAGCTGTCGAAGTTTTGTC
CATGTTGTTGTCATCTCACTTGTACGTTGTCTGCATGGCTATTGATTTGAGAGTTATCGACCAAATGTTTCAAAAA
GAATTGAAGGGTTTGTTGCCAGTTTTGTTGGATTCCATTTTAAGTCTAGACCAACTCAAGCTGCTGATCCATTGA
TTGGTGCTTTAGCTTCTAGATTGGAAGCTACTGCTTCTTTGGATTCTGAAGCTAGATTTTTGTCCGCTTTCAAGCA
AACCTTGCATGTTATTTTAGCCTTTCCCAGTTGATTTGGAAGAAGCTAGATGGCCATCATTTGCTGCTTCTCAA
TCTACTTTGTTGTACAAGAGAACCAGAGATCAATACTTCGAAAACTCCGAATCTTTCTTGGCTGAAAAGTGGTTGG
GTAAAAGAACAAGCACTTGTACCACTTCGTCAGAAAAGAATTAGGTATCGGTCCTAGAAGAGGTGATGTTAGATT
GGGTAGACATGAAGGTTCCGTTTCCATTGATGTTTCTAAGATCTACGAATCCGTCAGATCCGGTGAATTATACAAG
TTTATGAACAGAATGTTTTAA
```

SEQ ID NO: 29    Protein sequence of PAL from *Puccinia graminis* f. sp. *tritici*
MAHADLCSAISRELEEHISNKREIILDGHGLTSTGVVGAARYNVQAKISNDPALITVVEESVEFLASKLDTAIYGV
TTFSERLDPRPTNACNFYFQGSADTRSDSTADLQMAFLEHQVSGVLPLSSRSTSAGLYLSDPMNNVMPEAITRGAI
LIRINSLVRGHSALREQVLETLITLLNKNLTPMVPLRGSISASGDLMPLSYVAAAICGHPAIRIIDRSSADGHIEI
MPASDALTKHGTTPIVLGPKEGLAISNGTAFSASAACLVAHDSHMLLMLAQGLTSMTVEAMMGQAQSFDPFTHETC
RPHPGQVEVAKTIRSMFEGSRLVIHMDEERSVDQEKDQGILRQDRYALRTAPQWLGPQLEELVTVNKTLCREINAT
TDNPLIDIKNKKILNGGNFQAMSITNSMEKTRSSLESIGKLSFAQAIELMNCTMSKGLPSCLAGDEPSTNYHTKGL
DINMAAYTAELGFLASPVSTHVQSAEQHNQSVNSLALVSARYTIQAVEVLSMLLSSHLYVVCMAIDLRVIDQMFQK
ELKGLLPVLLDSHFKSRPTQAADPLIGALASRLEATASLDSEARFLSAFKQTLHVILAFPVDLEEARSWPSFAASQ
STLLYKRTRDQYFENSESFLAEKWLGKKNKHLYHFVRKELGIGPRRGDVRLGRHEGSVSIDVSKIYESVRSGELYK
FMNRMF SEQ ID NO: 30    DNA sequence encoding tyrosine ammonia lyase (TAL) from
                 *Aeromonas salmonicida* subsp. *salmonicida* A449 (Asal) codon
                 optimized for expression in *S. cerevisiae*
```
ATGAACAAGTCCG TABLE 1-continued Nucleic acid and amino acid sequences.

```
TGCTATGACAGGTGTTTCTTGTTTGTTGTTGGAAACTTTGAGAGCCCAAGTTCAACAAGCTGAAATTATTGCTGCT
TTGGCATTGGAAGGTTTGTCTGCTTCAGCTGATGCTTTTATGGCTGATGGTCATGATATTGCTAAACCACATCCAG
GTCAAATTAGATCTGCTGCTAATATGAGAGCTTTGTTGGCTGATTCTGCTAGATTGTCTGGTCATGGTGAATTGTC
TGCTGAAATGAAAACTAGAGCTGGTGAAGCTAAGAATACTGGTACTGGTGTTTTCATTCAAAAGGCCTACACCTTG
AGATGTATCCCACAAGTTTTAGGTGCAGTTAGAGATACCTTGGATCATTGTGCTACTGTTGTCGAAAGAGAATTGA
ACTCCTCTAACGATAACCCTTTGTTCTTTGAAGATGGTGAATTATTCCACGGTGGTAACTTTCATGGTCAACAAGT
AGCTTTTGCCATGGATTTTTTGGCTATTGCTGCAACTCAATTGGGTGTTGTTTCTGAAAGAAGATTGAACAGATTA
TTGTCCCCACACTTGAACAACAATTTGCCAGCTTTTTTGGCAGCTGCTAACGAAGGTTTATCTTGTGGTTTTGCTG
GTGCTCAATATCCAGCTACTGCTTTGATTGCTGAAAACAGAACTATTTGCTCCCCAGCCTCTATTCAATCTGTTCC
ATCAAATGGTGATAATCAAGACGTTGTCTCCATGGGTTTAATTGCAGCTAGAAACGCTAGAAGAATCTTGGACAAC
AATCAATATATCTTGGCCTTGGAATTATTGGCTTCTTGTCAAGCTGCTGAATTGGCTGGTGCTGTTGAACAATTGG
CTCCAGCTGGTAGAGCTGTTTTTGCTTTTGTTAGAGAAAGAGTCCCCATTCTTGTCCATCGATAGATATATGACCGA
TGACATTGAAGCTATGGCTGCTTTGTTGAGACAAGGTGCTTTGGTTGAAGTTGTTAGAGGTGCTGGTATTGAATTG
GCCTAA
```

SEQ ID NO: 33    Protein sequence of TAL from *Ralstonia metallidurans*

MPHAHPADIDGHHLTPDTVAAIARGQRAAIVPEPVLGKVADARARFEQVAAANVPIYGVSTGFGELVHNWVDIEHG
RALQENLLRSHCAGVGPLFSRDEVRAMMVARANALARGYSAVRPAVIEQLLKYLEAGITPAVPQVGSLGASGDLAP
LSHVAITLIGEGKVLTEDGGTAPTAEVLRERGITPLALAYKEGLALINGTSAMTGVSCLLLETLRAQVQQAEIIAA
LALEGLSASADAFMAHGHDIAKPHPGQIRSAANMRALLADSARLSGHGELSAEMKTRAGEAKNTGTGVFIQKAYTL
RCIPQVLGAVRDTLDHCATVVERELNSSNDNPLFFEDGELFHGGNEHGQQVAFAMDFLAIAATQLGVVSERRLNRL
LSPHLNNNLPAFLAAANEGLSCGFAGAQYPATALIAENRTICSPASIQSVPSNGDNQDVVSMGLIAARNARRILDN
NQYILALELLASCQAAELAGAVEQLAPAGRAVFAFVRERVPFLSIDRYMTDDIEAMAALLRQGALVEVVRGAGIEL
A

SEQ ID NO: 34    DNA sequence encoding tyrosine ammonia lyase (TAL) from
                 *Streptomyces globisporus* codon optimized for expression in *S. cerevisiae*

```
ATGGCCTTGACTCAAGTCGAAACTGAAATCGTTCCAGTTTCTGTTGATGGTGAAACTTTGACTGTTGAAGCCGTTA
GAAGAGTTGCTGAAGAAAGAGCTACTGTTGACGTTCCAGCTGAATCTATTGCTAAAGCTCAAAAGTCCAGAGAAAT
CTTCGAAGGTATTGCCGAACAAAACATTCCAATCTACGGTGTTACTACTGGTTACGGTGAAATGATCTATATGCAA
GTCGACAAGTCCAAAGAAGTTGAATTGCAAACTAACTTGGTCAGATCTCATTCTGCTGGTGTTGGTCCATTATTCG
CTGAAGATGAAGCTAGAGCTATAGTTGCTGCTAGATTGAATACTTTGGCTAAAGGTCATTCAGCTGTCAGACCAAT
TATCTTGGAAAGATTGGCTCAATACTTGAACGAAGGTATCACTCCAGCTATTCCAGAAATTGGTTCTTTGGGTGCT
TCTGGTGATTTGGCTCCATTGTCTCATGTTGCTTCTACTTTGATTGGTGAAGGTTACGTTTTGAGAGATGGTAGAC
CAGTTGAAACTGCTCAAGTTTTGGCTGAAAGAGGTATTGAACCATTGGAATTCAAAGAAGGTTTGGCCTT
GATTAACGGTACTTCTGGTATGACTGGTTTGGGTTCTTTAGTTGTTGGTAGAGCTTTGGAACAAGCTCAACAAGCT
GAAATAGTTACCGCCTTGTTGATAGAAGCTGTTAGAGGTTCTACTTCTCCATTCTTAGCTGAAGGTCATGATATTG
CTAGACCACATGAAGGTCAAATTGATACTGCTGCTAATATGAGAGCTTTGATGAGAGGTTCTGGTTTGACAGTTGA
ACATGCTGATTTGAGAAGAGAATTACAAAAGGACAAAGAAGCCGGTAAGGACGTTCAAAGATCTGAAATCTACTTG
CAAAAGGCCTACTCCTTGAGAGCTATTCCTCAAGTTGTAGGTGCAGTTAGAGATACCTTGTATCATGCTAGACACA
AGTTGAGAATCGAATTGAATTCCGCTAACGACAACCCTTTGTTCTTTGAAGGTAAAGAAATTTTCCACGGTGCCAA
CTTTCATGGTCAACCTATTGCTTTTGCTATGGACTTCGTTACCATTGCTTTGACTCAATTGGGTGTTTTAGCCGAA
AGACAAATCAACAGAGTTTTGAACAGACACTTGTCTTACGGTTTGCCAGAATTTTTGGTTTCAGGTGATCCAGGTT
TACATTCTGGTTTTGCTGGTGCTCAATATCCAGCTACTGCTTTGGTTGCTGAAAACAGAACTATTGGTCCAGCTTC
TACACAATCTGTTCCATCTAATGGTGATAATCAAGACGTTGTCTCCATGGGTTTGATTTCTGCTAGAAATGCAAGA
AGAGTCTTGTCCAACAACAACAAGATTTTGGCAGTCGAATATTTGGCTGCTGCTCAAGCTGTTGATATTTCTGGTA
GATTCGATGGTTTGTCTCCAGCTGCTAAAGCAACTTATGAAGCTGTAAGAAGATTGGTTCCAACCTTGGGTGTTGA
CAGATATATGGCTGATGATATTGAATTGGTTGCCGATGCTTTGTCTAGAGGTGAATTTTTGAGAGCCATTGCTAGA
GAAACCGACATCCAATTGAGATAA
```

SEQ ID NO: 35    Protein sequence of TAL from *Streptomyces globisporus*

MALTQVETEIVPVSVDGETLTVEAVRRVAEERATVDVPAESTAKAQKSREIFEGIAEQNIPTYGVTTGYGEMIYMQ
VDKSKEVELQTNLVRSHSAGVGPLFAEDEARAIVAARLNTLAKGHSAVRPTILERLAQYLNEGITPAIPEIGSLGA
SGDLAPLSHVASTLIGEGYVLRDGRPVETAQVLAERGIEPLELREKEGLALINGTSGMTGLGSLVVGRALEQAQQA
EIVTALLIEAVRGSTSPFLAEGHDIARPHEGQIDTAANMRALMRGSGLTVEHADLRRELQKDKEAGKDVQRSETYL
QKAYSLRAIPQVVGAVRDTLYHARHKLRIELNSANDNPLFFEGKEIFHGANFHGQPIAFAMDFVTIALTQLGVLAE
RQINRVLNRHLSYGLPEFLVSGDPGLHSGFAGAQYPATALVAENRTIGPASTQSVPSNGDNQDVVSMGLISARNAR
RVLSNNNKILAVEYLAAAQAVDISGREDGLSPAAKATYEAVRRLVPTLGVDRYMADDIELVADALSRGEFLRAIAR
ETDIQLR

SEQ ID NO: 36    DNA sequence encoding phenylalanine ammonia lyase/tyrosine
                 ammonia lyase (PAUTAL) from *Rhodotorula graminis* codon
                 optimized for expression in *S. cerevisiae*

```
ATGGCCCCATCTTTGGATTCTTTGGCTACTACTTTGGCTAACGTTTCACTAATGGTTCTCATGCTGCTCCAACAA
AATCTGCTGCTGGTCCAACTTCTGCTTTGAGAAGAACTCCAGGTTTGGATGGTCATGCTGCACATCAATCTCAATT
GGAAATCGTTCAAGAATTATTGTCCGATCCAACCGATGATGTTGTTGAATTGTCTGGTTACTCTTTGACCGTTAGA
GATGTTGTAGGTGCTGCTAGAAAAGGTAGAAGAGTTAGAGTTCAAAACGACGACGAAATTAGAGCCAGAGTTGATA
AGTCTGTTGATTTCTTGAAGGCCCAATTGCAAACTCTGTTTACGGTGTTACTACTGGTTTTGGTGGTTCTGCTGA
TACAAGAACTGAAGATGCTGTTTCCTTGCAAAAGGCCTTGATTGAACATCAATTGTGTGGTGTTACTCCAACCTCT
GTTTCTTCATTTTCTGTTGGTAGAGGTTTGGAAAACACCTTGCCATTGGAAGTTGTTAGAGGTGCTATGGTTATTA
GAGTCAACTCATTGACTAGAGGTCATTCCGCTGTTAGATTGGTTGTTTTGGAAGCTTTGACCAACTTCTTGAACCA
TAGAATTACTCCAATCGTCCCATTGAGAGGTTCTATTTCTGCTTCTGGTGATTTGTCTCCATTGTCTTATATTGCT
GGTGCTATTACTGGTCACCCAGATGTTAAGGTTCATGTTTTACATGAAGGTACTGAAAAGATCATGTTCGCCAGAG
AAGCTATTTCTGTTTTGGTTTGGAAGCAGTTGTCTTGGGTCCAAAAGAAGGTTTGGGTTTGGTTAATGGTACTGC
TGTTTCAGCTTCTATGGCTACTTTGTCATTGCATGATTCCCACATGTTGTCCTTGTTGTCTCAAGCTTTAACTGCC
TTGACTGTTGAAGCTATGGTTGGTCAACAAGGTTCTTTTGCTCCATTCATTCATGATGTCTGTAGACCACATCCAG
GTCAAGTTGAAGTTGCTAGAAACATCAGAACTTTGTTGTCCGGTTCATCTTTCGCTGTTGAACATGAAGAAGAAGT
```

TABLE 1-continued

Nucleic acid and amino acid sequences.

```
TAAGGTTAAGGACGACGAAGGTATTTTGAGACAAGATAGATATCCATTGAGAACTTCCCCACAATTTTTGGGTCCA
TTGGTTGAAGATATGATGCATGCTTACTCTACCTTGTCCTTAGAAAACAACACTACTACCGATAACCCTTTGTTGG
ATGTCGAAAACAAACAAACTGCTCATGGTGGTAATTTTCAAGCTTCTGCTGTCTCTATCTCTATGGAAAAAACTAG
ATTGGCTTTGGCCTTGATCGGTAAGTTGAATTTCACTCAATGCACCGAATTATTGAACGCTGCTATGAATAGAGGT
TTACCATCTTGTTTGGCTGCTGAAGATCCATCTTTGAACTATCATGGTAAGGGTTTGGATATTCATATTGCTGCTT
ACGCTTCAGAATTGGGTCATTTGGCTAATCCAGTTACTACTTTTGTTCAACCAGCCGAAATGGGTAATCAAGCCGT
TAATTCTTTAGCCTTGATTTCCGCTAGAAGAACTGCTGAAGCTAACGATGTTTTGTCTTTGTTGTTGGCTTCTCAC
TTGTACIGTACATTGCAAGCAGTTGATTTGAGAGCCATGGAATTGGATTTCAAGAAGCAATTCGATCCTTTGTTGC
CTACCTTGTTACAACAACATTTGGGTACTGGTTTGGACGTTAATGCTTTGGCTTTAGAAGTCAAGAAGGCTTTGAA
CAAGAGATTGGAACAAACTACCACCTACGATTTGGAACCTAGATGGCATGATGCTTTTTCTTATGCTACTGGTACT
GTCGTTGAATTATTGAGTTCTTCCCCATCTGCTAACGTTACTTTGACTGCTGTTAACGCTTGGAAAGTTGCATCTG
CTGAAAAGGCTATTTCCTTGACAAGAGAAGTCAGAAACAGATTCTGGCAAACTCCATCTTCTCAAGCTCCAGGTCA
TGCTTATTTGTCACCAAGAACTAGAGTCTTGTACTCCTTCGTTAGAGAAGAATTAGGTGTCCAAGCTAGAAGAGGT
GATGTTTTTGTTGGTGTTCAACAAGAAACCATCGGTTCCAATGTTTCAAGAATCTACGAAGCCATTAAGGACGGTA
GAATCAATCACGTTTTGGTTAAGATGTTGGCTTAA
```

SEQ ID NO: 37    Protein sequence of PAL/TAL from Rhodotorula graminis
MAPSLDSLATTLANGFTNGSHAAPTKSAAGPTSALRRTPGLDGHAAHQSQLEIVQELLSDPTDDVVELSGYSLTVR
DVVGAARKGRRVRVQNDDEIRARVDKSVDELKAQLQNSVYGVTTGFGGSADTRTEDAVSLQKALIEHQLCGVTPTS
VSSFSVGRGLENTLPLEVVRGAMVIRVNSLTRGHSAVRLVVLEALTNELNHRITPIVPLRGSISASGDLSPLSYIA
GAITGHPDVKVHVLHEGTEKIMFAREAISLEGLEAVVLGPKEGLGLVNGTAVSASMATLSLHDSHMLSLLSQALTA
LTVEAMVGQQGSFAPFIHDVCRPHPGQVEVARNIRTLLSGSSFAVEHEEEVKVKDDEGILRQDRYPLRTSPQFLGP
LVEDMMHAYSTLSLENNTTTDNPLLDVENKQTAHGGNFQASAVSISMEKTRLALALIGKLNFTQCTELLNAAMNRG
LPSCLAAEDPSLNYHGKGLDIHIAAYASELGHLANPVTTFVQPAEMGNQAVNSLALISARRTAEANDVLSLLLASH
LYCTLQAVDLRAMELDPKKQFDPLLPTLLQQHLGTGLDVNALALEVKKALNKRLEQTTTYDLEPRWHDAFSYATGT
VVELLSSSPSANVTLTAVNAWKVASAEKAISLTREVRNRFWQTPSSQAPAHAYLSPRTRVLYSEVREELGVQARRG
DVFVGVQQETIGSNVSRIYEAIKDGRINHVLVKMLA SEQ ID NO: 38    DNA sequence encoding phenylalanine ammonia lyase (PAL) from
                 Bambusa oldhamii codon optimized for expression in S. cerevisiae
```
ATGGCTGGTAATGGTCCAATCGTTAAGGATGATCCATTGAATTGGGGTGCTGCTGCTGCAGAATTGACTGGTTCTC
ATTTTGATGAAGTCAAGAGAATGGTTGCCCAATTCAGAGAACCTGTTATTAAGATTGAAGGTGCCTCTTTGAGAGT
TGGTCAAGTTGCTGCTGTTGCTCAAGCTAAAGATGTTTCTGGTGTTGCTGTTGAATTGGATGAAGAAGCTAGACCA
AGAGTTAAGGCTTCTTCTGAATGGATTTTGAACTGTTTGGCTCATGGTGGTGATATCTATGGTGTTACTACTGGTT
TTGGTGGTACTTCCCATAGAAGAACAAAAGATGGTCCAGCATTGCAAGTTGAATTATTGAGACATTTGAACGCCGG
TATTTTCGGTACTGGTACTGATGGTCATACTTTGCCATCTGAAGTTACTAGAGCTGCTATGTTGGTTAGAATCAAC
ACTTTGTTGCAAGGTTACTCCGGTATCAGATTCGAAATTTTGGAAGCCATTACCAAGTTGATCAATACTGGTGTTA
CACCATGTTTGCCATTGAGAGGTACTATTACTGCTTCTGGTGATTTGGTTCCATTGTCTTATATTGCCGGTTTGAT
TACTGGTAGACCAAATGCTCAAGCAGTTGCTCCAGATGGTAGAAAAGTTGATGCTGCTGAAGCTTTTAAGATTGCT
GGTATAGAAGGTGGTTTCTTCAAGTTGAACCCAAAAGAAGGTTTGGCTATCGTTAACGGTACTTCTGTTGGTTCTG
CTTTGGCTGCTACTGTCTTGTATGATTGCAATGTTTTGGCCGTTTTGTCCGAAGTTTTGTCTGCTGTTTTTGCGA
AGTTATGAACGGTAAGCCAGAATACACTGATCATTTGACCCATAAGTTGAAACATCACCCAGGTTCTATTGAAGCT
GCTGCTATTATGGAACATATTTTGGCTGGTTCCTCTTTCATGTCCCATGCTAAAAAAGTTAACGAAATGGACCCTT
TGTTGAAGCCTAAGCAAGATAGATATGCTTTGAGAACTTCTCCACAATGGTTGGGTCCACAAATTGAAGTTATAAG
AGCAGCCACCAAGTCCATCGAAAGAGAAGTTAATTCCGTTAATGACAACCCAGTTATCGATGTTCATAGAGGTAAG
GCTTTACATGGTGGTAATTTTCAAGGTACTCCAATCGGTGTTTCTATGGACAACACTAGATTGGCTATTGCTAACA
TCGGTAAGTTGATGTTCGCTCAATTTTCCGAATTGGTCAACGAATTCTACAACAACGGTTTGACTTCTAATTTGGC
CGGTTCTAGAAATCCATCTTTGGATTACGGTTTCAAGGGTACTGAAATTGCTATGGCTTCTTACTGCTCCGAATTG
CAATATTTGGCTAACCCAATCACCAACCATGTTCAATCTGCTGAACAACACAATCAAGACGTTAACTCTTTGGGTT
TGGTTTCTGCTAGAAAAACAGCTGAAGCCGTTGATATCTTGAAGTTGATGAGTTCTACTTACATGGTTGCTTTGTG
CCAAGCTGTTGATTTGAGACACTTGGAAGAAAACATCAAGTCCTCTGTTAAGAACTGCGTTACCCAAGTTGCTAAA
AAGGTTTTGACTATGAACCCAACCGGTGATTTGTCATCTGCTAGATTTTCTGAAAAGAACTTGTTGACCGCCATTG
ATAGAGAATGCAAAGAATCCAGATCCTTCCCAGTCTACAGATTCGTTAGAGAAGAATTAGGTTGCGTTTACTTGAC
CGGTGAAAAATTGAAATCTCCAGGTGAAGAATGCAACAAGGTTTTCATTGGTATCTCCCAAGGTAAATTGATCGAC
CCAATGTTGGAATGCTTGAAAGAATGGAATGGTGAACCATTGCCAATCAACTGA SEQ ID NO: 39    Protein sequence of PAL from Bambusa oldhamii
MAGNGPIVKDDPLNWGAAAAELTGSHFDEVKRMVAQFREPVIKIEGASLRVGQVAAVAQAKDVSGVAVELDEEARP
RVKASSEWILNCLAHGGDIYGVTTGFGGTSHRRTKDGPALQVELLRHLNAGIFGTGTDGHTLPSEVTRAAMLVRIN
TLLQGYSGIRFEILEAITKLINTGVTPCLPLRGTITASGDLVPLSYIAGLITGRPNAQAVAPDGRKVDAAEAFKIA
GIEGGFFKLNPKEGLAIVNGTSVGSALAATVLYDCNVLAVLSEVLSAVECEVMNGKPEYTDHLTHKLKHHPGSIEA
AAIMEHILAGSSFMSHAKKVNEMDPLLKPKQDRYALRTSPQWLGPQIEVIRAATKSIEREVNSVNDNPVIDVHRGK
ALHGGNFQGTPIGVSMDNTRLAIANIGKLMFAQFSELVNEFYNNGLTSNLAGSRNPSLDYGFKGTEIAMASYCSEL
QYLANPITNHVQSAEQHNQDVNSLGLVSARKTAEAVDILKLMSSTYMVALCQAVDLRHLEENIKSSVKNCVTQVAK
KVLTMNPTGDLSSARFSEKNLLTAIDREAVETYADDPCSANYPLMQKLRAVLVDHALTSGDAEREPSVESKITKFE
EELRSALPREIEAARVAVADGTAPIANRIKESRSFPVYREVREELGCVYLTGEKLKSPGEECNKVFIGISQGKLID
PMLECLKEWNGEPLPIN SEQ ID NO: 40    DNA sequence encoding histidine ammonia lyase/phenylalanine
                 ammonia lyase (HAL/PAL) from Neosartorya fischeri codon optimized
                 for expression in S. cerevisiae
```
ATGCCAGCTTCTTGGGTTAGAGGTACTATGTTGGTTAGATGTAACTCTAACGCTAGAGGTCATTCTGCTGTTTCTT
TGCCAGCTATTGAATCCTTGTTGAGATTGATCGAAAACCACATTACTCCAGTTGTTCCATTGAGAGGTTCTATTTC
TGCTTCTGGTGATTTGATGCCATTGTCTTATATTGCTGGTGCTATTGAAGGTTCCCCAGATGTTTATGTTCAAGTT
CAAGATTCCGACAAGACCAGAATCATGAATTCTAGAGATGCTTTGTTGTCCACTGGTTTGGAAGCTCAAACTTTGG TABLE 1-continued Nucleic acid and amino acid sequences.

```
GTCCAAAAGAAGGTTTGGGTTTGGTTAATGGTACTTCTGCTTCAGCTGCTTTGGCTTCTTTGGCTATGTATGAAGC
TCATCAATTGGCCGTTTTGGTTCAAGCTTTGTCTGCTTTGACTGTTGAAGCTTTGATGGGTAATGCTGAATCTTTC
CATCCATTCATTTCCGCCATTAGACCACATGATGGTCAAATTGAATGTGCCAGAAACGTCATGTCTTTCTTGCAAG
GTTCTCAATTGGCTCAAAACTTGGAAAGAAACTTGAAGGACAGAAACAGACCAGGTTTGATCCAAGATAGATACGC
TTTGAGAACTGTTCCACAATGGATTGGTCCACAATTGGAAGATTGTTGTTGGCCCATAGACAAGTTACCGTTGAA
TTGAACTCTTCTTGCGATAACCCATTGGTTGATGCTCAATCCGATGATATTTTCTACGGTGGTAATTTCCAAGCCG
TTTCTATTACATCTGCTATGGAAAAGACTAGAACCTGCTTGCAAATGTTCGGTAGATTGTTGTTTGCTCAAGCCAC
CGAATTGATTGATCCATCTTTGAACAATGGTTTGCCTACCAATTTGGTTGCTGATGATCCATCCTTGTCTTTCACT
ATGAAGGGTGTTGATATTTCCATGGCTTCTTACATGGCTGAATTGGCTTACTTGGCTAATCCAGTTTCTTCTCATG
TTCAAACCGCCGAAATGCACAATCAATCTGTTAATTCTATGGCCTTCGTTTCCTCTAGATACACTATGCAAGCTGT
CGAAATCGTTTCTTTGATGTGTGCTTGCTCTGTTTACATTGGTTGCCAAGCTTTGGATTTGAGAGTCTTGCATTTG
ACATTCTTGCAAAGATCTACCCCACAATTGCATACTTTGACCTCTCATTTGTTCTCCGAACACTTGTTTGAACCAG
ATTTGGCTACTTTGAATGAAGCCTTGCTACCCATATTCAAAAGTCTTGGCCAACTACTACCAGATTGAACATTAC
CGATAGAGTTGAAGAAGTTGTTACCTCCGCTATTCCAATTTTGTGTAGAACTTTCGCTTCTTCCACTGGTACATCT
ACTTCTCAAGCTCCAACTTTCTCTGATTTGGAAACCTGGAAATCTAGAGCTTTGCTTTTGTTGAACGAAATCTACC
AAGATACTGCTCATGCCTTCTTCTCTTACCAACATACTGAAGAAATGTTGGGTACTTCCTCTAAGATCTTGTACCA
AACCGTTAGAAGACAATTGGGTGTTCCATTTCATCAAGGTTTCATTGAACATCCAACCGCTCAATCTGATACTTTG
GGTGGTAGACCAAAAAAGACTGTTGGTTCTTGGATCTCCATTATCTACGAAGCTATTAGAGAAGGTAGATTGATGG
ATCCTTTGATGGCATCTTTACAAGCTGGTGTTGCTGGTGAATCAGATACTGAAGCTGTTGATACTTTAAAGGACGG
TTCTTCTGGTAAGTGTTCTTCTTCAGGTTTGGACTGA
```

SEQ ID NO: 41    Protein sequence of HAL/PAL from *Neosartorya fischeri*
MPASWVRGTMLVRCNSNARGHSAVSLPAIESLLRLIENHITPVVPLRGSISASGDLMPLSYIAGAIEGSPDVYVQV
QDSDKTRIMNSRDALLSTGLEAQTLGPKEGLGLVNGTSASAALASLAMYEAHQLAVLVQALSALTVEALMGNAESF
HPFISAIRPHDGQIECARNVMSFLQGSQLAQNLERNLKDRNRPGLIQDRYALRTVPQWIGPQLEDLLLAHRQVTVE
LNSSCDNPLVDAQSDDTFYGGNFQAVSITSAMEKTRTCLQMFGRLLFAQATELIDPSLNNGLPTNLVADDPSLSFT
MKGVDISMASYMAELAYLANPVSSHVQTAEMHNQSVNSMAEVSSRYTMQAVEIVSLMCACSVYIGCQALDLRVLHL
TFLQRSTPQLHTLTSHLFSEHLFEPDLATLNEALSTHIQKSWPTTTRLNITDRVEEVVTSAIPILCRTEASSTGTS
TSQAPTESDLETWKSRASALLNEIYQDTAHAFFSYQHTEEMLGTSSKILYQTVRRQLGVPFHQGFIEHPTAQSDTL
GGRPKKTVGSWISIIYEAIREGRLMDPLMASLQAGVAGESDTEAVDTLKDGSSGKCSSSGLD SEQ ID NO: 42    DNA sequence encoding partial tyrosine ammonia lyase (TAL) from
                 *Rhodotorula glutinis* codon optimized for expression in *S. cerevisiae*
```
ATGTCCTTGAGAAGAGATCACGGTGTTAGAAGATTGGGTAGACATCCAGATGGTGGTAGAGATTGGCTGCTGAAG
GTGTTAGATTGCATATTGCTTTGTCTCCATTCTCCTCAAGAAGAGCTTCTACTGATTCTAGAGGTCCATTCGCTTT
CGAAAACAGTTTGTTGGAACATCAATTGTGCGGTGTTTTGCCAACTTCTATGGATGGTTTTGCTTTGGGTTCTGGT
TTGGAAAATTCTTTGCCATTGGAAGTTGTTAGAGGTGCTATGACTTTGAGAGTCAACTCTTTGACAAGAGGTCATT
CTGCTGTTAGAATCGTTGTTTTGGAAGCTTTGACTAACTTCTTGAACCATGGTATTACTCCAATCGTTCCATTGAG
AGGTACTATTTCTGCTTCTGGTGATTTGTCACCATTGTCTTATATTGCTGCTTCCATTACTGGTCACCCAGATTCT
AAAGTTCATGTTGATGGTCAAATCATGTCCGCTCAAGAAGCTATTGCATTGAAAGGTTTACAACCAGTTGTCTTGG
GTCCAAAAGAAGGTTTGGGTTTAGTTAATGGTACTGCTGTTTCAGCTTCTATGGCTACTTTGGCTTTGACTGATGC
TCATGTTTTGTCTTTGTTGGCTCAAGCTAATACTGCTTTGACAGTTGAAGCTATGGTTGGTCATGCTGGTTCTTTT
CATCCATTCTTGCATGATGTTACTAGACCAGCTCCAGATCCAGACAGAGGTAGAGCTGCTACTTTAGGTTTGTTGT
TGGAAGGTTCTAAGTACTGCTTGTCTACTATGAGACCAAGATCCAGATCTAGAACTACTAGAGCTTCTTCTGGTAG
AACTGATACAAGATCTGCTGCTAGACCTAGATTTGTCGTTTTCAGAATTCCATCCTTGTCTGCCCATAGATCTGAT
CCTTTGTTGTTATGTTCTGGTGCTCAATGGTTGGGTCCATTGGTTTCTGATATGATTCATGCCCATTCTGTCTTGT
CTTTAGAAGCTGGTCAATCTACTACTGACAACCCATTGATTGACTTGGAAAACAAGATGACTCATCATGGTGGTGC
TTTTATGGCTTCTTCAGTTGGTAACAATATGGAAAAGAGATTGGTTTCCCCATCTCATTTGTGGGCTAGATTGGCT
TCTTTATCTTCTCCAAGATGTTCTACTCCAGCTTGTACTGCTAGATTTCCACCAGCTTCACCACCAAGAACTAGAT
TGTGTCCAACTACAGCTAGAGTTTCTACTTCTCCACCATTGCATACTTTGAGATCCTCTGTTACTTCTAGAACCCA
ATCCAGACCAACTTTCTCTAGACAAAGATGGGCTATTAGAAGATCTACCAGATCTCCATCTTCTAGACCAGTTGCT
CCTCCTAGAAGAACAACTTCTTCTAGATCATCATCCTCCAACTTCAACTGCTTCTTGTAGAAGATCCACTTGTGT
CTAGATGGTCATCCTCTACTAGAAAGTCTTTATCAAGATGGTCCCCAACCTGTTCTTCATCTACTTTAGCTAGATC
AAGACAACCTACCTCCAGAACAAGATCAGCTAATAGATCTACTTCTGGTTGCTCAAGAACTACAAGAACTACTTCA
TCTTCTGGTGGTACAACCAGATCAAGAAGTAGACCAGCACCATCATCTAAACCATCTCCAGGTACTAGATGTAGAT
CTAGAGCATCTACACCAGGTAGAAGTAGAGCTTTGAGAAGACCTTCTCCATCTCCTGCTCCATGTGCTACTAGATC
AGGTCCTCGTCGTAGAAGAAGAAGACCAAGAAGTTCAACTAGTAGAAGAGGTTTGGCTTCCTGTACTAGATCTTCA
GGTAAAACATCTGCTTCAAGACCAGCTGCTGCTACTAGTACTTCAGCTTCAAGAAGATCAAGATCCGGTCCAACTT
CTGCTGCATCAACAAGAAGATCCAGAACTGCTGCTTTGTTGAGATCATCTTCAAGATGTTGGCACAAGAGAACTTT
GGTTCAAGCTTCATTGGCTAGAGATTCTAAGTTGCCATTTTTGCCAGGTAGATTGAGACAAAGAAGATTCCCACCA
GATTGTCATTTTCCACATGCTCCATATCCATTGGGTTTCAGATCTCATTCTGGTCCAGTTGAAACCCATATTTCTT
TCGGTAGAAGACCATATTAA
```

SEQ ID NO: 43    Protein sequence of PAUTAL from *Rhodotorula glutinis*
MSLRRDHGVRRLGRHPDGGRDLAAEGVRLHIALSPESSRRASTDSRGPFAFENSLLEHQLCGVIPTSMDGEALGSG
LENSLPLEVVRGAMTLRVNSLTRGHSAVRIVVLEALTNELNHGTTPIVPLRGTISASGDLSPLSYIAASITGHPDS
KVHVDGQIMSAQEATALKGLQPVVLGPKEGLGLVNGTAVSASMATLALTDAHVLSLLAQANTALTVEAMVGHAGSF
HPFLHDVTRPAPDPDRGRAATLGLLLEGSKYCLSTMRPRSRSRTTRASSGRTDTRSAARPREVVERIPSLSAHRSD
PLLLCSGAQWLGPLVSDMIHAHSVLSLEAGQSTTDNPLIDLENKMTHHGGAFMASSVGNTMEKRLVSPSHLWARLA
SLSSPRCSTPACTARFPPASPPRTRLCPTTARVSTSPPLHTLRSSVTSRQSRPTFSRQRWAIRRSTRSPSSRPVA
PPRRTTSSRSSSPPTSASCRRSTCARWSSSTRKSLSRWSPTCSSSTLARSRQPTSRTRSANRSTSGCSRTTRTTS
SSGGTTRSRSRPAPSSKPSPGTRCRSRASTPGRSRALRRPSPSPAPCATRSGPRRRRRPRSSTSRRGLASCTRSS
GKTSASRPAAATSTSASRRSRSGPTSAASTRRSRTAALLRSSSRCWHKRTLVQASLARDSKLPFLPGRLRQRRFPP
DCHFPHAPYPLGFRSHSGPVETHISFGRRPY TABLE 1-continued Nucleic acid and amino acid sequences.

SEQ ID NO: 44    DNA sequence encoding phenylalanine ammonia lyase/tyrosine ammonia
                 lyase (PAL/TAL) from *Trichosporon cutaneum* codon optimized for
                 expression in *S. cerevisiae*

```
ATGTTCATCGAAACTAACGTTGCTAAGCCAGCTTCTACTAAGGCTATGAATGCTGGTTCTGCTAAAGCTGCTCCAG
TTGAACCATTTGCTACTTATGCTCATTCTCAAGCTACTAAGACCGTTTCTATTGATGGTCATACAATGAAGGTTGG
TGATGTTGTTGCTGTTGCTAGACATGGTGCTAAAGTTGAATTGGCTGCTTCTGTTGCTGGTCCAGTTAGAGCTTCA
GTTGATTTCAAAGAATCCAAAAAGCACACCTCCATCTACGGTGTTACTACTGGTTTTGGTGGTTCAGCTGATACAA
GAACTTCTGATACTGAAGCCTTGCAAATCTCCTTGTTGGAACATCAATTGTGTGGTTTCTTGCCAACTGATGCTAC
TTACGAAGGTATGTTGTTGGCTGCTATGCCAATTCCAATAGTTAGAGGTGCTATGGCTGTTAGAGTTAATTCTTGT
GTTAGAGGTCACTCCGGTGTTAGATTGGAAGTTTTACAATCTTTCGCCGACTTCATCAACAGAGGTTTGGTTCCAT
GTGTTCCATTGAGAGGTACTATTTCTGCTTCTGGTGATTTGTCTCCATTGTCTTTATATTGCTGGTGCTATTTGTGG
TCACCCAGATGTTAAGGTTTTTGATACTGCTGCTTCTCCACCAACTGTTTTGACTTCTCCTGAAGCTATTGCTAAG
TACGGTTTGAAAACTGTTAAGTTGGCCTCCAAAGAAGGTTTGGGTTTGGTTAATGGTACTGCTGTTTCTGCTGCTG
CTGGTGCATTGGCATTATATGATGCTGAATGTTTGGCCATCATGTCCCAAACTAACACAGTTTTGACTGTTGAAGC
TTTGGATGGTCATGTTGGTTCTTTTGCTCCATTCATCCAAGAAATTAGACCACATGCAGGTCAAATTGAAGCTGCC
AGAAATATCAGACATATGTTGGGTGGTTCTAAGTTGGCTGTTCATGAAGAATCTGAATTATTGGCTGATCAAGACG
CCGGTATTTTGAGACAAGATAGATATGCTTTGAGAACCTCCGCTCAATGGATTGGTCCACAATTGGAAGCTTTAGG
TTTGGCCAGACAACAAATTGAAACCGAATTGAACTCTACCACCGATAACCCATTGATTGATGTTGAAGGTGGTATG
TTTCATCACGGTGGTAATTTTCAAGCTATGGCAGTTACTTCTGCTATGGATTCTGCTAGAATTGTCTTGCAAAACT
TGGGTAAATTGTCCTTCGCTCAAGTCACTGAATTGATCAACTGTGAAATGAATCACGGTTTGCCATCTAATTTGGC
AGGTTCTGAACCATCTACTAATTACCATTGCAAGGGTTTGGATATTCATTGTGGTGCTTATTGTGCTGAATTGGGT
TTTTTTGGCTAACCCAATGTCTAACCATGTTCAATCTACCGAAATGCACAATCAATCCGTTAACTCTATGGCTTTTG
CTTCCGCTAGAAGAACTATGGAAGCTAACGAAGTTTTGTCCTTGTTGTTGGGTTCACAAATGTACTGTGCTACCCA
AGCCTTGGATTTGAGAGTTATGGAAGTTAAGTTCAAGATGGCCATTGTCAAGTTGTTGAACGAAACTTTGACCAAG
CACTTTGCTGCTTTTTTGACTCCAGAACAATTGGCTAAGTTGAACACTCATGCTGCTATCACCTTGTACAAAAGAT
TGAATCAAACCCCATCTTGGGATTCCGCTCCAAGATTTGAAGATGCTGCTAAACATTTGGTTGGTGTTATTATGGA
TGCCTTGATGGTTAACGATGATATCACTGACTTGACTAACTTGCCAAAGTGGAAGAAAGAATTCGCTAAAGAAGCT
GGTAACTTGTACAGATCCATTTTGGTTGCTACTACTGCTGATGGTAGAAACGATTTGGAACCAGCTGAATATTTGG
GTCAAACTAGAGCTGTTTACGAAGCCGTTAGATCAGAATTGGGTGTCAAAGTTAGAAGAGGTGATGTAGCTGAAGG
TAAGAGTGGTAAATCTATCGGTTCTTCCGTTGCCAAAATCGTTGAAGCTATGAGAGATGGTAGATTGATGGGTGCT
GTTGGTAAGATGTTCTGA
```

SEQ ID NO: 45    Protein sequence of PAL/TAL from *Trichosporon cutaneum*
```
MFIETNVAKPASTKAMNAGSAKAAPVEPFATYAHSQATKTVSIDGHTMKVGDVVAVARHGAKVELAASVAGPVRAS
VDFKESKKHTSIYGVTTGFGGSADTRTSDTEALQISLLEHQLCGFLPTDATYEGMLLAAMPIPIVRGAMAVRVNSC
VRGHSGVRLEVLQSFADFINRGLVPCVPLRGTISASGDLSPLSYIAGAICGHPDVKVFDTAASPPTVLTSPEAIAK
YGLKTVKLASKEGLGLVNGTAVSAAAGALALYDAECLAIMSQTNTVLTVEALDGHVGSFAPFIQEIRPHAGQIEAA
RNIRHMLGGSKLAVHEESELLADQDAGILRQDRYALRTSAQWIGPQLEALGLARQQIETELNSTTDNPLIDVEGGM
FHHGGNFQAMAVTSAMDSARIVLQNLGKLSFAQVTELINCEMNHGLPSNLAGSEPSTNYHCKGLDIHCGAYCAELG
FLANPMSNHVQSTEMHNQSVNSMAFASARRTMEANEVLSLLLGSQMYCATQALDLRVMEVKFKMAIVKLLNETLTK
HFAAFLTPEQLAKLNTHAAITLYKRLNQTPSWDSAPRFEDAAKHLVGVIMDALMVNDDITDLTNLPKWKKEFAKEA
GNLYRSILVATTADGRNDLEPAEYLGQTRAVYEAVRSELGVKVRRGDVAEGKSGKSIGSSVAKIVEAMRDGRLMGA
VGKMF
```

SEQ ID NO: 46    DNA sequence encoding phenylalanine ammonia lyase/tyrosine
                 ammonia lyase (PAL/TAL) from *Phanerochaete chrysosporium* codon
                 optimized for expression in *S. cerevisiae*

```
ATGCCATCCAGAATCGACTACTACACTTCTTCTGGTAATGGTTACGCCCAATCCAGAAAATCTTCTGCTATCTATC
CAGCTTCTGCTTCTACTGGTCATGCTGCTCCATCTACTGAAAGAAAACCAGAATTATTGGACAAGTTCGTTGAAGC
CTACGACGAATTGCAATCTTACAGAGAAGGTAAGCCAGTTATCGTTGATGGTCATAACTTGTCTATTCCAGCTGTT
GCTGCTACAGCTAGATTTGGTGCTGCTGTTGTTTTGGACGAAAATCCTGAAACTCACGAAAGAGTCTTGCAATCTA
GAAGAGTTATCGTCGATAAGGTCAGTACCCAAAGATCTGTTTATGGTGTTCTACAGGTTTTGGTGGTTCTGCTGA
TACAAGAACTTCTGATCCATTGCAATTGGGTCATGCCTTGTTACAACATCAACACGTTGGTGTTTTGCCAACTCAA
ACTGAATCTCCATTGCCAGCTTTGCCATTGGGTGATCCATTAGCTACTACTTCTATGCCTGAAGCTTGGGTTAGAG
GTGCTATTTTGATTAGAATGAACTCCTTGATCAGAGGTCACTCTGGTGTTAGATGGGAATTGATTGAAAAGATGGG
TGAATTATTGAGAGAAAACATCACCCCATTGGTTCCATTGAGAGGTTCTATTTCTGCTTCAGGTGATTTGTCTCCA
TTGTCTTATATTGCCGGTACTTTGATTGGTTCCCCAGCTATTAGAGTTTTTGATGGTCCAGCTTCATATGGTGCCA
GAAGAATTTGCCATCCAATATTGCTTTGGCCAATCATGGTGTTGCTCCAATTCCATTGTCATCCAAAGAACATTTG
GGGTATCTTGAACGGTACTGCTTTTTCAGCTTCTGTTGGTGCTTTGGCTTTGAATGAAGCTGTTCATTTGTCTTTG
TTGGCTCAAGTATGTACTGCTATGGGTACTGAAGCTATGATTGGTGCAGTTGGTTCTTTCGATGCTTTCATTCATG
ATACTGCTAGACCACATCCAGGTCAAGTTGAAGTTGCTAGAAATGTTAGAACCTGTTGGAAGATTCTCAAATGGC
TGTTAAGGCCGAAGATGAAGTTCATATTGCTGAAGATGAAGGTGAATTGAGACAAGACAGATACCCATTGAGAACT
GCTGCTCAATTTTGGGTCCACAAATCGAAGATATTTGTCTGCTCACGAAACCGTTACCTTGGAATGTAATTCTA
CTACCGATAACCCATTGATCGATGGTGAAACTGGTACTGTTCATCATGGTGGTAATTTTCAAGCTATGGCCGTTAC
TAATGCTATGGAAAAAACCAGATTGGCTATCCATCATATCGGTAAGTTGTTTGTTGCTCAAGCTACCGAATTGATC
AACCCAATGATGAATGAGGTTTGCCACCTAATTTGGCTGCTACTGATCCATCTCATAATTACTTTGCTAAGGGTG
TTGATATTCATTTGGCAGCTTACGTTGGTGAATTGGGTTTTTTGGCTTCTCCAGTTTCCTCCCATATTCAATCTGC
TGAAATGCATAATCAAGCCGTTAATTCCTTGGCTTTGGTTTCTGCTAGATATACCATTTCCGCTTTGGATGTCTTA
TCTTTGTTGACTGCTGCTTACTTGTACGTTTTGTGTCAAGCTTTTGGATTTGAGAGCTATGGCTAGATAACGACTTGAT
CATCTTTGTCAGCCATCGTTAGAGAATTATTACCAAAGCACTTTCCATCCGCTGCTAAAAGAGCTGACGCTTTGTT
GCCAATTTTGGAAAGAACTATTTTCAGAGCCTTGAACTCCTCTTCTTCTGCTGACTGTAAAGCTAGAATGGTTTCA
GTTGCTGCTTCAACTACTACTCCATTGGTTGATTTTTTGTCAGCTGATGCAGCTTTGGCATCTGAATTGGCTAATA
TTACTGCTTTCAGAACCGAATTAGCTACCAGAGCTGCTGATGCTTTGACTACTTTGGAAACTCAATATTGGAAGG
TGCTAGAGGTGCAGCTCCAGCATCTAAATACTTGGGTAAAACTAGACCAGTCTACGAATTTGTTAGAGTCACTTTG
AACGTTCCAATGCACGGTAGAGAAAACTTGCATAACTTTGAAATGGGTCAGGTGTTGAAGATGGTATTATTGGTA
ACAACATCTCCACCATCTACGAAGCAATTAGAGATGGTAAGATGCAAAACGTCGTAATGCAATTGGTCAAGTCCAT
TAAGGCTTAA
```

TABLE 1-continued

Nucleic acid and amino acid sequences.

SEQ ID NO: 47    Protein sequence of PAL/TAL from *Phanerochaete chrysosporium*
MPSRIDYYTSSGNGYAQSRKSSAIYPASASTGHAAPSTERKPELLDKFVEAYDELQSYREGKPVIVDGHNLSIPAV
AATARFGAAVVLDENPETHERVLQSRRVIVDKVSTQRSVYGVSTGFGGSADTRTSDPLQLGHALLQHQHVGVLPTQ
TESPLPALPLGDPLATTSMPEAWVRGAILIRMNSLIRGHSGVRWELIEKMGELLRENITPLVPLRGSISASGDLSP
LSYIAGTLIGSPAIRVFDGPASYGARRILPSNIALANHGVAPIPLSSKEHLGILNGTAFSASVGALALNEAVHLSL
LAQVCTAMGTEAMIGAVGSFDAFIHDTARPHPGQVEVARNVRTLLEDSQMAVKAEDEVHIAEDEGELRQDRYPLRT
AAQFLGPQIEDILSAHETVTLECNSTTDNPLIDGETGTVHHGGNFQAMAVTNAMEKTRLAIHHIGKLLFAQATELI
NPMMNRGLPPNLAATDPSHNYFAKGVDIHLAAYVGELGFLASPVSSHIQSAEMHNQAVNSLALVSARYTISALDVL
SLLTAAYLYVLCQALDLRAMHNDLQSSLSAIVRELLPKHFPSAAKRADALLPILERTIFRALNSSSSADCKARMVS
VAASTTTPLVDFLSADAALASELANITAFRTELATRAADALTTLRTQYLEGARGAAPASKYLGKTRPVYEFVRVTL
NVPMHGRENLHNFEMGPGVEDGIIGNNISTIYEAIRDGKMQNVVMQLVKSIKA SEQ ID NO: 48    DNA sequence encoding tyrosine ammonia lyase 2 (TAL2) from
                 *Rhodotorula glutinis* codon optimized for expression in *S. cerevisiae*
ATGGCCCCATCCGTTGATTCTATTGCTACTTCTGTTGCTAACTCCTTGTCCAATGGTTTACATGCTGCTGCTGCAG
CTAATGGTGGTGATGTTCATAAGAAAACTGCTGGTGCTGGTTCTTTGTTGCCAACTACTGAAACTACTCAATTGGA
CATCGTCGAAAGAATTTTGGCTGATGCTGGTGCAACTGATCAAATCAAATTGGATGGTTACACTTTGACCTTGGGT
GATGTTGTTGGTGCTGCTAGAAGAGGTAGATCTGTTAAGGTTGCTGATTCCCCACATATCAGAGAAAGATTGATG
CCTCTGTCGAATTCTTGAGAACCCAATTGGATAACTCTGTTTACGGTGTTACTACTGGTTTTGGTGGTTCTGCTGA
TACAAGAACTGAAGATGCTATCTCCTTGCAAAAGGCTTTGTTGGAACATCAATTGTGTGGTGTTTTGCCAACTTCT
ATGGATGGTTTTGCTTTGGGTAGAGGTTTGGAAAATTCATTGCCATTGGAAGTTGTTAGAGGTGCCATGACTATCA
GAGTTAATTCTTTGACTAGAGGTCACTCCGCTGTTAGAATAGTTGTTTTGGAAGCTTTGACTAACTTCTTGAACCA
TGGTATTACTCCAATCGTTCCATTGAGAGGTACTATTTCTGCTTCTGGTGATTTGTCTCCATTGTCTTATATTGCT
GCTTCCATTACTGGTCACCCAGATTCTAAAGTTCATGTTGATGGTAAGATCATGTCCGCTCAAGAAGCTATTGCTT
TGAAAGGTTTACAACCAGTTGTCTTGGGTCCAAAAGAAGGTTTGGGTTTGGTTAATGGTACTGCTGTTTCAGCTTC
TATGGCTACATTGGCTTTGACTGATGCTCATGTTTTGTCTTTGTTGGCTCAAGCTTTAACTGCTTTGACAGTTGAA
GCTATGGTTGGTCATGCTGGTTCATTTCATCCATTCTTGCATGATGTTACTAGACCACATCCAACCCAAATTGAAG
TTGCCAGAAACATTAGAACCTTGTTGGAAGGTTCCAAGTATGCTGTTCATCACGAAACTGAAGTTAAGGTTAAGGA
TGACGAAGGTATCTTGAGACAAGATAGATACCCATTGAGATGTTCTCCACAATGGTTGGGTCCATTGGTTTCTGAT
ATGATTCATGCTCATGCCGTCTTGTCTTTAGAAGCTGGTCAATCTACTACTGACAACCCATTGATTGACTTGGAAA
ACAAGATGACTCATCATGGTGGTGCTTTTATGGCTTCTTCTGTAGGTAACACTATGGAAAAGACTAGATTGGCTGT
TGCTTTGATGGGTAAGGTTTCTTTCACTCAATTGACCGAAATGTTGAACGCTGGTATGAATAGAGCTTTGCCATCA
TCTTTGGCTGCTGAAGATCCATCTTTATCTTACCACTGTAAGGGTTTGGATATTGCAGCTGCTGCTTATACTTCTG
AATTGGGTCATTTGGCTAACCCAGTTTCTACTCATGTTCAACCAGCTGAAATGGGTAATCAAGCTATCAATTCTTT
GGCCTTGATTTCCGCTAGAAGAACAGCTGAAGCTAATGATGTTTTGAGTTTGTTGTTGGCTACCCACTTGTATTGC
GTTTTACAAGCTGTTGATTTGAGAGCCATGGAATTCGAACATACCAAAGCTTTCGAACCTATGGTCACCGAATTAT
TGAAGCAACATTTTGGTGCTTTGGCTACCGCTGAAGTTGAAGATAAGGTAAGAAAGTCCATCTACAAGAGATTGCA
ACAAAACAATTCCTACGATTTGGAACAAAGATGGCACGATACTTTTTCAGTTGCTACTGGTGCTGTTGTTGAAGGT
TTGGCAGGTCAAGAAGTATCTTTGGCTTCTTTGAATGCTTGGAAAGTTGCTTGTGCTGAAAAGGCTATTGCATTGA
CTAGATCCGTTAGAGATTCTTTTTGGGCTGCTCCATCTTCTTCATCTCCAGCTTTGAAATACTTGTCTCCAAGAAC
TAGAGTCTTGTACTCCTTCGTTAGAGAAGAAGTTGGTGTTAAGGCAAGAAGAGGTGACGTTTATTTGGGTAAACAA
GAAGTCACCATCGGTACAAACGTTTCCAGAATCTATGAAGCCATTAAGTCCGGTAGAATTGCTCCAGTTTTGGTTA
AGATGATGGCCTGA SEQ ID NO: 49    Protein sequence of PAL/TAL2 from *Rhodotorula glutinis*
MAPSVDSIATSVANSLSNGLHAAAAANGGDVHKKTAGAGSLLPTTETTQLDIVERILADAGATDQIKLDGYTLTLG
DVVGAARRGRSVKVADSPHIREKIDASVEFLRTQLDNSVMGVTTGFGGSADTRTEDAISLQKALLEHQLCGVLPTS
MDGFALGRGLENSLPLEVVRGAMTIRVNSLTRGHSAVRIVVLEALTNFLNHGITPIVPLRGTISASGDLSPLSYIA
ASITGHPDSKVHVDGKIMSAQEATALKGLQPVVLGPKEGLGLVNGTAVSASMATLALTDAHVLSLLAQALTALTVE
AMVGHAGSFHPFLHDVTRPHPTQIEVARNIRTLLEGSKYAVHHETEVKVKDDEGILRQDRYPLRCSPQWLGPLVSD
MIHAHAVLSLEAGQSTTDNPLIDLENKMTHHGGAFMASSVGNTMEKTRLAVALMGKVSFTQLTEMLNAGMNRALPS
CLAAEDPSLSYHCKGLDIAAAAYTSELGHLANPVSTHVQPAEMGNQAINSLALISARRTAEANDVLSLLLATHLYC
VLQAVDLRAMEFEHTKAFEPMVTELLKQHFGALATAEVEDKVRKSTYKRLQQNNSYDLEQRWHDTFSVATGAVVEA
LAGQEVSLASLNAWKVACAEKAIALTRSVRDSFWAAPSSSSPALKYLSPRTRVLYSFVREEVGVKARRGDVYLGKQ
EVTIGTNVSRIYEAIKSGRIAPVLVKMMA Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A recombinant host comprising a recombinant gene encoding a tyrosine ammonia lyase (TAL) polypeptide, wherein the host is capable of producing a phenylpropanoid or a phenylpropanoid derivative compound, and wherein the TAL polypeptide sequence has at least 90% identity to the amino acid sequence set forth in SEQ ID NO:31, and uses tyrosine as a preferred substrate.

2. The host of claim 1, wherein the gene encoding a TAL polypeptide encodes a polypeptide having at least 95% identity to the amino acid sequence set forth in SEQ ID NO:31.

3. The host of claim 1, wherein the gene encoding a TAL polypeptide encodes a polypeptide having the amino acid sequence set forth in SEQ ID NO:31.

4. The host of claim 1, wherein the gene encoding the TAL polypeptide is overexpressed in comparison to the direct parental strain.

5. The host of claim 1, wherein the recombinant host is capable of producing an increased yield of a phenylpropanoid or a phenylpropanoid derivative compound, as compared to a recombinant host not comprising the TAL gene.

6. The host of claim 1, further comprising a recombinant gene encoding:
   (a) a stilbene synthase (STS) polypeptide; or
   (b) a chalcone synthase (CHS) polypeptide.

7. The host of claim 1, further comprising one or more of:
   (a) a gene encoding a L-phenylalanine ammonia lyase (PAL) polypeptide;
   (b) a gene encoding a cinnamate-4-hydroxylase (C4H) polypeptide;
   (c) a gene encoding a NADPH:cytochrome P450 reductase polypeptide;
   (d) a gene encoding a 4-coumarate-CoA ligase (4CL) polypeptide; or
   (e) a gene encoding a chalcone isomerase (CHI) polypeptide
   wherein at least one of the genes is a recombinant gene.

8. The host of claim 1, wherein the phenylpropanoid compound is coumaric acid.

9. The host of claim 1, wherein the phenylpropanoid derivative compound is a stilbenoid compound or a chalcone compound.

10. The host of claim 9, wherein the stilbene is resveratrol or a resveratrol derivative.

11. The host of claim 9, wherein the chalcone is naringenin or a naringenin derivative.

12. The host of claim 1, wherein the host comprises a microorganism that is a yeast cell, a plant cell, a mammalian cell, an insect cell, a fungal cell, or a bacterial cell.

13. The host of claim 12, wherein the bacterial cell comprises *Escherichia* bacteria cells, *Lactobacillus* bacteria cells, *Lactococcus* bacteria cells, Cornebacterium bacteria cells, *Acetobacter* bacteria cells, *Acinetobacter* bacteria cells, or *Pseudomonas* bacterial cells.

14. The host of claim 13, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

15. The host of claim 14, wherein the yeast cell is a Saccharomycete.

16. The host of claim 15, wherein the yeast cell is a cell from the *Saccharomyces cerevisiae* species.

17. A method of producing a phenylpropanoid or a phenylpropanoid derivative compound, comprising growing a recombinant host of claim 1 in a culture medium under conditions in which the recombinant genes are expressed, wherein the phenylpropanoid or the phenylpropanoid derivative compound is synthesized by the recombinant host.

18. The method of claim 17, wherein the gene encoding the TAL polypeptide is overexpressed in comparison to the direct parental strain.

19. The method of claim 17, wherein the recombinant host produces an increased yield of a phenylpropanoid or a phenylpropanoid derivative compound, as compared to a recombinant host not comprising the TAL gene.

20. The method of claim 17, wherein the phenylpropanoid derivative compound is a stilbenoid compound or a chalcone compound.

21. The method of claim 20, wherein the chalcone compound is naringenin or a naringenin derivative.

22. The method of claim 20, wherein the stilbene compound is resveratrol or a resveratrol derivative.

23. The method of claim 17, further comprising recovering the phenylpropanoid or the phenylpropanoid derivative compound from the culture media.

24. The method of claim 17, further comprising isolating the phenylpropanoid or the phenylpropanoid derivative compound from the culture medium.

25. The method of claim 17, wherein the host comprises a microorganism that is a yeast cell, a plant cell, a mammalian cell, an insect cell, a fungal cell, or a bacterial cell.

26. The method of claim 25, wherein the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

27. The method of claim 25, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

28. The method of claim 27, wherein the yeast cell is a Saccharomycete.

29. The method of claim 28, wherein the yeast cell is a cell from the *Saccharomyces cerevisiae* species.

* * * * *